(12) United States Patent
Berger et al.

(10) Patent No.: US 11,034,650 B2
(45) Date of Patent: *Jun. 15, 2021

(54) **COMPOUNDS USEFUL FOR TREATING A *MANNHEIMIA HAEMOLYTICA* OR *HISTOPHILUS SOMNI* INFECTION**

(71) Applicant: Intervet Inc., Madison, NJ (US)

(72) Inventors: Michael Berger, Wiesbaden (DE); Thorsten Meyer, Wiesbaden (DE); Joachim Ullrich, Stadecken-Elsheim (DE); Ralf Warrass, Alzey (DE)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,001

(22) PCT Filed: Dec. 22, 2017

(86) PCT No.: PCT/EP2017/084346
§ 371 (c)(1),
(2) Date: Jun. 20, 2019

(87) PCT Pub. No.: WO2018/115421
PCT Pub. Date: Jun. 28, 2018

(65) Prior Publication Data
US 2019/0352256 A1    Nov. 21, 2019

(30) Foreign Application Priority Data

Dec. 23, 2016  (EP) .................... 16206790

(51) Int. Cl.
| | | |
|---|---|---|
| A61K 31/165 | (2006.01) | |
| A61P 11/00 | (2006.01) | |
| C07D 259/00 | (2006.01) | |
| C07D 205/04 | (2006.01) | |
| C07D 207/14 | (2006.01) | |
| C07D 213/56 | (2006.01) | |
| C07D 217/18 | (2006.01) | |
| C07D 233/64 | (2006.01) | |
| C07D 267/10 | (2006.01) | |
| C07D 277/28 | (2006.01) | |
| C07D 295/00 | (2006.01) | |
| C07D 307/56 | (2006.01) | |
| C07D 333/20 | (2006.01) | |
| C07D 409/12 | (2006.01) | |
| C07C 259/06 | (2006.01) | |
| A61P 31/04 | (2006.01) | |
| C07C 317/50 | (2006.01) | |
| C07C 323/60 | (2006.01) | |
| C07D 235/14 | (2006.01) | |
| C07D 295/155 | (2006.01) | |
| C07D 307/52 | (2006.01) | |
| C07D 405/12 | (2006.01) | |
| C07D 413/12 | (2006.01) | |
| C07D 417/12 | (2006.01) | |

(52) U.S. Cl.
CPC ............ *C07C 259/06* (2013.01); *A61P 11/00* (2018.01); *A61P 31/04* (2018.01); *C07C 317/50* (2013.01); *C07C 323/60* (2013.01); *C07D 213/56* (2013.01); *C07D 217/18* (2013.01); *C07D 235/14* (2013.01); *C07D 267/10* (2013.01); *C07D 277/28* (2013.01); *C07D 295/155* (2013.01); *C07D 307/52* (2013.01); *C07D 333/20* (2013.01); *C07D 405/12* (2013.01); *C07D 409/12* (2013.01); *C07D 413/12* (2013.01); *C07D 417/12* (2013.01); *C07C 2601/02* (2017.05); *C07C 2601/04* (2017.05); *C07C 2601/08* (2017.05); *C07C 2601/14* (2017.05); *C07C 2601/16* (2017.05)

(58) Field of Classification Search
CPC ..... A61K 31/165; A61P 11/00; C07D 259/00; C07D 205/04; C07D 207/14; C07D 213/56; C07D 217/18; C07D 233/64; C07D 267/10; C07D 277/28; C07D 295/00; C07D 307/52; C07D 333/20; C07D 409/12
See application file for complete search history.

(56) References Cited

FOREIGN PATENT DOCUMENTS

| CN | 105777464 A | 7/2016 |
|---|---|---|
| EP | 2562155 A1 | 2/2013 |
| WO | 2004062601 A2 | 7/2004 |
| WO | 2008154642 A2 | 12/2008 |
| WO | 2012/031298 A2 | 3/2012 |
| WO | 2013/170030 A1 | 11/2013 |
| WO | 2014165075 A1 | 10/2014 |

(Continued)

OTHER PUBLICATIONS

Angen et al, Proposal of *Histophilus somni* gen. nov., sp. nov., International Journal of Systematic and Evolutionary Microbiology, 2003, pp. 1449-1456, vol. 53.

(Continued)

*Primary Examiner* — Brenda L Coleman
(74) *Attorney, Agent, or Firm* — David J. Kerwick

(57) ABSTRACT

The present invention discloses compounds of formula (I) that are useful in the treatment of respiratory diseases of animals, especially Bovine or Swine Respiratory disease (BRD and SRD).

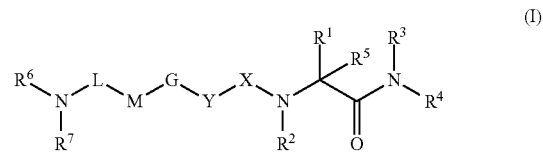

4 Claims, No Drawings

(56) References Cited

FOREIGN PATENT DOCUMENTS

WO    2015/024010 A2    2/2015

OTHER PUBLICATIONS

Extended European Search Report for 16206790.4 dated Jul. 12, 2017, 9 pages.
Hale, M.R., et al., Exploring the UDP pocket of LpxC through amino acid analogs, Bioorganic & Medicinal Chemistry Letters, 2013, pp. 2362-2367, 23.
International Search Report for application No. PCTEP2017084346 dated Feb. 26, 2018, 8 pages.
Rose, S et al, Multiplex PCR to Identify Macrolide Resistance Determinants in Mannheimia haemolytica and Pasteurella multocida, Antimicrobial Agents and Chemotherapy, 2012, pp. 3664-3669, vol. 56 No. 7.
Stephens,L et al, Morphological, Biochemical, Antigenic, and Cytochemical Relationships Among Haemophilus somnus, Haemophilus agni, Haemophilus haemoglobinophilus, Histophilus ovis, and Actinobacillus seminis, Journal of Clinical Microbiology,, 1983, p. 728-737, vol. 17, No. 5.
Titecat, M. et al., High susceptibility of MDR and XDR Gram-negative pathogens to biphenyl-diacetylene-based difluoromethyl-allo-threonyl-hydroxamate LpxC inhibitors, J. Antimicrob. Chemother., Jun. 20, 2016, pp. 2874-2882, 71.
Gao, N. et al., Overexpression of Pseudomonas aeruginosa LpxC with its inhibitors in an acrB-deficient *Escherichia coli* strain, Protein Expression and Purification, 2014, pp. 57-64, 104.
International Search Report for application No. PCTEP2017084346 dated Jan. 4, 2019, 13 pages.

COMPOUNDS USEFUL FOR TREATING A *MANNHEIMIA HAEMOLYTICA* OR *HISTOPHILUS SOMNI* INFECTION

CROSS-REFERENCE TO RELATED APPLICATIONS

This application is a national stage entry under 35 U.S.C. § 371 of PCT/EP2017/084346, filed on Dec. 22, 2017, which claims priority to EP 16206790.4, filed on Dec. 23, 2016; the content of PCT/EP2017/084346 is hereby incorporated by reference in its entirety.

The present invention relates to the field of compounds for the treatment of respiratory diseases of animals, especially of Bovine or Swine Respiratory disease (BRD or SRD).

BACKGROUND

Bovine respiratory disease (BRD) is the most common and costly disease affecting beef cattle in the world. It is a complex, bacterial infection that causes pneumonia in calves and can possibly be fatal. The infection is usually a sum of three codependent factors: Stress, an underlying viral infection, and a new bacterial infection. The diagnosis of the disease is complex since there are multiple possible causes. The disease manifests itself most often in calves within four weeks of weaning, when calves are sorted and often sold to different farms. This gives it a common nickname, "Shipping Fever." BRD is of major economic importance to the North American and the global cattle industries. The United States feedlot industry estimates an annual loss as high as 1 billion dollars due to loss of production, increased labor expenses, drug costs, and death because of bovine respiratory disease (BRD). *Mannheimia haemolytica*, *Pasteurella multocida*, *Histophilus somni*, and *Mycoplasma bovis* are the bacterial agents that have been most consistently implicated in BRDViral agents include Bovine Viral Diarrhea (BVD), Infectious Bovine Rhinotracheitis (IBR), Bovine Respiratory Synctial Virus (BRSV), and Parainfluenza Type-3 Virus (PI-3).

*Pasteurella* is a genus of Gram-negative, facultatively anaerobic bacteria *Pasteurella multocida* is the cause of a range of diseases in mammals and birds, including fowl cholera in poultry, atrophic rhinitis in pigs, and bovine hemorrhagic septicemia in cattle and buffalo.

*Histophilus somni* is also known as *Haemophilus agni*, *Histophilus ovis Haemophilus somnus*, and *Haemophilus somnifer*.

*Histophilus somni* is a bacterium that lives in the nasal passages of cattle. Generally speaking, *H. somni* infects vascular tissue (blood vessels) and endothelium of organs, causing inflammation, thrombosis (formation of a vascular obstruction) that interrupts the blood supply, and causes local cellular death. *H. somni* typically colonize in the respiratory tract, reproductive tract, and circulatory system of many herd animals such as cattle, sheep, and American bison. If *H. somni* infects the lungs, pneumonia can result in rapid death. If *H. somni* gains access to the bloodstream, it spreads throughout the body, a condition known as septicemia.

*Mannheimia haemolytica* is a species of the *Mannheimia* genus. *Mannheimia haemolytica* is a gram negative bacterium normally found in the upper respiratory tract of healthy cattle, sheep and wild sheep. *Mannheimia haemolytica* was formerly known as: *Pasteurella haemolytica*. *M. haemolytica* descends into the lungs when cattle experience stress such as shipping, weaning, overcrowding, or viral infections and causes fibrinous and necrotizing bronchopneumonia, a chief component of the bovine respiratory disease (BRD). *M. haemolytica* is the bacterium most commonly isolated from the lungs of cattle affected with BRD in the United States.

Vaccinations exist for several biological BRD precursors, but the multitude of possible precursors complicates the process of choosing a vaccine regime. Bacteria may be treated with common antibiotics. Fear of antibiotic resistance caution the use of broad spectrum antibiotics and instead prefer compounds that selectively kill bacteria.

There exists a need for such compounds that treat bovine respiratory disease (BRD) associated with *Mannheimia haemolytica*, *Pasteurella multocida* and *Histophilus somni*.

Preferably these compounds are active against the bacterial causes of BRD. Preferably the compounds are active against *Mannheimia haemolytica*, *Pasteurella multocida* and *Histophilus somni*. Preferably the compounds are also active against resistant (e.g. macrolide) strains of these bacteria.

Such strains for *Mannheimia haemolytica* and *Pasteurella multocida* are e.g. described in Rose S, et al: "Multiplex PCR to identify macrolide resistance determinants in *Mannheimia haemolytica* and *Pasteurella multocida* "Antimicrobial Agents and Chemotherapy, 56, 7 (2012) p. 3664-3669.

Respiratory disease in swine is arguably the most important health concern for swine producers today. As with respiratory disease in humans and other species, respiratory disease in swine is often the result of a combination of primary and opportunistic infectious agents. In addition, adverse environmental and management conditions play an important role in the multifactorial nature of respiratory disease in pigs. The term swine respiratory disease (SRD) was used to describe pneumonia of multiple etiology causing clinical disease and failure to gain weight later in the finishing process (15 to 20 weeks of age). *Actinobacillus pleuropneumoniae* is a gram-negative bacterium which is the most common cause of pleuropneumonia in pigs. Outbreaks of *A. pleuropneumoniae* are usually precipitated by stress, environmental changes, or viral or mycoplasmal infection. The disease may present clinically as a peracute form with sudden death; an acute form with clinical signs characterized by fever, lethargy, dyspnea, cyanosis, recumbency, and froth from the nose; or a subacute/chronic form which develops after disappearance of acute signs with intermittent cough, slow growth, and exercise intolerance. *P. multocida* is a gram-negative bacterium which is a cause of atrophic rhinitis and pneumonia in pigs. *Bordetella bronchiseptica* is a gram-negative bacterium that causes rhinitis and mild to moderate turbinate atrophy and predisposes to infection with toxigenic strains of *P. multocida* which causes the progressive form of atrophic rhinitis.

*Mycoplasma hyopneumoniae* is the primary pathogen associated with enzootic pneumonia, which occurs when *M. hyopneumoniae* is combined with opportunistic bacteria such as *P. multocida*. *Haemophilus parasuis* is a gram-negative bacterium which causes polyserositis (Glässer's disease) and pneumonia in swine. Clinical signs include fever, anorexia, swollen joints with lameness, dyspnea, and central nervous system signs. Because of the incomplete efficacy of vaccines, antibacterials are needed to treat *H. parasuis* infections.

Consequently there is a need for compounds for the treatment and control of swine respiratory disease (SRD) especially when associated with *Pasteurella multocida*, *Actinobacillus pleuropneumoniae*, *Bordetella bronchiseptica* or

*Haemophilus parasuis*. Preferably these compounds are active against the bacterial causes of SRD. Preferably the compounds are active against *Pasteurella multocida* and *Actinobacillus pleuropneumoniae*. Preferably the compounds are also active against *Bordetella bronchiseptica*. In one embodiment they are active against *Mycoplasma* spp. It is therefore desirable, that such antibacterial compounds have an effect on such bacterial pathogens involved in BRD and/or SRD but are not active against pathogens (especialy multiresistant) that are important in human health, such as *Straphylococcus* spp. and *Streptrococcus* spp., *Acinetobacter* species, especially *Acinetobacter baumanii*.

SUMMARY OF THE INVENTION

Surprisingly it was found that at least one of the objects can be met by providing a compound according to the formula (I):

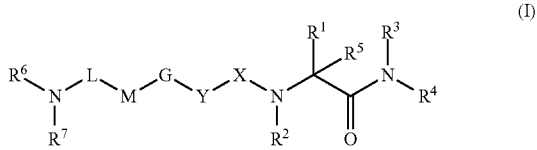

or a stereoisomer, pharmaceutically acceptable salt, ester, solvate, or prodrug thereof, wherein $R^1$ is selected from the group consisting of H, $C(R^{11}R^{12}R^{13})$, $C(=O)R^{11}$, $—C(=NR^{14})R^{11}$;

$R^{11}$ is selected from the group consisting of H, and $C_{1-6}$-alkyl;

$R^{12}$ is selected from the group consisting of

H, $C_{1-6}$-alkyl, and $C_{1-6}$-alkyl substituted with a substituent from the group consisting of $—SR^8$, $—OR^9$, $—C(=O)OR^9$, $—NR^9R^{10}$, $—SO_2NR^9R^{10}$, $—SO_2R^8$;

$R^{13}$ is selected from the group consisting of

H, $C_{1-6}$-alkyl, aryl, $—SR^8$, $—OR^9$, $—NR^9R^{10}$, $—SO_2R^8$, nitro, $—C(=O)NR^9R^{10}$, and $C_{1-6}$-alkyl substituted with a substituent selected from the group consisting of $—SR^8$, $—C(=O)NR^9R^{10}$, $—SO_2R^8$, $—SO_2NR^9R^{10}$, nitro, cyano, $—OR^9$, $—C(=O)OR^9$, $—NR^9C(=NR^{14})NR^9R^{10}$;

or $R^{13}$ and $R^2$ together with the N atom which $R^2$ is attached to, form a saturated or unsaturated heterocycle having 3 to 6 ring atoms wherein 1 ring atom is N and 0, 1 or 2 further ring atoms are selected from N, S, and O the rest of the ring atoms being C;

wherein when $R^{13}$ is OH or $NH_2$ and $R^{12}$ is methyl then $R^{11}$ cannot be H or $R^{11}$ cannot be methyl when $R^{13}$ is $NH_2$;

$R^{14}$ is selected from the group consisting of H, $C_{1-6}$-alkyl, $—OR^9$;

$R^2$, $R^3$ is selected from the group consisting of

H, $C_{1-6}$-alkyl, and $C_{1-6}$-alkyl substituted with a substituent from the group consisting of halogen, hydroxyl, $C_{1-6}$-alkoxy, aryloxy, ester, thiol, $C_{1-6}$-alkyl, carbonyl, $—SR^8$, $—SO_2R^8$, $—SO_2NR^9R^{10}$, $—C(=O)NR^9R^{10}$, cyano, $—NR^9R^{10}$, $—C(=O)OR^9$, aryl, heteroaryl, heterocycle, $C_{3-8}$-cycloalkyl;

$R^4$ is selected from the group consisting of

H, $C_{1-6}$-alkyl, $C_{2-6}$-alkenyl, $C_{2-6}$-alkynyl, $C_{3-10}$-cycloalkyl, $—OR^9$, $C(=O)OR^9$, $C(=O)R^8$, aryl, heteroaryl, heterocyclyl, $C_1$-$C_6$-alkyl substituted with aryl, $C_1$-$C_6$-alkyl substituted with heteroaryl, $C_1$-$C_6$-alkyl substituted with heterocyclyl wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalkyl, $C_{1-6}$-alkyloxy, $NR^9R^{10}$, carbonyl, nitro, $C(=O)OR^9$, halogen, halo-$C_{1-6}$-alkyl, $C_{1-6}$-alkyloxy-$C_{1-6}$-alkyl, cyano, hydroxy, $—SR^8$, $—SO_2R^8$, $—SO_2NR^9R^{10}$, $C(=O)NR^9R^{10}$;

$R^5$ is selected from the group consisting of H, and $C_{1-6}$-alkyl;

$R^6$, $R^7$ are independently selected from the group consisting of

H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or $R^6$, $R^7$ together with the N atom to which they are attached can form a saturated or unsaturated heterocyclic ring having 3 to 12 ring atoms, wherein 1 ring atom is N and 0, 1, 2, or 3 further ring atoms are selected from N, S, and O, the rest of the ring atoms being C;

wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of $C_{1-6}$-alkyl, $C_{3-8}$-cycloalkyl, $C_{1-6}$-alkyloxy, $—NR^9R^{10}$, carbonyl, $—C(=O)OR^9$, halogen atom, $C_{1-6}$-alkyl substituted with halo, $C_{1-6}$-alkyloxy-$C_{1-6}$-alkyl, aryl, heteroaryl, $C_1$-$C_6$-alkyl substituted with aryl, cyano, hydroxyl, $—SR^8$, $—SO_2R^8$, $—SO_2NR^9R^{10}$, $—C(=O)NR^9R^{10}$, $C_{1-6}$-alkyl substituted with hydroxyl;

$R^8$ is selected from the group consisting of H, $C_{1-6}$-alkyl;
$R^9$, $R^{10}$ are independently selected from the group consisting of H, and $C_{1-6}$-alkyl;

L is selected from the group consisting of $C_{1-6}$-alkyl, $C_{2-6}$-alkenyl, $C_{2-6}$-alkynyl, $C_{3-10}$-cycloalkyl, $—(NR^{L3})_{0-1}—(CH_2)_{0-4}—NR^{L3}—)_{0-4}—$, $—(NR^{L3})_{0-1}—(CR^{L1}R^{L2})_{0-4}—NR^{L3}—(CR^{L1}R^{L2})—$, $—(CR^{L1}R^{L2})_{0-4}—O—(CR^{L1}R^{L2})$, $—(CH_2)_{0-4}—NR^{L3}—(CR^{L1}R^{L2})—C(=O)NH—(CH_2)_{0-4}—$, $—C(=O)—(CR^{L1}R^{L2})NR^{L3}C(=O)—$, $—C(=O)NR^{L3}—$, $—NR^{L3}C(=O)—$, $—NR^{L3}—$, $—SO_2NR^{L3}—$, $—NR^{L3}—C(=O)—NR^{L3}—$;

wherein $R^{L1}$, $R^{L2}$, $R^{L3}$, are independently selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of $C_{3-10}$-cycloalkyl, aryl, heterocyclyl, heteroaryl, $C_{2-4}$alkenyl, $C_{2-4}$alkynyl, $—C(R^{M1})=C(R^{M1})—C\equiv C—$, $—C(R^{M1})=C(R^{M1})—$, wherein each cycloalkyl, aryl, heterocyclyl, or heteroaryl is optionally substituted with a substituent selected from the group consisting of $C_{1-6}$-alkyl, $C_{3-8}$-cycloalkyl, $C_{1-6}$-alkyloxy, $NR^{M2}R^{M3}$, carbonyl, $—C(=O)OR^{M2}$, halo, halo-$C_{1-6}$-alkyl, $C_{1-6}$-alkyloxy-$C_{1-6}$-alkyl, aryl, heteroaryl, $C_1$-$C_6$-alkyl substituted with aryl, cyano, hydroxy, $—SR^{M2}$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-C$_{1-6}$-alkyl;

wherein R$^{M1}$ is selected from the group consisting of H, C$_{1-6}$-alkyl, halo, hydroxyl, and amino;

wherein R$^{M2}$, R$^{M3}$ are independently selected from the group consisting of H, and C$_{1-6}$-alkyl;

wherein R$^{M4}$ is selected from the group consisting of H, C$_{1-6}$-alkyl, and amino;

G is selected from the group consisting of
—(C(R$^{G2}$R$^{G3}$)$_{0-4}$—O—(C(R$^{G2}$R$^{G3}$)$_{0-4}$—,
—(C(R$^{G2}$R$^{G3}$)$_{0-4}$—S—(C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—,
—NR$^{G1}$C(=O)—, —C(=O)NR$^{G1}$—,
—(C(R$^{G2}$R$^{G3}$)$_{0-4}$—NR$^{G1}$—C(R$^{G2}$R$^{G3}$)—C(=O)NR$^{G1}$—, —CR$^{G2}$=CR$^{G2}$—, —CR$^{G2}$=CR$^{G2}$—CR$^{G2}$=CR$^{G2}$—, —C≡C—, —C≡C—C≡C—,
—CR$^{G2}$=CR$^{G2}$—C≡C—, —C≡C—CR$^{G2}$=CR$^{G2}$,
—C(=O)—C≡C—, —C≡C—C(=O)— —SO$_2$—,
—S(=O)—, —S(=O)C(R$^{G2}$R$^{G3}$)—. —C(R$^{G2}$R$^{G3}$)S(=O)—, —C(R$^{G2}$R$^{G3}$)—SO$_2$—, —SO$_2$C(R$^{G2}$R$^{G3}$)—;

wherein
R$^{G1}$ is H or C$_{1-6}$-alkyl
each R$^{G2}$, R$^{G3}$ is independently selected from the group consisting of
H, halogen atom, or C$_{1-6}$-alkyl;

Y is selected from the group consisting of
C$_{3-10}$-cycloalkyl, aryl, heterocyclyl, heteroaryl,
wherein each cycloalkyl, aryl, heterocyclyl, or heteroaryl is optionally substituted with a substituent selected from the group consisting of
C$_{1-6}$-alkyl, C$_{3-8}$-cycloalkyl, C$_{1-6}$-alkyloxy, NR$^{Y1}$R$^{Y2}$, carbonyl, —C(=O)—OR$^{Y1}$, halo, halo-C$_{1-6}$-alkyl, C$_{1-6}$-alkyloxy-C$_{1-6}$-alkyl, aryl, heteroaryl, C$_1$-C$_6$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-C$_{1-6}$-alkyl;

wherein R$^{Y1}$, R$^{Y2}$ are independently selected from the group consisting of H, and C$_{1-6}$-alkyl;

wherein R$^{Y3}$ is selected from the group consisting of H, C$_{1-6}$-alkyl, and amino;

X is selected from the group consisting of
—C(=O)—, —C$_{1-6}$-alkyl-C(=O)—, —C$_{2-6}$-alkenyl-C(=O)—, —C$_{2-6}$-alkynyl-C(=O)—, and —(CR$^{X1}$R$^{X2}$)—, —S(=O)—, —SO$_2$—;

wherein
each R$^{X1}$, R$^{X2}$ is selected from the group consisting of H, halogen atom, substituted C$_{1-6}$-alkyl, or un-substituted C$_{1-6}$-alkyl;
wherein the substituents on the substituted C$_{1-6}$-alkyl may be selected from the group consisting of halogen, hydroxyl, alkoxy, aryloxy, ester, thiol, C$_{1-6}$-alkyl, carbonyl, —SR$^{X3}$, —SO$_2$R$^5$, —C(=O)NR$^{X3}$R$^{X4}$, cyano, —NR$^{X3}$R$^{X4}$, —C(=O)—OR$^{X3}$, aryl, heteroaryl, heterocycle, C$_{3-8}$-cycloalkyl;
wherein R$^{X3}$, R$^{X4}$ are independently selected from the group consisting of H, or C$_{1-6}$-alkyl;
wherein R$^{X5}$ is selected from the group consisting of H, C$_{1-6}$-alkyl, and amine.

Suitably, in an embodiment of the invention and/or embodiments thereof, R$^6$, R$^7$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl, or NR$^6$R$^7$ is NO$_2$ or R$^6$, R$^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O, the rest of the ring atoms being C;

wherein the alkyl, alkenyl, alkynyl, cycloalkyl, aryl, heterocyclyl, heteroaryl, alkyloxy or the heterocyclic ring formed by R$^6$, R$^7$ together with the N atom to which they are attached is optionally substituted with a substituent selected from the group consisting of
C$_{1-6}$-alkyl, C$_{3-8}$-cycloalkyl, C$_{1-6}$-alkyloxy, —NR$^9$R$^{10}$, carbonyl, —C(=O)—OR$^9$, halogen atom, C$_{1-6}$-alkyl substituted with halo, C$_{1-6}$-alkyloxy-C$_{1-6}$-alkyl, aryl, heteroaryl, C$_1$-C$_6$-alkyl substituted with aryl, cyano, hydroxy, —SR$^8$, —SO$_2$R$^8$, —SO$_2$NR$^9$R$^{10}$, —C(=O)NR$^9$R$^{10}$, C$_{1-6}$-alkyl substituted with hydroxy;

wherein
R$^8$ is selected from the group consisting of H, C$_{1-6}$-alkyl;
R$^9$, R$^{10}$ are independently selected from the group consisting of H, and C$_{1-6}$-alkyl.

In yet another embodiment of the invention and/or embodiments thereof, R$^6$, R$^7$ are independently selected from
H, C$_{1-6}$-alkyl, C$_{2-6}$-alkenyl, C$_{2-6}$-alkynyl, C$_{3-10}$-cycloalkyl, C$_{1-6}$-alkyloxy-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl, or NR$^6$R$^7$ is NO$_2$ or R$^6$, R$^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O.

In yet another embodiment of the invention and/or embodiments thereof, R$^6$, R$^7$ are independently selected from
H, C$_{1-6}$-alkyl, C$_{2-6}$-alkenyl, C$_{3-10}$-cycloalkyl, C$_{1-6}$-alkyloxy-C$_{1-6}$-alkyl, C$_1$-C$_6$-alkyl substituted with aryl, C$_1$-C$_6$-alkyl substituted with heteroaryl, or NR$^6$R$^7$ is NO$_2$ or R$^6$, R$^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O.

In yet another embodiment of the invention and/or embodiments thereof L is selected from the group consisting of
C$_{1-6}$-alkyl, C$_{2-6}$-alkenyl, C$_{2-6}$-alkynyl, C$_{3-10}$-cycloalkyl,
—(NR$^{L3}$)$_{0-1}$—(CH$_2$)$_{0-4}$—NR$^{L3}$—(CH$_2$)$_{0-4}$—,
—(NR$^{L3}$)$_{0-1}$—(CR$^{L1}$R$^{L2}$)$_{0-4}$—NR$^{L3}$—(CR$^{L1}$R$^{L2}$)—,
—(CR$^{L1}$R$^{L2}$)$_{0-4}$—O—(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—,
—C(=O)—(CR$^{L1}$R$^{L2}$)NR$^{L3}$C(=O)—, —C(=O)NR$^{L3}$—, —NR$^{L3}$C(=O)—, —NR$^{L3}$—, —SO$_2$NR$^{L3}$—, NR$^{L3}$—C(=O)—NR$^{L3}$— wherein
R$^{L1}$, R$^{L2}$, R$^{L3}$, are independently selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or
R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O.

In yet another embodiment of the invention and/or embodiments thereof L is selected from the group consisting of $C_{1-6}$-alkyl, $C_{2-6}$-alkenyl, $C_{2-6}$-alkynyl, $C_{3-10}$-cycloalkyl, —$NR^{L3}$—, wherein $R^{L3}$, is selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

Suitably L is selected from the group consisting of $C_{1-6}$-alkyl, or $C_{2-6}$-alkenyl. Preferably L is —$CH_2$—, —$CH_2CH_2$—, —$CH_2CH_2CH_2$—, or —$CH_2CH_2CH_2CH_2$—, more preferably L is —$CH_2$—, —$CH_2CH_2$—, or —$CH_2CH_2CH_2$—, more preferably L is —$CH_2$—, or —$CH_2CH_2$—.

In another embodiment of the invention and/or embodiments thereof M is selected from the group consisting of $C_{3-10}$-cycloalkyl, aryl, heterocyclyl, heteroaryl, $C_{2-4}$alkenyl, $C_{2-4}$alkynyl, —$C(R^{M1})$=$C(R^{M1})$—C≡C—, —$C(R^{M1})$=$C(R^{M1})$—, wherein each cycloalkyl, aryl, heterocyclyl, or heteroaryl is optionally substituted with a substituent selected from the group consisting of $C_{1-6}$-alkyl, $C_{3-8}$-cycloalkyl, $C_{1-6}$-alkyloxy, $NR^{M2}R^{M3}$, carbonyl, —C(=O)—$OR^{M2}$, halo, halo-$C_{1-6}$-alkyl, $C_{1-6}$-alkyloxy-$C_{1-6}$-alkyl, aryl, heteroaryl, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(=O)$NR^{M2}R^{M3}$—, hydroxy-$C_{1-6}$-alkyl;

wherein $R^{M1}$ is selected from the group consisting of H, $C_{1-6}$-alkyl, halo, hydroxyl, and amino;

wherein $R^{M2}$, $R^{M3}$ are independently selected from the group consisting of H, and $C_{1-6}$-alkyl;

wherein $R^{M4}$ is selected from the group consisting of H, $C_{1-6}$-alkyl, and amino.

Suitably M is selected from the group consisting of $C_{3-10}$-cycloalkyl, aryl, heterocyclyl, heteroaryl, $C_{2-4}$alkenyl, $C_{2-4}$alkynyl, —$C(R^{M1})$=$C(R^{M1})$—C≡C—, —$C(R^{M1})$=$C(R^{M1})$—. More suitably M is selected from the group consisting of aryl, heterocyclyl, heteroaryl, —$C(R^{M1})$=$C(R^{M1})$—C≡C—, —$C(R^{M1})$=$C(R^{M1})$—. More suitably M is selected from the group consisting of aryl, heteroaryl, —$C(R^{M1})$=$C(R^{M1})$—C≡C—, —$C(R^{M1})$=$C(R^{M1})$—.

In another embodiment of the invention and/or embodiments thereof G is selected from the group consisting of —$(C(R^{G2}R^{G3}))_{0-4}$—O—$(C(R^{G2}R^{G3}))_{0-4}$—,
—$(C(R^{G2}R^{G3}))_{0-4}$—S—$(C(R^{G2}R^{G3}))_{0-4}$—, —$(C(R^{G2}R^{G3}))_{0-4}$—$NR^{G1}$—$(C(R^{G2}R^{G3}))_{0-4}$—, —C(=O)—,
—$NR^{G1}C$(=O)—, —C(=O)$NR^{G1}$—,
—$(C(R^{G2}R^{G3}))_{0-4}$—$NR^{G1}$—$C(R^{G2}R^{G3})$—C(=O)$NR^{G1}$—, —$CR^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡C—C(=O)— —$SO_2$—, —S(=O)—, —S(=O)$C(R^{G2}R^{G3})$—. —$C(R^{G2}R^{G3})S$(=O)—, —$C(R^{G2}R^{G3})$—$SO_2$—, —$SO_2C(R^{G2}R^{G3})$—;

wherein $R^{G1}$ is H or $C_{1-6}$-alkyl each $R^{G2}$, $R^{G3}$ is independently selected from the group consisting of H, halogen atom, or $C_{1-6}$-alkyl.

In suitable embodiments, G is selected from the group consisting of —C≡C—, —C≡C—C≡C—, —$CR^{G2}$=$CR^{G2}$—C≡C—, —C≡C—$CR^{G2}$=$CR^{G2}$, wherein $R^{G2}$ is selected from the group consisting of H, halogen atom, or $C_{1-6}$-alkyl.

In another suitable embodiments, G is selected from the group consisting of $CR^{G2}$=$CR^{G2}$—, —C≡C—, —C≡C—C≡C—, —C≡C—C(=O)—.

wherein $R^{G2}$ is selected from the group consisting of

H, halogen atom, or $C_{1-6}$-alkyl.

In some embodiments of the invention and/or embodiments thereof the compound is a compound according to formula (II)

(II)

or a stereoisomer, pharmaceutically acceptable salt, ester, solvate, or prodrug thereof, wherein L, M, Y, X, $R^1$, $R^2$, $R^3$, $R^4$, $R^5$, $R^6$, and $R^7$ are defined as in any of the embodiments described herein.

In some embodiments of the invention and/or embodiments thereof, Y is selected from the group consisting of $C_{3-10}$-cycloalkyl, aryl, heterocyclyl, heteroaryl, wherein each cycloalkyl, aryl, heterocyclyl, or heteroaryl is optionally substituted with a substituent selected from the group consisting of $C_{1-6}$-alkyl, $C_{3-8}$-cycloalkyl, $C_{1-6}$-alkyloxy, $NR^{Y1}R^{Y2}$, carbonyl, —C(=O)—$OR^{Y1}$, halo, halo-$C_{1-6}$-alkyl, $C_{1-6}$-alkyloxy-$C_{1-6}$-alkyl, aryl, heteroaryl, $C_1$-$C_6$-alkyl substituted with aryl, cyano, hydroxy, —$SR^{Y2}$, —$SO_2R^{Y3}$, —$OSO_2R^{Y3}$, —$SO_2NR^{Y1}R^{Y2}$, —C(=O)$NR^{M2}R^{M3}$—, hydroxy-$C_{1-6}$-alkyl;

wherein R Y, $R^{Y2}$ are independently selected from the group consisting of H, and $C_{1-6}$-alkyl;

wherein $R^{Y3}$ is selected from the group consisting of H, $C_{1-6}$-alkyl, and amino. In embodiments of the invention and/or embodiments thereof, Y is selected from aryl, or heteroaryl. Suitably Y is aryl. Suitably Y is phenyl. Suitably Y is para-phenyl.

In some embodiments of the invention and/or embodiments thereof the cycloalkyl, aryl, heterocyclyl, or heteroaryl of Y is optionally substituted with a substituent selected from the group consisting of $C_{1-6}$-alkyl, $C_{1-6}$-alkyloxy, $NR^{Y1}R^{Y2}$, carbonyl, —C(=O)—OR Y, halo, halo-$C_{1-6}$-alkyl, $C_{1-6}$-alkyloxy-$C_{1-6}$-alkyl, $C_1$-$C_6$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-C$_{1-6}$-alkyl.

Suitably the cycloalkyl, aryl, heterocyclyl, or heteroaryl of Y is optionally substituted with a substituent selected from the group consisting of C$_{1-6}$-alkyl, halo, halo-C$_{1-6}$-alkyl, hydroxy-C$_{1-6}$-alkyl. Suitably, the cycloalkyl, aryl, heterocyclyl, or heteroaryl of Y is not substituted.

In some embodiments of the invention and/or embodiments thereof the compound is a compound according to formula (III)

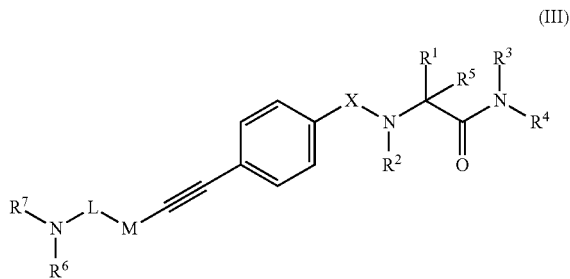

(III)

or a stereoisomer, pharmaceutically acceptable salt, ester, solvate, or prodrug thereof, wherein L, M, X, R$^1$, R$^2$, R$^3$, R$^4$, R$^5$, R$^6$, and R$^7$ are defined as in any of the embodiments described herein.

In some embodiments of the invention and embodiments thereof, X is selected from the group consisting of
—C(=O)—, —C$_{1-6}$-alkyl-C(=O)—, —C$_{2-6}$-alkenyl-C(=O)—, —C$_{2-6}$-alkynyl-C(=O)—, and —(C(R$^{X1}$)$_2$—, —S(=O)—, —SO$_2$—;
wherein
R$^{X1}$, R$^{X2}$, is selected from the group consisting of
H, halogen atom, substituted C$_{1-6}$-alkyl, or un-substituted C$_{1-6}$-alkyl;
wherein the substituents on the substituted C$_{1-6}$-alkyl may be selected from the group consisting of halogen, hydroxyl, alkoxy, aryloxy, ester, thiol, C$_{1-6}$-alkyl, carbonyl, —SR$^{X3}$, —SO$_2$R$^{X5}$, —C(=O)NR$^{X3}$R$^{X4}$, cyano, —NR$^{X3}$R$^{X4}$, —C(=O)—OR$^{X3}$, aryl, heteroaryl, heterocycle, C$_{3-8}$-cycloalkyl;
wherein R$^{X3}$, R$^{X4}$ are independently selected from the group consisting of H, or C$_{1-6}$-alkyl;
wherein R$^{X5}$ is selected from the group consisting of H, C$_{1-6}$-alkyl, and amine.

Suitably X is selected from the group consisting of —C(=O)—, —C$_{1-6}$-alkyl-C(=O)—, S(=O)—, —SO$_2$—. Suitably X is selected from —C(=O)—, and S(=O)—.

In some embodiments of the invention and/or embodiments thereof the compound is a compound according to formula (IV)

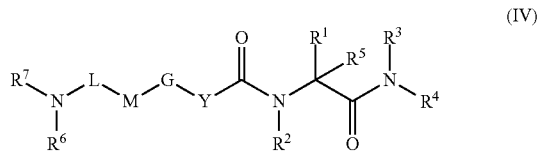

(IV)

or a stereoisomer, pharmaceutically acceptable salt, ester, solvate, or prodrug thereof, wherein L, M, G, Y, R$^1$, R$^2$, R$^3$, R$^4$, R$^5$, R$^6$, and R$^7$ are defined as in any of the embodiments described herein.

In another embodiments of the invention and/or embodiments thereof R$^2$, R$^3$ is independently selected from the group consisting of H, substituted C$_{1-6}$-alkyl, or un-substituted C$_{1-6}$-alkyl. Suitably R$^2$ and R$^3$ are H.

In embodiments of the invention and/or embodiments thereof R$^4$ is selected from the group consisting of H, C$_{1-6}$-alkyl, C$_{2-6}$-alkenyl, C$_{2-6}$-alkynyl, C$_{3-10}$-cycloalkyl, —OR$^8$, C(=O)OR$^{8'}$ C(=O)R$^8$, aryl, heterocyclyl, heteroaryl, C$_1$-C$_6$-alkyl substituted with aryl, C$_1$-C$_6$-alkyl substituted with heteroaryl, C$_1$-C$_6$-alkyl substituted with heterocyclyl
wherein each alkyl, alkenyl, alkynyl, cycloalkyl, aryl, heterocyclyl, heteroaryl, is optionally substituted with a substituent selected from the group consisting of
C$_{1-6}$-alkyl, C$_{3-8}$-cycloalkyl, C$_{1-6}$-alkyloxy, NR$^9$R$^{10}$, carbonyl, nitro, C(=O)OR$^6$, halogen, halo-C$_{1-6}$-alkyl, C$_{1-6}$-alkyloxy-C$_{1-6}$-alkyl, cyano, hydroxy, —SR$^8$, —SO$_2$R$^8$, —SO$_2$NR$^9$R$^{10}$, C(=O)NR$^9$R$^{10}$.

Suitably in embodiments of the invention and/or embodiments thereof R$^4$ is selected from the group consisting of H, C$_{1-6}$-alkyl, —OR$^8$, C(=O)OR$^{8'}$ C(=O)R$^8$. More suitably R$^4$ is selected from the group consisting of H, —OR$^8$. Suitably R$^4$ is —OR$^8$, more suitably R$^8$ is OH.

Suitably R$^1$ is selected from the group consisting of C(R$^{11}$R$^{12}$R$^{13}$), C(=O)R$^{11}$, —C(=NR$^{14}$)R$^{11}$. Suitably R$^1$ is C(R$^{11}$R$^{12}$R$^{13}$). Suitably R$^1$ is C(=O)R$^{11}$. Suitably R$^1$ is —C(=NR$^{14}$)R$^{11}$.

In another suitable embodiment of the present invention and/or embodiments thereof, R$^{12}$ is selected from the group consisting of
H, C$_{1-6}$-alkyl, and C$_{1-6}$-alkyl substituted with a substituent from the group consisting of —SR$^8$, '—OR$^9$, —C(=O)OR$^9$, —NR$^9$R$^{10}$, —SO$_2$NR$^9$R$^{10}$, —SO$_2$R$^8$.

Suitably in certain embodiments of the present invention and/or embodiments thereof, the substituted C$_{1-6}$-alkyl in R$^{12}$ is substituted with a substituent selected from the group consisting of
—SR$^8$, '—OR$^9$, —NR$^9$R$^{10}$, —SO$_2$NR$^9$R$^{10}$, —SO$_2$R$^8$.

In some embodiments of the present invention and/or embodiments thereof, R$^{13}$ is selected from the group consisting of
H, C$_{1-6}$-alkyl, —SR$^8$, —OR$^9$, —NR$^9$R$^{10}$, —SO$_2$R$^8$, nitro, —C(=O)NR$^9$R$^{10}$, and C$_{1-6}$-alkyl substituted with a substituent selected from the group consisting of —SR$^8$, —C(=O)NR$^9$R$^{10}$, —SO$_2$R$^8$, —SO$_2$NR$^9$R$^{10}$, nitro, cyano, —OR$^9$, —C(=O)OR$^9$, —NR$^9$C(=NR$^{14}$)NR$^9$R$^{10}$.

Suitably in certain embodiments of the present invention and/or embodiments thereof, the substituted C$_{1-6}$-alkyl in R$^{13}$ is substituted with a substituent selected from the group consisting of —SR$^8$, —C(=O)NR$^9$R$^{10}$, —SO$_2$R$^8$, —S$_2$NR$^9$R$^{10}$, nitro, cyano, —OR$^9$, —C(=O)OR$^9$, —NR$^9$C(=NR$^{14}$)NR$^9$R$^{10}$.

In some embodiments of the present invention and/or embodiments thereof, the aryl in R$^{13}$ is phenyl or hydroxyphenyl.

Suitably in certain embodiments of the present invention and/or embodiments thereof, R$^{13}$ and R$^2$ together with the N atom which R$^2$ is attached to, form a heterocycle selected from the group consisting of aziridine, azirine, azetidine, dihydroazete, azete, diazetidine, pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine.

Suitably in certain embodiments of the present invention and/or embodiments thereof, when $R^{13}$ is OH or $NH_2$ and $R^{12}$ is methyl then $R^{11}$ cannot be H.

Suitably in certain embodiments of the present invention and/or embodiments thereof, when $R^{13}$ is $NH_2$ and $R^{12}$ is methyl $R^{11}$ cannot be methyl.

Suitably in certain embodiments of the present invention and/or embodiments thereof, when $R^{13}$ is OH and $R^{12}$ is methyl then $R^{11}$ cannot be methyl.

Suitably in certain embodiments of the present invention and/or embodiments thereof, when $R^{13}$ is $NH_2$ and $R^{12}$ is H then $R^{11}$ cannot be H.

Suitably in certain embodiments of the present invention and/or embodiments thereof, when $R^{13}$ is OH and $R^{12}$ is H then $R^{11}$ cannot be H.

Suitably in certain embodiments of the present invention and/or embodiments thereof, when $R^{13}$ is $CH_3$ and $R^{12}$ is $CH_3$ then $R^{11}$ cannot be H.

The invention is also directed to method for treating an animal with an infection by a bacteria comprising administering to the subject in need thereof an effective amount of a compound of the present invention and/or embodiments thereof with a pharmaceutically acceptable carrier, wherein the bacteria is at least one of the bacteria selected from the group *Pasteurella multocida*, *Mannheimia haemolytica* and *Histophilus somni*. Suitably the subject is a mammal and in some embodiments, a ruminant or swine.

In yet another aspect, the invention is directed to a compound according to the present invention and/or embodiments thereof with a pharmaceutically acceptable carrier for use in the treatment of bovine respiratory disease or swine respiratory disease.

The invention provides further a pharmaceutical composition comprising an effective amount of a compound according to the invention and/or embodiments thereof with a pharmaceutically acceptable carrier thereof.

DETAILED DESCRIPTION

It was found that compounds according to formula (I) or the stereoisomer, pharmaceutically acceptable salt, ester, solvate, or prodrug thereof, are useful in the treatment of an infection by a bacteria causing Bovine Respiratory disease, such as *Mannheimia haemolytica Histophilus somni*, and *Pasteurella multocida*, In particular the compounds according to the invention and/or any embodiments thereof are useful in the treatment of an infection by *Mannheimia haemolytica* and/or *Histophilus somni*. Optionally, the compounds according to the invention and/or any embodiments thereof are useful in the treatment of an infection by *Pasteurella multocida*. Advantageously, the compounds according to the invention and/or any embodiments thereof are useful in the treatment of an infection by *Mannheimia haemolytica*, *Histophilus somni* and *Pasteurella multocida*.

Increasingly there is a fear of multi-resistant bacteria. There is therefore a need for a specific antibiotic that can be used in an infection of a specific bacterium. Advantageously the compounds according to the invention and/or any embodiments thereof is effective against *Mannheimia haemolytica*, *Histphilus somni* and/or *Pasteurella multocida* but not against other bacteria, such as those that are important in human health, such as *Straphylococcus* spp. and *Streptrococcus* spp., *Acinetobacter* species, especially *Acinetobacter baumanii*.

The following abbreviations and definitions are used throughout this application: Generally, reference to a certain element such as hydrogen or H is meant to include all isotopes of that element. For example, if an R group is defined to include hydrogen or H, it also includes deuterium and tritium.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example: $-CH(CH_3)_2$, $-CH(CH_3)(CH_2CH_3)$, $-CH(CH_2CH_3)_2$, $-C(CH_3)_3$, $-C(CH_2CH_3)_3$, $-CH_2CH(CH_3)_2$, $-CH_2CH(CH_3)(CH_2CH_3)$, $-CH_2CH(CH_2CH_3)_2$, $-CH_2C(CH_3)_3$, $-CH_2C(CH_2CH_3)_3$, $-CH(CH_3)CH(CH_3)(CH_2CH_3)$, $-CH_2CH_2CH(CH_3)_2$, $-CH_2CH_2CH(CH_3)(CH_2CH_3)$, $-CH_2CH_2CH(CH_2CH_3)_2$, $-CH_2CH_2C(CH_3)_3$, $-CH_2CH_2C(CH_2CH_3)_3$, $-CH(CH_3)CH_2CH(CH_3)_2$, $-CH(CH_3)CH(CH_3)CH(CH_3)_2$, $-CH(CH_2CH_3)CH(CH_3)CH(CH_3)(CH_2CH_3)$, and others. Thus the phrase alkyl groups includes primary alkyl groups, secondary alkyl groups, and tertiary alkyl groups. Preferred alkyl groups include straight and branched chain alkyl groups having 1 to 12 carbon atoms.

The phrase "substituted alkyl" refers to an alkyl group as defined above in which one or more bonds to a carbon (s) or hydrogen (s) are replaced by a bond to non-hydrogen and non-carbon atoms. If not further defined the "substituted alkyl" may be substituted by a group such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon (s) or hydrogen (s) atom is replaced by a higher-order bond (e. g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon (s) or hydrogen (s) atoms is replaced by a bond to an aryl, heterocyclyl group, or cycloalkyl group. Exemplary substituted alkyl groups include, among others, alkyl groups in which one or more bonds to a carbon or hydrogen atom is/are replaced by one or more bonds to fluorine atoms.

Another exemplary substituted alkyl group is the trifluoromethyl group and other alkyl groups that contain the trifluoromethyl group. Other exemplary substituted alkyl groups include those in which one or more bonds to a carbon or hydrogen atom is replaced by a bond to an oxygen atom such that the substituted alkyl group contains a hydroxyl, alkoxy, or aryloxy group. Still other exemplary substituted alkyl groups include alkyl groups that have an amine, or a substituted or unsubstituted alkylamine, dialkylamine, arylamine, (alkyl) (aryl) amine, diarylamine, heterocyclylamine, diheterocyclylamine, (alkyl) (heterocyclyl) amine, or (aryl) (heterocyclyl) amine group.

The phrase "alkenyl" refers to straight and branched chain and cyclic groups such as those described with respect to alkyl groups as defined above, except that at least one double bond exists between two carbon atoms. Examples include, but are not limited to vinyl, —CH=C(H)(CH₃), —CH=C(CH₃)₂, —C(CH₃)=C(H)₂, —C(CH)=C(H)(CH₃), —C(CH₂CH₃)=CH₂, cyclohexenyl, cyclopentenyl, cyclohexadienyl, butadienyl, pentadienyl, and hexadienyl among others.

The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —C≡C(H), —C≡C(CH₃), —C≡C(CH₂CH₃), —C(H₂)C≡C(H), —C(H)₂C≡C(CH₃), and —C(H)₂C≡C(CH₂CH₃) among others.

The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "cycloalkyl" refers to a non-aromatic monocyclic or polycyclic alkyl group consisting solely of carbon and hydrogen atoms, and which may be saturated or unsaturated. Cycloalkyl may include fused or bridged ring systems, having from three to fifteen carbon atoms, preferably having from three to ten carbon atoms ($C_3$-$C_{10}$-cycloalkyl), and which may be saturated or unsaturated. Monocyclic radicals include, for example, cyclopropyl, cyclobutyl, cyclopentyl, cyclohexyl, cycloheptyl, cyclooctyl, and the like. Polycyclic radicals include, for example, adamantine, norbornane, decalinyl, 7,7-dimethyl-bicyclo[2.2.1]heptanyl, and the like. If not further defined, cycloalkyl may be substituted with substituents as indicated above with substituted alkyl group.

The phrase "heterocyclic ring" refers to both aromatic, "heteroaryl" and nonaromatic, "heterocyclyl", ring compounds including monocyclic, bicyclic, and polycyclic ring compounds such as, but not limited to, quinuclidinyl, containing 3 or more ring members of which one or more is a heteroatom such as, but not limited to, N, O, and S.

Heterocyclyl refers to a 3- to 18-membered non-aromatic ring radical which consists of two to seventeen carbon atoms and from one to ten heteroatoms selected from the group consisting of nitrogen, oxygen and sulfur. Unless stated otherwise specifically in the specification, the heterocyclyl radical may be a monocyclic, bicyclic or polycyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e. g. 4H-1,2,4-triazolyl, lu-1,2,3-triazolyl, 2H-1,2,3-triazolyl etc.), tetrazolyl, (e. g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e. g. 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e. g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e. g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e. g. 2H-1,4-benzothiazinyl, etc.), dihydrobenzothiazinyl (e. g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e. g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene,' tetrahydrothiophene oxide, and tetrahydrothiophene 1,1-dioxide. Exemplary heterocyclyl groups contain 5 or 6 ring members. Other exemplary heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran. The phrase "substituted heterocyclyl" refers to a heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus the phrase includes, but is not limited to, groups such as phenyl, biphenyl, anthracenyl, naphtenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. An exemplary unsubstituted aryl group is phenyl. Unsubstituted aryl groups may be bonded to one or more carbon atom(s), oxygen atom(s), nitrogen atom(s), and/or sulfur atom (s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e. g. dihydronaphthyl or tetrahydronaphthyl). Thus, the phrase "substituted aryl" includes, but is not limited to tolyl, and hydroxyphenyl among others. If not further defined the "substituted aryl group" may be substituted by a group such as straight and branched chain alkyl groups, —$CH_3$, —$C_2H_5$, —$CH_2OH$, —OH, —$OCH_3$, —$OC_2H_5$, —$OCF_3$, —CN, —$NO_2$, —$CO_2H$, —$CO_2CH_3$, —$CONH_2$, —$NH_2$, —F, —Cl, Br, —$CF_3$, —$N(CH_3)_2$, —$NHSO_2CH_3$, —$NHCOCH_3$.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon. Exemplary substituents may include Cl, Br, F, I, OH, CN, $C_{1-3}$-alkyl, $C_{1-6}$-alkoxy, $C_{1-6}$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Exemplary substituents include straight and branched chain alkyl groups, —$CH_3$, —$C_2H_5$, —$CH_2OH$, —OH, —$OCH_3$, —$OC_2H_5$, —$OCF_3$, —CN, —$NO_2$, —$CO_2H$, —$CO_2CH_3$, —$CONH_2$, —$NH_2$, —F, —Cl, —Br, —$CF_3$, —$N(CH_3)_2$, —$NHSO_2CH_3$, —$NHCOCH_3$.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl) benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl) phenyl]acetamide, 1,4-diphenylbenzene, N-[4-(2-phenylethynyl) phenyl]-2-[benzylamino] acetamide, 2-amino-N-[4-(2-phenylethynyl) phenyl] propanamide, 2-amino-N-[4-(2-phenylethynyl) phenyl] acetamide, 2-(cyclopropylamino)-N-[4-(2-phenylethynyl) phenyl] acetamide, 2-(ethylamino)-N-[4-(2-phenylethynyl) phenyl] acetamide, 2-[(2-methylpropyl) amino]-N-[4-(2-phenylethynyl) phenyl] acetamide, 5-phenyl-2H-benzo [d] 1,3-dioxolene, 2-chloro-1-methoxy 4-phenylbenzene, 2-[(imidazolylmethyl) amino]-N-[4-(2-phenylethynyl) phenyl] acetamide, 4-phenyl-1-phenoxybenzene, N-(2-aminoethyl) [4-(2-phenylethynyl) phenyl] carboxamide, 2-{[(4-fluorophenyl) methyl] amino}-N-[4-(2-phenylethynyl) phenyl] acetamide, 2-{[(4-methylphenyl) methyl] amino}-N-[4-(2-phenylethynyl) phenyl] acetamide, 4-phenyl-1-(trifluoromethyl) benzene, 1-butyl-4-phenylbenzene, 2-(cyclohexylamino)-N-[4-(2-phenylethynyl) phenyl] acetamide, 2-(ethylmethylamino)-N-[4-(2-phenylethynyl) phenyl] acetamide, 2-(butylamino)-N-[4-(2-phenylethynyl) phenyl] acetamide, N-[4-(2-phenylethynyl) phenyl]-2-(4-pyridylamino) acetamide, N-[4-(2-phenylethynyl) phenyl]-2-(quinuclidin-3-ylamino) acetamide, N-[4-(2-phenylethynyl) phenyl]pyrrolidin-2-ylcarboxamide, 2-amino-3-methyl-N-[4-(2-phenylethynyl) phenyl] butanamide, 4-(4-phenylbuta-1,3-diynyl) phenylamine, 2-(dimethylamino)-N-[4-(4-phenylbuta-1,3-diynyl) phenyl]acetamide, 2-(ethylamino)-N-[4-(4-phenylbuta-l, 3-diynyl) phenyl] acetamide, 4-ethyl-1-phenylbenzene, 1-[4-(2-phenylethynyl) phenyl] ethan-1-one, N-(1-carbamoyl-2-hydroxypropyl) [4-(4-phenylbuta-1,3-diynyl) phenyl] carboxamide, N-[4-(2-phenylethynyl) phenyl] propanamide, 4-methoxyphenyl phenyl ketone, phenyl-N-benzamide, (tert-butoxy)-N-[(4-phenylphenyl) methyl] carboxamide, 2-(3-phenylphenoxy) ethanehydroxamic acid, 3-phenylphenyl propanoate, 1-(4-ethoxyphenyl)-4-methoxybenzene, and [4-(2-phenylethynyl) phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl) pyridine, phenylpyrazole, 5-(2-phenylethynyl)-1,3-dihydropyrimidine-2, 4-dione, 4-phenyl-1,2,3-thiadiazole, 2-(2-phenylethynyl) pyrazine, 2-phenylthiophene, phenylimidazole, 3-(2-piperazinylphenyl)furan, 3-(2,4-dichlorophenyl)-4-methylpyrrole, and the like. Optionally substituted heteroarylaryl groups include: 5-(2-phenylethynyl) pyrimidine-2-ylamine, 1-methoxy-4-(2-thienyl) benzene, 1-methoxy-3-(2-thienyl) benzene, 5-methyl-2-phenylpyridine, 5-methyl-3-phenylisoxazole, 2-[3-(trifluoromethyl) phenyl] furan, 3-fluoro-5-(2-furyl)-2-methoxy-1-prop-2-enylbenzene, (hydroxyimino) (5-phenyl (2-thienyl)) methane, 5-[(4-methylpiperazinyl) methyl]-2-phenylthiophene, 2-(4-ethylphenyl) thiophene, 4-methylthio-1-(2-thienyl) benzene, 2-(3-nitrophenyl) thiophene, (tert-butoxy)-N-[(5-phenyl (3-pyridyl)) methyl] carboxamide, hydroxy-N-[(5-phenyl (3-pyridyl)) methyl] amide, 2-(phenyhnethylthio) pyridine, and benzylimidazole.

The term "heteroaryl" refers to a biaryl group where both of the aryl groups is a heteroaryl group. Exemplary heteroaryl groups include, for example, 3-pyridylimidazole, 2-imidazolylpyrazine, and the like. Preferred optionally substituted heteroaryl groups include: 2-(4-piperazinyl-3-pyridyl) furan, diethyl (3-pyrazin-2-yl (4-pyridyl)) amine, and dimethyl {2-[2-(5-methylpyrazin-2-yl) ethynyl] (4-pyridyl)} amine.

"Optionally substituted" refers to the optional replacement of hydrogen with one or more monovalent or divalent radicals. Optionally substituted groups include those described herein, for each group in which a distinct definition for substitution is supplied. Additionally, suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

The term "protected" with respect to hydroxyl groups, amine groups, and sulfhydryl groups refers to forms of these functionalities that are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) that can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioether such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid. As salts of inorganic bases, the invention includes, for example, alkali metals such as sodium or potassium; alkaline earth metals such as calcium and magnesium or aluminum; and ammonia. As salts of organic bases, the invention includes, for example, trimethylamine, triethylamine, pyridine, picoline, ethanolamine, diethanolamine, and triethanolamine. As salts of inorganic acids, the instant invention includes, for example, hydrochloric acid, hydroboric acid, nitric acid, sulfuric acid, and phosphoric acid. As salts of organic acids, the instant invention includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

Representative examples of particular esters include, but are not limited to, formates, acetates, propionates, butyrates, acrylates and ethylsuccinates.

The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "antibacterial agent" refers to agents synthesized or modified in the laboratory that have either bactericidal or bacteriostatic activity.

An "active" agent in this context will inhibit the growth of *Mannheimia haemolytica, Histophilus somni*, and/or *Pasteurella multocidaa*.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The present invention provides compounds that are useful in the treatment of an infection by *Mannheimia haemolytica*, and/or *Histophilus somni* and/or *Pasteurella multocida*, pharmaceutical formulations including the compounds and methods of treating an infection caused by *Mannheimia haemolytica* and/or *Histophilus somni*.

The invention provides a compound according to the invention and/or embodiments thereof, wherein $R^1$ is selected from the group consisting of $C(R^{11}R^{12}R^{13})$, $C(=O)R^{11}$, $-C(=NR^{14})R^{11}$. Suitably $R^1$ is $C(R^{11}R^{12} R^{13})$. Suitably $R^1$ is $C(=O)R^{11}$. Suitably $R^1$ is $-C(=NR^{14})R^{11}$.

In some embodiments of the invention and/or embodiments thereof the compound is a compound according to formula (V)

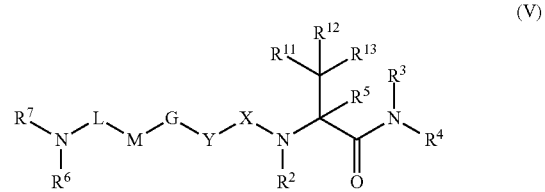

(V)

or a stereoisomer, pharmaceutically acceptable salt, ester, solvate, or prodrug thereof, wherein L, M, G, Y, X, $R^2$, $R^3$, $R^4$, $R^5$, $R^6$, $R^7$, R, R, $R^{12}R^{13}$ are defined as in any of the embodiments described herein.

In some embodiments of the invention and/or embodiments thereof the compound is a compound according to formula (VI)

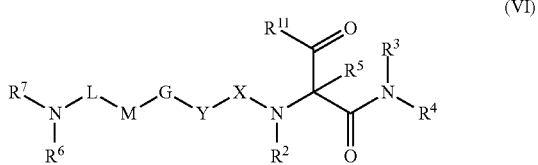

(VI)

or a stereoisomer, pharmaceutically acceptable salt, ester, solvate, or prodrug thereof, wherein L, M, G, Y, X, $R^2$, $R^3$, $R^4$, $R^5$, $R^6$, $R^7$, and $R^{11}$, are defined as in any of the embodiments described herein. In some embodiments of the invention and/or embodiments thereof the compound is a compound according to formula (VII)

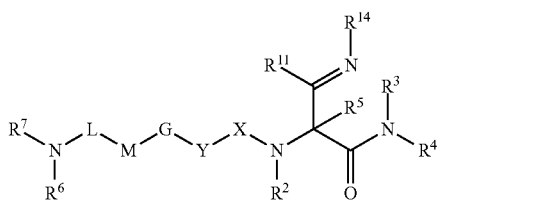

or a stereoisomer, pharmaceutically acceptable salt, ester, solvate, or prodrug thereof, wherein L, M, G, Y, X, $R^2$, $R^3$, $R^4$, $R^5$, $R^6$, $R^7$, and $R^{11}$, $R^{14}$ are defined as in any of the embodiments described herein. Suitably $R^{11}$ is selected from the group consisting of H, and $C_{1-6}$-alkyl, more suitably $C_{1-6}$-alkyl.

In another suitable embodiment of the present invention and/or embodiments thereof, $R^{12}$ is selected from the group consisting of H, $C_{1-6}$-alkyl, and $C_{1-6}$-alkyl substituted with a substituent from the group consisting of —$SR^8$, '—$OR^9$, —C(=O)$OR^9$, —$NR^9R^{10}$, —$SO_2NR^9R^{10}$, —$SO_2R^8$.

In another suitable embodiment of the present invention and/or embodiments thereof, $R^{12}$ is selected from the group consisting of H, $C_{1-6}$-alkyl, and $C_{1-6}$-alkyl substituted with a substituent from the group consisting of —$SR^8$, '—$OR^9$, —C(=O)$OR^9$, —$NR^9R^{10}$, —$SO_2NR^9R^{10}$, —$SO_2R^8$.

Suitably in certain embodiments of the present invention and/or embodiments thereof, the substituted $C_{1-6}$-alkyl in $R^{12}$ is substituted with a substituent selected from the group consisting of

—$SR^8$, '—$OR^9$, —$NR^9R^{10}$, —$SO_2NR^9R^{10}$, —$SO_2R^8$.

Suitably in certain embodiments of the present invention and/or embodiments thereof, the substituted $C_{1-6}$-alkyl in $R^{12}$ is substituted with a substituent selected from the group consisting of

—$SCH_3$, '—OH, —$NH_2$, —$SO_2CH_3$.

In some embodiments of the present invention and/or embodiments thereof, $R^{13}$ is selected from the group consisting of H, $C_{1-6}$-alkyl, aryl, —$SR^8$, —$OR^9$, —$NR^9R^{10}$, —$SO_2R^8$, nitro, —C(=O)$NR^9R^{10}$, and $C_{1-6}$-alkyl substituted with a substituent selected from the group consisting of —$SR^8$, —C(=O)$NR^9R^{10}$, —$SO_2NR^9R^{10}$, —$SO_2R^8$, nitro, cyano, —$OR^9$, —C(=O)$OR^9$, —$NR^9C$(=$NR^{14}$)$NR^9R^{10}$.

In some embodiments of the present invention and/or embodiments thereof, $R^{13}$ is selected from the group consisting of H, $C_{1-6}$-alkyl, aryl, —$SR^8$, —$SO_2R^8$, nitro, —C(=O)$NR^9R^{10}$, and $C_{1-6}$-alkyl substituted with a substituent selected from the group consisting of —$SR^8$, —C(=O)$NR^9R^{10}$, —$SO_2NR^9R^{10}$, —$SO_2R^8$, nitro, cyano, —$OR^9$, —C(=O)$OR^9$, —$NR^9C$(=$NR^{14}$)$NR^9R^{10}$.

In some embodiments of the present invention and/or embodiments thereof, $R^{13}$ is selected from the group consisting of H, $C_{1-6}$-alkyl, —$SR^8$, —$OR^9$, —$NR^9R^{10}$, —$SO_2R^8$, nitro, —C(=O)$NR^9R^{10}$, and $C_{1-6}$-alkyl substituted with a substituent selected from the group consisting of —$SR^8$, —C(=O)$NR^9R^{10}$, —$SO_2NR^9R^{10}$, —$SO_2R^8$, nitro, cyano, —$OR^9$, —C(=O)$OR^9$, —$NR^9C$(=$NR^{14}$)$NR^9R^{10}$.

In some embodiments of the present invention and/or embodiments thereof, $R^{13}$ is selected from the group consisting of H, $C_{1-6}$-alkyl, —$SR^8$, —$SO_2R^8$, nitro, —C(=O)$NR^9R^{10}$, and $C_{1-6}$-alkyl substituted with a substituent selected from the group consisting of —$SR^8$, —C(=O)$NR^9R^{10}$, —$SO_2NR^9R^{10}$, —$SO_2R^8$, nitro, cyano, —$OR^9$, —C(=O)$OR^9$, —$NR^9C$(=$NR^{14}$)$NR^9R^{10}$.

In some embodiments of the present invention and/or embodiments thereof, $R^{13}$ is selected from the group consisting of H, $C_{1-6}$-alkyl, —$SR^8$, —$OR^9$, —$NR^9R^{10}$, —$SO_2R^8$, and $C_{1-6}$-alkyl substituted with a substituent selected from the group consisting of —$SR^8$, —C(=O)$NR^9R^{10}$, —$SO_2R^8$, —$SO_2NR^9R^{10}$, nitro, cyano, —$OR^9$, —C(=O)$OR^9$, —$NR^9C$(=$NR^{14}$)$NR^9R^{10}$.

In some embodiments of the present invention and/or embodiments thereof, $R^{13}$ is selected from the group consisting of H, $C_{1-6}$-alkyl, —$SR^8$, —$SO_2R^8$, and $C_{1-6}$-alkyl substituted with a substituent selected from the group consisting of —$SR^8$, —C(=O)$NR^9R^{10}$, —$SO_2R^8$, —$SO_2NR^9R^{10}$, nitro, cyano, —$OR^9$, —C(=O)$OR^9$, —$NR^5C$(=$NR^{14}$)$NR^9R^{10}$.

In some embodiments of the present invention and/or embodiments thereof, $R^{13}$ is selected from the group consisting of H, $C_{1-6}$-alkyl, —$SR^8$, —$OR^9$, —$NR^9R^{10}$, —$SO_2R^8$.

In some embodiments of the present invention and/or embodiments thereof, $R^{13}$ is selected from the group consisting of H, $C_{1-6}$-alkyl, —$SR^8$, —$SO_2R^8$.

In some embodiments of the present invention and/or embodiments thereof, $R^{13}$ is selected from the group consisting of $C_{1-6}$-alkyl, —$SR^8$, —$OR^9$, —$NR^9R^{10}$, —$SO_2R^8$.

In some embodiments of the present invention and/or embodiments thereof, $R^{13}$ is selected from the group consisting of $C_{1-6}$-alkyl, —$SR^8$, —$SO_2R^8$.

In some embodiments of the present invention and/or embodiments thereof, $R^{13}$ is selected from the group consisting of

—$SR^8$, —$OR^9$, —$NR^9R^{10}$, —$SO_2R^8$.

In some embodiments of the present invention and/or embodiments thereof, $R^{13}$ is selected from the group consisting of
—$SR^8$, —$OR^9$, —$SO_2R^8$.

In some embodiments of the present invention and/or embodiments thereof, $R^{13}$ is selected from the group consisting of
—$SR^8$, and —$SO_2R^8$.

In some embodiments of the present invention and/or embodiments thereof, $R^{13}$ is selected from the group consisting of
—$SR^8$, and —$SO_2R^8$
and wherein $R^{11}$ and $R^{12}$ are methyl.

In some embodiments of the present invention and/or embodiments thereof, $R^{13}$ is not OH or $NH_2$.

Suitably in certain embodiments of the present invention and/or embodiments thereof, the substituted $C_{1-6}$-alkyl in $R^{13}$ is substituted with a substituent selected from the group consisting of —$SR^8$, —$C(=O)NR^9R^{10}$, —$SO_2R^8$, —$SO_2NR^9R^{10}$, nitro, cyano, —$OR^9$, —$C(=O)OR^9$, —$NR^9C(=NR^{14})NR^9R^{10}$.

Suitably in certain embodiments of the present invention and/or embodiments thereof, the substituted $C_{1-6}$-alkyl in $R^{13}$ is substituted with a substituent selected from the group consisting of —$SR^8$, —$C(=O)NR^9R^{10}$, —$SO_2R^8$, —$SO_2NR^9R^{10}$, nitro, —$OR^9$, —$C(=O)OR^9$.

Suitably in certain embodiments of the present invention and/or embodiments thereof, the substituted $C_{1-6}$-alkyl in $R^{13}$ is substituted with a substituent selected from the group consisting of —$SR^8$, —$SO_2NR^9R^{10}$, —$SO_2R^8$, —$OR^9$.

Suitably in certain embodiments of the present invention and/or embodiments thereof, the substituted $C_{1-6}$-alkyl in $R^{13}$ is substituted with a substituent selected from the group consisting of —$SCH_3$, —$SO_2CH_3$, —OH.

In some embodiments of the present invention and/or embodiments thereof, $R^{13}$ and $R^2$ together with the N atom which $R^2$ is attached to, form a saturated or unsaturated heterocycle having 3 to 6 ring atoms wherein 1 ring atom is N and 0, 1 or 2 further ring atoms are selected from N, S, and O the rest of the ring atoms being C.

Suitably in certain embodiments of the present invention and/or embodiments thereof, $R^{13}$ and $R^2$ together with the N atom which $R^2$ is attached to, form a heterocycle selected from the group consisting of aziridine, azirine, azetidine, dihydroazete, azete, diazetidine, pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, pyrazolidine, imidazolidine, pyrrazoline, imidazoline, pyrrazole, imidazole, triazole, oxazole, isoxazole, isothiazole, thiazole, oxadiazole, thiadiazole, piperidine, pyridine, piperazine, pyridazine, pyrimidine, pyrazine, triazine, morpholine, oxazine, thiomorpholine, thiazine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, pyrazolidine, imidazolidine, pyrrazoline, imidazoline, pyrrazole, imidazole, triazole, oxazole, isothiazole, thiazole, piperidine, pyridine, piperazine, pyrimidine, pyrazine, morpholine, thiomorpholine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, imidazole, oxazole, thiazole, piperidine, pyridine, piperazine, pyrimidine, morpholine.

Suitably in certain embodiments of the present invention and/or embodiments thereof, $R^{13}$ and $R^2$ together with the N atom which $R^2$ is attached to, form a heterocycle selected from the group consisting of pyrrolidine, imidazoline, oxazole, thiazole, piperidine, pyridine, morpholine.

Suitably in certain embodiments of the present invention and/or embodiments thereof, $R^{13}$ and $R^2$ together with the N atom which $R^2$ is attached to, form a heterocycle selected from the group consisting of pyrrolidine, pyrroline, pyrrole, imidazole, oxazole, isoxazole, isothiazole, thiazole, thiadiazole, piperidine, pyridine, piperazine, pyrimidine, pyrazine, morpholine, thiomorpholine.

Suitably when $R^{13}$ is OH or $NH_2$ and $R^{12}$ is methyl then $R^{11}$ cannot be H.

Suitably when $R^{13}$ is $NH_2$ and $R^{12}$ is methyl $R^{11}$ cannot be methyl.

Suitably when $R^{13}$ is OH and $R^{12}$ is methyl then $R^{11}$ cannot be methyl.

Suitably when $R^{13}$ is $NH_2$ and $R^{12}$ is H then $R^{11}$ cannot be H.

Suitably when $R^{13}$ is OH and $R^{12}$ is H then $R^{11}$ cannot be H.

Suitably when $R^{13}$ is $CH_3$ and $R^{12}$ is $CH_3$ then $R^{11}$ cannot be H.

Suitably in certain embodiments of the present invention and/or embodiments thereof, $R^{14}$ is selected from the group consisting of H, $C_{1-6}$-alkyl, —$OR^9$. Suitably in certain embodiments of the present invention and/or embodiments thereof, $R^{14}$ is selected from the group consisting of H, $C_{1-6}$-alkyl, —OH.

Optionally, in an embodiment of the invention and/or embodiments thereof $R^6$, $R^7$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of $C_{1-6}$-alkyl, $C_{3-8}$-cycloalkyl, $C_{1-6}$-alkyloxy, —$NR^9R^{10}$, carbonyl, —$C(=O)$—$OR^9$, halogen atom, $C_{1-6}$-alkyl substituted with halo, $C_{1-6}$-alkyloxy-$C_{1-6}$-alkyl, aryl, heteroaryl, $C_1$-$C_6$-alkyl substituted with aryl, cyano, hydroxy, —$SR^8$, —$SO_2R^8$, —$SO_2NR^9R^{10}$, —$C(=O)NR^9R^{10}$, $C_{1-6}$-alkyl substituted with hydroxy;

wherein $R^8$ is selected from the group consisting of H, and $C_{1-6}$-alkyl;

$R^9$, $R^{10}$ are independently selected from the group consisting of H, and $C_{1-6}$-alkyl.

Optionally, in an embodiment of the invention and/or embodiments thereof, $R^6$, $R^7$ are independently selected from the group consisting of

- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or
- $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of
  $C_{1-6}$-alkyl, $C_{3-8}$-cycloalkyl, —$NR^9R^{10}$, carbonyl, halogen, $C_{1-6}$-alkyl substituted with halo, aryl, heteroaryl, $C_1$-$C_6$-alkyl substituted with aryl, cyano, hydroxy, —$SR^8$, —$SO_2R^8$, —$SO_2NR^9R^{10}$, —$C(=O)NR^9R^{10}$, $C_{1-6}$-alkyl substituted with hydroxy;
  wherein
  $R^8$ is selected from the group consisting of H, $C_{1-6}$-alkyl;
  $R^9$, $R^{10}$ are independently selected from the group consisting of H, and $C_{1-6}$-alkyl.

Optionally, in an embodiment of the invention and/or embodiments thereof, $R^6$, $R^7$ are independently selected from the group consisting of

- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or
- $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of
  $C_{1-6}$-alkyl, —$NR^9R^{10}$, carbonyl, halogen, cyano, hydroxy, —$SR^8$, —$SO_2R^8$, —$SO_2NR^9R^{10}$, —$C(=O)NR^9R^{10}$;
  wherein
  $R^8$ is selected from the group consisting of H, $C_{1-6}$-alkyl;
  $R^9$, $R^{10}$ are independently selected from the group consisting of H, and $C_{1-6}$-alkyl.

Optionally, in an embodiment of the invention and/or embodiments thereof, $R^6$, $R^7$ are independently selected from the group consisting of

- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or
- $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of
  $C_{1-6}$-alkyl, carbonyl, halogen, amino, cyano, hydroxyl.

Optionally, in an embodiment of the invention and/or embodiments thereof, $R^6$, $R^7$ are independently selected from

- H, $C_{1-6}$-alkyl, $C_{2-6}$-alkenyl, $C_{2-6}$-alkynyl, $C_{3-10}$-cycloalkyl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or
- $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

Suitably, in an embodiment of the invention and/or embodiments thereof, $R^6$, $R^7$ are independently selected from the group consisting of

- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl, or $NR^6R^7$ is $NO_2$ or
- $R^6$, $R^7$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  wherein the alkyl, alkenyl, alkynyl, cycloalkyl, aryl, heterocyclyl, heteroaryl, alkyloxy or the heterocyclic ring formed by $R^6$, $R^7$ together with the N atom to which they are attached is optionally substituted with a substituent selected from the group consisting of
  $C_{1-6}$-alkyl, $C_{3-8}$-cycloalkyl, $C_{1-6}$-alkyloxy, —$NR^9R^{10}$, carbonyl, —$C(=O)$—OR9, halogen atom, $C_{1-6}$-alkyl substituted with halo, $C_{1-6}$-alkyloxy-$C_{1-6}$-alkyl, aryl, heteroaryl, $C_1$-$C_6$-alkyl substituted with aryl, cyano, hydroxy, —$SR^8$, —$SO_2R^8$, —$SO_2NR^9R^{10}$, —$C(=O)NR^9R^{10}$, $C_{1-6}$-alkyl substituted with hydroxy;
  wherein
  $R^8$ is selected from the group consisting of H, $C_{1-6}$-alkyl;
  $R^9$, $R^{10}$ are independently selected from the group consisting of H, and $C_{1-6}$-alkyl.

In yet another embodiment of the invention and/or embodiments thereof, $R^6$, $R^7$ together with the N atom to which they are attached can form a saturated or unsaturated heterocyclic ring having 3 to 10 ring atoms, wherein 1 ring atom is N and wherein 0, 1, 2, or 3 further ring atoms are selected from N, S, and O.

In yet another embodiment of the invention and/or embodiments thereof, $R^6$, $R^7$ together with the N atom to which they are attached can form a saturated or unsaturated heterocyclic ring having 3 to 8 ring atoms, wherein 1 ring atom is N and wherein 0, 1, 2, or 3 further ring atoms are selected from N, S, and O.

In yet another embodiment of the invention and/or embodiments thereof, $R^6$, $R^7$ together with the N atom to which they are attached can form a saturated or unsaturated heterocyclic ring selected from the group consisting of azetidinyl, azetyl, diazetidinyl, pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, oxadiazolyl, thiadiazolyl, oxazolidonyl, piperidinyl, pyridinyl, piperazinyl, pyridazinyl, pyrimidinyl, pyrazinyl, triazinyl, morpholinyl, oxazinyl, thiomorpholinyl, thiazinyl, thiomorpholinyl dioxide, indolyl, indolinyl, isoindolyl, benzimidazolyl, azaindolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^6$, $R^7$ together with the N atom to which they are attached can form a saturated or unsaturated heterocyclic ring selected from the group consisting of pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, thiadiazolyl, oxazolidonyl, piperidinyl, pyridinyl, piperazinyl, pyridazinyl, pyrimidinyl, pyrazinyl, triazinyl, morpholinyl, thiomorpholinyl, thiazinyl, thiomorpholinyl dioxide, indolyl, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^6$, $R^7$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^6$, $R^7$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^6$, $R^7$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl, Suitably, in an embodiment of the invention and/or embodiments thereof —$NR^6R^7$ is selected from the group consisting of

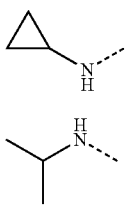

(a-1)

(a-2)

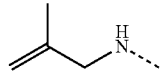

(a-3)

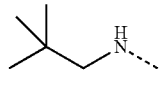

(a-4)

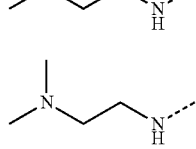

(a-5)

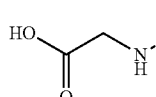

(a-6)

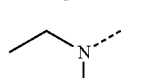

(a-7)

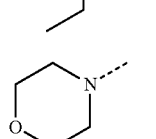

(a-8)

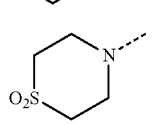

(a-9)

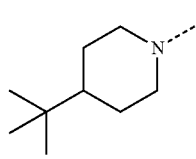

(a-10)

(a-11)

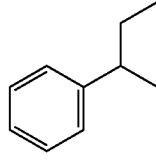

(a-12)

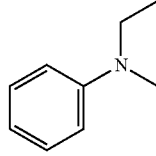

(a-13)

(a-14)

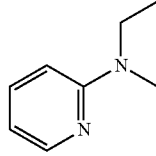

(a-15)

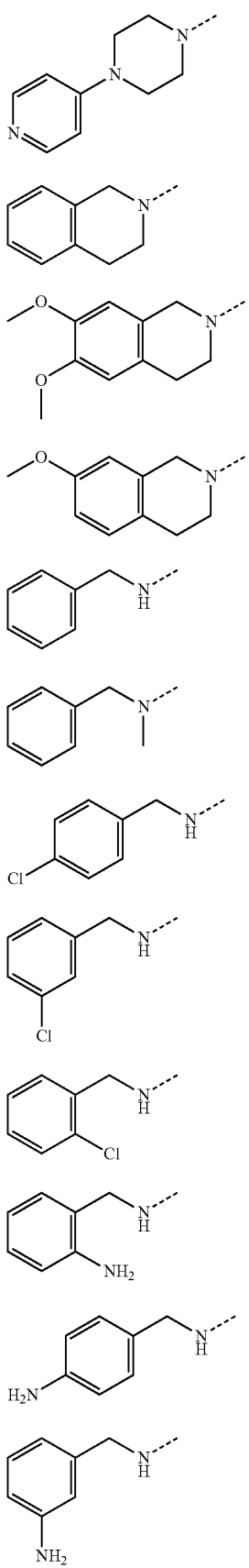
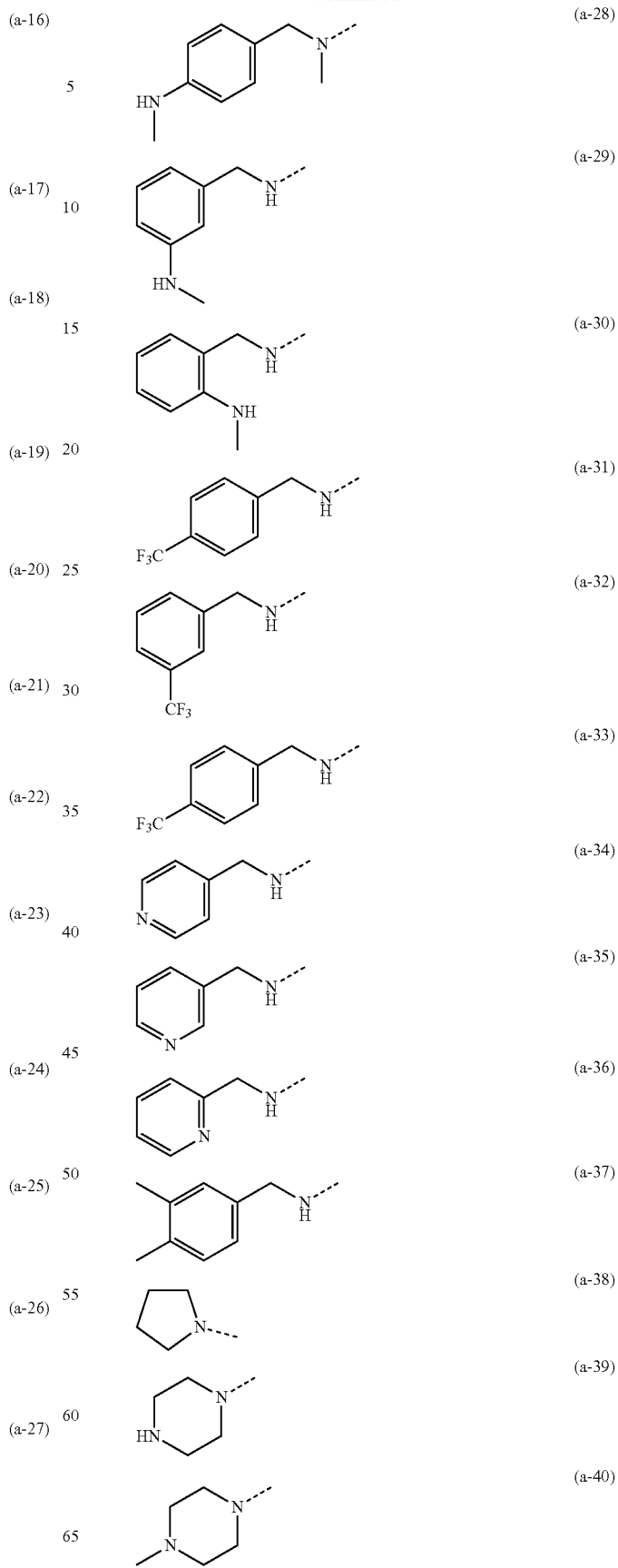

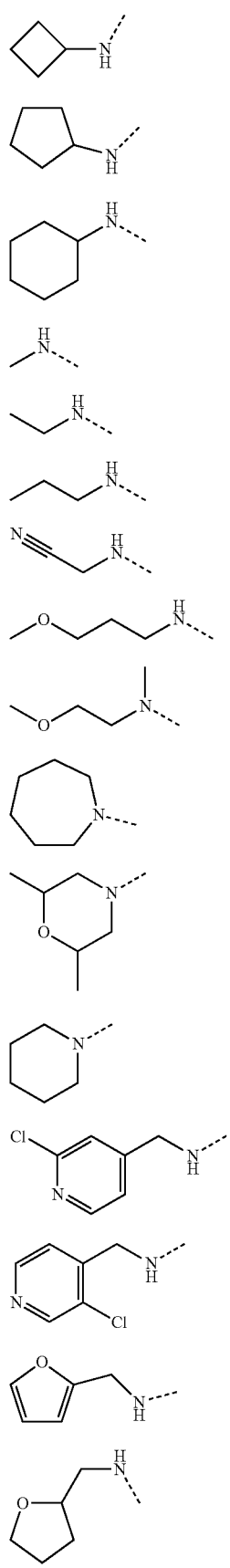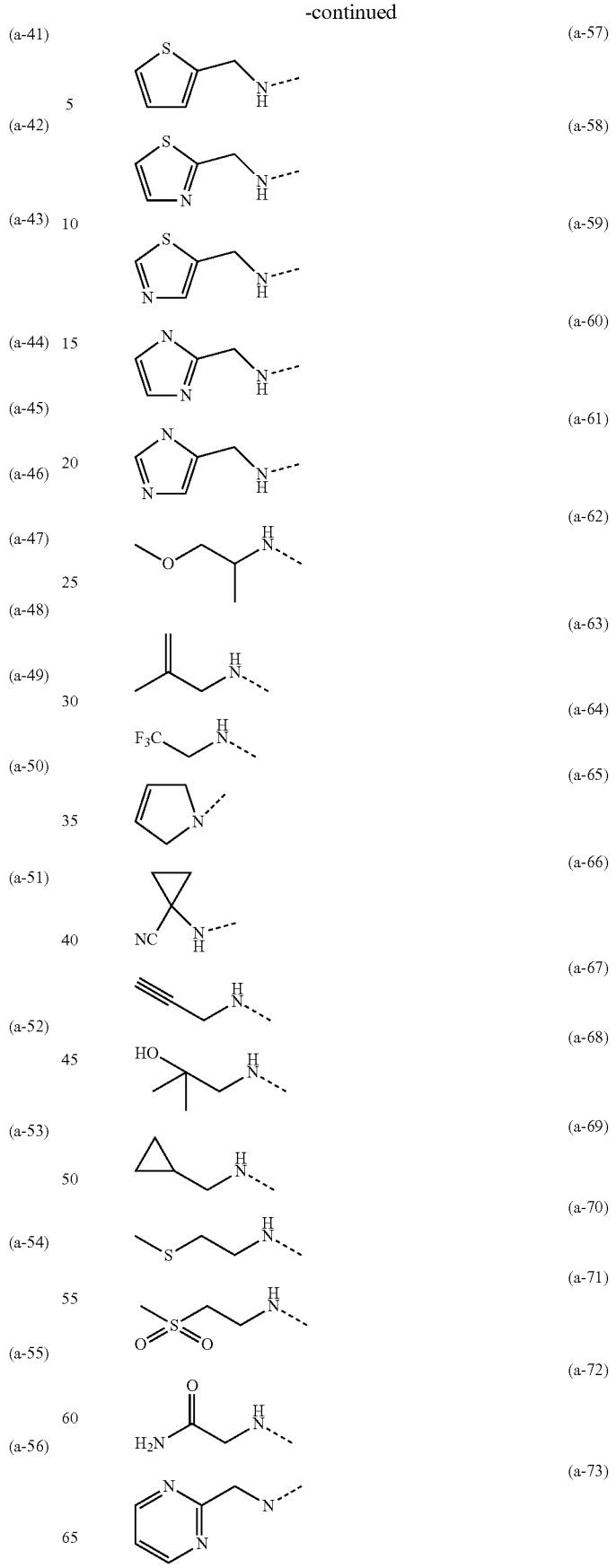

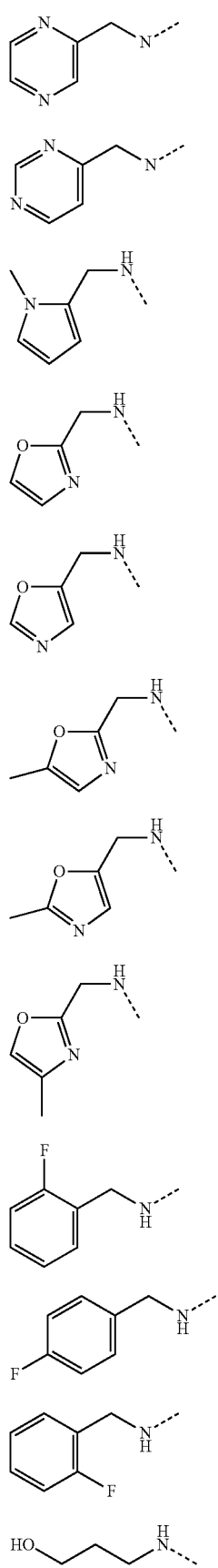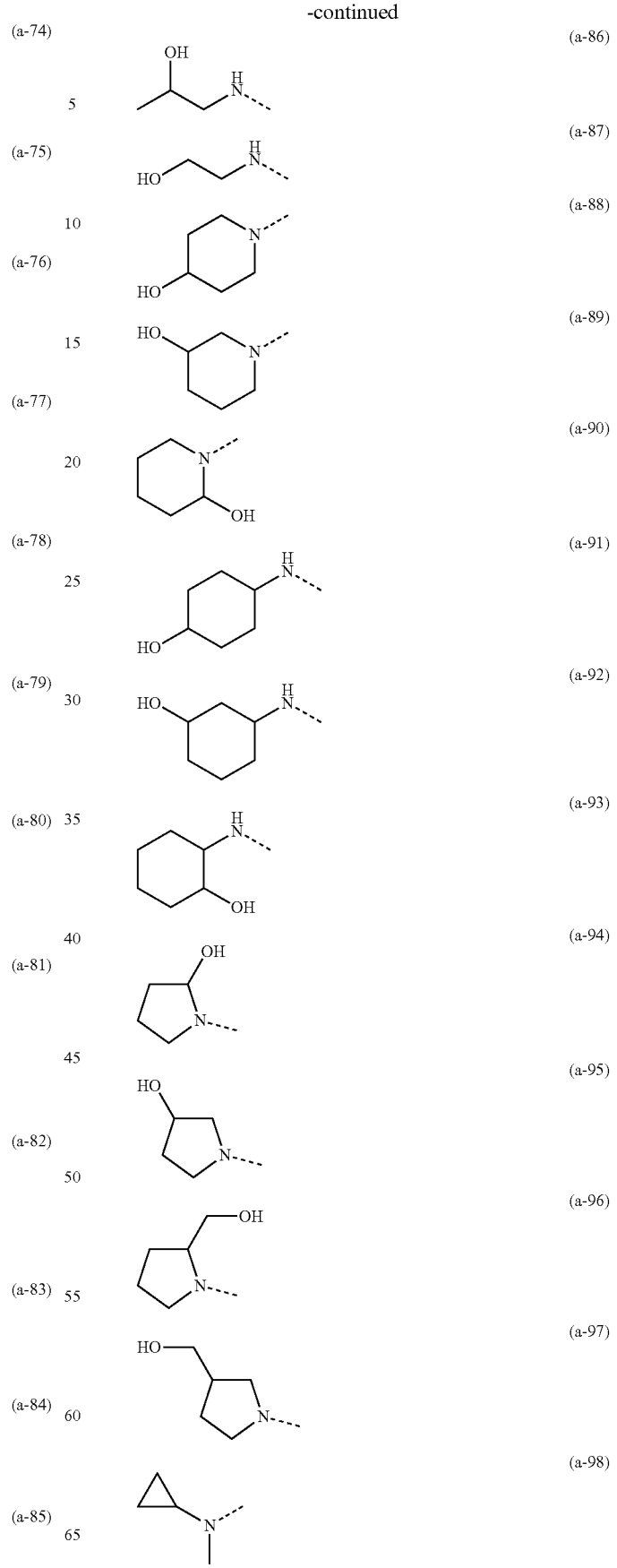

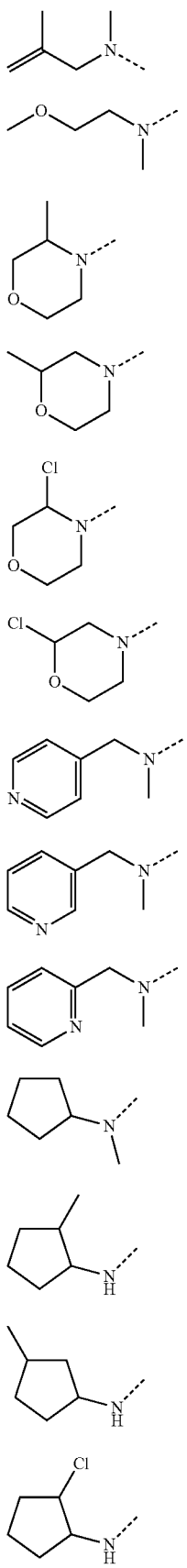
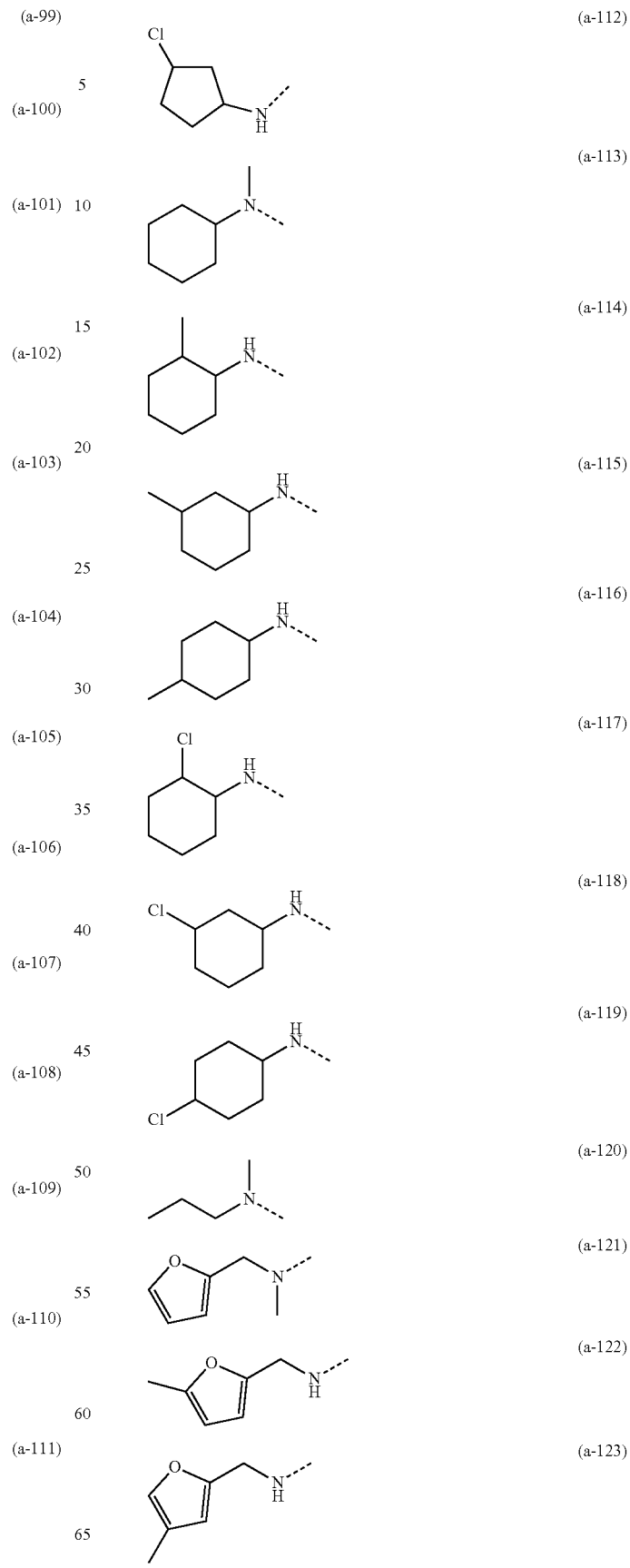

-continued (a-124) 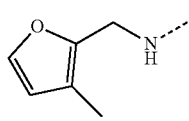

(a-125) 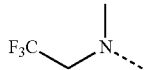

(a-126) 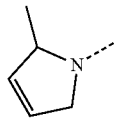

(a-127) 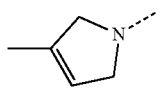

(a-128) 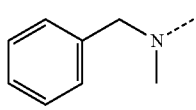

(a-129) 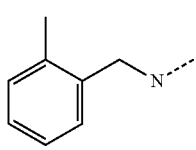

(a-130) 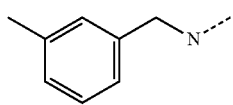

(a-131) 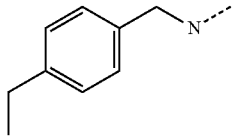

(a-132) 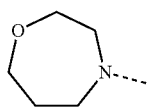

(a-133) 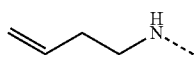

(a-134) 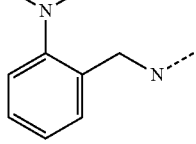

(a-135) 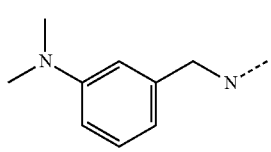

(a-136) 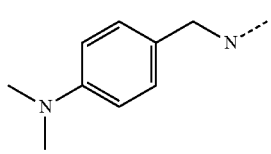

-continued (a-137) 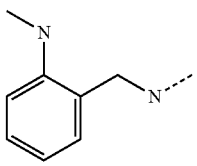

(a-138) 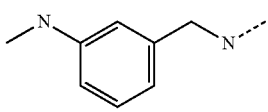

(a-139) 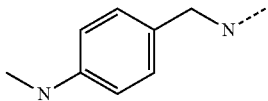

(a-140) 

(a-141) 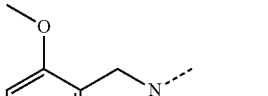

(a-142) 

(a-143) 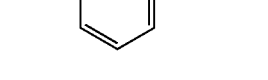

Suitably, in an embodiment of the invention and/or embodiments thereof —NR$^6$R$^7$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

Suitably, in an embodiment of the invention and/or embodiments thereof —NR$^6$R$^7$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

Suitably, in an embodiment of the invention and/or embodiments thereof —NR$^6$R$^7$ is selected from the group consisting of (a-1), (a-3), (a-5), (a-9), (a-20), (a-34), (a-35), (a-36), (a-42), (a-46), (a-55), (a-64), and (a-65).

Suitably, in an embodiment of the invention and/or embodiments thereof NR$^6$R$^7$ is selected from the group consisting of (a-1), (a-3), (a-5), (a-20), (a-34), (a-35), (a-36), (a-46), (a-55), and (a-65).

Suitably in an embodiment of the invention and/or embodiments thereof, when R$^6$ is H then R$^7$ is not H.

In embodiments, L is selected from the group consisting of $C_{1-6}$-alkyl, $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})NR^{L3}C(=O)$—, —C(=O)$NR^{L3}$—, —$NR^{L3}C(=O)$—, —$NR^{L3}$—, —$SO_2NR^{L3}$—, $NR^{L3}$—C(=O)—$NR^{L3}$—
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of
$C_{1-6}$-alkyl, $C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$)_{0-4}$—O—$)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$, —$(CH_2)_{0-4}$—$NR^{L3}$—$(CR^{L1}R^{L2})$—C(=O)NH—$(CH_2)_{0-4}$—, —C(=O)—$(CR^{L1}R^{L2}).NR^{L3}C(=O)$—, —C(=O)$NR^{L3}$—, —$NR^{L3}C(=O)$—, —$NR^{L3}$—, —$SO_2NR^{L3}$—, $NR^{L3}$—C(=O)—$NR^{L3}$—
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of
$C_{1-6}$-alkyl, $C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$NR^{L3}$—, —$SO_2NR^{L3}$—,
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of
$C_{1-6}$-alkyl, $C_{2-6}$-alkenyl, $C_{2-6}$-alkynyl, $C_{3-10}$-cycloalkyl, —$NR^{L3}$—,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

Suitably L is selected from the group consisting of $C_{1-6}$-alkyl, or $C_{2-6}$-alkenyl.

Suitably L is $C_{1-6}$-alkyl. Suitably L is —$CH_2$—, —$CH_2CH_2$—, —$CH_2CH_2CH_2$—, or —$CH_2CH_2CH_2CH_2$—. Suitably L is —$CH_2$—, —$CH_2CH_2$—, or —$CH_2CH_2CH_2$—. Suitably L is —$CH_2$—, or —$CH_2CH_2$—.

In some embodiments of the invention and/or embodiments thereof the compounds are compounds according to formula (VIII)

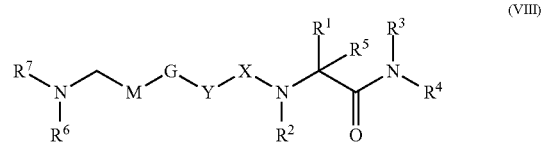

(VIII)

or a stereoisomer, pharmaceutically acceptable salt, ester, solvate, or prodrug thereof, wherein M, G, Y, X, $R^1$, $R^2$, $R^3$, $R^4$, $R^5$, $R^6$, and $R^7$ are defined as in any of the embodiments described herein.

In some embodiments, M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—,
wherein each cycloalkyl, aryl, heterocyclyl, or heteroaryl is optionally substituted with a substituent selected from the group consisting of
$C_{1-6}$-alkyl, $C_{3-8}$-cycloalkyl, $C_{1-6}$-alkyloxy, $NR^{M2}R^{M3}$, carbonyl, —C(=O)—$OR^{M2}$, halo, halo-$C_{1-6}$-alkyl, $C_{1-6}$-alkyloxy-$C_{1-6}$-alkyl, aryl, heteroaryl, $C_1$-$C_6$-alkyl substituted with aryl, cyano, hydroxy, —$SR^{M2}$, —$SO_2R^{M4}$, —$OS_2R^{M4}$, —$SO_2NR^{M2}R^{M3}$, —C(=O)$NR^{M2}R^{M3}$—, hydroxy-$C_{1-6}$-alkyl;
wherein $R^{M1}$ is selected from the group consisting of H, $C_{1-6}$-alkyl, halo, hydroxyl, and amino;
wherein $R^{M2}$, $R^{M3}$ are independently selected from the group consisting of H, and $C_{1-6}$-alkyl;
wherein $R^{M4}$ is selected from the group consisting of H, $C_{1-6}$-alkyl, and amino.

In some embodiments, M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—.

Suitably M is selected from the group consisting of
aryl, heterocyclyl, heteroaryl, —C($R^{M1}$)=C($R^{M1}$)—C≡C—, —C($R^{M1}$)=C($R^{M1}$)—.

Suitably M is selected from the group consisting of
aryl, heteroaryl, —C($R^{M1}$)=C($R^{M1}$)—C≡C—, —C($R^{M1}$)=C($R^{M1}$)—.

Suitably M is selected from the group consisting of
aryl, and heteroaryl.

Suitably M is selected from the group consisting of
phenyl, thiazolyl, pyridinyl, pyrimidinyl, thiophenyl, furanyl, pyrrolyl, imidazolyl, oxazolyl, pyrazinyl, pyranyl, thiopyranyl, oxazinyl, thiazynyl, —C($R^{M1}$)=C($R^{M1}$)—C≡C—, —C($R^{M1}$)=C($R^{M1}$)—.

Suitably M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.

Suitably M is selected from the group consisting of
phenyl, thiazolyl, pyridinyl, pyrimidinyl, thiophenyl, furanyl, —C($R^{M1}$)=C($R^{M1}$)—C≡C—, —C($R^{M1}$)=C($R^{M1}$)—.

Suitably M is selected from the group consisting of phenyl, thiazolyl, pyridinyl, pyrimidinyl, thiophenyl, furanyl, —C(H)═C(H)—C≡C—, —C(H)═C(H)—.

Suitably the cycloalkyl, aryl, heterocyclyl, or heteroaryl of M is optionally substituted with a substituent selected from the group consisting of
$C_{1-6}$-alkyl, $C_{1-6}$-alkyloxy, $NR^{M2}R^{M3}$, carbonyl, —C(═O)—$OR^{M2}$, halo, halo-$C_{1-6}$-alkyl, $C_{1-6}$-alkyloxy-$C_{1-6}$-alkyl, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(═O)$NR^{M2}R^{M3}$—, hydroxy-$C_{1-6}$-alkyl.

Suitably the cycloalkyl, aryl, heterocyclyl, or heteroaryl of M is optionally substituted with a substituent selected from the group consisting of
$C_{1-6}$-alkyl, $C_{1-6}$-alkyloxy, $NR^{M2}R^{M3}$, carbonyl, —C(═O)—$OR^{M2}$, halo, halo-$C_{1-6}$-alkyl, $C_{1-6}$-alkyloxy-$C_{1-6}$-alkyl, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, —C(═O)$NR^{M2}R^{M3}$—, hydroxy-$C_{1-6}$-alkyl.

Suitably the cycloalkyl, aryl, heterocyclyl, or heteroaryl of M is optionally substituted with a substituent selected from the group consisting of
$C_{1-6}$-alkyl, halo, amino, halo-$C_{1-6}$-alkyl, $C_{1-6}$-alkyloxy-$C_{1-6}$-alkyl, $C_1$-$C_6$-alkyl substituted with aryl, cyano, hydroxy, —$SR^{M2}$, —$SO_2R^{M4}$, —$OSO_2R^{M4}$, —$SO_2NR^{M2}R^{M3}$, hydroxy-$C_{1-6}$-alkyl.

Suitably the cycloalkyl, aryl, heterocyclyl, or heteroaryl of M is optionally substituted with a substituent selected from the group consisting of
$C_{1-6}$-alkyl, halo, halo-$C_{1-6}$-alkyl, hydroxy-$C_{1-6}$-alkyl.

Suitably $R^{M1}$ is selected from the group consisting of H, $C_{1-6}$-alkyl, halo, hydroxyl, and amino. Suitably $R^{M1}$ is selected from the group consisting of H, $C_{1-6}$-alkyl, and halo. Suitably $R^{M1}$ is selected from the group consisting of H, and $C_{1-6}$-alkyl.

Suitably, $R^{M2}$, $R^{M3}$ are independently selected from the group consisting of H, and $C_{1-6}$-alkyl.

Suitably $R^{M4}$ is selected from the group consisting of H, $C_{1-6}$-alkyl, and amino. Suitably $R^{M4}$ is selected from the group consisting of H, and $C_{1-6}$-alkyl.

Particular suitable groups of M are selected from the group consisting of

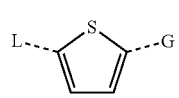
(m-1)

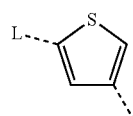
(m-2)

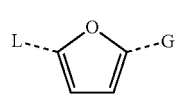
(m-3)

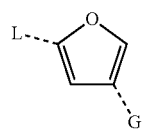
(m-4)

-continued

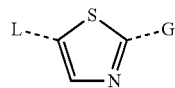
(m-5)

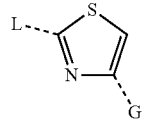
(m-6)

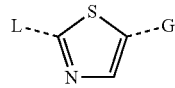
(m-7)

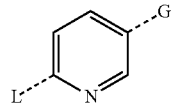
(m-8)

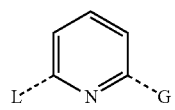
(m-9)

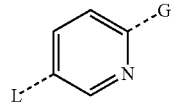
(m-10)

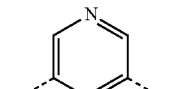
(m-11)

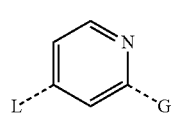
(m-12)

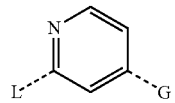
(m-13)

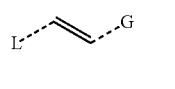
(m-14)

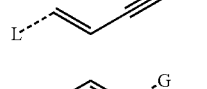
(m-15)

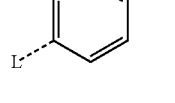
(m-16)

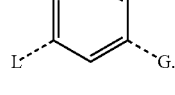
(m-17)

Particular suitable groups of M are selected from the group consisting of
(m-1), (m-3), (m-5), (m-8), (m-14), (m-15), (m-16), (m-17).

Particular suitable groups of M are selected from the group consisting of
(m-1), (m-8), (m-16).

In another embodiment of the invention and/or embodiments thereof G is selected from the group consisting of —(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—(C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{G3}$)$_{0-4}$—NR$^{G1}$—C(R$^{G2}$R$^{G3}$)—C(=O)NR$^{G1}$—, —CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$C≡C—, —C≡C—CR$^{G2}$=CR$^{G2}$—, —C(=O)—C≡C—, —C≡C—C(=O)—, —SO$_2$—, —S(=O)—, —S(=O)C(R$^{G2}$R$^{G3}$)—, —C(R$^{G2}$R$^{G3}$)S(=O)—, —C(R$^{G2}$R$^{G3}$)—SO$_2$—, —SO$_2$C(R$^{G2}$R$^{G3}$)—;
wherein
R$^{G1}$ is H or C$_{1-6}$-alkyl each R$^{G2}$, R$^{G3}$ is independently selected from the group consisting of
H, halogen atom, or C$_{1-6}$-alkyl.

In suitable embodiments, G is selected from the group consisting of —(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—(C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{G3}$)$_{0-4}$—NR$^{G1}$—C(R$^{G2}$R$^{G3}$)C(=O)NR$^{G1}$—, —CR$^{G2}$=CR$^{G2}$—, —C≡C—, —C≡C—C≡C—, —C≡C—C(=O)—, —SO$_2$—, —S(=O)—, —S(=O)C(R$^{G2}$R$^{G3}$)—, —C(R$^{G2}$R$^{G3}$)S(=O)—, —C(R$^{G2}$R$^{G3}$)—SO$_2$—, —SO$_2$C(R$^{G2}$R$^{G3}$)—;
wherein
R$^{G1}$ is H or C$_{1-6}$-alkyl
each R$^{G2}$, R$^{G3}$ is independently selected from the group consisting of
H, halogen atom, or C$_{1-6}$-alkyl.

Suitably G is selected from the group consisting of CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—, wherein R$^{G2}$ is selected from the group consisting of H, halogen atom, or C$_{1-6}$-alkyl.

In suitable embodiments, G is selected from the group consisting of —C≡C—, —C≡C—C≡C—, —CR$^{G2}$=CR$^{G2}$—C≡C—, —C≡C—CR$^{G2}$=CR$^{G2}$, wherein R$^{G2}$ is selected from the group consisting of H, halogen atom, or C$_{1-6}$-alkyl.

In another suitable embodiments, G is selected from the group consisting of CR$^{G2}$=CR$^{G2}$—, —C≡C—, —C≡C—C≡C—, —C≡C—C(=O)—.
wherein
R$^{G2}$ is selected from the group consisting of
H, halogen atom, or C$_{1-6}$-alkyl.

In another suitable embodiments, G is selected from the group consisting of —C≡C—, —C≡C—C≡C—.

In another suitable embodiments, G is —C≡C—.

In some embodiments of the invention and/or embodiments thereof the compound is a compound according to formula (II)

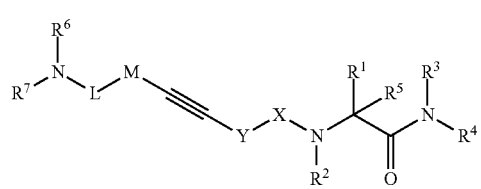

(II)

or a stereoisomer, pharmaceutically acceptable salt, ester, solvate, or prodrug thereof, wherein L, M, Y, X, R$^1$, R$^2$, R$^3$, R$^4$, R$^5$, R$^6$, and R$^7$ are defined as in any of the embodiments described herein.

In some embodiments of the invention and/or embodiments thereof the compound is a compound according to formula (IX)

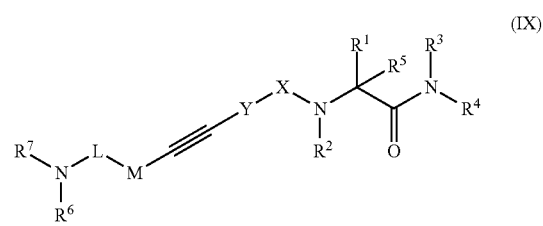

(IX)

or a stereoisomer, pharmaceutically acceptable salt, ester, solvate, or prodrug thereof, wherein M, Y, X, R$^1$, R$^2$, R$^3$, R$^4$, R$^5$, R$^6$, and R$^7$ are defined as in any of the embodiments described herein.

In some embodiments of the invention and/or embodiments thereof the compound is a compound according to formula (X)

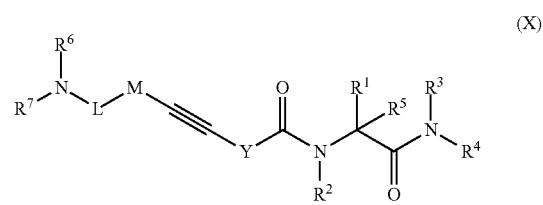

(X)

or a stereoisomer, pharmaceutically acceptable salt, ester, solvate, or prodrug thereof, wherein L, M, Y, R$^1$, R$^2$, R$^3$, R$^4$, R$^5$, R$^6$, and R$^7$ are defined as in any of the embodiments described herein.

In some embodiments of the invention and/or embodiments thereof the compound is a compound according to formula (XI)

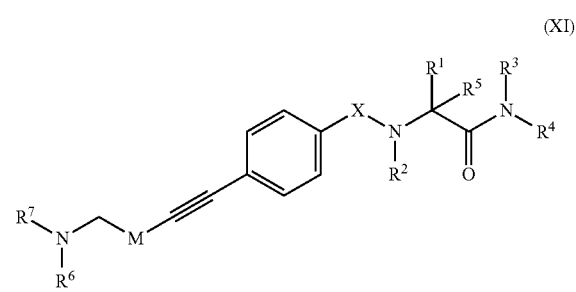

(XI)

or a stereoisomer, pharmaceutically acceptable salt, ester, solvate, or prodrug thereof, wherein M, X, R$^1$, R$^2$, R$^3$, R$^4$, R$^5$, R$^6$, and R$^7$ are defined as in any of the embodiments described herein.

In some embodiments of the invention and/or embodiments thereof the compound is a compound according to formula (XII)

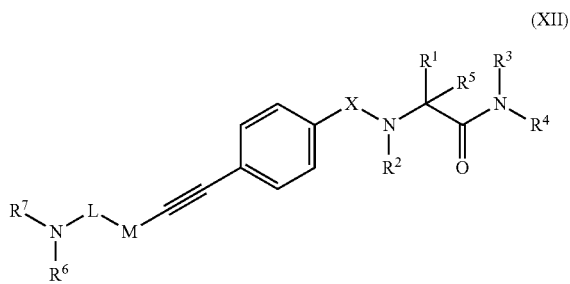

(XII)

or a stereoisomer, pharmaceutically acceptable salt, ester, solvate, or prodrug thereof, wherein L, M, X, $R^1$, $R^2$, $R^3$, $R^4$, $R^5$, $R^6$, and $R^7$ are defined as in any of the embodiments described herein.

In some embodiments of the invention and/or embodiments thereof the compound is a compound according to formula (XIII)

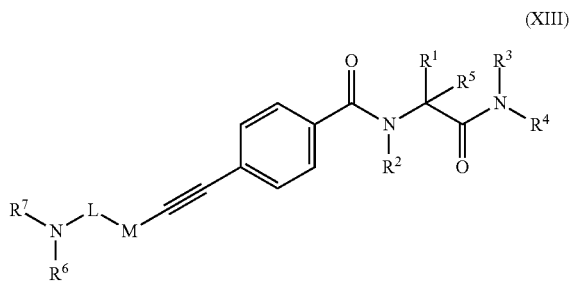

(XIII)

or a stereoisomer, pharmaceutically acceptable salt, ester, solvate, or prodrug thereof, wherein L, M, $R^1$, $R^2$, $R^3$, $R^4$, $R^5$, $R^6$, and $R^7$ are defined as in any of the embodiments described herein.

In some embodiments of the invention and/or embodiments thereof the compound is a compound according to formula (XIV)

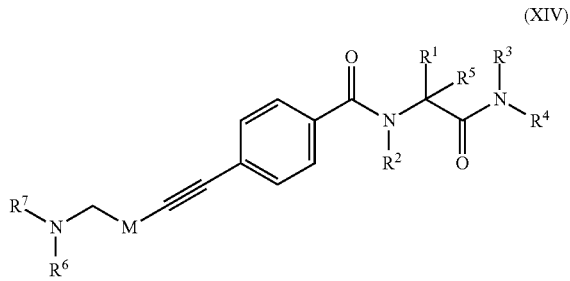

(XIV)

or a stereoisomer, pharmaceutically acceptable salt, ester, solvate, or prodrug thereof, wherein M, $R^1$, $R^2$, $R^3$, $R^4$, $R^5$, $R^6$, and $R^7$ are defined as in any of the embodiments described herein.

In embodiments of the invention and embodiments thereof, Y is selected from the group consisting of
$C_{3-10}$-cycloalkyl, aryl, heterocyclyl, heteroaryl,
wherein each cycloalkyl, aryl, heterocyclyl, or heteroaryl is optionally substituted with a substituent selected from the group consisting of
$C_{1-6}$-alkyl, $C_{3-8}$-cycloalkyl, $C_{1-6}$-alkyloxy, $NR^{Y1}R^{Y2}$, carbonyl, —C(=O)—$OR^{Y1}$, halo, halo-$C_{1-6}$-alkyl, $C_{1-6}$-alkyloxy-$C_{1-6}$-alkyl, aryl, heteroaryl, $C_1$-$C_6$-alkyl substituted with aryl, cyano, hydroxy, —$SR^{Y2}$, —$SO_2R^{Y3}$, —$OSO_2R^{Y3}$, —$SO_2NR^{Y1}R^{Y2}$, —C(=O)$NR^{Y1}R^{Y2}$—, hydroxy-$C_{1-6}$-alkyl;

wherein $R^{Y1}$, $R^{Y2}$ are independently selected from the group consisting of H, and $C_{1-6}$-alkyl;
wherein $R^{Y3}$ is selected from the group consisting of H, $C_{1-6}$-alkyl, and amino.

In embodiments of the invention and/or embodiments thereof, Y is selected from
aryl, or heteroaryl.

Suitably Y is aryl. Suitably Y is phenyl. Suitably Y is para-phenyl.

Suitably the cycloalkyl, aryl, heterocyclyl, or heteroaryl of Y is optionally substituted with a substituent selected from the group consisting of
$C_{1-6}$-alkyl, $C_{1-6}$-alkyloxy, $NR^{Y1}R^{Y2}$, carbonyl, —C(=O)—$OR^{Y1}$, halo, halo-$C_{1-6}$-alkyl, $C_{1-6}$-alkyloxy-$C_{1-6}$-alkyl, $C_1$-$C_6$-alkyl substituted with aryl, cyano, hydroxy, —$SR^{Y2}$, —$SO_2R^{Y3}$, —$OSO_2R^{Y3}$, —$SO_2NR^{Y1}R^{Y2}$, —C(=O)$NR^{Y1}R^{Y2}$—, hydroxy-$C_{1-6}$-alkyl.

Suitably the cycloalkyl, aryl, heterocyclyl, or heteroaryl of Y is optionally substituted with a substituent selected from the group consisting of
$C_{1-6}$-alkyl, $C_{1-6}$-alkyloxy, $NR^{Y1}R^{Y2}$, carbonyl, —C(=O)—$OR^{Y1}$, halo, halo-$C_{1-6}$-alkyl, $C_{1-6}$-alkyloxy-$C_{1-6}$-alkyl, $C_1$-$C_6$-alkyl substituted with aryl, cyano, hydroxy, —$SR^{Y2}$, —$SO_2R^{Y3}$, —$OSO_2R^{Y3}$, —$SO_2NR^{Y1}R^{Y2}$, —C(=O)$NR^{Y1}R^{Y2}$—, hydroxy-$C_{1-6}$-alkyl.

Suitably the cycloalkyl, aryl, heterocyclyl, or heteroaryl of Y is optionally substituted with a substituent selected from the group consisting of
$C_{1-6}$-alkyl, $NR^{Y1}R^{Y2}$, halo, halo-$C_{1-6}$-alkyl, $C_{1-6}$-alkyloxy-$C_{1-6}$-alkyl, $C_1$-$C_6$-alkyl substituted with aryl, cyano, hydroxy, hydroxy-$C_{1-6}$-alkyl.

Suitably the cycloalkyl, aryl, heterocyclyl, or heteroaryl of Y is optionally substituted with a substituent selected from the group consisting of
$C_{1-6}$-alkyl, halo, halo-$C_{1-6}$-alkyl, hydroxy-$C_{1-6}$-alkyl.

Suitably, the cycloalkyl, aryl, heterocyclyl, or heteroaryl of Y is not substituted.

In some embodiments of the invention and/or embodiments thereof the compounds are compounds according to formula (XV)

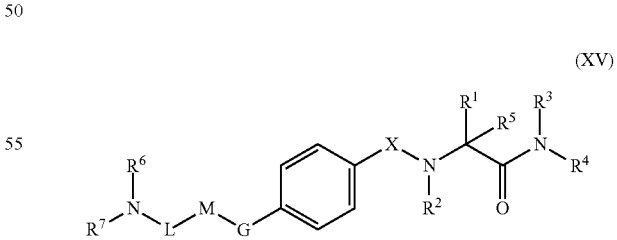

(XV)

or a stereoisomer, pharmaceutically acceptable salt, ester, solvate, or prodrug thereof, wherein L, M, G, X, $R^1$, $R^2$, $R^3$, $R^4$, $R^5$, $R^6$, and $R^7$, are defined as in any of the embodiments described herein.

In some embodiments of the invention and/or embodiments thereof the compounds are compounds according to formula (XVI)

(XVI)

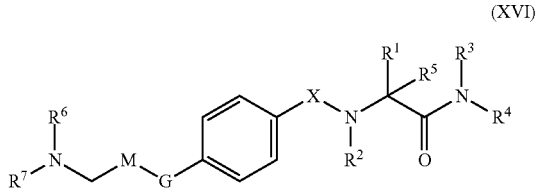

or a stereoisomer, pharmaceutically acceptable salt, solvate, or prodrug thereof, wherein M, G, X, $R^1$, $R^2$, $R^3$, $R^4$, $R^5$, $R^6$, and $R^7$, are defined as in any of the embodiments described herein.

In embodiments of the invention and embodiments thereof, X is selected from the group consisting of —C(=O)—, —$C_{1-6}$-alkyl-C(=O)—, —$C_{2-6}$-alkenyl-C(=O)—, —$C_{2-6}$-alkynyl-C(=O)—, and —(C($R^{X1}$)$_2$—, —S(=O)—, —$SO_2$—;
wherein
$R^{X1}$, $R^{X2}$, is selected from the group consisting of
H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, ester, thiol, $C_{1-6}$-alkyl, carbonyl, —$SR^{X3}$, —$SO_2R^{X5}$, —C(=O)$NR^{X3}R^{X4}$, cyano, —$NR^{X3}R^{X4}$, —C(=O)—$OR^{X3}$, aryl, heteroaryl, heterocycle, $C_{3-8}$-cycloalkyl;
wherein $R^{X3}$, $R^{X4}$ are independently selected from the group consisting of H, or $C_{1-6}$-alkyl;
wherein $R^{X5}$ is selected from the group consisting of H, $C_{1-6}$-alkyl, and amine.
Suitably X is selected from the group consisting of —C(=O)—, —$C_{1-6}$-alkyl-C(=O)—, S(=O)—, —$SO_2$—.
Suitably X is selected from —C(=O)—, and S(=O)—.
Suitably $R^{X1}$, $R^{X2}$, are independently selected from the group consisting of H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, carbonyl, —$SR^{X3}$, —$SO_2R^{X5}$, —C(=O)$NR^{X3}R^{X4}$, cyano, —$NR^{X3}R^{X4}$, —C(=O)—$OR^{X3}$.
Suitably the substituents on the substituted $C_{1-6}$-alkyl of X is selected from the group consisting of halogen, hydroxyl, carbonyl, —$SR^{X3}$, —$SO_2R^{X5}$, —C(=O)$NR^{X3}R^{X4}$, —$NR^{X3}R^{X4}$.
Suitably the substituents on the substituted $C_{1-6}$-alkyl of X is selected from the group consisting of halogen or amino.
Suitably $R^{X1}$, $R^{X2}$, are independently selected from the group consisting of H, halogen atom, or un-substituted $C_{1-6}$-alkyl.
Suitably, $R^{X3}$, $R^{X4}$ are independently selected from the group consisting of H, or $C_{1-6}$-alkyl;
Suitably $R^{X5}$ is selected from the group consisting of H, $C_{1-6}$-alkyl, and amine.
In some embodiments of the invention and/or embodiments thereof the compounds are compounds according to formula (IV)

(IV)

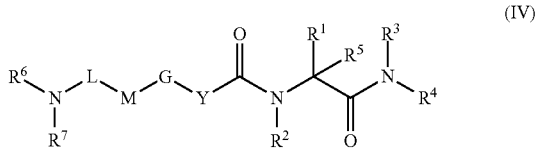

or a stereoisomer, pharmaceutically acceptable salt, ester, solvate, or prodrug thereof, wherein L, M, G, Y, $R^1$, $R^2$, $R^3$, $R^4$, $R^5$, $R^6$, and $R^7$, are defined as in any of the embodiments described herein.

In some embodiments of the invention and/or embodiments thereof the compounds are compounds according to formula (XVII)

(XVII)

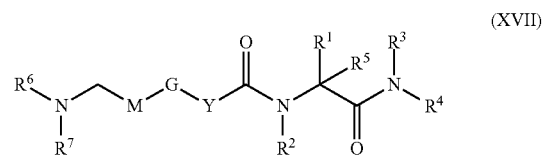

or a stereoisomer, pharmaceutically acceptable salt, ester, solvate, or prodrug thereof, wherein M, G, Y, $R^1$, $R^2$, $R^3$, $R^4$, $R^5$, $R^6$, and $R^7$, are defined as in any of the embodiments described herein.

In some embodiments of the invention and/or embodiments thereof the compounds are compounds according to formula (XVIII)

(XVIII)

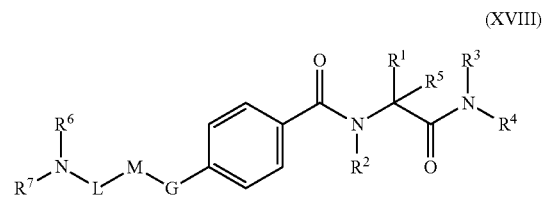

or a stereoisomer, pharmaceutically acceptable salt, ester, solvate, or prodrug thereof, wherein L, M, G, $R^1$, $R^2$, $R^3$, $R^4$, $R^5$, $R^6$, and $R^7$, are defined as in any of the embodiments described herein.

In some embodiments of the invention and/or embodiments thereof the compounds are compounds according to formula (XIX)

(XIX)

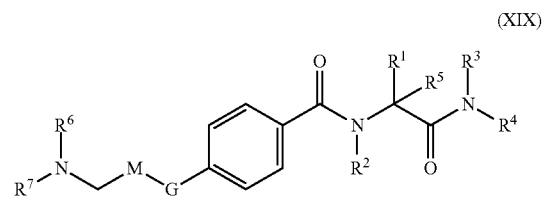

or a stereoisomer, pharmaceutically acceptable salt, ester, solvate, or prodrug thereof, wherein M, G, $R^1$, $R^2$, $R^3$, $R^4$, $R^5$, $R^6$, and $R^7$, are defined as in any of the embodiments described herein.

In some embodiments of the invention and/or embodiments thereof the compounds are compounds according to formula (XX)

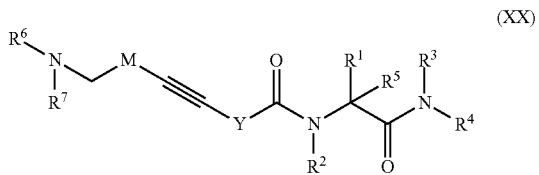

(XX)

or a stereoisomer, pharmaceutically acceptable salt, ester, solvate, or prodrug thereof, wherein M, Y, $R^1$, $R^2$, $R^3$, $R^4$, $R^5$, $R^6$, and $R^7$, are defined as in any of the embodiments described herein.

In suitable embodiments of the invention and/or embodiments thereof $R^5$ is selected from the group consisting of H, and $C_{1-6}$-alkyl. Suitably $R^5$ is H.

In some embodiments of the invention and/or embodiments thereof the compounds are compounds according to formula (XXII)

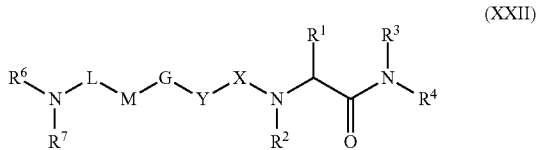

(XXII)

or a stereoisomer, pharmaceutically acceptable salt, ester, solvate, or prodrug thereof, wherein L, M, G, Y, X, $R^1$, $R^2$, $R^3$, $R^4$, $R^6$, and $R^7$, are defined as in any of the embodiments described herein.

In embodiments of the invention and/or embodiments thereof $R^2$, $R^3$ is independently selected from the group consisting of H, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, ester, thiol, $C_{1-6}$-alkyl, carbonyl, —$SR^8$, —$SO_2R^8$, —$SO_2NR^9R^{10}$, —C(=O)$NR^9R^{10}$, cyano, —$NR^9R^{10}$, —C(=O)—$OR^9$, aryl, heteroaryl, heterocycle, $C_{3-8}$-cycloalkyl.

Suitably $R^2$, $R^3$ is independently selected from the group consisting of H, substituted $C_{1-6}$-alkyl, or un-substituted $C_{1-6}$-alkyl. Suitably $R^2$ and $R^3$ are H.

In some embodiment, the substituents on the substituted $C_{1-6}$-alkyl of $R^2$ and/or $R^3$ may be selected from the group consisting of hydroxyl, alkoxy, aryloxy, ester, thiol, $C_{1-6}$-alkyl, carbonyl, —$SR^8$, —$SO_2R^8$, —$SO_2NR^9R^{10}$, —C(=O)$NR^9R^{10}$, cyano, —$NR^9R^{10}$, —C(=O)—$OR^9$, aryl, heteroaryl, heterocycle, $C_{3-8}$-cycloalkyl.

In some embodiment, the substituents on the substituted $C_{1-6}$-alkyl of $R^2$ and/or $R^3$ may be selected from the group consisting of hydroxyl, $C_{1-6}$-alkyl, carbonyl, —$SR^8$, —$SO_2NR^9R^{10}$, —$SO_2R^8$, —C(=O)$NR^9R^{10}$, cyano, —$NR^9R^{10}$, —C(=O)—$OR^9$.

$R^8$ is selected from the group consisting of H, $C_{1-6}$-alkyl, and amine.

$R^9$, $R^{10}$ are independently selected from the group consisting of H, and $C_{1-6}$-alkyl.

In some embodiment, the substituents on the substituted $C_{1-6}$-alkyl of $R^2$ and/or $R^3$ may be selected from the group consisting of hydroxyl, $C_{1-6}$-alkyl, —$NR^9R^{10}$.

In some embodiments of the invention and/or embodiments thereof the compounds are compounds according to formula (XXI)

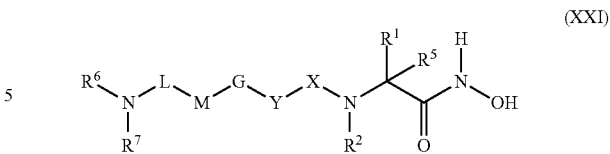

(XXI)

or a stereoisomer, pharmaceutically acceptable salt, ester, solvate, or prodrug thereof, wherein L, M, G, Y, X, $R^1$, $R^2$, $R^5$, $R^6$, and $R^7$, are defined as in any of the embodiments described herein.

In embodiments of the invention and/or embodiments thereof $R^4$ is selected from the group consisting of H, $C_{1-6}$-alkyl, $C_{2-6}$-alkenyl, $C_{2-6}$-alkynyl, $C_{3-10}$-cycloalkyl, —$OR^8$, C(=O)$OR^{8'}$ C(=O)$R^8$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalkyl, $C_{1-6}$-alkyloxy, $NR^9R^{10}$, carbonyl, nitro, C(=O)$OR^9$, halogen, halo-$C_{1-6}$-alkyl, $C_{1-6}$-alkyloxy-$C_{1-6}$-alkyl, cyano, hydroxy, —$SR^8$, —$SO_2R^8$, —$SO_2NR^9R^{10}$, —C(=O)$NR^9R^{10}$.

In embodiments of the invention and/or embodiments thereof $R^4$ is selected from the group consisting of H, $C_{1-6}$-alkyl, $C_{2-6}$-alkenyl, $C_{2-6}$-alkynyl, —$OR^9$, C(=O)$OR^{9'}$ C(=O)$R^9$, $C_1$-$C_6$-alkyl substituted with aryl, $C_1$-$C_6$-alkyl substituted with heteroaryl, $C_1$-$C_6$-alkyl substituted with heterocyclyl.

In embodiments of the invention and/or embodiments thereof $R^4$ is selected from the group consisting of H, $C_{1-6}$-alkyl, —$OR^9$, C(=O)$OR^{9'}$ C(=O)$R^9$.

In embodiments of the invention and/or embodiments thereof $R^4$ is selected from the group consisting of H, —$OR^9$. Suitably $R^4$ is —$OR^9$, more suitably $R^9$ is OH.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalkyl, $C_{1-6}$-alkyloxy, $NR^9R^{10}$, carbonyl, nitro, C(=O)$OR^9$, halogen, halo-$C_{1-6}$-alkyl, $C_{1-6}$-alkyloxy-$C_{1-6}$-alkyl, cyano, hydroxy, —$SR^8$, —$SO_2R^8$, —$SO_2NR^9R^{10}$, —C(=O)$NR^9R^{10}$.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalkyl, $NR^9R^{10}$, carbonyl, nitro, halogen, halo-$C_{0-6}$-alkyl, $C_{1-6}$-alkyloxy-$C_{1-6}$-alkyl, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^9R^{10}$, halogen, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^9R^{10}$, halogen.

In embodiments of the invention and/or embodiments thereof $R^8$ is selected from the group consisting of H, $C_{1-6}$-alkyl, and amine. Suitably $R^8$ is H or $C_{1-6}$-alkyl.

In embodiments of the invention and/or embodiments thereof $R^9$, $R^{10}$ are independently selected from the group consisting of H, and $C_{1-6}$-alkyl.

In some embodiments of the invention and/or embodiments thereof the compounds are compounds according to formula (XXIII)

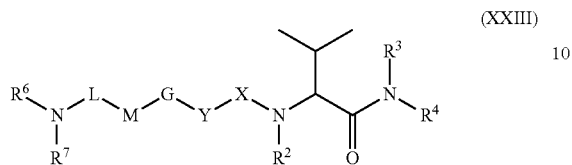

(XXIII)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXIV)

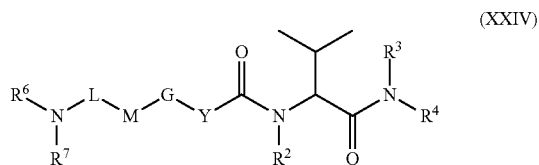

(XXIV)

or a stereoisomer, pharmaceutically acceptable salt, ester, solvate, or prodrug thereof, wherein M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXV)

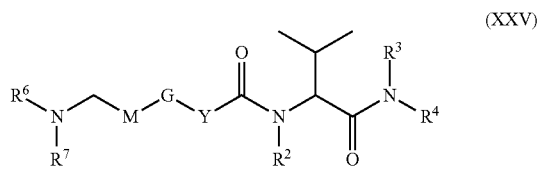

(XXV)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXVI)

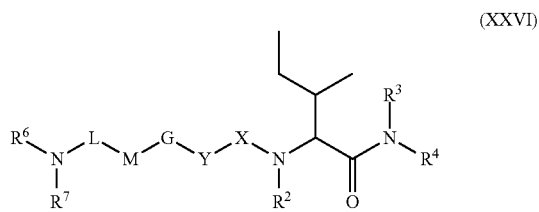

(XXVI)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXVII)

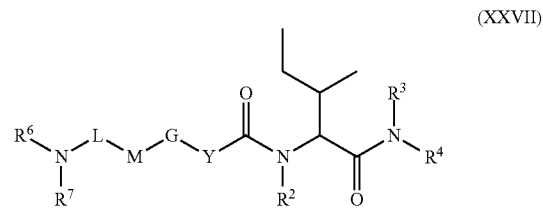

(XXVII)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXVIII)

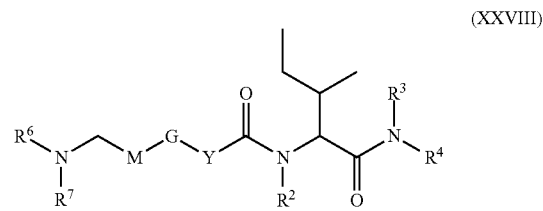

(XXVIII)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXIX)

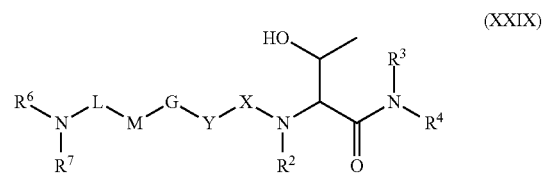

(XXIX)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXX)

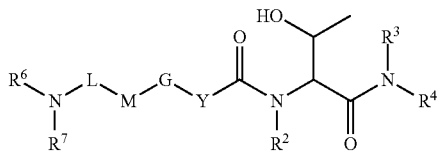

(XXX)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXXI)

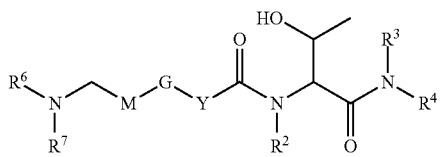

(XXXI)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXXII)

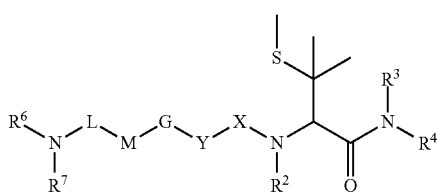

(XXXII)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXXIII)

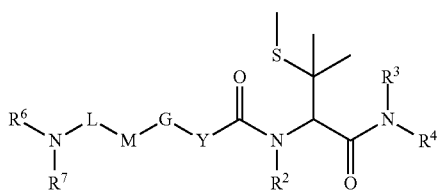

(XXXIII)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXXIV)

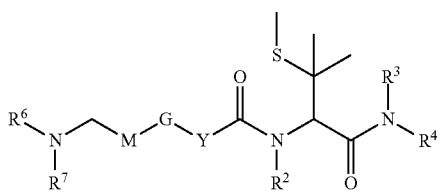

(XXXIV)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXXV)

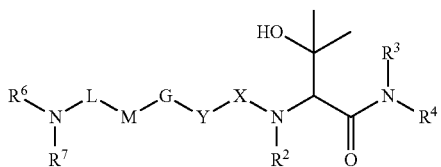

(XXXV)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XXXVI)

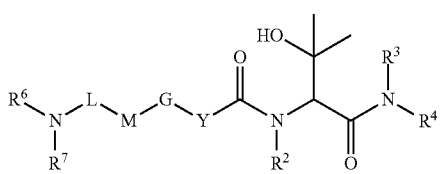

(XXXVI)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XXXVII)

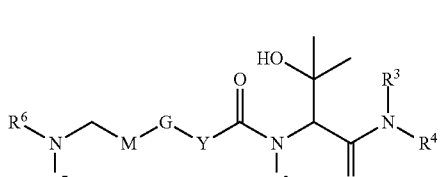

(XXXVII)

or a stereoisomer, pharmaceutically acceptable salt, ester, solvate, or prodrug thereof, wherein M, G, Y, R², R³, R⁴, R⁶, and R⁷, are defined as in any of the embodiments described herein.

In some embodiments of the invention and/or embodiments thereof the compounds are compounds according to formula (XXXVIII)

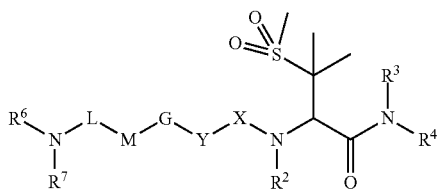

(XXXVIII)

or a stereoisomer, pharmaceutically acceptable salt, ester, solvate, or prodrug thereof, wherein L, M, G, Y, X, R², R³, R⁴, R⁶, and R⁷, are defined as in any of the embodiments described herein.

In some embodiments of the invention and/or embodiments thereof the compounds are compounds according to formula (XXXIX)

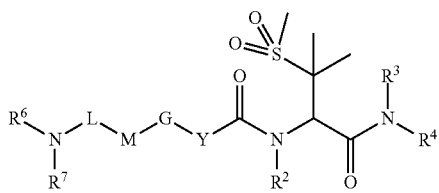

(XXXIX)

or a stereoisomer, pharmaceutically acceptable salt, ester, solvate, or prodrug thereof, wherein L, M, G, Y, R², R³, R⁴, R⁶, and R⁷, are defined as in any of the embodiments described herein.

In some embodiments of the invention and/or embodiments thereof the compounds are compounds according to formula (XL)

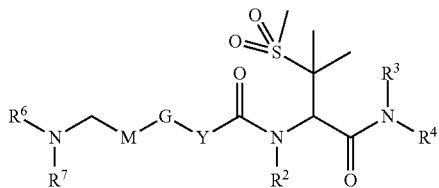

(XL)

or a stereoisomer, pharmaceutically acceptable salt, ester, solvate, or prodrug thereof, wherein M, G, Y, R², R³, R⁴, R⁶, and R⁷, are defined as in any of the embodiments described herein.

In some embodiments of the invention and/or embodiments thereof the compounds are compounds according to formula (XLI)

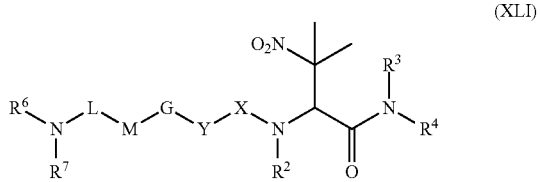

(XLI)

or a stereoisomer, pharmaceutically acceptable salt, ester, solvate, or prodrug thereof, wherein L, M, G, Y, X, R², R³, R⁴, R⁶, and R⁷, are defined as in any of the embodiments described herein.

In some embodiments of the invention and/or embodiments thereof the compounds are compounds according to formula (XLII)

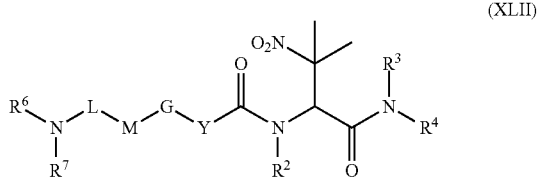

(XLII)

or a stereoisomer, pharmaceutically acceptable salt, ester, solvate, or prodrug thereof, wherein L, M, G, Y, R², R³, R⁴, R⁶, and R⁷, are defined as in any of the embodiments described herein.

In some embodiments of the invention and/or embodiments thereof the compounds are compounds according to formula (XLIII)

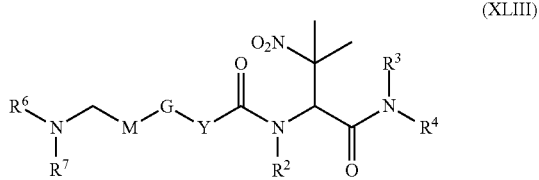

(XLIII)

or a stereoisomer, pharmaceutically acceptable salt, ester, solvate, or prodrug thereof, wherein M, G, Y, R², R³, R⁴, R⁶, and R⁷, are defined as in any of the embodiments described herein.

In some embodiments of the invention and/or embodiments thereof the compounds are compounds according to formula (XLIV)

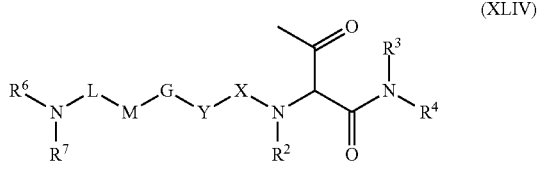

(XLIV)

or a stereoisomer, pharmaceutically acceptable salt, ester, solvate, or prodrug thereof, wherein L, M, G, Y, X, R², R³, R⁴, R⁶, and R⁷, are defined as in any of the embodiments described herein.

In some embodiments of the invention and/or embodiments thereof the compounds are compounds according to formula (XLV)

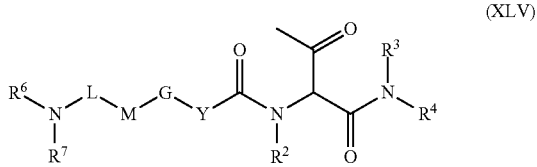
(XLV)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XLVI)

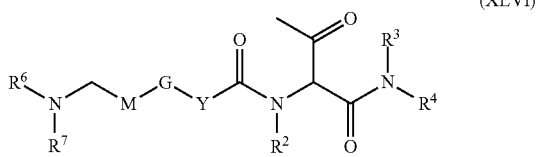
(XLVI)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (XLVII)

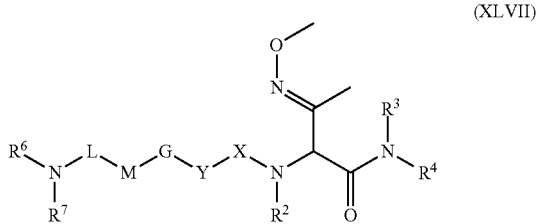
(XLVII)

or a stereoisomer, pharmaceutically acceptable salt, ester, solvate, or prodrug thereof, wherein L, M, G, Y, X, $R^2$, $R^3$, $R^4$, $R^6$, and $R^7$, are defined as in any of the embodiments described herein.

In some embodiments of the invention and/or embodiments thereof the compounds are compounds according to formula (XLVIII)

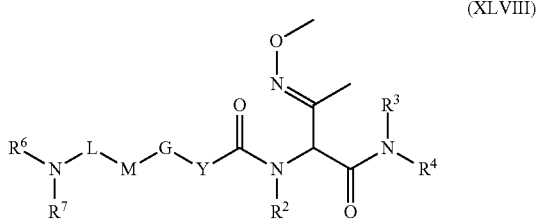
(XLVIII)

or a stereoisomer, pharmaceutically acceptable salt, ester, solvate, or prodrug thereof, wherein L, M, G, Y, $R^2$, $R^3$, $R^4$, $R^6$, and $R^7$, are defined as in any of the embodiments described herein.

In some embodiments of the invention and/or embodiments thereof the compounds are compounds according to formula (XLIX)

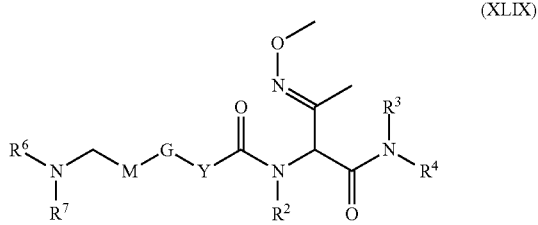
(XLIX)

or a stereoisomer, pharmaceutically acceptable salt, ester, solvate, or prodrug thereof, wherein M, G, Y, $R^2$, $R^3$, $R^4$, $R^6$, and $R^7$, are defined as in any of the embodiments described herein.

In some embodiments of the invention and/or embodiments thereof the compounds are compounds according to formula (L)

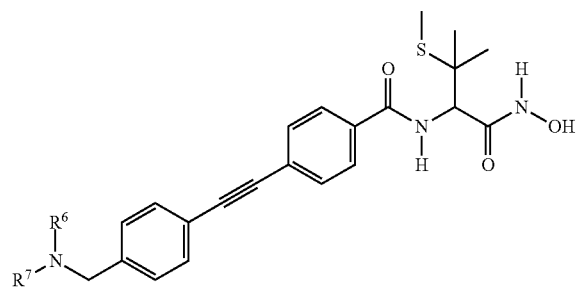
(L)

or a stereoisomer, pharmaceutically acceptable salt, ester, solvate, or prodrug thereof, wherein $R^6$, and $R^7$, are defined as in any of the embodiments described herein.

In some embodiments of the invention and/or embodiments thereof the compounds are compounds according to formula (LI)

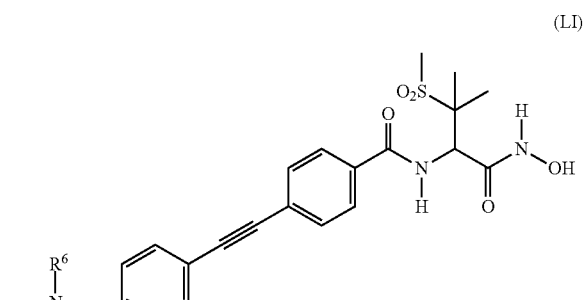
(LI)

or a stereoisomer, pharmaceutically acceptable salt, ester, solvate, or prodrug thereof, wherein R, and $R^7$, are defined as in any of the embodiments described herein.

In some embodiments of the invention and/or embodiments thereof the compounds are compounds according to formula (LII)

(LII)

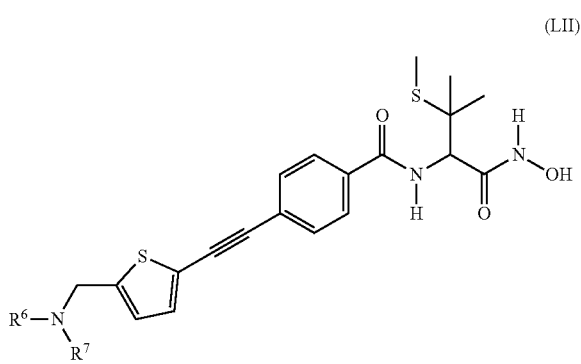

or a stereoisomer, pharmaceutically acceptable salt, ester, solvate, or prodrug thereof, wherein $R^6$, and $R^7$, are defined as in any of the embodiments described herein.

In some embodiments of the invention and/or embodiments thereof the compounds are compounds according to formula (LIII)

(LIII)

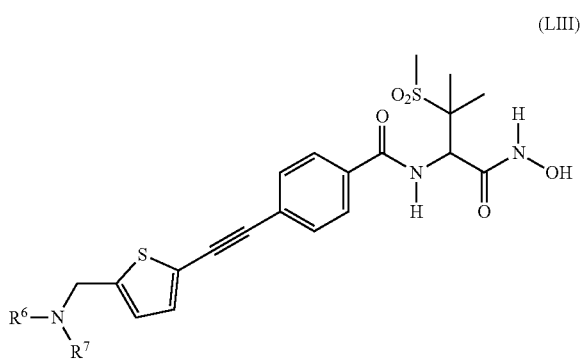

or a stereoisomer, pharmaceutically acceptable salt, ester, solvate, or prodrug thereof, wherein $R^6$, and $R^7$, are defined as in any of the embodiments described herein.

The invention is also directed to method for treating an animal with an infection by a bacteria comprising administering to the subject in need thereof an effective amount of a compound of the present invention and/or embodiments thereof with a pharmaceutically acceptable carrier, wherein the bacteria is at least one of the bacteria selected from the group *Mannheimia haemolytica* and *Histophilus somni*. Suitably the subject is a mammal and in some embodiments, a ruminant or swine.

Further the invention is directed to a compound according to the present invention and/or embodiments thereof with a pharmaceutically acceptable carrier for use in the treatment of a infection by a bacteria in a subject, wherein the bacteria is at least one of the bacteria selected from the group *Mannheimia haemolytica* and *Histophilus somni*. Suitably the subject is a mammal and in some embodiments, a ruminant or swine.

The invention provides further a pharmaceutical composition comprising an effective amount of a compound according to the invention and/or embodiments thereof with a pharmaceutically acceptable carrier thereof.

Suitably the compound of the present invention and/or embodiments thereof, is co-administered with other therapeutic agents that are selected for their particular usefulness against the condition that is being treated.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The compound of the present invention and/or embodiments thereof may also be used in the treatment of Bovine Respiratory Disease and/or Swine Respiratory disease.

Pharmaceutical Compositions

Pharmaceutical compositions of the present invention and/or embodiments thereof comprise a therapeutically effective amount of a compound of the present invention and/or embodiments thereof formulated together with one or more pharmaceutically acceptable carriers.

As used herein, the term "pharmaceutically acceptable carrier" means a non-toxic, inert solid, semi-solid or liquid filler, diluent, encapsulating material or formulation auxiliary of any type. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention and/or embodiments thereof can be administered to animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

The term "pharmaceutically acceptable salt" includes a salt with an inorganic base, organic base, inorganic acid, organic acid, or basic or acidic amino acid.

Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt. In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group Ia) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as C1-C6-alkyl halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

As salts of basic amino acids, the instant invention includes, for example, arginine, lysine and ornithine. Acidic amino acids include, for example, aspartic acid and glutamic acid.

The term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "antibacterial agent" refers to agents synthesized or modified in the laboratory that have either bactericidal or bacteriostatic activity. An "active" agent in this context will inhibit the growth of *P. aeruginosa* and other gram-negative bacteria. The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

Liquid dosage forms for oral administration include pharmaceutically acceptable emulsions, micro-emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U. S. P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution that, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly (anhydrides). Depot injectable formulations may also be prepared by entrapping the drug in liposomes or microemulsions that are compatible with body tissues.

Compositions for rectal or vaginal administration can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e. g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli.

Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5 pm.

Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 um. Predominantly in this application means that at least 70% but preferably more than 90% of all generated aerosol particles are 1 to 5 pm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances.

Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin.

The rate can be controlled by either providing a rate controlling membrane or by dispersing the compound in a polymer matrix or gel.

According to the treatment by the compounds of the present invention and/or embodiments thereof, bacterial infections are treated or prevented in an animal by administering to the animal a therapeutically effective amount of a compound of the invention, in such amounts and for such time as is necessary to achieve the desired result.

By a "therapeutically effective amount" of a compound of the invention and/or embodiments thereof is meant a sufficient amount of the compound to treat bacterial infections, at a reasonable benefit/risk ratio applicable to any medical treatment. It will be understood, however, that the total daily usage of the compounds and compositions of the present invention will be decided by the attending physician or veterinary doctor within the scope of sound medical judgment. The specific therapeutically effective dose level for any particular animal will depend upon a variety of factors including the disorder being treated and the severity of the disorder; the activity of the specific compound employed; the specific composition employed; the age, body weight, general health, sex and diet of the animal; the time of administration, route of administration, and rate of excretion of the specific compound employed; the duration of the treatment; drugs used in combination or coincidental with the specific compound employed; and like factors well known in the medical arts.

Methods of formulation are well known in the art and are disclosed, for example, in Remington: The Science and Practice of Pharmacy, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

A "kit" as used in the instant application includes a container for containing the pharmaceutical compositions and may also include divided containers such as a divided bottle or a divided foil packet.

The container can be in any conventional shape or form as known in the art that is made of a pharmaceutically acceptable material, for example a paper or cardboard box, a glass or plastic bottle or jar, a resealable bag (for example, to hold a "refill" of tablets for placement into a different container), or a blister pack with individual doses for pressing out of the pack according to a therapeutic schedule.

The container employed can depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil that is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Compositions of the present compounds may also be used in combination with other known antibacterial agents of similar spectrum to (1) synergistically enhance treatment of severe Gram-negative infections covered by the spectrum of this compound or (2) add coverage in severe infections in which multiple organisms are suspected in which another agent of a different spectrum may be required in addition to this compound. Potential agents include members of the aminoglycosides, penicillins, cephalosporins, fluoroquinolones, macrolides, glycopeptides, lipopeptides and oxazolidinones. The treatment can involve administering a composition having both active agents or administration of the inventive compounds followed by or preceded by administration of an additional active antibacterial agent.

Types of animals that may benefit from the practice of the invention include any that are susceptible to infection by an etiological agent of Bovine respiratory Disease (BRD) or alternatively, swine respiratory disease (SRD).

Exemplary animals include but are not limited to: members of the biological subfamily Bovinae which includes medium- to large-sized ungulates such as domestic dairy and beef cattle, bison, African buffalo, the water buffalo, etc. The animals may be so-called livestock raised in an agricultural setting for the production of dairy products or meat; or may be raised to perform work; or may be in another setting, e.g. in a zoo, animal reserve, etc., or raised for some other reason, e.g. as pets, show animals, for breeding purposes, etc.

Especially preferred is the use of the compounds of the current invention in beef cattle. Beef cattle are cattle raised for meat production (as distinguished from dairy cattle, used for milk production). There are three main stages in beef production: cow-calf operations, backgrounding, and feedlot operations. Especially preferred is the use of the compounds of the current invention in feedlot operations. The compounds of the invention can be used in beef (and dairy) cattle of every age, in calf, heifers, steer, cows. The compound of the invention can be used in animals of different weight, including heavy animals of a weight higher than 350 kg.

Other exemplary animals that can be treated with the compounds and compositions of the current invention are small ruminants, such a sheep or goats or pseudoruminants, such as e.g. camels or lamas. In one embodiment the compounds of the current invention is used to treat respiratory diseases such as enzootic pneumonia of lambs and/or adult sheep (ewes, rams) that are kept for meat or as breeding stock. Enzootic pneumonia is an acute infectious disease of sheep characterised by fever, nasal discharge, pneumonitis and pleuritis.

The compounds of the current invention can be alternatively used to treat Swine respiratory disease (SRD),that is a disease of animals of the family Suidae. Suidae are commonly called pigs, swine, hogs, or boars. The compounds of the current invention can be administered in general to all swine animals; to sucker, weaner, boars, barrows, gilts or sows. It can be used in one or more of the phases of swine farming for meat: suckling pigs, feeder pigs, grower, and finisher pigs or in backfatter pigs. Alternatively it can be used in breeding stocks, i.e. in breeding sows, gilts or boars or the offspring of such animal as replacement breeding stock.

In one embodiment, the animal that is treated is a bovine animal and the disease that is treated is BRD. In another embodiment the animal is a suidae (porcine) animal and the disease that is treated is SRD. The compounds of the current invention can be used to treat diseased animals that display clinical symptoms of Bovine Respiratory disease or Swine respiratory disease.

The compounds of the current invention can additionally or alternatively be used to treat animals with subclinical infections with *Pasteurella* spp., *Mannheimia* spp., and *Histophilus* spp. infections. A subclinical infection is nearly or completely asymptomatic (no disease signs or symptoms). Therefore identifying affected animals early in the course of BRD or SRD is difficult and subclinical infection is mainly detected at the slaughterhouse when checking the lungs for lesions. However, subclinical BRD or SRD infection result in lower average daily gains (ADG).

In addition to treatment purposes, the compositions and methods of the invention are also suitable for metaphylactic use. For example, in case of an outbreak of Bovine Respiratory disease or Swine respiratory disease, administration of the compounds of the current invention to non-affected (or sub-clinical infected) animals, especially those which are in close contact with those showing clinical signs of disease, could prevent the spread of the infection.

In addition, prophylactic treatment might be undertaken in bovines considered to be vulnerable to infection and/or in whom infection could have grave consequences, e.g. calves, show cattle, pregnant females, prize bulls or boars, etc., whether or not an outbreak of the disease is known to have occurred. Another option is the prophylactic administration of compounds according to the current invention in animals before shipping and other stress inducing events to prevent outbreak of the disease in such animals.

The same concept of prophylactic or metaphylactic treatment, as described in the herein applies to swine animals at risk for SRD.

In some embodiments, one or more, preferably one compound according to this invention is used to treat an infection by a pathogen that is resistant to one or more other antibacterial agents. In some embodiments, the compound according to this invention is active against a pathogen, that is resistant to one or more of the following antibacterials: macrolide antibiotics, aminoglycosides, fluoroquinolones, or cephalosporins, especially one ormore selected grom the group of tylosin, erythromycin, tildipirosin, timicosin, tulathromycin, gamithromycin, gentamicin, neomycin, enrofloxacin, ciprofloxacindanafloxaxin, oxytetracycline, chlortetracycline, cefquinome, ceftiofur or florfenicol, sulfonamides or penicillin.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Dosage forms useful in the current invention can be liquid, semi-solid or solid dosage forms. Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is mixed and reconstituted with a diluent (e.g. water) as a solution, or as a suspension immediately prior to injection. The principal advantage of this dosage form is that it overcomes the problem of instability in solution or suspension.

One dosage route (administration route) is the parenteral, especially injection administration (e.g. subcutaneous injection, intravenous injection, intramuscular injection, etc.). Parenteral formulations and delivery systems for non-oral routes comprise liquids (e.g. solutions, suspensions, emulsions, and dry powders for reconstitution), semi-solids and solids (e.g. implants). The majority of implants, that are used in veterinary medicine, are compressed tablets or dispersed matrix systems in which the drug is uniformly dispersed within a nondegradable polymer or alternatively extrusion products. In one embodiment the compounds of the current invention are administered subcutaneously.

Another possible dosage route is the oral dosage route, wherein the compound according to this invention is administered via the mouth. Oral dosage forms suitable for oral administration comprise liquids (e.g. injectable, drench, in-feed or drinking water formulations), semi-solids (e.g. pastes, gels), and solids (e.g. tablets, capsules, powders, granules, chewable treats, premixes and medicated blocks). A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, it may, for example, be fed as a discrete feed or as a chewable treat. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a small amount of a liquid or solid carrier. This "premix" is, in turn, dispersed in the animal's regular feed using, for example, a conventional mixer.

Several modified-release delivery systems have been developed, that take advantage of the unique anatomy of the ruminant forestomach, i.e. for intra-ruminal administration. An intraruminal bolus is a specific formulation for ruminants and pseudo-ruminants (cattle, sheep, goats, buffalos, camelids, deer etc.). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to the current invention may alternatively be administered topically (e.g., transdermal via a spot-on, pour-on or spray, or alternatively as a nasal spray or by inhalation).

For instance the compounds according to this invention may be administered topically using a transdermal formulation (i.e. a formulation that passes through the skin). Alternatively the compounds according to this invention may be administered topically via the mucosa, e.g. as nasal spray.

Further aspects regarding formulation of drugs and various excipients are found in, for example, Gennaro, A. R., et al., eds., Remington: The Science and Practice of Pharmacy (Lippincott Williams & Wilkins, 20th Ed., 2000).

In carrying out the method of this invention, a specified compound according to the invention is preferably administered parenterally to an infected or susceptible animal.

In another embodiment the compound is administered orally (especially in case of SRD).

When the compound according to this invention is administered orally or parenterally by subcutaneous injection, the total dose is generally greater than about 0.01 mg/kg (i.e., milligram of compound according to this invention per kilogram body weight of the treated animal). In some such embodiments, the total dose is from about 0.01 to about 100 mg/kg, from about 0.01 to about 50 mg/kg, from about 0.1 to about 25 mg/kg, or from about 1 to about 20. For BRD or SRD, for example, the dose is generally from about 0.5 to about 15 mg/kg, from about 1 to about 10 mg/kg. The same dose range may be suitable for other dosage routes. The desired dose, however, may be less in some instances where the compound according to this invention is administered intravenously.

The dose used to control *Pasteurella multocida, Mannheimia haemolytica* or *Histophilus somni* infections or especially BRD will vary with the compound, the severity of the infection, and the age, weight, and condition of the animal. The total dose required for several days protection will generally, however, be in the range of from about 1 to about 40 mg/kg bodyweight, and preferably will be in the range of from about 2.5 to about 35 mg/kg. Similar dosages are administered to pigs to treat SRD. Protection for up to about seven days can be provided by a single injection; the length of protection will depend upon the dose given. The total dose can also be divided into smaller doses given at intervals, such as once daily for two to seven days. Obviously, other suitable dosage regimens can be constructed.

A single administration of a composition comprising a compound according to this invention can be sufficient to treat an infection and to clinically and/or bacteriologically cure BRD or SRD, or at least diminish the clinical symptoms in diseased animals; this is called "one shot" administration. Although the administration of such a "one-shot" single dose is very suitable, it is contemplated that multiple doses can be used, e.g. two administrations 12-24 hours apart or alternatively, two administrations, 48-72 hours apart.

Factors affecting the preferred dosage may include, for example, infection to be treated, the type (e.g., species and breed), age, size, sex, diet, activity, and condition of the of the infected animal; the dosage route; pharmacological considerations, such as the activity, efficacy, pharmacokinetic, and toxicology profiles of the particular compound of the invention and the composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art.

The effective dosage will vary; for example for prophylactic treatment relatively low doses would be administered over an extended time.

The compounds of this invention may be formulated for parenteral administration by methods recognized in the veterinary pharmaceutical art. Effective injectable compositions containing these compounds may be in either suspension or solution form. In the preparation of suitable formulations it will be recognized that, in general, the water solubility of the acid addition salts is greater than that of the corresponding free bases. Similarly, the free bases are more soluble in dilute acids or in acidic solutions than in neutral or basic solutions.

In the solution form a compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions employ a liquid suspending medium, with or without adjuvants, as a vehicle. The suspending medium can be, aqueous or non-aqueous, e.g. water, polyethylene glycol, benzyl alcohol, N methyl pyrrolidone, triacetin, inert oils such as vegetable oils or highly refined mineral oils.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents. Many substances which affect the hydrophilicity, density, and surface tension of the liquid suspending medium can assist in making injectable suspensions in individual cases. For example, silicone antifoams, sorbitol, and sugars can be useful suspending agents. Other conventional iingredients such as preservatives, buffers, surfactats, or thickeners can be present in the injectable formulation.

The compounds of this invention exhibit unexpectedly high antibacterial activity against *Mannheimia haemolytica* and *Pasteurella multocida*. For example, representative compounds were tested against ***, *Mannheimia haemolytica* and *Pasteurella multocida*, using the conventional broth-dilution assay. The minimal inhibitory concentrations (MIC's) of representative compounds against these species are summarized in Table C.

The concentration of the compounds according to this invention in the applied dosage form may vary widely depending on, for example, the dosage route. In general, the concentration for injectable or oral administration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

Preferred concentration in drinking water are from 0.01 to 0.05% weight by volume, particularly 0.01 to 0.025%, and in-feed from 100 to 400 ppm (g/metric ton), particularly 100 to 200 ppm.

In another aspect the present invention thus provides the administration of a pharmaceutical composition comprising an antibacterial effective amount of one or more, preferably one compound according to this invention and one or more pharmaceutically acceptable excipients to an animal, especially a bovine animal or alternatively a porcine animal, especially for the treatment of BRD or SRD.

The formulation type chosen for a dosage form in any instance will depend upon the particular purpose envisaged and the physical, chemical and biological properties of the compound according to this invention.

If the compound according to this invention is administered parentally via an injection, the concentration of the compound according to this invention in the composition/formulation/dosage form preferably is sufficient to provide the desired therapeutically effective amount of the compound according to this invention in a volume that is acceptable for parenteral (subcutaneous) administration and allows an injection volume of less than 20 ml/per injection site.

In one embodiment the composition of a compound according to the invention is administered in a non-edible tissue of the animal that is removed at slaughter and does not enter the human food chain, e.g. in the ear or at the base of the ear (at the junction of the pinna with the cranium), or behind the ear, e.g. as described in WO1998041207 or WO2003079923, the content of which is incorporated by reference. Injection in alternative animal tissues of food producing animals, that do not enter the (human) food chain after slaughtering of the animal are also envisaged.

Examples of Contemplated Combination Therapies

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different diseases or conditions.

Contemplated active ingredient(s) that may be administered in combination with the compounds of the current invention include, for example, antibacterials, anti-inflammatories, pharmaceutically acceptable anthelmintics, insecticides and acaricides, insect growth regulators, hormones, immunostimulats, dermatological preparations (e.g. antiseptics and disinfectants), and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anti-inflammatory compounds, more preferably selected from the group consisting of non-steroidal anti-inflammatory agents (NSAID's), such as e.g. flunixin meglumine, meloxicam, carprofen, ketoprofen, phenylbutazone, or Aspirin. In one embodiment one compound according to the invention is combined with flunixin. In another embodiment one compound of the invention is combined with meloxicam. Preferably such combination is used to treat BRD in cattle.

Combination means that a compound of the current invention is administered in a common formulation with the one or more pharmaceutically acceptable active compounds which differ in structure. Alternatively the compound according to the invention is administered to the animal in parallel (not more than approximately 30 minutes apart) from one or more pharmaceutically acceptable active compounds which differ in structure.

In another embodiment the one or more pharmaceutically acceptable active compounds which differ in structure b) are antibacterials especially one or more selected grom the group of tylosin, erythromycin, tildipirosin, timicosin, tulathromycin, gamithromycin, gentamicin, neomycin, enrofloxacin,ciprofloxacindanafloxaxin, oxytetracycline, chlortetracycline, cefquinome, ceftiofur or florfenicol, sulfonamides or penicillin.

Veterinary formulations for use in the present invention may be prepared by mixing the ingredients in the required proportions. The formulation is then packaged into an appropriate container containing single or multiple doses ready for administration (ready to use—RTU) or alternatively, can be mixed with a diluent before administration.

Features of the invention have been described in embodiments in the present application; however for brevity not all combinations of the features are literally described. Combinations of features as described above are however expressly considered to be part of the invention.

The invention will now be further described by the following, non-limiting, examples: Synthesis Examples Example 1: General Procedure for the Synthesis of Aldehyde Containing Resins

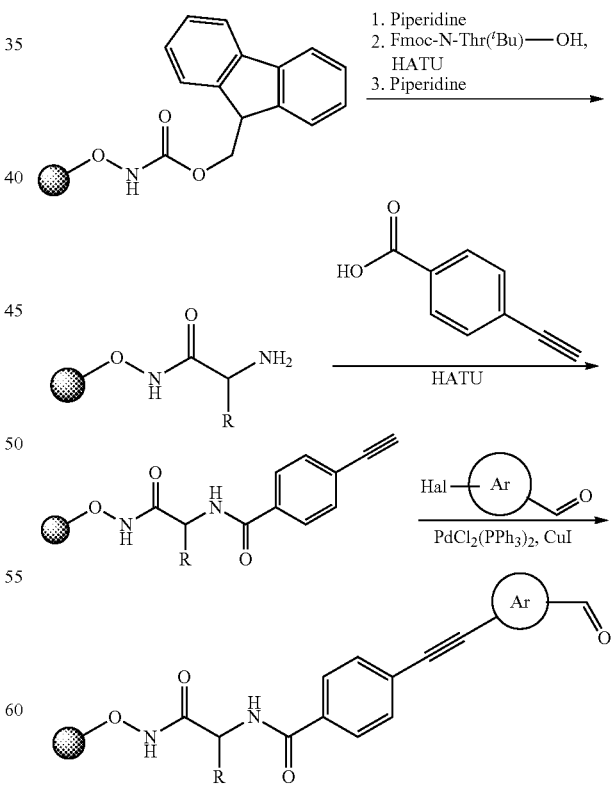

A suspension of N-Fmoc-hydroxylamine 2-chlorotrityl resin (12.0 g, 6.0 mmol) in dichloromethane (160 mL) was shaken for 2 hours and drained. The resin was treated with 20% v/v piperidine in DMF (150 mL) for 30 minutes, washed with DMF (5×80 mL) and drained completely. In a separate flask, the N-Fmoc-protected amino acid (18.0 mmol), HATU (6.5 g, 17.1 mmol) and DIEA (6.3 mL, 36.0 mmol) were dissolved in DMF (50 mL), stirred for three minutes and then added to the resin. After mixing under an atmosphere of nitrogen for 2 hours, the mixture was drained, washed with DMF (3×80 mL), and again treated with N-Fmoc-protected amino acid (18.0 mmol), HATU (6.5 g, 17.1 mmol) and DIEA (6.3 mL, 36.0 mmol). Mixing was continued for 2 hours, when the resin was drained, washed with DMF (5×80 mL) and drained again. The resin then was treated with 20% v/v piperidine in DMF (150 mL) for 30 minutes, drained and washed with DMF (5×80 mL) and drained again. A solution of 4-ethynylbenzoic acid (2.63 g, 18 mmol), HATU (6.5 g, 17.1 mmol) and DIEA (6.3 ml, 36.0 mmol) in DMF (50 mL) was then added to the resin and mixing under an atmosphere of nitrogen was continued for 2 hours. The mixture was then drained, washed with DMF (5×80 mL) and drained. A solution of the halo-aryl- or halo-heteroarylaldehyde (24.0 mmol) and DIEA (10.5 mL, 60.0 mmol) in DMF (150 mL) was purged with a stream of nitrogen for two minutes and added to the resin. After mixing for 5 min, $PdCl_2(PPh_3)_2$ (842 mg, 1.2 mmol) and CuI (571 mg, 3.0 mmol) were added and the mixture was mixed under an atmosphere of nitrogen for 48 hours. The resin was drained, washed with DMF (4×100 mL), DCM (4×100 mL) and dried in vacuo to give the aldehyde containing resin which was used in the next steps without further purification.

Using this procedure, the corresponding amino acid-containing aldehyde resins were obtained using Fmoc-N-(S)-Val-OH, Fmoc-N-(S)-Ser($^t$Bu)-OH, Fmoc-N-(S)-Ile-OH, Fmoc-N-3-OTBS-(S)-Val-OH and Fmoc-N-3-MeS-(S)-Val-OH, Fmoc-N-2-amino-3-methoxyimino-(2S)-butanoic acid and (2S)-Fmoc-N-2-amino-2-(2-methyl-1,3-dioxolan-2-yl)acetic acid.

Using this procedure, all aldehyde-containing resins were obtained using 4-iodobenzaldehyde, 3-iodobenzaldehyde, 5-bromopicolinaldehyde and 5-bromothiophene-2-carbaldehyde.

Example 2: General Procedure for the Oxidation of Methylsulfon-Containing Resins Prepared from Fmoc-N-3-MeS-(S)-Val-OH and N-Fmoc-hydroxylamine 2-chlorotrityl Resin A suspension of N-Fmoc-hydroxylamine 2-chlorotrityl resin (20.0 g, 10 mmol) in dichloromethane (200 mL) was shaken for 2 hours and drained. The resin was treated with 20% piperidine in DMF (320 mL) for 30 minutes, washed with DMF (5×200 mL) and drained completely. In a separate flask, a solution of (R)-2-((((9H-fluoren-9-yl)methoxy)carbonyl)amino)-3-methyl-3-(methylthio)butanoic acid (7.71 g, 20 mmol), HATU (72 g, 19 mmol) and DIEA (10.5 mL, 60 mmol) in DMF (40 mL) was stirred for three minutes and then added to the resin and mixing under an atmosphere of nitrogen was continued for 2 hours. The resin was drained, washed with DMF (3×200 mL) and drained again. The resin was then treated with 3-chlorobenzoperoxoic acid (6.9 g, 40 mmol) in DCM (200 mL) for 3 hours. The resin was washed with DMF (3×200 mL), drained and was then treated with 20% piperidine v/v in DMF (320 mL) for 30 minutes. After draining again and washing with DMF (5×200 mL), the resin was drained completely and 4-ethynylbenzoic acid (4.38 g, 30 mmol), HATU (10.5 g, 28.5 mmol) and DIEA (10.5 ml, 60 mmol) dissolved in DMF (40 mL) were added to the resin. Mixing under an atmosphere of nitrogen was continued for 2 hours after which the resin was drained, washed with DMF (5×200 mL) and drained again. A solution of the respective halo-aryl- or halo-heteroarylaldehyde (40 mmol) and DIEA (17.5 ml, 100 mmol) in DMF (400 mL) was purged with a stream of nitrogen for two minutes and then added to the resin. After mixing for 5 minutes and then added to the resin. After mixing for 5 minutes, $PdCl_2(PPh_3)_2$ (1.40 g, 2.0 mmol) and CuI (950 mg, 5.0 mmol) were added and the mixture was mixing was continued under an atmosphere of nitrogen for 48 hours. The resin was drained, washed with DMF (4×200 mL) and MeOH (3×200 mL) and dried in vacuo.

Using this procedure, all aldehyde resins were obtained using 4-iodobenzaldehyde, 5-bromopicolinaldehyde and 5-bromothiophene-2-carbaldehyde.

Example 3: General Procedure for the Reductive Amination of the Aldehyde-Containing Resins with Primary and Secondary Amines A solution of the amine (1.5 mmol) and trimethyl orthoformate (180 µL, 1.625 mmol) in THF (20 mL) was added to the aldehyde-containing resin (105 mg, 0.25 mmol). An atmosphere of nitrogen was established and after mixing for 5 minutes, acetic acid (180 µL, 3.08 mmol) followed by a solution of $NaBH_3CN$ (71 mg, 1.125 mmol) in methanol (1 mL) was added. Mixing was continued for 44 hours after which the resin was filtered, drained and washed with DMF (2×10 mL) and methanol (3×10 mL), drained again and dried in vacuo. Cleavage from the resin was achieved by treatment with trifluoroacetic acid (10 mL) for 30 minutes. The solution was collected and concentrated to dryness to give a crude residue which was purified by preparative HPLC using a e.g. Gilson GX-281 semi-preparative HPLC system equipped with a Luna 200×25 mm (C18, 10µ) or a Gemini 150×30 mm (C18, 5µ) column applying a gradient consisting of 0.1% TFA/water and acetonitrile.

The product containing fractions were collected, concentrated by freeze-drying and the residual trifluoroacetic acid was removed by another reverse-phase chromatography using a gradient consisting of aqueous ammonium hydrogencarbonate (7.5 mmol/L) and acetonitrile.

Using this procedure, the following compounds can be synthesized: Compound No.: 1-216, 219-275, 289-374, 378-415.

Example 4: Synthesis of (2S)-3-[tert-butyl(dimethyl)silyl]oxy-2-(9H-fluoren-9-ylmethoxycarbonylamino)-3-methyl-butanoic Acid

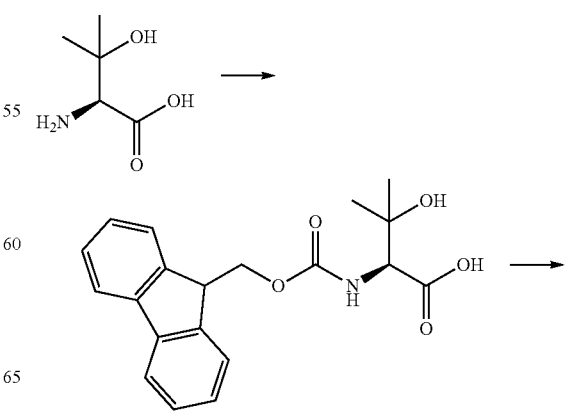

Step 1: (S)-2-((((9H-Fluoren-9-yl)methoxy)carbonyl)amino)-3-hydroxy-3-methylbutanoic Acid

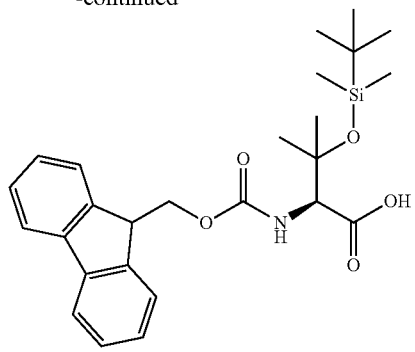

To a solution of (S)-2-amino-3-hydroxy-3-methylbutanoic acid hydrochloride (30.1 g, 177 mmol) in a mixture of dioxane (500 mL) and water (250 mL) was added an aqueous NaHCO$_3$ solution (44.7 g in 500 mL water) at 20° C. The reaction mixture was stirred at this temperature for 30 minutes. Then a solution of (9H-fluoren-9-yl)methyl (2,5-dioxopyrrolidin-1-yl) carbonate (59.9 g, 177 mmol) in dioxane (625 mL) was added. The resulting mixture was then stirred at room temperature for 3 hours. The dioxane was removed in vacuo and the remaining solution washed with methyl-tert-butylether (3×1000 mL). The aqueous phase was then acidified with 1.0 M hydrochloric acid until the pH 2-3 was reached and was 50 then extracted with ethyl acetate (4×800 mL). The organic phases were combined, washed with brine, dried, filtered and concentrated to give the title compound.

Step 2: (2S)-3-[tert-Butyl(dimethyl)silyl]oxy-2-(9H-fluoren-9-ylmethoxycarbonylamino)-3-methyl-butanoic Acid N,N-Diisopropylethylamine (36.4 g, 281 mmol) was added to a solution of (S)-2-((((9H-fluoren-9-yl)methoxy)carbonyl)amino)-3-hydroxy-3-methylbutanoic acid (20 g, 56.3 mmol) in dichloromethane (500 mL) at 0° C. over a period of 20 minutes. Then, tert-butyldimethylsilyl trifluoromethanesulfonate (59.5 g, 225 mmol) was added dropwise to the mixture and after stirring for 4 hours at 0° C. All volatiles were removed in vacuo and to the residue ethyl acetate (400 mL) was added. 1.0 M hydrochloric acid was added until pH 2-3 was reached and the aqueous layer was extracted with ethyl acetate (4×300 mL). The combined organic phases were washed with brine, dried, filtered and concentrated to give the crude product which was purified by column chromatography on silica gel (petroleum ether/ethyl acetate) to provide the title compound as a solid. $^1$H NMR (400 MHz, CDCl$_3$): δ 7.77 (d, J=7.6 Hz, 2H), 7.61 (dd, J=6.8 Hz, J=6.4 Hz, 2H), 7.30-7.41 (m, 4H), 5.56 (d, J=9.2 Hz, 1H), 4.2 (d, J=6.8 Hz, 2H), 4.23-4.30 (m, 2H), 1.45 (s, 3H), 1.30 (s, 3H), 0.92 (s, 9H), 0.19 (s, 3H), 0.18 (s, 3H).

Example 5: Synthesis of (2R)-2-(9H-fluoren-9-yl-methoxycarbonylamino)-3-methyl-3-methylsulfanyl-butanoic Acid

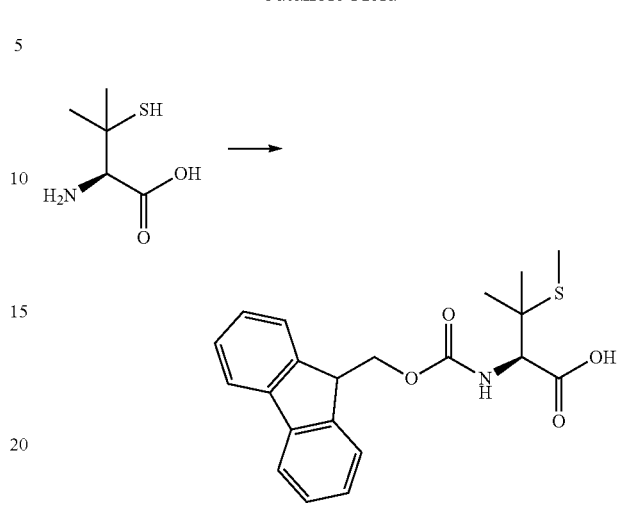

To a solution of (R)-2-amino-3-mercapto-3-methylbutanoic acid in methanol was added sodium (3.08 g, 134 mmol) followed by iodomethane (5 g, 35.2 mmol). The reaction mixture was stirred for 3 hours at 25° C. and then concentrated in vacuo. The residue was treated with 1 M hydrochloric acid until pH 7 was reached and the mixture was then diluted with water (50 mL). NaHCO$_3$ (5.6 g, 67 mmol) and a solution of (9H-fluoren-9-yl)methyl (2,5-dioxopyrrolidin-1-yl) carbonate in acetone was added. After stirring at 25° C. for 3 hours, the solution was concentrated in vacuo and treated with 1 M hydrochloric acid until pH 4 was reached. The mixture was then extracted with ethyl acetate (4×50 mL) and the combined organic layers were evaporated to dryness and the residue submitted to column chromatography on silica gel (ethyl acetate/petroleum ether 1:100 to 1:10) to provide the title compound as a solid. MS: 385.8 (M+1). $^1$H NMR (400 MHz, CDCl$_3$): δ 7.77 (d, J=7.6 Hz, 2H), 7.61 (d, J=7.2 Hz, 2H), 7.32-7.43 (m, 4H), 5.57 (d, J=7.6 Hz, 1H), 4.3-4.5 (m, 3H), 4.25 (t, J=6.8 Hz, 1H), 2.10 (s, 3H), 1.43 (s, 3H), 1.39 (s, 3H).

Example 6: Synthesis of (2S)-2-(9H-fluoren-9-yl-methoxycarbonylamino)-2-(2-methyl-1,3-dioxolan-2-yl) Acetic Acid -continued

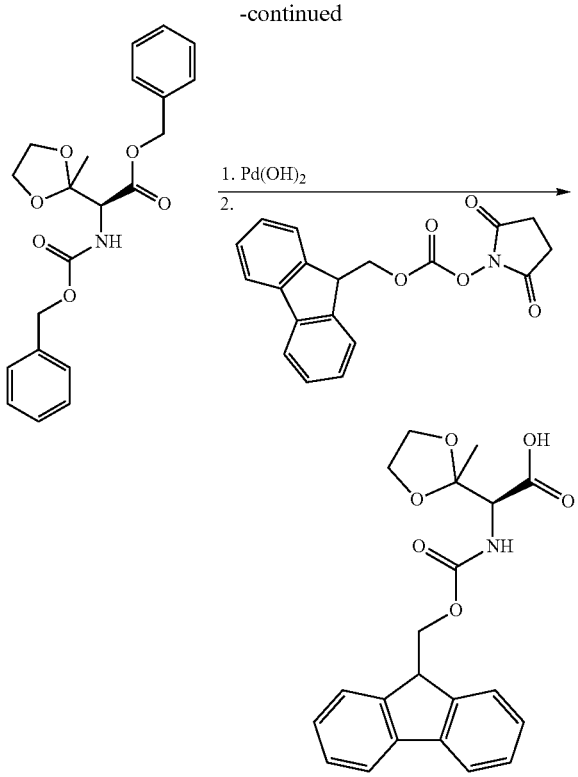

Step 1: Synthesis of benzyl (2S)-2-(benzyloxycarbonylamino)-3-oxo-butanoate

To a mixture of (benzyl (2S,3R)-2-(benzyloxycarbonylamino)-3-hydroxy-butanoate (20 g, 58.2 mmol) in dichloromethane (300 mL) was added Dess-Martin Periodinane (37.1 g, 87 mmol) and NaHCO$_3$ (0.489 g, 5.82 mmol) at 0° C. The mixture was then stirred at room temperature for 16 hours and concentrated under reduced pressure to remove all volatiles. To the mixture was then added saturated Na$_2$SO$_3$ (400 mL) and ethyl acetate (400 mL) and both layers shaken vigorously. The aqueous phase was separated and extracted with ethyl acetate (1×400 mL). The combined organic layers were washed with brine (3×400 mL), dried over Na$_2$SO$_4$, filtered and concentrated under reduced pressure to provide the crude title compound which was used in the next step without further purification.

Step 2: Synthesis of benzyl (2S)-2-(benzyloxycarbonylamino)-2-(2-methyl-1,3-dioxolan-2-yl) Acetate A solution of benzyl (2S)-2-(benzyloxycarbonylamino)-3-oxo-butanoate (40 g, 117 mmol), 4-methylbenzenesulfonic acid hydrate (22.29 g, 117 mmol) in ethane-1,2-diol (400 mL) and tetrahydrofuran (50 mL) was stirred at ambient temperature for 16 hours. The reaction mixture was then concentrated under reduced pressure and the residue was purified by reverse phase preparative HPLC applying a water/acetonitrile gradient without additives to provide the title compound.

Step 3: (2S)-2-amino-2-(2-methyl-1,3-dioxolan-2-yl) acetic Acid

A mixture of benzyl (2S)-2-(benzyloxycarbonylamino)-2-(2-methyl-1,3-dioxolan-2-yl) acetate (8 g, 20.76 mmol) and Pd(OH)$_2$ on carbon (1 g, 20% purity) in methanol (200 mL) was stirred at ambient temperature under an atmosphere of hydrogen (50 psi) for 16 hours. The mixture was filtered and concentrated under reduced pressure to provide the crude title compound which was used in the next step without further purification.

Step 4: (2S)-2-(9H-fluoren-9-ylmethoxycarbonylamino)-2-(2-methyl-1,3-dioxolan-2-yl) acetic Acid To a mixture of (S)-2-amino-2-(2-methyl-1,3-dioxolan-2-yl) acetic acid (4 g, 24.82 mmol) and NaHCO$_3$ (6.26 g, 74.5 mmol) in acetone (50 mL) and water (50 mL) was added a solution of (9H-fluoren-9-yl)methyl (2,5-dioxopyrrolidin-1-yl) carbonate (9.21 g, 27.3 mmol) in acetone (20 mL) under stirring at ambient temperature and stirring was continued for 2 hours. All volatiles were then removed under reduced pressure and the residue was combined with water (20 mL). The resulting mixture was washed with ethyl acetate (50 mL), the aqueous layer was acidified with 3 M HCl to pH=4. The precipitate was collected by filtration and washed with water (30 mL) and dried under freeze-drying condition to provide the title compound. $^1$H NMR (400 MHz, DMSO-d$_6$): δ 7.89 (d, J=7.6 Hz, 2H), 7.78 (d, J=7.6 Hz, 2H), 7.69 (m, 2H), 7.42 (dd, J=7.6 Hz, 2H), 7.33 (dd, J=7.6 Hz, 2H) 4.1-4.4 (m, 4H), 3.7-4.0 (m, 4H), 1.38 (s, 3H).

Example 7: Synthesis of (2S)-2-(9H-fluoren-9-ylmethoxycarbonylamino)-3-methoxyimino-butanoic Acid

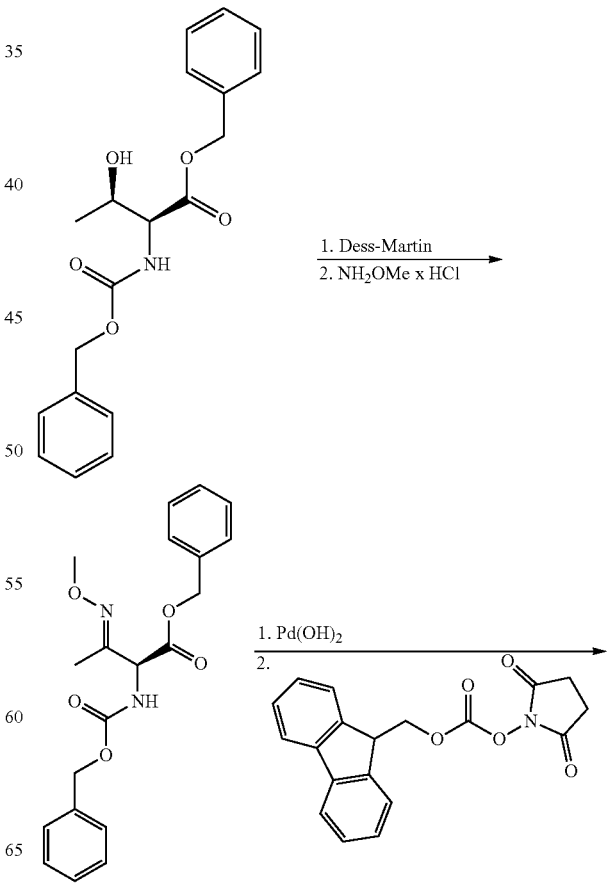

Step 4: Synthesis of (2S)-2-(9H-fluoren-9-yl-methoxycarbonylamino)-3-methoxyimino-butanoic Acid (9H-Fluoren-9-yl)methyl (2,5-dioxopyrrolidin-1-yl) carbonate (69.2 g, 205 mmol) was added to a solution of (S)-2-amino-3-(methoxyimino)-butanoic acid (20 g, 137 mmol) in a mixture if acetone (400 mL) and saturated aqueous $NaHCO_3$ (400 mL). The solution was stirred ambient temperature for 10 hours. Water was then added to the reaction mixture and the formed precipitate collected by filtration. The filter cake was then purified by flash C18 reverse phase chromatography applying a water/acetonitrile gradient to provide the title compound. $^1$H NMR (400 MHz, $CDCl_3$): δ 7.89 (d, J=7.6 Hz, 2H), 7.68 (d, J=7.6 Hz, 2H), 7.42 (dd, J=7.6 Hz, 2H), 7.33 (dd, J=7.6 Hz, 2H), 6.7 (b, 1H), 4.1-4.4 (m, 4H), 3.72 (s, 3H), 1.62 (s, 3H).

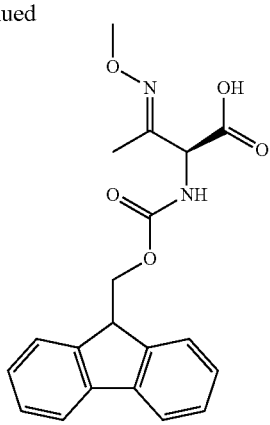

Step 1: Synthesis of benzyl (2S)-2-(benzyloxycarbonylamino)-3-oxo-butanoate

To a mixture of (benzyl (2S,3R)-2-(benzyloxycarbonylamino)-3-hydroxy-butanoate (20 g, 58.2 mmol) in dichloromethane (300 mL) was added Dess-Martin Periodinane (37.1 g, 87 mmol) and $NaHCO_3$ (0.489 g, 5.82 mmol) at 0° C. The mixture was then stirred at room temperature for 16 hours and concentrated under reduced pressure to remove all volatiles. To the mixture was then added saturated $Na_2SO_3$ (400 mL) and ethyl acetate (400 mL) and both layers shaken vigorously. The aqueous phase was separated and extracted with ethyl acetate (1×400 mL). The combined organic layers were washed with brine (3×400 mL), dried over $Na_2SO_4$, filtered and concentrated under reduced pressure to provide the crude title compound which was used in the next step without further purification.

Step 2: Synthesis of benzyl (2S)-2-(benzyloxycarbonylamino)-3-methoxyimino-butanoate Benzyl (2S)-2-(benzyloxycarbonylamino)-3-oxo-butanoate (0.5 g, 1.46 mmol) was added to a solution of methoxylamine hydrochloride (183 mg, 2.197 mmol) and titanium (IV) isopropoxide (83 mg, 0.29 mmol) in DIEA (0.767 mL) and tetrahydrofuran (10 mL) at 20° C. The reaction mixture was heated at 72° C. for 12 hours and then diluted with water (10 mL). The aqueous layer was extracted with dichloromethane and the combined organic extracts were washed with 10% aqueous HCl (50 mL), saturated $NaHCO_3$ (50 mL) and brine (50 mL) and then dried over $Na_2SO_4$. It was then filtered and concentrated under reduced pressure to give a residue which was purified by column chromatography on silica gel (petroleum ether/ethyl acetate) to provide the title compound.

Step 3: (2S)-2-Amino-3-methoxyimino-butanoic Acid

To a solution of benzyl (2S)-2-(benzyloxycarbonylamino)-3-methoxyimino-butanoate (50 g, 135 mmol) in methanol (1000 mL) was added palladium on carbon (15%, 10 g) and an atmosphere of nitrogen (15 psi) was established. The reaction mixture was then stirred at 20° C. for 90 minutes and all solids removed by filtration. The solution was collected and concentrated to provide the title compound.

Example 8: General Procedure for the Synthesis of Crotonaldehyde-Containing Resin

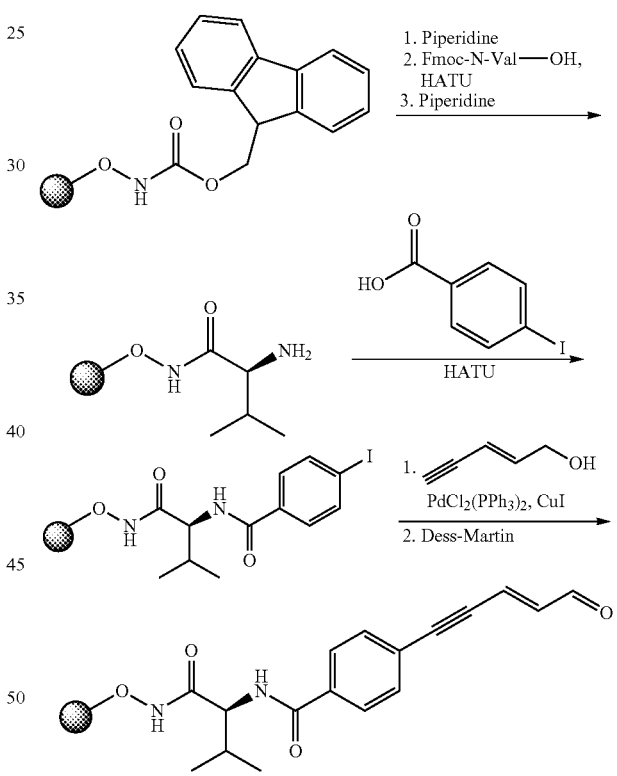

A suspension of N-Fmoc-hydroxylamine 2-chlorotrityl resin (50.0 g, 25 mmol) in dichloromethane (500 mL) was shaken for 2 hours and drained. The resin was then treated with 20% piperidine in DMF (500 mL) for 30 minutes, washed with DMF (5×200 mL) and drained completely. In a separate flask, Fmoc-N-Val-OH (75 mmol), HATU (27 g, 71.3 mmol) and DIEA (26.0 mL, 150 mmol) were dissolved in DMF (100 mL), stirred for three minutes and then added to the resin. After mixing under an atmosphere of nitrogen for 2 hours, the mixture was drained, washed with DMF (3×200 mL), treated a second time with the DMF solution of Fmoc-N-Thr($^t$Bu)-OH (30 g, 75 mmol), HATU (27 g, 71.3 mmol) and DIEA (26.0 mL, 150 mmol). The mixture was left shaking for another 2 hours, washed with DMF (5×200 mL) and drained. The resin was then treated with 20% piperidine in DMF (500 mL) for 30 minutes, washed with DMF (5×200 mL) and drained completely. 4-iodobenzoic acid (19 g, 75 mmol), HATU (27 g, 71.3 mmol) and DIEA (26 mL, 150 mmol) dissolved in DMF (100 mL) were then added to the resin and the mixture was mixed under an atmosphere of nitrogen for 1 hour. The mixture was drained, washed with DMF (3×200 mL), MeOH (3×200 mL) and drained, dried in vacuo.

A solution of (E)-pent-2-en-4-yn-1-ol (8.21 g, 100 mmol) and DIEA (44 mL, 250 mmol) in DMF (250 mL) was purged with a stream of nitrogen for two minutes and then added to the resin. After mixing for 5 minutes, $PdCl_2(PPh_3)_2$ (3.51 g, 5.0 mmol) and CuI (2.38 g, 12.5 mmol) were added and the mixture was shaken under an atmosphere of nitrogen for 48 hours. The resin was drained, washed with DMF (4×150 mL), dichloromethane (4×100 mL) and drained again. The resin was then treated with Dess-Martin periodinane (21.2 g, 50 mmol) and $Na_2CO_3$ (10.6 g, 100 mmol) in dichloromethane for 1 hour, and drained completely. The resin was washed with DMF (3×150 mL) and MeOH (3×150 mL) and dried in vacuo.

Example 9: General Procedure for the Reductive Amination of the Crotonaldehyde-Containing Resins with Primary and Secondary Amines A solution of the amine (2.4 mmol) and trimethyl orthoformate (287 μL, 2.6 mmol) in THF (20 mL) was added to a vial containing the resin (186 mg). After purging the vessel with nitrogen for 5 minutes, it was treated with acetic acid (282 μL, 4.92 mmol) followed by a solution of $NaBH_3CN$ (113 mg, 1.8 mmol) in MeOH (1.0 mL) and mixing under an atmosphere of nitrogen was continued for 48 hours. The resin was drained, washed with DMF (2×10 mL) and MeOH (3×10 mL) and drained again and dried under reduced pressure. Cleavage from the resin was achieved by treatment with 30% v/v TFA/DCM (20 mL) and for 30 minutes. The solution was collected and concentrated to dryness to give a crude residue which was purified by preparative HPLC using a Gilson GX-281 semi-preparative HPLC system equipped with a Luna 200×25 mm (C18, 10μ, 100 A) or a Gemini 150×30 mm (C18, 5 um, 110 A) column applying a gradient consisting of 0.1% TFA/water and acetonitrile. The product containing fractions were collected, concentrated by freeze-drying and the residual trifluoroacetic acid was removed by another reverse-phase chromatography using a gradient consisting of aqueous ammonium hydrogencarbonate (7.5 mmol/L) and acetonitrile.

Using this procedure, the following compound can be synthesized: Compound No.: 217.

Example 10: Synthesis of N-[(1S)-2-(hydroxyamino)-1-(hydroxymethyl)-2-oxo-ethyl]-4-[2-(4-nitrophenyl)ethynyl] benzamide [375] and 4-[2-(4-aminophenyl)ethynyl]-N-[(1S)-2-(hydroxyamino)-1-(hydroxymethyl)-2-oxo-ethyl] benzamide [376]

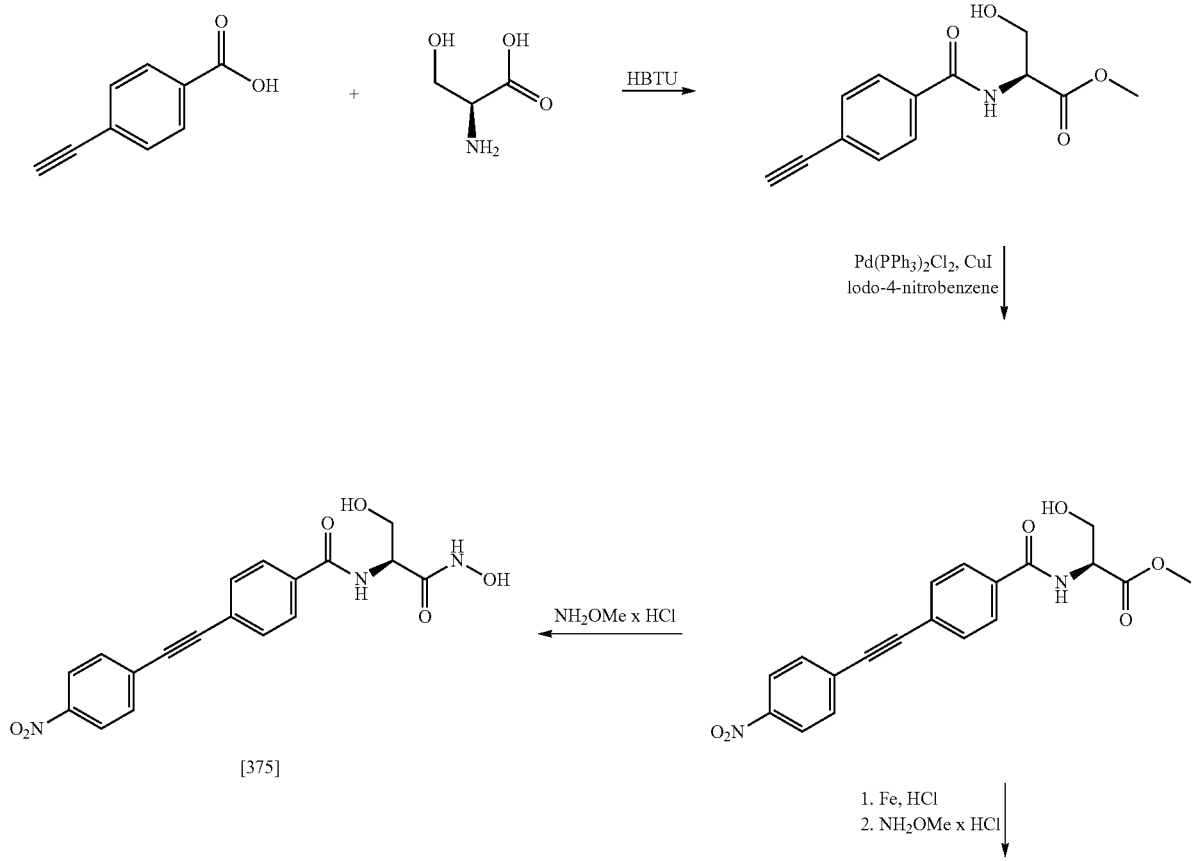

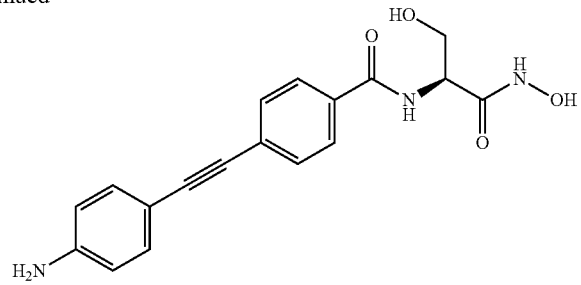

[376]

Step 1: Synthesis of methyl (2S)-2-[(4-ethynylbenzoyl)amino]-3-hydroxy-propanoate 4-Ethynylbenzoic acid (300 mg, 2.05 mmol) and HBTU (779 mg, 2.0 mmol) were dissolved in DMF (1 mL) and stirred at ambient temperature. After 5 minutes, (S)-methyl 2-amino-3-hydroxypropanoate hydrochloride (351 mg, 2.26 mmol), tetrahydrofuran (4 mL) and triethylamine (0.658 ml, 4.7 mmol) were added and stirring was continued for 1 hour at ambient temperature. The reaction mixture was diluted with ethyl acetate and washed twice with NaHCO$_3$ solution. The organic layer was washed with brine, dried over MgSO$_4$ and concentrated under reduced pressure. The residue was purified by column chromatography (silica, pentane/ethyl acetate) to provide the title compound.

Step 2: Synthesis of methyl (2S)-3-hydroxy-2-[[4-[2-(4-nitrophenyl)ethynyl]benzoyl]amino]propanoate Iodo-4-nitrobenzene (528 mg, 2.12 mmol) and triethylamine (0.34 ml, 2.44 mmol) were added to a solution of Pd(PPh$_3$)$_2$Cl$_2$ (29.8 mg, 0.042 mmol) and CuI (12.1 mg, 0.064 mmol) in tetrahydrofuran (5 mL) under an atmosphere of nitrogen. To this mixture was then added dropwise a solution of (S)-methyl 2-(4-ethynylbenzamido)-3-hydroxypropanoate (262 mg, 1.06 mmol) in tetrahydrofuran (2 mL). The reaction mixture was taken up on silica gel and purified by column chromatography on silica gel (pentane/ethyl acetate) to provide the title compound.

Step 3: Synthesis of N-[(1S)-2-(hydroxyamino)-1-(hydroxymethyl)-2-oxo-ethyl]-4-[2-(4-nitrophenyl)ethynyl]benzamide [375]

Sodium (14 mg, 0.61 mmol) was added to dry methanol (1 mL) and the mixture was stirred for 20 minutes. Hydroxylamine hydrochloride (40.6 mg, 0.58 mmol) was then added and stirring at ambient temperature was continued for 45 minutes. Then, a solution of methyl (2S)-3-hydroxy-2-[[4-[2-(4-nitrophenyl)ethynyl]benzoyl]amino]propanoate (50 mg, 0.14 mmol) in methanol/tetrahydrofuran 1:1 (1 mL) was added and the reaction mixture stirred overnight. All volatiles were then removed under reduced pressure and the resulting residue was purified by reverse phase preparative HPLC using an Atlantis® C18 column applying a gradient consisting of 0.1% aqueous formic acid and acetonitrile to provide the title compound. $^1$H NMR (300 MHz, DMSO-d$_6$): δ 10.71 (b, 1H), 8.86 (b, 1H), 8.45 (d, J=7.96 Hz, 1H), 8.30 (m, 2H), 7.99 (d, J=8.4 Hz, 2H), 7.87 (m, 2H), 7.74 (d, J=8.4 Hz, 2H), 4.98 (t, J=5.8 Hz, 1H), 4.43 (m, 1H), 3.69 (m, 2H).

Step 4: Synthesis of methyl (2S)-2-[[4-[2-(4-aminophenyl)ethynyl]benzoyl]amino]-3-hydroxy-propanoate Methyl (2S)-3-hydroxy-2-[[4-[2-(4-nitrophenyl)ethynyl]benzoyl]amino]propanoate (100 mg, 0.27 mmol), 2 M hydrochloric acid (0.54 ml, 1.1 mmol) and iron (106 mg, 1.9 mmol) were stirred in ethanol (2.5 mL) at 80° C. for 3.5 hours. The reaction mixture was then concentrated under reduced pressure and the resulting residue taken up in water and extracted with dichloromethane (2×). The organic layers were combined, washed with brine, dried over MgSO$_4$ and concentrated under reduced pressure to provide the title compound which was used in the next step without further purification.

Step 5: Synthesis of 4-[2-(4-aminophenyl)ethynyl]-N-[(1S)-2-(hydroxyamino)-1-(hydroxymethyl)-2-oxo-ethyl]benzamide [376]

Sodium (11.6 mg, 0.5 mmol) was added to dry methanol (1 mL) and stirred for 20 minutes. Hydroxylamine hydrochloride (33.6 mg, 0.48 mmol) was then added and stirring at ambient temperature was continued for 45 minutes. Then, a solution of methyl (2S)-2-[[4-[2-(4-aminophenyl)ethynyl]benzoyl]amino]-3-hydroxy-propanoate (38 mg, 0.11 mmol) in methanol/tetrahydrofuran 1:1 (1 mL) was added and the reaction mixture stirred for 2 hours. Then, another methanolic solution of hydroxylamine prepared from sodium (11.6 mg, 0.5 mmol), hydroxylamine hydrochloride (33.6 mg, 0.48 mmol) and methanol (1 mL) was added to the reaction mixture and heated at 40° C. overnight. The reaction mixture was allowed to attain room temperature and all volatiles were then removed under reduced pressure and the resulting residue was purified by reverse phase preparative HPLC using an Atlantis® C18 column applying a gradient consisting of 0.1% $^1$H NMR (300 MHz, DMSO-d$_6$) δ 10.69 (s, 1H), 8.85 (s, 1H), 8.34 (d, J=8.0 Hz, 1H), 7.90 (d, J=8.5 Hz, 2H), 7.54 (d, J=8.4 Hz, 2H), 7.23 (d, J=8.5 Hz, 2H), 6.57 (d, J=8.6 Hz, 2H), 5.64 (s, 2H), 4.98 (t, J=5.6 Hz, 1H), 4.42 (q, J=6.2 Hz, 1H), 3.68 (s, 2H).

Example 11: Synthesis of N-[(1S,2R)-2-hydroxy-1-(hydroxycarbamoyl)propyl]-4-[2-(4-nitrophenyl)ethynyl]benzamide [377]

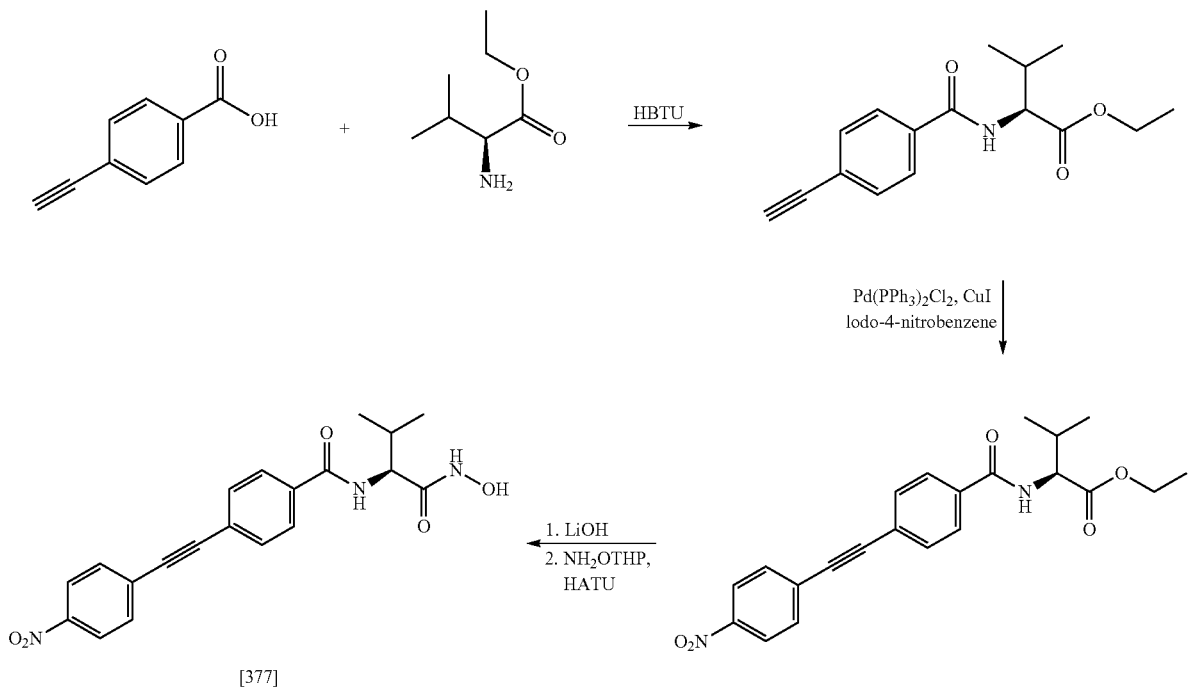

[377]

Step 1: Synthesis of (2S)-ethyl-2-[(4-ethynylbenzoyl)amino]-3-methyl-butanoate 4-Ethynylbenzoic acid (600 mg, 4.11 mmol) and HBTU (1557 mg, 4.11 mmol) were dissolved in DMF (3 mL) and stirred at ambient temperature for 5 minutes. (S)-ethyl 2-amino-3-methylbutanoate hydrochloride (820 mg, 4.52 mmol), tetrahydrofuran (7 mL) and triethylamine (1.316 ml, 9.44 mmol) were then added and the resulting reaction mixture was stirred at ambient temperature for 1 hour. The mixture was then diluted with ethyl acetate and extracted twice with NaHCO$_3$ solution. The organic layer was washed with brine and dried over MgSO4 and concentrated. The resulting residue was purified by column chromatography on silica gel (pentane/ethyl acetate) to provide the title compound.

Step 2: Synthesis of ethyl (2S)-3-methyl-2-[[4-[2-(4-nitrophenyl)ethynyl]benzoyl]amino]butanoate A solution of triethylamine (0.235 ml, 1.683 mmol) in tetrahydrofuran (5 mL) was added to Pd(PPh$_3$)$_2$Cl$_2$ (20.54 mg, 0.029 mmol), CuI (8.36 mg, 0.044 mmol), (2S)-ethyl-2-[(4-ethynylbenzoyl)amino]-3-methyl-butanoate (200 mg, 0.732 mmol) and iodo-4-nitrobenzene (364 mg, 1.463 mmol) under argon and the resulting reaction mixture was stirred for 30 minutes. The reaction mixture was concentrated and the residue was purified by column chromatography on silica gel (pentane/ethyl acetate) to provide the title compound.

Step 3: Synthesis of (2S)-3-methyl-2-[[4-[2-(4-nitrophenyl)ethynyl]benzoyl]amino]butanoic acid To a solution of ethyl (2S)-3-methyl-2-[[4-[2-(4-nitrophenyl)ethynyl]benzoyl]amino]butanoate (133 mg, 0.337 mmol) in tetrahydrofuran (4 mL) was added LiOH (48.5 mg, 2.023 mmol) and the mixture was stirred at ambient temperature for 1 hour. Water (1 drop) was added and the mixture was allowed to stir overnight. The reaction mixture was acidified and extracted with ethyl acetate. The organic layer was washed with brine, dried over MgSO$_4$ and concentrated under reduced pressure to provide the title compound with was used in the next step without further purification.

Step 4: Synthesis of N-[(1S)-1-(hydroxycarbamoyl)-2-methyl-propyl]-4-[2-(4-nitrophenyl)ethynyl]benzamide [377]

(2S)-3-methyl-2-[[4-[2-(4-nitrophenyl)ethynyl]benzoyl]amino]butanoic acid (33 mg, 0.09 mmol) and HATU (37.7 mg, 0.1 mmol) were stirred for 3 minutes in a 1:1 mixture of tetrahydrofuran and DMF at ambient temperature. O-(tetrahydro-2H-pyran-2-yl)hydroxylamine (11.6 mg, 0.1 mmol) and triethylamine (0.025 ml, 0.18 mmol) were added and the mixture was left stirring for another hour. All volatiles were then removed under reduced pressure and the resulting residue was purified by reverse phase preparative HPLC using an Atlantis® C18 column applying a gradient consisting of 0.1% aqueous formic acid and acetonitrile to provide the title compound. $^1$H NMR (600 MHz, DMSO-d$_6$) δ 11.25 (s, 1H), 8.51 (d, J=8.6 Hz, 1H), 8.23 (d, J=8.9 Hz, 2H), 7.91 (d, J=8.9 Hz, 2H), 7.80 (d, J=8.9 Hz, 2H), 7.66 (d, J=8.5 Hz, 2H), 4.08 (td, J=8.0, 17.3 Hz, 1H), 2.03 (m, J=5.9 Hz, 1H), 0.86 (m, J=3.5 Hz, 3H).

Example 12: Synthesis of methyl 2-[[4-[2-(4-formylphenyl)ethynyl]benzoyl]amino]-3-methyl-3-nitrobutanoate

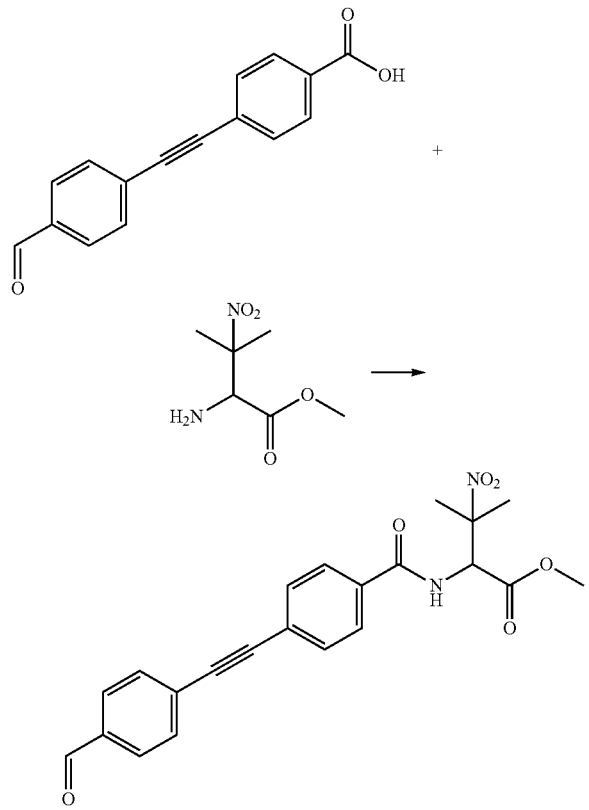

4-((4-formylphenyl)ethynyl)benzoic acid (1316 mg, 5.26 mmol) was mixed with tetrahydrofuran (20 mL) and 2 drops of DMF. Oxalyl chloride (0.506 mL, 5.8 mmol) was then added dropwise and the reaction mixture stirred at room temperature for 4 hours. More tetrahydrofuran (100 mL) was added to the slurry and after 1 hour, methyl 2-amino-3-methyl-3-nitrobutanoate (927 mg, 5.26 mmol) was added to the yellow solution. The reaction mixture was allowed to stir at ambient temperature overnight, was then diluted with ethyl acetate and washed with saturated aqueous sodium hydrogen carbonate. The organic phase was separated, dried over MgSO$_4$, filtered and evaporated under reduced pressure to provide the title compound which was used in the next steps without further purification. MS: 409.1 (M+1).

Example 13: General Procedure for the Synthesis of Compounds in Solution Phase Containing a Nitro-Valine as the Amino Acid To a mixture of methyl 2-[[4-[2-(4-formylphenyl)ethynyl]benzoyl]amino]-3-methyl-3-nitro-butanoate (65 mg, 0.16 mmol) in tetrahydrofuran (1 mL) was added the respective amine (0.16 mmol) and the solution was stirred for 30 min at room temperature. Then, sodium triacetoxyborohydride (135 mg, 0.64 mmol) was added and the reaction mixture stirred at room temperature until all of the methyl 2-[[4-[2-(4-formylphenyl)ethynyl]benzoyl]amino]-3-methyl-3-nitro-butanoate was consumed. Dichloromethane was then added and the mixture washed with 0.1 N HCl. The organic phase was separated, dried over with MgSO$_4$, filtered and evaporated to dryness under reduced pressure. The resulting residue was dissolved in a 1:1 mixture of methanol and tetrahydrofuran (1 mL) and hydroxylamine (50% in water, 0.3 mL, 4.9 mmol) and KCN (1.8 mg, 0.028 mmol) were added. The resulting reaction mixture was stirred until all the starting material was consumed or until the reaction did not progress any further. The mixture was then purified by preparative reverse-phase HPLC using an XBridge column and a gradient consisting of acetonitrile/water+0.1% formic acid or for the more basic compounds a gradient consisting of acetonitrile/water+0.1% ammonia to provide the title compounds.

Using this procedure, the following compounds can be synthesized: Compound No.: 218, 276-288.

Specific Compounds

Table A provides for each of the exemplified compounds the structure according to Formula 1 below.

Compounds of Formula A:

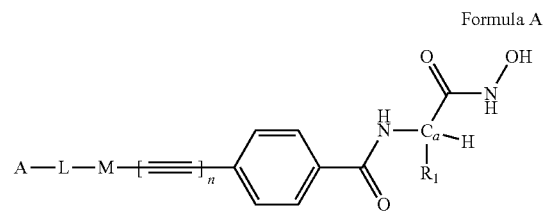

Formula A

The residue A in Table A is described either in form of a molecular formula or in form of a chemical name, in this latter case A is an amine which is inked with its nitrogen atom to residue L.

In the column C$_a$ the stereochemistry of the atom C$_a$ is denoted. If there is no entry in column C$_a$ then both stereoisomers regarding C$_a$ are present.

The values for M in Table A have the following meaning:

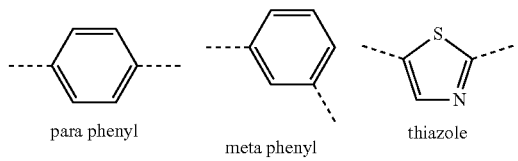

para phenyl          meta phenyl          thiazole

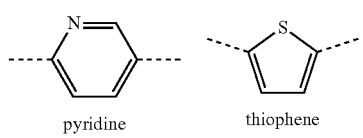

pyridine          thiophene

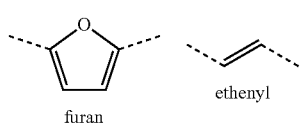

furan          ethenyl

The orientation of the residues with regard to Formula 1 is as drawn.

TABLE A

| No | A | L | M | n | R₁ | $C_a$ |
|---|---|---|---|---|---|---|
| 1 | cyclopropylamine | —CH₂— | meta phenyl | 1 | —CH₂OH | (S) |
| 2 | (CH₃)₂CHNH— | —CH₂— | meta phenyl | 1 | —CH₂OH | (S) |
| 3 | CH₂CHCH₂NH— | —CH₂— | meta phenyl | 1 | —CH₂OH | (S) |
| 4 | (CH₃)₃CCH₂NH— | —CH₂— | meta phenyl | 1 | —CH₂OH | (S) |
| 5 | CH₃O(CH₂)₂NH— | —CH₂— | meta phenyl | 1 | —CH₂OH | (S) |
| 6 | (CH₃)₂N(CH₂)₂NH— | —CH₂— | meta phenyl | 1 | —CH₂OH | (S) |
| 7 | CO₂HCH₂NH— | —CH₂— | meta phenyl | 1 | —CH₂OH | (S) |
| 8 | (C₂H₅)₂N— | —CH₂— | meta phenyl | 1 | —CH₂OH | (S) |
| 9 | morpholine | —CH₂— | meta phenyl | 1 | —CH₂OH | (S) |
| 10 | 4-tert-butyl-piperidine | —CH₂— | meta phenyl | 1 | —CH₂OH | (S) |
| 11 | 4-phenyl-piperidine | —CH₂— | meta phenyl | 1 | —CH₂OH | (S) |
| 12 | 4-phenyl-piperazine | —CH₂— | meta phenyl | 1 | —CH₂OH | (S) |
| 13 | 1-(pyridin-2-yl)-piperazine | —CH₂— | meta phenyl | 1 | —CH₂OH | (S) |
| 14 | 1,2,3,4-tetrahydro-isoquinoline | —CH₂— | meta phenyl | 1 | —CH₂OH | (S) |
| 15 | heliamine | —CH₂— | meta phenyl | 1 | —CH₂OH | (S) |
| 16 | benzylamine | —CH₂— | meta phenyl | 1 | —CH₂OH | (S) |
| 17 | N-methylbenzylamine | —CH₂— | meta phenyl | 1 | —CH₂OH | (S) |
| 18 | 4-chlorobenzylamine | —CH₂— | meta phenyl | 1 | —CH₂OH | (S) |
| 19 | 4-methoxybenzylamine | —CH₂— | meta phenyl | 1 | —CH₂OH | (S) |
| 20 | 4-dimethylaminobenzylamine | —CH₂— | meta phenyl | 1 | —CH₂OH | (S) |
| 21 | 4-trifluoromethylbenzylamine | —CH₂— | meta phenyl | 1 | —CH₂OH | (S) |
| 22 | 4-pyridylmethanamine | —CH₂— | meta phenyl | 1 | —CH₂OH | (S) |
| 23 | 3,4-dimethylbenzylamine | —CH₂— | meta phenyl | 1 | —CH₂OH | (S) |
| 24 | cyclopropylamine | —CH₂— | meta phenyl | 1 | —CH(CH₃)₂ | (S) |
| 25 | (CH₃)₂CHNH— | —CH₂— | meta phenyl | 1 | —CH(CH₃)₂ | (S) |
| 26 | CH₂CHCH₂NH— | —CH₂— | meta phenyl | 1 | —CH(CH₃)₂ | (S) |
| 27 | (CH₃)₃CCH₂NH— | —CH₂— | meta phenyl | 1 | —CH(CH₃)₂ | (S) |
| 28 | CH₃O(CH₂)₂NH— | —CH₂— | meta phenyl | 1 | —CH(CH₃)₂ | (S) |
| 29 | (CH₃)₂N(CH₂)₂NH— | —CH₂— | meta phenyl | 1 | —CH(CH₃)₂ | (S) |
| 30 | CO₂HCH₂NH— | —CH₂— | meta phenyl | 1 | —CH(CH₃)₂ | (S) |
| 31 | (C₂H₅)₂N— | —CH₂— | meta phenyl | 1 | —CH(CH₃)₂ | (S) |
| 32 | morpholine | —CH₂— | meta phenyl | 1 | —CH(CH₃)₂ | (S) |
| 33 | 1,1-dioxo-thiomorpholine | —CH₂— | meta phenyl | 1 | —CH(CH₃)₂ | (S) |
| 34 | 4-tert-butyl-piperidine | —CH₂— | meta phenyl | 1 | —CH(CH₃)₂ | (S) |
| 35 | 4-phenyl-piperidine | —CH₂— | meta phenyl | 1 | —CH(CH₃)₂ | (S) |
| 36 | 4-phenyl-piperazine | —CH₂— | meta phenyl | 1 | —CH(CH₃)₂ | (S) |
| 37 | 1-(pyridin-2-yl)-piperazine | —CH₂— | meta phenyl | 1 | —CH(CH₃)₂ | (S) |
| 38 | 1,2,3,4-tetrahydro-isoquinoline | —CH₂— | meta phenyl | 1 | —CH(CH₃)₂ | (S) |
| 39 | heliamine | —CH₂— | meta phenyl | 1 | —CH(CH₃)₂ | (S) |
| 40 | benzylamine | —CH₂— | meta phenyl | 1 | —CH(CH₃)₂ | (S) |
| 41 | N-methylbenzylamine | —CH₂— | meta phenyl | 1 | —CH(CH₃)₂ | (S) |
| 42 | 4-chlorobenzylamine | —CH₂— | meta phenyl | 1 | —CH(CH₃)₂ | (S) |
| 43 | 4-methoxybenzylamine | —CH₂— | meta phenyl | 1 | —CH(CH₃)₂ | (S) |
| 44 | 4-dimethylaminobenzylamine | —CH₂— | meta phenyl | 1 | —CH(CH₃)₂ | (S) |
| 45 | 4-trifluoromethylbenzylamine | —CH₂— | meta phenyl | 1 | —CH(CH₃)₂ | (S) |
| 46 | 4-pyridylmethanamine | —CH₂— | meta phenyl | 1 | —CH(CH₃)₂ | (S) |
| 47 | 3,4-dimethylbenzylamine | —CH₂— | meta phenyl | 1 | —CH(CH₃)₂ | (S) |
| 48 | (CH₃)₂CHNH— | —CH₂— | meta phenyl | 1 | (S)—CH(CH₃)C₂H₅ | (S) |
| 49 | CH₂CHCH₂NH— | —CH₂— | meta phenyl | 1 | (S)—CH(CH₃)C₂H₅ | (S) |
| 50 | (CH₃)₃CCH₂NH— | —CH₂— | meta phenyl | 1 | (S)—CH(CH₃)C₂H₅ | (S) |
| 51 | CH₃O(CH₂)₂NH— | —CH₂— | meta phenyl | 1 | (S)—CH(CH₃)C₂H₅ | (S) |
| 52 | (CH₃)₂N(CH₂)₂NH— | —CH₂— | meta phenyl | 1 | (S)—CH(CH₃)C₂H₅ | (S) |
| 53 | CO₂HCH₂NH— | —CH₂— | meta phenyl | 1 | (S)—CH(CH₃)C₂H₅ | (S) |
| 54 | (C₂H₅)₂N— | —CH₂— | meta phenyl | 1 | (S)—CH(CH₃)C₂H₅ | (S) |
| 55 | morpholine | —CH₂— | meta phenyl | 1 | (S)—CH(CH₃)C₂H₅ | (S) |
| 56 | 1,1-dioxo-thiomorpholine | —CH₂— | meta phenyl | 1 | (S)—CH(CH₃)C₂H₅ | (S) |
| 57 | 4-tert-butyl-piperidine | —CH₂— | meta phenyl | 1 | (S)—CH(CH₃)C₂H₅ | (S) |
| 58 | 4-phenyl-piperidine | —CH₂— | meta phenyl | 1 | (S)—CH(CH₃)C₂H₅ | (S) |
| 59 | 4-phenyl-piperazine | —CH₂— | meta phenyl | 1 | (S)—CH(CH₃)C₂H₅ | (S) |
| 60 | 1-(pyridin-2-yl)-piperazine | —CH₂— | meta phenyl | 1 | (S)—CH(CH₃)C₂H₅ | (S) |
| 61 | 1,2,3,4-tetrahydro-isoquinoline | —CH₂— | meta phenyl | 1 | (S)—CH(CH₃)C₂H₅ | (S) |
| 62 | heliamine | —CH₂— | meta phenyl | 1 | (S)—CH(CH₃)C₂H₅ | (S) |
| 63 | benzylamine | —CH₂— | meta phenyl | 1 | (S)—CH(CH₃)C₂H₅ | (S) |
| 64 | N-methylbenzylamine | —CH₂— | meta phenyl | 1 | (S)—CH(CH₃)C₂H₅ | (S) |
| 65 | 4-chlorobenzylamine | —CH₂— | meta phenyl | 1 | (S)—CH(CH₃)C₂H₅ | (S) |
| 66 | 4-methoxybenzylamine | —CH₂— | meta phenyl | 1 | (S)—CH(CH₃)C₂H₅ | (S) |
| 67 | 4-dimethylaminobenzylamine | —CH₂— | meta phenyl | 1 | (S)—CH(CH₃)C₂H₅ | (S) |
| 68 | 4-trifluoromethylbenzylamine | —CH₂— | meta phenyl | 1 | (S)—CH(CH₃)C₂H₅ | (S) |
| 69 | 4-pyridylmethanamine | —CH₂— | meta phenyl | 1 | (S)—CH(CH₃)C₂H₅ | (S) |
| 70 | 3,4-dimethylbenzylamine | —CH₂— | meta phenyl | 1 | (S)—CH(CH₃)C₂H₅ | (S) |
| 71 | cyclopropylamine | —CH₂— | para phenyl | 1 | —CH₂OH | (S) |
| 72 | (CH₃)₂CHNH— | —CH₂— | para phenyl | 1 | —CH₂OH | (S) |
| 73 | CH₂CHCH₂NH— | —CH₂— | para phenyl | 1 | —CH₂OH | (S) |
| 74 | CH₃O(CH₂)₂NH— | —CH₂— | para phenyl | 1 | —CH₂OH | (S) |
| 75 | (CH₃)₂N(CH₂)₂NH— | —CH₂— | para phenyl | 1 | —CH₂OH | (S) |

TABLE A-continued

| No | A | L | M | n | R₁ | $C_a$ |
|---|---|---|---|---|---|---|
| 76 | (C₂H₅)₂N— | —CH₂— | para phenyl | 1 | —CH₂OH | (S) |
| 77 | morpholine | —CH₂— | para phenyl | 1 | —CH₂OH | (S) |
| 78 | 1,1-dioxo-thiomorpholine | —CH₂— | para phenyl | 1 | —CH₂OH | (S) |
| 79 | 4-tert-butyl-piperidine | —CH₂— | para phenyl | 1 | —CH₂OH | (S) |
| 80 | 4-phenyl-piperidine | —CH₂— | para phenyl | 1 | —CH₂OH | (S) |
| 81 | 4-phenyl-piperazine | —CH₂— | para phenyl | 1 | —CH₂OH | (S) |
| 82 | 1-(pyridin-2-yl)-piperazine | —CH₂— | para phenyl | 1 | —CH₂OH | (S) |
| 83 | 1,2,3,4-tetrahydro-isoquinoline | —CH₂— | para phenyl | 1 | —CH₂OH | (S) |
| 84 | heliamine | —CH₂— | para phenyl | 1 | —CH₂OH | (S) |
| 85 | benzylamine | —CH₂— | para phenyl | 1 | —CH₂OH | (S) |
| 86 | N-methylbenzylamine | —CH₂— | para phenyl | 1 | —CH₂OH | (S) |
| 87 | 4-chlorobenzylamine | —CH₂— | para phenyl | 1 | —CH₂OH | (S) |
| 88 | 4-methoxybenzylamine | —CH₂— | para phenyl | 1 | —CH₂OH | (S) |
| 89 | 4-trifluoromethylbenzylamine | —CH₂— | para phenyl | 1 | —CH₂OH | (S) |
| 90 | 4-pyridylmethanamine | —CH₂— | para phenyl | 1 | —CH₂OH | (S) |
| 91 | 3,4-dimethylbenzylamine | —CH₂— | para phenyl | 1 | —CH₂OH | (S) |
| 92 | cyclopropylamine | —CH₂— | para phenyl | 1 | —CH(CH₃)₂ | (S) |
| 93 | (CH₃)₂CHNH— | —CH₂— | para phenyl | 1 | —CH(CH₃)₂ | (S) |
| 94 | CH₂CHCH₂NH— | —CH₂— | para phenyl | 1 | —CH(CH₃)₂ | (S) |
| 95 | (CH₃)₃CCH₂NH— | —CH₂— | para phenyl | 1 | —CH(CH₃)₂ | (S) |
| 96 | CH₃O(CH₂)₂NH— | —CH₂— | para phenyl | 1 | —CH(CH₃)₂ | (S) |
| 97 | (C₂H₅)₂N— | —CH₂— | para phenyl | 1 | —CH(CH₃)₂ | (S) |
| 98 | morpholine | —CH₂— | para phenyl | 1 | —CH(CH₃)₂ | (S) |
| 99 | 1,1-dioxo-thiomorpholine | —CH₂— | para phenyl | 1 | —CH(CH₃)₂ | (S) |
| 100 | 4-phenyl-piperidine | —CH₂— | para phenyl | 1 | —CH(CH₃)₂ | (S) |
| 101 | 1-(pyridin-2-yl)-piperazine | —CH₂— | para phenyl | 1 | —CH(CH₃)₂ | (S) |
| 102 | 1,2,3,4-tetrahydro-isoquinoline | —CH₂— | para phenyl | 1 | —CH(CH₃)₂ | (S) |
| 103 | heliamine | —CH₂— | para phenyl | 1 | —CH(CH₃)₂ | (S) |
| 104 | benzylamine | —CH₂— | para phenyl | 1 | —CH(CH₃)₂ | (S) |
| 105 | N-methylbenzylamine | —CH₂— | para phenyl | 1 | —CH(CH₃)₂ | (S) |
| 106 | 4-chlorobenzylamine | —CH₂— | para phenyl | 1 | —CH(CH₃)₂ | (S) |
| 107 | 4-methoxybenzylamine | —CH₂— | para phenyl | 1 | —CH(CH₃)₂ | (S) |
| 108 | 4-dimethylaminobenzylamine | —CH₂— | para phenyl | 1 | —CH(CH₃)₂ | (S) |
| 109 | 4-trifluoromethylbenzylamine | —CH₂— | para phenyl | 1 | —CH(CH₃)₂ | (S) |
| 110 | 4-pyridylmethanamine | —CH₂— | para phenyl | 1 | —CH(CH₃)₂ | (S) |
| 111 | 3,4-dimethylbenzylamine | —CH₂— | para phenyl | 1 | —CH(CH₃)₂ | (S) |
| 112 | cyclopropylamine | —CH₂— | para phenyl | 1 | (S)—CH(CH₃)C₂H₅ | (S) |
| 113 | CH₂CHCH₂NH— | —CH₂— | para phenyl | 1 | (S)—CH(CH₃)C₂H₅ | (S) |
| 114 | (CH₃)₃CCH₂NH— | —CH₂— | para phenyl | 1 | (S)—CH(CH₃)C₂H₅ | (S) |
| 115 | CH₃O(CH₂)₂NH— | —CH₂— | para phenyl | 1 | (S)—CH(CH₃)C₂H₅ | (S) |
| 116 | (CH₃)₂N(CH₂)₂NH— | —CH₂— | para phenyl | 1 | (S)—CH(CH₃)C₂H₅ | (S) |
| 117 | CO₂HCH₂NH— | —CH₂— | para phenyl | 1 | (S)—CH(CH₃)C₂H₅ | (S) |
| 118 | (C₂H₅)₂N— | —CH₂— | para phenyl | 1 | (S)—CH(CH₃)C₂H₅ | (S) |
| 119 | morpholine | —CH₂— | para phenyl | 1 | (S)—CH(CH₃)C₂H₅ | (S) |
| 120 | 4-tert-butyl-piperidine | —CH₂— | para phenyl | 1 | (S)—CH(CH₃)C₂H₅ | (S) |
| 121 | 4-phenyl-piperidine | —CH₂— | para phenyl | 1 | (S)—CH(CH₃)C₂H₅ | (S) |
| 122 | 4-phenyl-piperazine | —CH₂— | para phenyl | 1 | (S)—CH(CH₃)C₂H₅ | (S) |
| 123 | 1-(pyridin-2-yl)-piperazine | —CH₂— | para phenyl | 1 | (S)—CH(CH₃)C₂H₅ | (S) |
| 124 | 1,2,3,4-tetrahydro-isoquinoline | —CH₂— | para phenyl | 1 | (S)—CH(CH₃)C₂H₅ | (S) |
| 125 | heliamine | —CH₂— | para phenyl | 1 | (S)—CH(CH₃)C₂H₅ | (S) |
| 126 | benzylamine | —CH₂— | para phenyl | 1 | (S)—CH(CH₃)C₂H₅ | (S) |
| 127 | N-methylbenzylamine | —CH₂— | para phenyl | 1 | (S)—CH(CH₃)C₂H₅ | (S) |
| 128 | 4-chlorobenzylamine | —CH₂— | para phenyl | 1 | (S)—CH(CH₃)C₂H₅ | (S) |
| 129 | 4-methoxybenzylamine | —CH₂— | para phenyl | 1 | (S)—CH(CH₃)C₂H₅ | (S) |
| 130 | 4-dimethylaminobenzylamine | —CH₂— | para phenyl | 1 | (S)—CH(CH₃)C₂H₅ | (S) |
| 131 | 4-trifluoromethylbenzylamine | —CH₂— | para phenyl | 1 | (S)—CH(CH₃)C₂H₅ | (S) |
| 132 | 4-pyridylmethanamine | —CH₂— | para phenyl | 1 | (S)—CH(CH₃)C₂H₅ | (S) |
| 133 | 3,4-dimethylbenzylamine | —CH₂— | para phenyl | 1 | (S)—CH(CH₃)C₂H₅ | (S) |
| 134 | 4-dimethylaminobenzylamine | —CH₂— | para phenyl | 1 | —CH₂OH | (S) |
| 135 | 4-phenyl-piperazine | —CH₂— | para phenyl | 1 | —CH(CH₃)₂ | (S) |
| 136 | (CH₃)₃CCH₂NH— | —CH₂— | para phenyl | 1 | —CH₂OH | (S) |
| 137 | CO₂HCH₂NH— | —CH₂— | para phenyl | 1 | —CH₂OH | (S) |
| 138 | (CH₃)₂N(CH₂)₂NH— | —CH₂— | para phenyl | 1 | —CH(CH₃)₂ | (S) |
| 139 | CO₂HCH₂NH— | —CH₂— | para phenyl | 1 | —CH(CH₃)₂ | (S) |
| 140 | 4-tert-butyl-piperidine | —CH₂— | para phenyl | 1 | —CH(CH₃)₂ | (S) |
| 141 | (CH₃)₂CHNH— | —CH₂— | para phenyl | 1 | (S)—CH(CH₃)C₂H₅ | (S) |
| 142 | 1,1-dioxo-thiomorpholine | —CH₂— | para phenyl | 1 | (S)—CH(CH₃)C₂H₅ | (S) |
| 143 | 1,1-dioxo-thiomorpholine | —CH₂— | meta phenyl | 1 | —CH₂OH | (S) |
| 144 | cyclopropylamine | —CH₂— | meta phenyl | 1 | (S)—CH(CH₃)C₂H₅ | (S) |
| 145 | pyrrolidine | —CH₂— | para phenyl | 1 | —CH₂OH | (S) |
| 146 | N-methylpiperazine | —CH₂— | para phenyl | 1 | —CH₂OH | (S) |
| 147 | cyclobutylamine | —CH₂— | para phenyl | 1 | —CH₂OH | (S) |
| 148 | cyclopentylamine | —CH₂— | para phenyl | 1 | —CH₂OH | (S) |
| 149 | cyclohexylamine | —CH₂— | para phenyl | 1 | —CH₂OH | (S) |
| 150 | CH₃NH— | —CH₂— | para phenyl | 1 | —CH₂OH | (S) |

TABLE A-continued

| No | A | L | M | n | R₁ | Cₐ |
|---|---|---|---|---|---|---|
| 151 | C₂H₅NH— | —CH₂— | para phenyl | 1 | —CH₂OH | (S) |
| 152 | CH₃(CH₂)₂NH— | —CH₂— | para phenyl | 1 | —CH₂OH | (S) |
| 153 | CH₃O(CH₂)₃NH— | —CH₂— | para phenyl | 1 | —CH₂OH | (S) |
| 154 | CH₃O(CH₂)₂N(CH₃)— | —CH₂— | para phenyl | 1 | —CH₂OH | (S) |
| 155 | 2,6-dimethylmorpholine | —CH₂— | para phenyl | 1 | —CH₂OH | (S) |
| 156 | piperidine | —CH₂— | para phenyl | 1 | —CH₂OH | (S) |
| 157 | 3-pyridylmethanamine | —CH₂— | para phenyl | 1 | —CH₂OH | (S) |
| 158 | 2-pyridylmethanamine | —CH₂— | para phenyl | 1 | —CH₂OH | (S) |
| 159 | furfurylamine | —CH₂— | para phenyl | 1 | —CH₂OH | (S) |
| 160 | 2-thienylmethanamine | —CH₂— | para phenyl | 1 | —CH₂OH | (S) |
| 161 | 4-methylbenzylamine | —CH₂— | para phenyl | 1 | —CH₂OH | (S) |
| 162 | tetrahydrofurfurylamine | —CH₂— | para phenyl | 1 | —CH₂OH | (S) |
| 163 | imidazol-2-ylmethanamine | —CH₂— | para phenyl | 1 | —CH₂OH | (S) |
| 164 | CH₃OCH₂CH(CH₃)NH— | —CH₂— | para phenyl | 1 | —CH₂OH | (S) |
| 165 | 2,6-dimethylmorpholine | —CH₂— | para phenyl | 1 | —CH(CH₃)₂ | (S) |
| 166 | piperidine | —CH₂— | para phenyl | 1 | —CH(CH₃)₂ | (S) |
| 167 | 3-pyridylmethanamine | —CH₂— | para phenyl | 1 | —CH(CH₃)₂ | (S) |
| 168 | (2-chloro-4-pyridyl)methanamine | | | | | |
| 169 | 2-pyridylmethanamine | —CH₂— | para phenyl | 1 | —CH(CH₃)₂ | (S) |
| 170 | furfurylamine | —CH₂— | para phenyl | 1 | —CH(CH₃)₂ | (S) |
| 171 | 2-thienylmethanamine | —CH₂— | para phenyl | 1 | —CH(CH₃)₂ | (S) |
| 172 | 4-methylbenzylamine | —CH₂— | para phenyl | 1 | —CH(CH₃)₂ | (S) |
| 173 | imidazol-2-ylmethanamine | —CH₂— | para phenyl | 1 | —CH(CH₃)₂ | (S) |
| 174 | pyrrolidine | —CH₂— | para phenyl | 1 | (S)—CH(CH₃)C₂H₅ | (S) |
| 175 | N-methylpiperazine | —CH₂— | para phenyl | 1 | (S)—CH(CH₃)C₂H₅ | (S) |
| 176 | C₂H₅NH— | —CH₂— | para phenyl | 1 | (S)—CH(CH₃)C₂H₅ | (S) |
| 177 | CH₃O(CH₂)₃NH— | —CH₂— | para phenyl | 1 | (S)—CH(CH₃)C₂H₅ | (S) |
| 178 | CH₃O(CH₂)₂N(CH₃)— | —CH₂— | para phenyl | 1 | (S)—CH(CH₃)C₂H₅ | (S) |
| 179 | 3-pyridylmethanamine | —CH₂— | para phenyl | 1 | (S)—CH(CH₃)C₂H₅ | (S) |
| 180 | 2-pyridylmethanamine | —CH₂— | para phenyl | 1 | (S)—CH(CH₃)C₂H₅ | (S) |
| 181 | furfurylamine | —CH₂— | para phenyl | 1 | (S)—CH(CH₃)C₂H₅ | (S) |
| 182 | 2-thienylmethanamine | —CH₂— | para phenyl | 1 | (S)—CH(CH₃)C₂H₅ | (S) |
| 183 | tetrahydrofurfurylamine | —CH₂— | para phenyl | 1 | (S)—CH(CH₃)C₂H₅ | (S) |
| 184 | imidazol-2-ylmethanamine | —CH₂— | para phenyl | 1 | (S)—CH(CH₃)C₂H₅ | (S) |
| 185 | CH₃OCH₂CH(CH₃)NH— | —CH₂— | para phenyl | 1 | (S)—CH(CH₃)C₂H₅ | (S) |
| 186 | 1,4-oxazepane | —CH₂— | para phenyl | 1 | (S)—CH(CH₃)C₂H₅ | (S) |
| 187 | piperidine | —CH₂— | para phenyl | 1 | (S)—CH(CH₃)C₂H₅ | (S) |
| 188 | thiazol-2-ylmethanamine | —CH₂— | para phenyl | 1 | (S)—CH(CH₃)C₂H₅ | (S) |
| 189 | 4-methylbenzylamine | —CH₂— | para phenyl | 1 | (S)—CH(CH₃)C₂H₅ | (S) |
| 190 | (2-chloro-4-pyridyl)methanamine | —CH₂— | para phenyl | 1 | (S)—CH(CH₃)C₂H₅ | (S) |
| 191 | 2,6-dimethylmorpholine | —CH₂— | para phenyl | 1 | (S)—CH(CH₃)C₂H₅ | (S) |
| 192 | NCCH₂NH— | —CH₂— | para phenyl | 1 | (S)—CH(CH₃)C₂H₅ | (S) |
| 193 | CH₃(CH₂)₂NH— | —CH₂— | para phenyl | 1 | (S)—CH(CH₃)C₂H₅ | (S) |
| 194 | CH₃NH— | —CH₂— | para phenyl | 1 | (S)—CH(CH₃)C₂H₅ | (S) |
| 195 | cyclohexylamine | —CH₂— | para phenyl | 1 | (S)—CH(CH₃)C₂H₅ | (S) |
| 196 | cyclopentylamine | —CH₂— | para phenyl | 1 | (S)—CH(CH₃)C₂H₅ | (S) |
| 197 | cyclobutylamine | —CH₂— | para phenyl | 1 | (S)—CH(CH₃)C₂H₅ | (S) |
| 198 | CH₃OCH₂CH(CH₃)NH— | —CH₂— | para phenyl | 1 | —CH(CH₃)₂ | (S) |
| 199 | thiazol-2-ylmethanamine | —CH₂— | para phenyl | 1 | —CH(CH₃)₂ | (S) |
| 200 | tetrahydrofurfurylamine | —CH₂— | para phenyl | 1 | —CH(CH₃)₂ | (S) |
| 201 | C₂H₅NH— | —CH₂— | para phenyl | 1 | —CH(CH₃)₂ | (S) |
| 202 | 1,4-oxazepane | —CH₂— | para phenyl | 1 | —CH(CH₃)₂ | (S) |
| 203 | CH₃O(CH₂)₂N(CH₃)— | —CH₂— | para phenyl | 1 | —CH(CH₃)₂ | (S) |
| 204 | NCCH₂NH— | —CH₂— | para phenyl | 1 | —CH(CH₃)₂ | (S) |
| 205 | CH₃O(CH₂)₃NH— | —CH₂— | para phenyl | 1 | —CH(CH₃)₂ | (S) |
| 206 | CH₃(CH₂)₂NH— | —CH₂— | para phenyl | 1 | —CH(CH₃)₂ | (S) |
| 207 | CH₃NH— | —CH₂— | para phenyl | 1 | —CH(CH₃)₂ | (S) |
| 208 | cyclohexylamine | —CH₂— | para phenyl | 1 | —CH(CH₃)₂ | (S) |
| 209 | cyclopentylamine | —CH₂— | para phenyl | 1 | —CH(CH₃)₂ | (S) |
| 210 | cyclobutylamine | —CH₂— | para phenyl | 1 | —CH(CH₃)₂ | (S) |
| 211 | N-methylpiperazine | —CH₂— | para phenyl | 1 | —CH(CH₃)₂ | (S) |
| 212 | pyrrolidine | —CH₂— | para phenyl | 1 | —CH(CH₃)₂ | (S) |
| 213 | thiazol-2-ylmethanamine | —CH₂— | para phenyl | 1 | —CH₂OH | (S) |
| 214 | (2-chloro-4-pyridyl)methanamine | —CH₂— | para phenyl | 1 | —CH₂OH | (S) |
| 215 | 1,4-oxazepane | —CH₂— | para phenyl | 1 | —CH₂OH | (S) |
| 216 | NCCH₂NH— | —CH₂— | para phenyl | 1 | —CH₂OH | (S) |
| 217 | morpholine | —CH₂— | ethenyl | 1 | —CH(CH₃)₂ | (S) |
| 218 | cyclopropylamine | —CH₂— | para phenyl | 1 | —C(CH₃)₂NO₂ | |
| 219 | cyclopropylamine | —CH₂— | para phenyl | 1 | —C(CH₃)₂OH | (S) |
| 220 | CH₂CHCH₂NH— | —CH₂— | para phenyl | 1 | —C(CH₃)₂OH | (S) |
| 221 | CH₃O(CH₂)₂NH— | —CH₂— | para phenyl | 1 | —C(CH₃)₂OH | (S) |
| 222 | morpholine | —CH₂— | para phenyl | 1 | —C(CH₃)₂OH | (S) |
| 223 | benzylamine | —CH₂— | para phenyl | 1 | —C(CH₃)₂OH | (S) |
| 224 | 4-methoxybenzylamine | —CH₂— | para phenyl | 1 | —C(CH₃)₂OH | (S) |
| 225 | pyrrolidine | —CH₂— | para phenyl | 1 | —C(CH₃)₂OH | (S) |

TABLE A-continued

| No | A | L | M | n | R₁ | C_a |
|---|---|---|---|---|---|---|
| 226 | cyclobutylamine | —CH$_2$— | para phenyl | 1 | —C(CH$_3$)$_2$OH | (S) |
| 227 | cyclopentylamine | —CH$_2$— | para phenyl | 1 | —C(CH$_3$)$_2$OH | (S) |
| 228 | 3-pyridylmethanamine | —CH$_2$— | para phenyl | 1 | —C(CH$_3$)$_2$OH | (S) |
| 229 | (2-chloro-4-pyridyl)methanamine | —CH$_2$— | para phenyl | 1 | —C(CH$_3$)$_2$OH | (S) |
| 230 | 2-pyridylmethanamine | —CH$_2$— | para phenyl | 1 | —C(CH$_3$)$_2$OH | (S) |
| 231 | furfurylamine | —CH$_2$— | para phenyl | 1 | —C(CH$_3$)$_2$OH | (S) |
| 232 | 2-thienylmethanamine | —CH$_2$— | para phenyl | 1 | —C(CH$_3$)$_2$OH | (S) |
| 233 | 4-methylbenzylamine | —CH$_2$— | para phenyl | 1 | —C(CH$_3$)$_2$OH | (S) |
| 234 | tetrahydrofurfurylamine | —CH$_2$— | para phenyl | 1 | —C(CH$_3$)$_2$OH | (S) |
| 235 | cyclopropylamine | —CH$_2$— | para phenyl | 1 | —C(CH$_3$)$_2$SCH$_3$ | (R) |
| 236 | CH$_2$CHCH$_2$NH— | —CH$_2$— | para phenyl | 1 | —C(CH$_3$)$_2$SCH$_3$ | (R) |
| 237 | CH$_3$O(CH$_2$)$_2$NH— | —CH$_2$— | para phenyl | 1 | —C(CH$_3$)$_2$SCH$_3$ | (R) |
| 238 | morpholine | —CH$_2$— | para phenyl | 1 | —C(CH$_3$)$_2$SCH$_3$ | (R) |
| 239 | benzylamine | —CH$_2$— | para phenyl | 1 | —C(CH$_3$)$_2$SCH$_3$ | (R) |
| 240 | 4-methoxybenzylamine | —CH$_2$— | para phenyl | 1 | —C(CH$_3$)$_2$SCH$_3$ | (R) |
| 241 | 4-pyridylmethanamine | —CH$_2$— | para phenyl | 1 | —C(CH$_3$)$_2$SCH$_3$ | (R) |
| 242 | pyrrolidine | —CH$_2$— | para phenyl | 1 | —C(CH$_3$)$_2$SCH$_3$ | (R) |
| 243 | cyclobutylamine | —CH$_2$— | para phenyl | 1 | —C(CH$_3$)$_2$SCH$_3$ | (R) |
| 244 | cyclopentylamine | —CH$_2$— | para phenyl | 1 | —C(CH$_3$)$_2$SCH$_3$ | (R) |
| 245 | CH$_3$(CH$_2$)$_2$NH— | —CH$_2$— | para phenyl | 1 | —C(CH$_3$)$_2$SCH$_3$ | (R) |
| 246 | NCCH$_2$NH— | —CH$_2$— | para phenyl | 1 | —C(CH$_3$)$_2$SCH$_3$ | (R) |
| 247 | 3-pyridylmethanamine | —CH$_2$— | para phenyl | 1 | —C(CH$_3$)$_2$SCH$_3$ | (R) |
| 248 | (2-chloro-4-pyridyl)methanamine | —CH$_2$— | para phenyl | 1 | —C(CH$_3$)$_2$SCH$_3$ | (R) |
| 249 | 2-pyridylmethanamine | —CH$_2$— | para phenyl | 1 | —C(CH$_3$)$_2$SCH$_3$ | (R) |
| 250 | furfurylamine | —CH$_2$— | para phenyl | 1 | —C(CH$_3$)$_2$SCH$_3$ | (R) |
| 251 | 2-thienylmethanamine | —CH$_2$— | para phenyl | 1 | —C(CH$_3$)$_2$SCH$_3$ | (R) |
| 252 | 4-methylbenzylamine | —CH$_2$— | para phenyl | 1 | —C(CH$_3$)$_2$SCH$_3$ | (R) |
| 253 | tetrahydrofurfurylamine | —CH$_2$— | para phenyl | 1 | —C(CH$_3$)$_2$SCH$_3$ | (R) |
| 254 | thiazol-2-ylmethanamine | —CH$_2$— | para phenyl | 1 | —C(CH$_3$)$_2$SCH$_3$ | (R) |
| 255 | cyclopropylamine | —CH$_2$— | para phenyl | 1 | —C(CH$_3$)$_2$SO$_2$CH$_3$ | (R) |
| 256 | CH$_2$CHCH$_2$NH— | —CH$_2$— | para phenyl | 1 | —C(CH$_3$)$_2$SO$_2$CH$_3$ | (R) |
| 257 | CH$_3$O(CH$_2$)$_2$NH— | —CH$_2$— | para phenyl | 1 | —C(CH$_3$)$_2$SO$_2$CH$_3$ | (R) |
| 258 | morpholine | —CH$_2$— | para phenyl | 1 | —C(CH$_3$)$_2$SO$_2$CH$_3$ | (R) |
| 259 | benzylamine | —CH$_2$— | para phenyl | 1 | —C(CH$_3$)$_2$SO$_2$CH$_3$ | (R) |
| 260 | 4-methoxybenzylamine | —CH$_2$— | para phenyl | 1 | —C(CH$_3$)$_2$SO$_2$CH$_3$ | (R) |
| 261 | 4-pyridylmethanamine | —CH$_2$— | para phenyl | 1 | —C(CH$_3$)$_2$SO$_2$CH$_3$ | (R) |
| 262 | pyrrolidine | —CH$_2$— | para phenyl | 1 | —C(CH$_3$)$_2$SO$_2$CH$_3$ | (R) |
| 263 | cyclobutylamine | —CH$_2$— | para phenyl | 1 | —C(CH$_3$)$_2$SO$_2$CH$_3$ | (R) |
| 264 | cyclopentylamine | —CH$_2$— | para phenyl | 1 | —C(CH$_3$)$_2$SO$_2$CH$_3$ | (R) |
| 265 | CH$_3$(CH$_2$)$_2$NH— | —CH$_2$— | para phenyl | 1 | —C(CH$_3$)$_2$SO$_2$CH$_3$ | (R) |
| 266 | NCCH$_2$NH— | —CH$_2$— | para phenyl | 1 | —C(CH$_3$)$_2$SO$_2$CH$_3$ | (R) |
| 267 | 3-pyridylmethanamine | —CH$_2$— | para phenyl | 1 | —C(CH$_3$)$_2$SO$_2$CH$_3$ | (R) |
| 268 | (2-chloro-4-pyridyl)methanamine | —CH$_2$— | para phenyl | 1 | —C(CH$_3$)$_2$SO$_2$CH$_3$ | (R) |
| 269 | 2-pyridylmethanamine | —CH$_2$— | para phenyl | 1 | —C(CH$_3$)$_2$SO$_2$CH$_3$ | (R) |
| 270 | furfurylamine | —CH$_2$— | para phenyl | 1 | —C(CH$_3$)$_2$SO$_2$CH$_3$ | (R) |
| 271 | 2-thienylmethanamine | —CH$_2$— | para phenyl | 1 | —C(CH$_3$)$_2$SO$_2$CH$_3$ | (R) |
| 272 | 4-methylbenzylamine | —CH$_2$— | para phenyl | 1 | —C(CH$_3$)$_2$SO$_2$CH$_3$ | (R) |
| 273 | tetrahydrofurfurylamine | —CH$_2$— | para phenyl | 1 | —C(CH$_3$)$_2$SO$_2$CH$_3$ | (R) |
| 274 | thiazol-2-ylmethanamine | —CH$_2$— | para phenyl | 1 | —C(CH$_3$)$_2$SO$_2$CH$_3$ | (R) |
| 275 | 4-pyridylmethanamine | —CH$_2$— | para phenyl | 1 | —C(CH$_3$)$_2$OH | (S) |
| 276 | benzylamine | —CH$_2$— | para phenyl | 1 | —C(CH$_3$)$_2$NO$_2$ | |
| 277 | 4-chlorobenzylamine | —CH$_2$— | para phenyl | 1 | —C(CH$_3$)$_2$NO$_2$ | |
| 278 | 4-pyridylmethanamine | —CH$_2$— | para phenyl | 1 | —C(CH$_3$)$_2$NO$_2$ | |
| 279 | 4-trifluoromethylbenzylamine | —CH$_2$— | para phenyl | 1 | —C(CH$_3$)$_2$NO$_2$ | |
| 280 | CH$_2$CHCH$_2$NH— | —CH$_2$— | para phenyl | 1 | —C(CH$_3$)$_2$NO$_2$ | |
| 281 | (CH$_3$)$_2$CHNH— | —CH$_2$— | para phenyl | 1 | —C(CH$_3$)$_2$NO$_2$ | |
| 282 | 2-pyridylmethanamine | —CH$_2$— | para phenyl | 1 | —C(CH$_3$)$_2$NO$_2$ | |
| 283 | 4-methylbenzylamine | —CH$_2$— | para phenyl | 1 | —C(CH$_3$)$_2$NO$_2$ | |
| 284 | 4-fluorobenzylamine | —CH$_2$— | para phenyl | 1 | —C(CH$_3$)$_2$NO$_2$ | |
| 285 | CH$_3$O(CH$_2$)$_3$NH— | —CH$_2$— | para phenyl | 1 | —C(CH$_3$)$_2$NO$_2$ | |
| 286 | 3-pyridylmethanamine | —CH$_2$— | para phenyl | 1 | —C(CH$_3$)$_2$NO$_2$ | |
| 287 | furfurylamine | —CH$_2$— | para phenyl | 1 | —C(CH$_3$)$_2$NO$_2$ | |
| 288 | CF$_3$CH$_2$NH— | —CH$_2$— | para phenyl | 1 | —C(CH$_3$)$_2$NO$_2$ | |
| 289 | 2-thienylmethanamine | —CH$_2$— | para phenyl | 1 | —C(CH$_3$)$_2$NO$_2$ | |
| 290 | cyclopropylamine | —CH$_2$— | thiophene | 1 | —C(CH$_3$)$_2$OH | (S) |
| 291 | CH$_2$CHCH$_2$NH— | —CH$_2$— | thiophene | 1 | —C(CH$_3$)$_2$OH | (S) |
| 292 | CH$_3$O(CH$_2$)$_2$NH— | —CH$_2$— | thiophene | 1 | —C(CH$_3$)$_2$OH | (S) |
| 293 | morpholine | —CH$_2$— | thiophene | 1 | —C(CH$_3$)$_2$OH | (S) |
| 294 | benzylamine | —CH$_2$— | thiophene | 1 | —C(CH$_3$)$_2$OH | (S) |
| 295 | 4-methoxybenzylamine | —CH$_2$— | thiophene | 1 | —C(CH$_3$)$_2$OH | (S) |
| 296 | 3-pyridylmethanamine | —CH$_2$— | thiophene | 1 | —C(CH$_3$)$_2$OH | (S) |
| 297 | 2-pyridylmethanamine | —CH$_2$— | thiophene | 1 | —C(CH$_3$)$_2$OH | (S) |
| 298 | furfurylamine | —CH$_2$— | thiophene | 1 | —C(CH$_3$)$_2$OH | (S) |
| 299 | (5-methyloxazol-2-yl)methanamine | —CH$_2$— | thiophene | 1 | —C(CH$_3$)$_2$OH | (S) |

TABLE A-continued

| No | A | L | M | n | R$_1$ | C$_a$ |
|---|---|---|---|---|---|---|
| 300 | cyclopropylamine | —CH$_2$— | thiophene | 1 | —C(CH$_3$)$_2$SCH$_3$ | (R) |
| 301 | CH$_2$CHCH$_2$NH— | —CH$_2$— | thiophene | 1 | —C(CH$_3$)$_2$SCH$_3$ | (R) |
| 302 | CH$_3$O(CH$_2$)$_2$NH— | —CH$_2$— | thiophene | 1 | —C(CH$_3$)$_2$SCH$_3$ | (R) |
| 303 | morpholine | —CH$_2$— | thiophene | 1 | —C(CH$_3$)$_2$SCH$_3$ | (R) |
| 304 | benzylamine | —CH$_2$— | thiophene | 1 | —C(CH$_3$)$_2$SCH$_3$ | (R) |
| 305 | 4-methoxybenzylamine | —CH$_2$— | thiophene | 1 | —C(CH$_3$)$_2$SCH$_3$ | (R) |
| 306 | 3-pyridylmethanamine | —CH$_2$— | thiophene | 1 | —C(CH$_3$)$_2$SCH$_3$ | (R) |
| 307 | 2-pyridylmethanamine | —CH$_2$— | thiophene | 1 | —C(CH$_3$)$_2$SCH$_3$ | (R) |
| 308 | furfurylamine | —CH$_2$— | thiophene | 1 | —C(CH$_3$)$_2$SCH$_3$ | (R) |
| 309 | CF$_3$CH$_2$NH— | —CH$_2$— | thiophene | 1 | —C(CH$_3$)$_2$SCH$_3$ | (R) |
| 310 | (5-methyloxazol-2-yl)methanamine | —CH$_2$— | thiophene | 1 | —C(CH$_3$)$_2$SCH$_3$ | (R) |
| 311 | cyclopropylamine | —CH$_2$— | thiophene | 1 | —C(CH$_3$)$_2$SO$_2$CH$_3$ | (R) |
| 312 | CH$_2$CHCH$_2$NH— | —CH$_2$— | thiophene | 1 | —C(CH$_3$)$_2$SO$_2$CH$_3$ | (R) |
| 313 | CH$_3$O(CH$_2$)$_2$NH— | —CH$_2$— | thiophene | 1 | —C(CH$_3$)$_2$SO$_2$CH$_3$ | (R) |
| 314 | morpholine | —CH$_2$— | thiophene | 1 | —C(CH$_3$)$_2$SO$_2$CH$_3$ | (R) |
| 315 | benzylamine | —CH$_2$— | thiophene | 1 | —C(CH$_3$)$_2$SO$_2$CH$_3$ | (R) |
| 316 | 4-methoxybenzylamine | —CH$_2$— | thiophene | 1 | —C(CH$_3$)$_2$SO$_2$CH$_3$ | (R) |
| 317 | 4-pyridylmethanamine | —CH$_2$— | thiophene | 1 | —C(CH$_3$)$_2$SO$_2$CH$_3$ | (R) |
| 318 | NCCH$_2$NH— | —CH$_2$— | thiophene | 1 | —C(CH$_3$)$_2$SO$_2$CH$_3$ | (R) |
| 319 | 3-pyridylmethanamine | —CH$_2$— | thiophene | 1 | —C(CH$_3$)$_2$SO$_2$CH$_3$ | (R) |
| 320 | 2-pyridylmethanamine | —CH$_2$— | thiophene | 1 | —C(CH$_3$)$_2$SO$_2$CH$_3$ | (R) |
| 321 | furfurylamine | —CH$_2$— | thiophene | 1 | —C(CH$_3$)$_2$SO$_2$CH$_3$ | (R) |
| 322 | 2-pyrimidinylmethanamine | —CH$_2$— | thiophene | 1 | —C(CH$_3$)$_2$SO$_2$CH$_3$ | (R) |
| 323 | (5-methyloxazol-2-yl)methanamine | —CH$_2$— | thiophene | 1 | —C(CH$_3$)$_2$SO$_2$CH$_3$ | (R) |
| 324 | cyclopropylamine | —CH$_2$— | pyridine | 1 | —C(CH$_3$)$_2$OH | (S) |
| 325 | CH$_3$O(CH$_2$)$_2$NH— | —CH$_2$— | pyridine | 1 | —C(CH$_3$)$_2$OH | (S) |
| 326 | morpholine | —CH$_2$— | pyridine | 1 | —C(CH$_3$)$_2$OH | (S) |
| 327 | benzylamine | —CH$_2$— | pyridine | 1 | —C(CH$_3$)$_2$OH | (S) |
| 328 | 4-methoxybenzylamine | —CH$_2$— | pyridine | 1 | —C(CH$_3$)$_2$OH | (S) |
| 329 | 4-pyridylmethanamine | —CH$_2$— | pyridine | 1 | —C(CH$_3$)$_2$OH | (S) |
| 330 | 3-pyridylmethanamine | —CH$_2$— | pyridine | 1 | —C(CH$_3$)$_2$OH | (S) |
| 331 | 2-pyridylmethanamine | —CH$_2$— | pyridine | 1 | —C(CH$_3$)$_2$OH | (S) |
| 332 | furfurylamine | —CH$_2$— | pyridine | 1 | —C(CH$_3$)$_2$OH | (S) |
| 333 | CF$_3$CH$_2$NH— | —CH$_2$— | pyridine | 1 | —C(CH$_3$)$_2$OH | (S) |
| 334 | (5-methyloxazol-2-yl)methanamine | —CH$_2$— | pyridine | 1 | —C(CH$_3$)$_2$OH | (S) |
| 335 | cyclopropylamine | —CH$_2$— | pyridine | 1 | —C(CH$_3$)$_2$SCH$_3$ | (R) |
| 336 | CH$_2$CHCH$_2$NH— | —CH$_2$— | pyridine | 1 | —C(CH$_3$)$_2$SCH$_3$ | (R) |
| 337 | CH$_3$O(CH$_2$)$_2$NH— | —CH$_2$— | pyridine | 1 | —C(CH$_3$)$_2$SCH$_3$ | (R) |
| 338 | morpholine | —CH$_2$— | pyridine | 1 | —C(CH$_3$)$_2$SCH$_3$ | (R) |
| 339 | benzylamine | —CH$_2$— | pyridine | 1 | —C(CH$_3$)$_2$SCH$_3$ | (R) |
| 340 | 4-methoxybenzylamine | —CH$_2$— | pyridine | 1 | —C(CH$_3$)$_2$SCH$_3$ | (R) |
| 341 | 4-pyridylmethanamine | —CH$_2$— | pyridine | 1 | —C(CH$_3$)$_2$SCH$_3$ | (R) |
| 342 | NCCH$_2$NH— | —CH$_2$— | pyridine | 1 | —C(CH$_3$)$_2$SCH$_3$ | (R) |
| 343 | 2-pyridylmethanamine | —CH$_2$— | pyridine | 1 | —C(CH$_3$)$_2$SCH$_3$ | (R) |
| 344 | furfurylamine | —CH$_2$— | pyridine | 1 | —C(CH$_3$)$_2$SCH$_3$ | (R) |
| 345 | CF$_3$CH$_2$NH— | —CH$_2$— | pyridine | 1 | —C(CH$_3$)$_2$SCH$_3$ | (R) |
| 346 | 2-pyrimidinylmethanamine | —CH$_2$— | pyridine | 1 | —C(CH$_3$)$_2$SCH$_3$ | (R) |
| 347 | (5-methyloxazol-2-yl)methanamine | —CH$_2$— | pyridine | 1 | —C(CH$_3$)$_2$SCH$_3$ | (R) |
| 348 | cyclopropylamine | —CH$_2$— | pyridine | 1 | —C(CH$_3$)$_2$SO$_2$CH$_3$ | (R) |
| 349 | CH$_3$O(CH$_2$)$_2$NH— | —CH$_2$— | pyridine | 1 | —C(CH$_3$)$_2$SO$_2$CH$_3$ | (R) |
| 350 | morpholine | —CH$_2$— | pyridine | 1 | —C(CH$_3$)$_2$SO$_2$CH$_3$ | (R) |
| 351 | benzylamine | —CH$_2$— | pyridine | 1 | —C(CH$_3$)$_2$SO$_2$CH$_3$ | (R) |
| 352 | 4-methoxybenzylamine | —CH$_2$— | pyridine | 1 | —C(CH$_3$)$_2$SO$_2$CH$_3$ | (R) |
| 353 | 2-pyridylmethanamine | —CH$_2$— | pyridine | 1 | —C(CH$_3$)$_2$SO$_2$CH$_3$ | (R) |
| 354 | furfurylamine | —CH$_2$— | pyridine | 1 | —C(CH$_3$)$_2$SO$_2$CH$_3$ | (R) |
| 355 | CF$_3$CH$_2$NH— | —CH$_2$— | pyridine | 1 | —C(CH$_3$)$_2$SO$_2$CH$_3$ | (R) |
| 356 | 2-pyrimidinylmethanamine | —CH$_2$— | pyridine | 1 | —C(CH$_3$)$_2$SO$_2$CH$_3$ | (R) |
| 357 | (5-methyloxazol-2-yl)methanamine | —CH$_2$— | pyridine | 1 | —C(CH$_3$)$_2$SO$_2$CH$_3$ | (R) |
| 358 | NCCH$_2$NH— | —CH$_2$— | thiophene | 1 | —C(CH$_3$)$_2$OH | (S) |
| 359 | thiazol-2-ylmethanamine | —CH$_2$— | thiophene | 1 | —C(CH$_3$)$_2$OH | (S) |
| 360 | 2-pyrimidinylmethanamine | —CH$_2$— | thiophene | 1 | —C(CH$_3$)$_2$OH | (S) |
| 361 | CH$_2$CHCH$_2$NH— | —CH$_2$— | pyridine | 1 | —C(CH$_3$)$_2$OH | (S) |
| 362 | thiazol-2-ylmethanamine | —CH$_2$— | pyridine | 1 | —C(CH$_3$)$_2$OH | (S) |
| 363 | 2-pyrimidinylmethanamine | —CH$_2$— | pyridine | 1 | —C(CH$_3$)$_2$OH | (S) |
| 364 | 4-pyridylmethanamine | —CH$_2$— | thiophene | 1 | —C(CH$_3$)$_2$SCH$_3$ | (R) |
| 365 | thiazol-2-ylmethanamine | —CH$_2$— | thiophene | 1 | —C(CH$_3$)$_2$SCH$_3$ | (R) |
| 366 | 2-pyrimidinylmethanamine | —CH$_2$— | thiophene | 1 | —C(CH$_3$)$_2$SCH$_3$ | (R) |
| 367 | 3-pyridylmethanamine | —CH$_2$— | pyridine | 1 | —C(CH$_3$)$_2$SCH$_3$ | (R) |
| 368 | thiazol-2-ylmethanamine | —CH$_2$— | pyridine | 1 | —C(CH$_3$)$_2$SCH$_3$ | (R) |
| 369 | thiazol-2-ylmethanamine | —CH$_2$— | thiophene | 1 | —C(CH$_3$)$_2$SO$_2$CH$_3$ | (R) |
| 370 | CH$_2$CHCH$_2$NH— | —CH$_2$— | pyridine | 1 | —C(CH$_3$)$_2$SO$_2$CH$_3$ | (R) |
| 371 | 4-pyridylmethanamine | —CH$_2$— | pyridine | 1 | —C(CH$_3$)$_2$SO$_2$CH$_3$ | (R) |
| 372 | NCCH$_2$NH— | —CH$_2$— | pyridine | 1 | —C(CH$_3$)$_2$SO$_2$CH$_3$ | (R) |

TABLE A-continued

| No | A | L | M | n | $R_1$ | $C_a$ |
|---|---|---|---|---|---|---|
| 373 | 3-pyridylmethanamine | —CH$_2$— | pyridine | 1 | —C(CH$_3$)$_2$SO$_2$CH$_3$ | (R) |
| 374 | thiazol-2-ylmethanamine | —CH$_2$— | pyridine | 1 | —C(CH$_3$)$_2$SO$_2$CH$_3$ | (R) |
| 375 | NO$_2$ | — | para phenyl | 1 | —CH$_2$OH | (S) |
| 376 | NH$_2$ | — | para phenyl | 1 | —CH$_2$OH | (S) |
| 377 | NO$_2$ | — | para phenyl | 1 | —CH(CH$_3$)$_2$ | (S) |
| 378 | cyclopropylamine | —CH$_2$— | para phenyl | 1 | C(N=OCH$_3$)CH$_3$ | (S) |
| 379 | CH2CHCH2NH— | —CH$_2$— | para phenyl | 1 | C(N=OCH$_3$)CH$_3$ | (S) |
| 380 | CH3O(CH2)2NH— | —CH$_2$— | para phenyl | 1 | C(N=OCH$_3$)CH$_3$ | (S) |
| 381 | morpholine | —CH$_2$— | para phenyl | 1 | C(N=OCH$_3$)CH$_3$ | (S) |
| 382 | benzylamine | —CH$_2$— | para phenyl | 1 | C(N=OCH$_3$)CH$_3$ | (S) |
| 383 | 4-methoxybenzylamine | —CH$_2$— | para phenyl | 1 | C(N=OCH$_3$)CH$_3$ | (S) |
| 384 | pyrrolidine | —CH$_2$— | para phenyl | 1 | C(N=OCH$_3$)CH$_3$ | (S) |
| 385 | cyclobutylamine | —CH$_2$— | para phenyl | 1 | C(N=OCH$_3$)CH$_3$ | (S) |
| 386 | cyclopentylamine | —CH$_2$— | para phenyl | 1 | C(N=OCH$_3$)CH$_3$ | (S) |
| 387 | CH3(CH2)2NH— | —CH$_2$— | para phenyl | 1 | C(N=OCH$_3$)CH$_3$ | (S) |
| 388 | 3-pyridylmethanamine | —CH$_2$— | para phenyl | 1 | C(N=OCH$_3$)CH$_3$ | (S) |
| 389 | (2-chloro-4-pyridyl)methanamine | —CH$_2$— | para phenyl | 1 | C(N=OCH$_3$)CH$_3$ | (S) |
| 390 | 2-pyridylmethanamine | —CH$_2$— | para phenyl | 1 | C(N=OCH$_3$)CH$_3$ | (S) |
| 391 | furfurylamine | —CH$_2$— | para phenyl | 1 | C(N=OCH$_3$)CH$_3$ | (S) |
| 392 | 2-thienylmethanamine | —CH$_2$— | para phenyl | 1 | C(N=OCH$_3$)CH$_3$ | (S) |
| 393 | 4-methylbenzylamine | —CH$_2$— | para phenyl | 1 | C(N=OCH$_3$)CH$_3$ | (S) |
| 394 | tetrahydrofurfurylamine | —CH$_2$— | para phenyl | 1 | C(N=OCH$_3$)CH$_3$ | (S) |
| 395 | thiazol-2-ylmethanamine | —CH$_2$— | para phenyl | 1 | C(N=OCH$_3$)CH$_3$ | (S) |
| 396 | cyclopropylamine | —CH$_2$— | para phenyl | 1 | —COCH$_3$ | (S) |
| 397 | CH2CHCH2NH— | —CH$_2$— | para phenyl | 1 | —COCH$_3$ | (S) |
| 398 | CH3O(CH2)2NH— | —CH$_2$— | para phenyl | 1 | —COCH$_3$ | (S) |
| 399 | morpholine | —CH$_2$— | para phenyl | 1 | —COCH$_3$ | (S) |
| 400 | benzylamine | —CH$_2$— | para phenyl | 1 | —COCH$_3$ | (S) |
| 401 | 4-methoxybenzylamine | —CH$_2$— | para phenyl | 1 | —COCH$_3$ | (S) |
| 402 | 4-pyridylmethanamine | —CH$_2$— | para phenyl | 1 | —COCH$_3$ | (S) |
| 403 | pyrrolidine | —CH$_2$— | para phenyl | 1 | —COCH$_3$ | (S) |
| 404 | cyclobutylamine | —CH$_2$— | para phenyl | 1 | —COCH$_3$ | (S) |
| 405 | cyclopentylamine | —CH$_2$— | para phenyl | 1 | —COCH$_3$ | (S) |
| 406 | CH$_3$(CH$_2$)$_2$NH— | —CH$_2$— | para phenyl | 1 | —COCH$_3$ | (S) |
| 407 | 3-pyridylmethanamine | —CH$_2$— | para phenyl | 1 | —COCH$_3$ | (S) |
| 408 | (2-chloro-4-pyridyl)methanamine | —CH$_2$— | para phenyl | 1 | —COCH$_3$ | (S) |
| 409 | 2-pyridylmethanamine | —CH$_2$— | para phenyl | 1 | —COCH$_3$ | (S) |
| 410 | furfurylamine | —CH$_2$— | para phenyl | 1 | —COCH$_3$ | (S) |
| 411 | 2-thienylmethanamine | —CH$_2$— | para phenyl | 1 | —COCH$_3$ | (S) |
| 412 | 4-methylbenzylamine | —CH$_2$— | para phenyl | 1 | —COCH$_3$ | (S) |
| 413 | tetrahydrofurfurylamine | —CH$_2$— | para phenyl | 1 | —COCH$_3$ | (S) |
| 414 | thiazol-2-ylmethanamine | —CH$_2$— | para phenyl | 1 | —COCH$_3$ | (S) |
| 415 | 4-pyridylmethanamine | —CH$_2$— | para phenyl | 1 | C(N=OCH$_3$)CH$_3$ | (S) |

Example 8: Analytics—HPLC Methods

Method 1
Chromatographic System:
Column: Chromolith FastGradient RP-18e from Merck, 2*50 mm
Oven: 35° C.
Eluents: Solvent A: water/HCO$_2$H (0.1%); Solvent B: acetonitrile/HCO$_2$H (0.1%)
Flow: 1.2 ml/min
Gradient:

| Time [min] | Solvent A [%] | Solvent B [%] |
|---|---|---|
| 0.0 | 90 | 10 |
| 2.0 | 0 | 100 |
| 2.7 | 0 | 100 |

Run time: 3.5 min (equilibration included)

Method 2
Chromatographic System:
Column: Chromolith FastGradient RP-18e from Merck, 2*50 mm
Oven: 30° C.
Eluents: Solvent A: water/HCO$_2$H (0.1%); Solvent B: acetonitrile/HCO$_2$H (0.1%)
Flow: 1.2 ml/min
Gradient:

| Time [min] | Solvent A [%] | Solvent B [%] |
|---|---|---|
| 0.0 | 98 | 2 |
| 0.2 | 98 | 2 |
| 2.2 | 2 | 98 |
| 2.7 | 2 | 98 |

Run time: 3.5 min (equilibration included)

Method—3
Chromatographic System:
Column: Xbridge BEH C18 Waters, 2.1×50 mm, 2.5μ
Oven: 40° C.
Eluents: Solvent A: water/HCO$_2$H (0.05%); Solvent B: acetonitrile/HCO$_2$H (0.05%)
Flow: 0.8 ml/min Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 1.8 | 98 | 2 |

Run time 2.2 min + 0.5 min equilibration time

Method—4
Chromatographic System:
Column: Phenomenex Jupiter Proteo C18 90 A, 4.6×50 mm, 4µ
Oven: 30° C.
Eluents: Solvent A: water/TFA (0.1%); Solvent B: acetonitrile/TFA (0.1%)
Flow: 1.0 ml/min
Gradient:

| Time [min] | Solvent A [%] | Solvent B [%] |
|---|---|---|
| 0.0 | 98 | 2 |
| 3.0 | 0 | 100 |
| 4.0 | 0 | 100 |
| 4.5 | 98 | 2 |
| 5 | 98 | 2 |

Run time: 5 min

Table B provides for each of the exemplified compounds of Table A the calculated molecular weight (MW), the observed mass signal (m/z), the HPLC retention time (Rt) in minutes and the number of the HPLC method as described above ("HPLC methods").

TABLE B

| No | Rt | m/z | MW | HPLC method |
|---|---|---|---|---|
| 1 | 2.15 | 394.1 | 393.4 | 4 |
| 2 | 2.17 | 396.2 | 395.5 | 4 |
| 3 | 2.17 | 394.1 | 393.4 | 4 |
| 4 | 2.37 | 424.2 | 423.5 | 4 |
| 5 | 2.14 | 412.3 | 411.5 | 4 |
| 6 | 1.99 | 425.2 | 424.5 | 4 |
| 7 | 2.04 | 412.0 | 411.4 | 4 |
| 8 | 2.18 | 410.2 | 409.5 | 4 |
| 9 | 2.10 | 424.2 | 423.5 | 4 |
| 10 | 2.63 | 478.3 | 477.6 | 4 |
| 11 | 2.60 | 498.2 | 497.6 | 4 |
| 12 | 2.53 | 499.3 | 498.6 | 4 |
| 13 | 2.04 | 500.3 | 499.6 | 4 |
| 14 | 2.42 | 470.2 | 469.5 | 4 |
| 15 | 2.37 | 530.2 | 529.6 | 4 |
| 16 | 2.39 | 444.1 | 443.5 | 4 |
| 17 | 2.42 | 458.2 | 457.5 | 4 |
| 18 | 2.52 | 478.2 | 477.9 | 4 |
| 19 | 2.43 | 474.1 | 473.5 | 4 |
| 20 | 2.12 | 487.2 | 486.6 | 4 |
| 21 | 2.62 | 512.2 | 511.5 | 4 |
| 22 | 1.99 | 445.2 | 444.5 | 4 |
| 23 | 2.58 | 472.2 | 471.6 | 4 |
| 24 | 2.41 | 406.2 | 405.5 | 4 |
| 25 | 2.43 | 408.3 | 407.5 | 4 |
| 26 | 2.43 | 407.2 | 405.5 | 4 |
| 27 | 2.60 | 436.3 | 435.6 | 4 |
| 28 | 2.40 | 424.3 | 423.5 | 4 |
| 29 | 2.21 | 437.2 | 436.6 | 4 |
| 30 | 2.31 | 424.2 | 423.5 | 4 |
| 31 | 2.44 | 422.3 | 421.5 | 4 |
| 32 | 2.36 | 436.3 | 435.5 | 4 |
| 33 | 2.47 | 484.1 | 483.6 | 4 |
| 34 | 2.84 | 490.4 | 489.7 | 4 |
| 35 | 2.81 | 510.2 | 509.6 | 4 |
| 36 | 2.72 | 511.3 | 510.6 | 4 |
| 37 | 2.27 | 512.3 | 511.6 | 4 |
| 38 | 2.65 | 482.2 | 481.6 | 4 |
| 39 | 2.60 | 542.2 | 541.6 | 4 |
| 40 | 2.61 | 456.3 | 455.6 | 4 |
| 41 | 2.65 | 470.2 | 469.6 | 4 |
| 42 | 2.74 | 490.1 | 490.0 | 4 |
| 43 | 2.66 | 486.2 | 485.6 | 4 |
| 44 | 2.34 | 499.2 | 498.6 | 4 |
| 45 | 2.81 | 524.3 | 523.6 | 4 |
| 46 | 2.22 | 457.2 | 456.5 | 4 |
| 47 | 2.79 | 484.3 | 483.6 | 4 |
| 48 | 2.53 | 422.3 | 421.5 | 4 |
| 49 | 2.53 | 420.2 | 419.5 | 4 |
| 50 | 2.70 | 450.3 | 449.6 | 4 |
| 51 | 2.50 | 438.3 | 437.5 | 4 |
| 52 | 2.31 | 451.2 | 450.6 | 4 |
| 53 | 2.42 | 438.2 | 437.5 | 4 |
| 54 | 2.56 | 436.2 | 435.6 | 4 |
| 55 | 2.48 | 450.2 | 449.5 | 4 |
| 56 | 2.58 | 498.1 | 497.6 | 4 |
| 57 | 2.94 | 504.4 | 503.7 | 4 |
| 58 | 2.88 | 524.4 | 523.7 | 4 |
| 59 | 2.83 | 525.3 | 524.7 | 4 |
| 60 | 2.38 | 526.3 | 525.6 | 4 |
| 61 | 2.75 | 496.3 | 495.6 | 4 |
| 62 | 2.69 | 556.2 | 555.7 | 4 |
| 63 | 2.71 | 470.3 | 469.6 | 4 |
| 64 | 2.74 | 484.3 | 483.6 | 4 |
| 65 | 2.82 | 504.2 | 504.0 | 4 |
| 66 | 2.74 | 500.3 | 499.6 | 4 |
| 67 | 2.44 | 513.2 | 512.7 | 4 |
| 68 | 2.89 | 538.2 | 537.6 | 4 |
| 69 | 2.32 | 471.2 | 470.6 | 4 |
| 70 | 2.88 | 499.3 | 497.6 | 4 |
| 71 | 2.10 | 394.2 | 393.4 | 4 |
| 72 | 2.13 | 396.2 | 395.5 | 4 |
| 73 | 2.13 | 394.1 | 393.4 | 4 |
| 74 | 2.08 | 412.2 | 411.5 | 4 |
| 75 | 1.93 | 425.2 | 424.5 | 4 |
| 76 | 2.13 | 410.2 | 409.5 | 4 |
| 77 | 2.04 | 424.2 | 423.5 | 4 |
| 78 | 2.13 | 472.1 | 471.5 | 4 |
| 79 | 2.62 | 478.2 | 477.6 | 4 |
| 80 | 2.57 | 498.2 | 497.6 | 4 |
| 81 | 2.50 | 499.7 | 498.6 | 4 |
| 82 | 1.98 | 500.2 | 499.6 | 4 |
| 83 | 2.40 | 470.2 | 469.5 | 4 |
| 84 | 2.34 | 530.2 | 529.6 | 4 |
| 85 | 2.36 | 444.1 | 443.5 | 4 |
| 86 | 2.39 | 458.2 | 457.5 | 4 |
| 87 | 2.51 | 478.1 | 477.9 | 4 |
| 88 | 2.41 | 474.1 | 473.5 | 4 |
| 89 | 2.61 | 512.2 | 511.5 | 4 |
| 90 | 1.93 | 445.1 | 444.5 | 4 |
| 91 | 2.57 | 472.3 | 471.6 | 4 |
| 92 | 2.37 | 406.1 | 405.5 | 4 |
| 93 | 2.40 | 408.1 | 407.5 | 4 |
| 94 | 2.40 | 406.1 | 405.5 | 4 |
| 95 | 2.57 | 436.1 | 435.6 | 4 |
| 96 | 2.35 | 424.1 | 423.5 | 4 |
| 97 | 2.41 | 422.1 | 421.5 | 4 |
| 98 | 2.32 | 436.2 | 435.5 | 4 |
| 99 | 2.41 | 484.1 | 483.6 | 4 |
| 100 | 2.77 | 510.2 | 509.6 | 4 |
| 101 | 2.23 | 512.2 | 511.6 | 4 |
| 102 | 2.61 | 482.2 | 481.6 | 4 |
| 103 | 2.57 | 542.2 | 541.6 | 4 |
| 104 | 2.59 | 456.2 | 455.6 | 4 |
| 105 | 2.63 | 470.2 | 469.6 | 4 |
| 106 | 2.72 | 490.1 | 490.0 | 4 |
| 107 | 2.63 | 486.1 | 485.6 | 4 |
| 108 | 2.31 | 499.2 | 498.6 | 4 |
| 109 | 2.79 | 524.3 | 523.6 | 4 |
| 110 | 2.18 | 457.1 | 456.5 | 4 |

TABLE B-continued

| No | Rt | m/z | MW | HPLC method |
|---|---|---|---|---|
| 111 | 2.80 | 484.2 | 483.6 | 4 |
| 112 | 2.48 | 420.2 | 419.5 | 4 |
| 113 | 2.49 | 420.2 | 419.5 | 4 |
| 114 | 2.66 | 450.3 | 449.6 | 4 |
| 115 | 2.46 | 438.2 | 437.5 | 4 |
| 116 | 2.27 | 451.2 | 450.6 | 4 |
| 117 | 2.37 | 438.1 | 437.5 | 4 |
| 118 | 2.51 | 436.3 | 435.6 | 4 |
| 119 | 2.43 | 450.3 | 449.5 | 4 |
| 120 | 2.91 | 504.4 | 503.7 | 4 |
| 121 | 2.85 | 524.3 | 523.7 | 4 |
| 122 | 2.82 | 525.4 | 524.7 | 4 |
| 123 | 2.33 | 526.3 | 525.6 | 4 |
| 124 | 2.71 | 496.2 | 495.6 | 4 |
| 125 | 2.66 | 556.2 | 555.7 | 4 |
| 126 | 2.66 | 470.2 | 469.6 | 4 |
| 127 | 2.71 | 484.3 | 483.6 | 4 |
| 128 | 2.80 | 504.1 | 504.0 | 4 |
| 129 | 2.71 | 500.2 | 499.6 | 4 |
| 130 | 2.39 | 513.2 | 512.7 | 4 |
| 131 | 2.88 | 538.3 | 537.6 | 4 |
| 132 | 2.29 | 471.2 | 470.6 | 4 |
| 133 | 2.87 | 498.2 | 497.6 | 4 |
| 134 | 2.08 | 487.2 | 486.6 | 4 |
| 135 | 2.72 | 511.2 | 510.6 | 4 |
| 136 | 2.32 | 424.2 | 423.5 | 4 |
| 137 | 1.94 | 412.1 | 411.4 | 4 |
| 138 | 2.20 | 438.2 | 436.6 | 4 |
| 139 | 2.26 | 424.1 | 423.5 | 4 |
| 140 | 2.84 | 490.3 | 489.7 | 4 |
| 141 | 2.50 | 422.2 | 421.5 | 4 |
| 142 | 2.57 | 498.2 | 497.6 | 4 |
| 143 | 2.21 | 472.1 | 471.5 | 4 |
| 144 | 2.51 | 420.2 | 419.5 | 4 |
| 145 | 2.25 | 408.0 | 407.5 | 4 |
| 146 | 2.14 | 437.1 | 436.5 | 4 |
| 147 | 2.33 | 408.0 | 407.5 | 4 |
| 148 | 2.41 | 422.1 | 421.5 | 4 |
| 149 | 2.51 | 436.1 | 435.5 | 4 |
| 150 | 2.16 | 368.1 | 367.4 | 4 |
| 151 | 2.21 | 382.0 | 381.4 | 4 |
| 152 | 2.30 | 396.0 | 395.5 | 4 |
| 153 | 2.29 | 426.0 | 425.5 | 4 |
| 154 | 2.26 | 426.1 | 425.5 | 4 |
| 155 | 2.35 | 452.1 | 451.5 | 4 |
| 156 | 2.31 | 422.1 | 421.5 | 4 |
| 157 | 2.11 | 445.0 | 444.5 | 4 |
| 158 | 2.32 | 445.0 | 444.5 | 4 |
| 159 | 2.35 | 434.0 | 433.5 | 4 |
| 160 | 2.43 | 450.0 | 449.5 | 4 |
| 161 | 2.61 | 458.0 | 457.5 | 4 |
| 162 | 2.31 | 438.1 | 437.5 | 4 |
| 163 | 2.08 | 434.1 | 433.5 | 4 |
| 164 | 2.30 | 426.1 | 425.5 | 4 |
| 165 | 2.60 | 464.1 | 463.6 | 4 |
| 166 | 2.58 | 434.1 | 433.5 | 4 |
| 167 | 2.36 | 457.1 | 456.5 | 4 |
| 168 | 2.61 | 491.1 | 491.0 | 4 |
| 169 | 2.58 | 457.1 | 456.5 | 4 |
| 170 | 2.61 | 446.1 | 445.5 | 4 |
| 171 | 2.66 | 462.0 | 461.6 | 4 |
| 172 | 2.80 | 470.1 | 469.6 | 4 |
| 173 | 2.33 | 446.0 | 445.5 | 4 |
| 174 | 2.63 | 434.1 | 433.5 | 4 |
| 175 | 2.50 | 463.1 | 462.6 | 4 |
| 176 | 2.59 | 408.1 | 407.5 | 4 |
| 177 | 2.65 | 452.1 | 451.6 | 4 |
| 178 | 2.64 | 452.1 | 451.6 | 4 |
| 179 | 2.47 | 471.1 | 470.6 | 4 |
| 180 | 2.67 | 471.1 | 470.6 | 4 |
| 181 | 2.69 | 460.1 | 459.5 | 4 |
| 182 | 2.76 | 476.0 | 475.6 | 4 |
| 183 | 2.66 | 464.1 | 463.6 | 4 |
| 184 | 2.43 | 460.0 | 459.6 | 4 |
| 185 | 2.66 | 452.1 | 451.6 | 4 |
| 186 | 2.60 | 464.1 | 463.6 | 4 |
| 187 | 2.68 | 448.1 | 447.6 | 4 |
| 188 | 2.49 | 477.2 | 476.6 | 4 |
| 189 | 2.78 | 484.2 | 483.6 | 4 |
| 190 | 2.57 | 505.2 | 505.0 | 4 |
| 191 | 2.56 | 478.2 | 477.6 | 4 |
| 192 | 2.46 | 419.2 | 418.5 | 4 |
| 193 | 2.51 | 422.2 | 421.5 | 4 |
| 194 | 2.40 | 394.2 | 393.5 | 4 |
| 195 | 2.67 | 462.2 | 461.6 | 4 |
| 196 | 2.60 | 448.2 | 447.6 | 4 |
| 197 | 2.53 | 434.2 | 433.5 | 4 |
| 198 | 2.41 | 438.2 | 437.5 | 4 |
| 199 | 2.38 | 463.1 | 462.6 | 4 |
| 200 | 2.40 | 450.2 | 449.5 | 4 |
| 201 | 2.32 | 394.2 | 393.5 | 4 |
| 202 | 2.34 | 450.2 | 449.5 | 4 |
| 203 | 2.37 | 438.2 | 437.5 | 4 |
| 204 | 2.35 | 405.2 | 404.5 | 4 |
| 205 | 2.40 | 438.2 | 437.5 | 4 |
| 206 | 2.42 | 408.2 | 407.5 | 4 |
| 207 | 2.28 | 380.2 | 379.5 | 4 |
| 208 | 2.59 | 448.2 | 447.6 | 4 |
| 209 | 2.49 | 434.2 | 433.5 | 4 |
| 210 | 2.41 | 420.2 | 419.5 | 4 |
| 211 | 2.19 | 449.2 | 448.6 | 4 |
| 212 | 2.37 | 420.2 | 419.5 | 4 |
| 213 | 2.13 | 451.1 | 450.5 | 4 |
| 214 | 2.22 | 479.1 | 478.9 | 4 |
| 215 | 2.06 | 438.2 | 437.5 | 4 |
| 216 | 2.06 | 393.1 | 392.4 | 4 |
| 217 | 1.32 | 386 | 385.4568 | 2 |
| 218 | 0.75 | 451 | 450.487 | 3 |
| 219 | 2.15 | 422.2 | 421.5 | 4 |
| 220 | 2.17 | 422.2 | 421.5 | 4 |
| 221 | 2.14 | 440.2 | 439.5 | 4 |
| 222 | 2.10 | 452.2 | 451.5 | 4 |
| 223 | 2.40 | 472.2 | 471.5 | 4 |
| 224 | 2.44 | 502.2 | 501.6 | 4 |
| 225 | 2.15 | 436.2 | 435.5 | 4 |
| 226 | 2.22 | 436.2 | 435.5 | 4 |
| 227 | 2.31 | 450.2 | 449.5 | 4 |
| 228 | 1.99 | 473.2 | 472.5 | 4 |
| 229 | 2.27 | 507.1 | 507.0 | 4 |
| 230 | 2.20 | 473.2 | 472.5 | 4 |
| 231 | 2.27 | 462.1 | 461.5 | 4 |
| 232 | 2.34 | 478.2 | 477.6 | 4 |
| 233 | 2.51 | 486.2 | 485.6 | 4 |
| 234 | 2.21 | 466.2 | 465.5 | 4 |
| 235 | 2.44 | 452.2 | 451.6 | 4 |
| 236 | 2.46 | 452.2 | 451.6 | 4 |
| 237 | 2.42 | 470.2 | 469.6 | 4 |
| 238 | 2.39 | 482.2 | 481.6 | 4 |
| 239 | 2.64 | 502.2 | 501.6 | 4 |
| 240 | 2.68 | 532.2 | 531.7 | 4 |
| 241 | 2.22 | 503.2 | 502.6 | 4 |
| 242 | 2.45 | 466.2 | 465.6 | 4 |
| 243 | 2.50 | 466.2 | 465.6 | 4 |
| 244 | 2.57 | 480.2 | 479.6 | 4 |
| 245 | 2.48 | 454.2 | 453.6 | 4 |
| 246 | 2.42 | 473.1 | 450.6 | 4 |
| 247 | 2.24 | 503.2 | 502.6 | 4 |
| 248 | 2.52 | 537.2 | 537.1 | 4 |
| 249 | 2.48 | 503.2 | 502.6 | 4 |
| 250 | 2.53 | 492.2 | 491.6 | 4 |
| 251 | 2.59 | 508.2 | 507.7 | 4 |
| 252 | 2.74 | 516.2 | 515.7 | 4 |
| 253 | 2.48 | 496.2 | 495.6 | 4 |
| 254 | 2.46 | 509.2 | 508.7 | 4 |
| 255 | 2.21 | 484.2 | 483.6 | 4 |
| 256 | 2.24 | 484.1 | 483.6 | 4 |
| 257 | 2.19 | 502.2 | 501.6 | 4 |
| 258 | 2.16 | 514.2 | 513.6 | 4 |
| 259 | 2.46 | 534.2 | 533.6 | 4 |
| 260 | 2.50 | 564.2 | 563.7 | 4 |
| 261 | 2.02 | 535.2 | 534.6 | 4 |
| 262 | 2.22 | 498.2 | 497.6 | 4 |
| 263 | 2.29 | 498.2 | 497.6 | 4 |
| 264 | 2.38 | 512.2 | 511.6 | 4 |
| 265 | 2.26 | 486.2 | 485.6 | 4 |
| 266 | 2.19 | 483.1 | 482.6 | 4 |

TABLE B-continued

| No | Rt | m/z | MW | HPLC method |
|---|---|---|---|---|
| 267 | 2.04 | 535.2 | 534.6 | 4 |
| 268 | 2.33 | 569.1 | 569.1 | 4 |
| 269 | 2.27 | 535.2 | 534.6 | 4 |
| 270 | 2.33 | 524.2 | 523.6 | 4 |
| 271 | 2.41 | 540.1 | 539.7 | 4 |
| 272 | 2.57 | 548.2 | 547.7 | 4 |
| 273 | 2.27 | 528.2 | 527.6 | 4 |
| 274 | 2.24 | 541.1 | 540.7 | 4 |
| 275 | 2.00 | 473.2 | 472.5 | 4 |
| 276 | 0.774 | 501 | 500.5457 | 3 |
| 277 | 0.816 | 535 | 534.9908 | 3 |
| 278 | 0.67 | 502 | 501.5338 | 3 |
| 279 | 0.871 | 569 | 568.5437 | 3 |
| 280 | 0.714 | 451 | 450.487 | 3 |
| 281 | 0.717 | 453 | 452.5029 | 3 |
| 282 | 0.75 | 502 | 501.5338 | 3 |
| 283 | 0.84 | 515 | 514.5723 | 3 |
| 284 | 0.805 | 519 | 518.5362 | 3 |
| 285 | 0.719 | 483 | 482.5289 | 3 |
| 286 | 0.753 | 502 | 501.5338 | 3 |
| 287 | 0.763 | 491 | 490.5078 | 3 |
| 288 | 0.988 | 491 | 492.4477 | 3 |
| 289 | 0.785 | 507 | 506.5734 | 3 |
| 290 | 2.24 | 450.1 | 427.5 | 4 |
| 291 | 2.19 | 428.1 | 427.5 | 4 |
| 292 | 2.15 | 446.1 | 445.5 | 4 |
| 293 | 2.20 | 458.2 | 457.5 | 4 |
| 294 | 2.42 | 478.2 | 477.6 | 4 |
| 295 | 2.45 | 508.1 | 507.6 | 4 |
| 296 | 2.09 | 479.1 | 478.6 | 4 |
| 297 | 2.22 | 479.1 | 478.6 | 4 |
| 298 | 2.28 | 468.1 | 467.5 | 4 |
| 299 | 2.39 | 482.1 | 481.6 | 4 |
| 300 | 2.45 | 458.2 | 457.6 | 4 |
| 301 | 2.47 | 458.2 | 457.6 | 4 |
| 302 | 2.43 | 476.2 | 475.6 | 4 |
| 303 | 2.40 | 488.1 | 487.6 | 4 |
| 304 | 2.65 | 508.2 | 507.7 | 4 |
| 305 | 2.67 | 538.2 | 537.7 | 4 |
| 306 | 2.26 | 509.1 | 508.7 | 4 |
| 307 | 2.49 | 509.1 | 508.7 | 4 |
| 308 | 2.53 | 498.2 | 497.6 | 4 |
| 309 | 2.73 | 500.1 | 499.6 | 4 |
| 310 | 2.62 | 512.2 | 511.7 | 4 |
| 311 | 2.23 | 490.2 | 489.6 | 4 |
| 312 | 2.25 | 490.2 | 489.6 | 4 |
| 313 | 2.21 | 508.1 | 507.6 | 4 |
| 314 | 2.17 | 520.1 | 519.6 | 4 |
| 315 | 2.45 | 540.2 | 539.7 | 4 |
| 316 | 2.50 | 570.1 | 569.7 | 4 |
| 317 | 2.04 | 541.1 | 540.7 | 4 |
| 318 | 2.28 | 489.1 | 488.6 | 4 |
| 319 | 2.05 | 541.2 | 540.7 | 4 |
| 320 | 2.28 | 541.1 | 540.7 | 4 |
| 321 | 2.33 | 530.2 | 529.6 | 4 |
| 322 | 2.18 | 542.1 | 541.6 | 4 |
| 323 | 2.43 | 544.2 | 543.7 | 4 |
| 324 | 2.09 | 423.2 | 422.5 | 4 |
| 325 | 2.06 | 441.2 | 440.5 | 4 |
| 326 | 2.03 | 453.2 | 452.5 | 4 |
| 327 | 2.34 | 473.2 | 472.5 | 4 |
| 328 | 2.37 | 503.2 | 502.6 | 4 |
| 329 | 1.92 | 474.2 | 473.5 | 4 |
| 330 | 1.94 | 474.2 | 473.5 | 4 |
| 331 | 2.14 | 474.2 | 473.5 | 4 |
| 332 | 2.20 | 463.2 | 462.5 | 4 |
| 333 | 2.20 | 465.2 | 464.4 | 4 |
| 334 | 2.30 | 477.3 | 476.5 | 4 |
| 335 | 2.35 | 453.2 | 452.6 | 4 |
| 336 | 2.38 | 453.2 | 452.6 | 4 |
| 337 | 2.36 | 471.1 | 470.6 | 4 |
| 338 | 2.31 | 483.3 | 482.6 | 4 |
| 339 | 2.58 | 503.2 | 502.6 | 4 |
| 340 | 2.61 | 533.2 | 532.7 | 4 |
| 341 | 2.18 | 504.2 | 503.6 | 4 |
| 342 | 2.35 | 452.1 | 451.5 | 4 |
| 343 | 2.41 | 504.2 | 503.6 | 4 |
| 344 | 2.46 | 493.2 | 492.6 | 4 |
| 345 | 2.48 | 495.2 | 494.5 | 4 |
| 346 | 2.33 | 505.2 | 504.6 | 4 |
| 347 | 2.56 | 507.2 | 506.6 | 4 |
| 348 | 2.13 | 485.2 | 484.6 | 4 |
| 349 | 2.12 | 503.2 | 502.6 | 4 |
| 350 | 2.08 | 515.2 | 514.6 | 4 |
| 351 | 2.39 | 535.2 | 534.6 | 4 |
| 352 | 2.43 | 565.2 | 564.7 | 4 |
| 353 | 2.19 | 536.2 | 535.6 | 4 |
| 354 | 2.25 | 525.2 | 524.6 | 4 |
| 355 | 2.26 | 527.1 | 526.5 | 4 |
| 356 | 2.10 | 537.2 | 536.6 | 4 |
| 357 | 2.36 | 539.2 | 538.6 | 4 |
| 358 | 2.03 | 427.2 | 426.5 | 4 |
| 359 | 2.19 | 485.2 | 484.6 | 4 |
| 360 | 2.13 | 480.2 | 479.6 | 4 |
| 361 | 2.10 | 423.3 | 422.5 | 4 |
| 362 | 2.11 | 480.2 | 479.6 | 4 |
| 363 | 2.06 | 475.2 | 474.5 | 4 |
| 364 | 2.24 | 509.2 | 508.7 | 4 |
| 365 | 2.47 | 515.2 | 514.7 | 4 |
| 366 | 2.40 | 510.2 | 509.6 | 4 |
| 367 | 2.19 | 504.2 | 503.6 | 4 |
| 368 | 2.39 | 510.2 | 509.6 | 4 |
| 369 | 2.25 | 547.2 | 546.7 | 4 |
| 370 | 2.16 | 485.2 | 484.6 | 4 |
| 371 | 1.98 | 536.3 | 535.6 | 4 |
| 372 | 2.10 | 484.1 | 483.5 | 4 |
| 373 | 1.99 | 536.3 | 535.6 | 4 |
| 374 | 2.16 | 542.2 | 541.6 | 4 |
| 375 | 1.443 | 370.1 | 369.33 | 1 |
| 376 | 1.389 | 340 | 339.349 | 2 |
| 377 | 1.864 | 382.1 | 381.386 | 1 |
| 378 | 2.38 | 435.2 | 434.5 | 5 |
| 379 | 2.40 | 435.2 | 434.5 | 5 |
| 380 | 2.37 | 453.2 | 452.5 | 5 |
| 381 | 2.34 | 465.2 | 464.5 | 5 |
| 382 | 2.60 | 485.2 | 484.5 | 5 |
| 383 | 2.63 | 515.2 | 514.6 | 5 |
| 384 | 2.39 | 449.2 | 448.5 | 5 |
| 385 | 2.44 | 449.2 | 448.5 | 5 |
| 386 | 2.52 | 463.2 | 462.5 | 5 |
| 387 | 2.43 | 437.2 | 436.5 | 5 |
| 388 | 2.20 | 486.2 | 485.5 | 5 |
| 389 | 2.48 | 520.2 | 520.0 | 5 |
| 390 | 2.42 | 486.2 | 485.5 | 5 |
| 391 | 2.48 | 475.2 | 474.5 | 5 |
| 392 | 2.55 | 491.2 | 490.6 | 5 |
| 393 | 2.70 | 499.3 | 498.6 | 5 |
| 394 | 2.43 | 479.2 | 478.5 | 5 |
| 395 | 2.40 | 492.2 | 491.6 | 5 |
| 396 | 2.24 | 406.2 | 405.4 | 5 |
| 397 | 2.26 | 406.2 | 405.4 | 5 |
| 398 | 2.22 | 424.2 | 423.5 | 5 |
| 399 | 2.20 | 436.2 | 435.5 | 5 |
| 400 | 2.49 | 456.2 | 455.5 | 5 |
| 401 | 2.53 | 486.2 | 485.5 | 5 |
| 402 | 2.05 | 457.2 | 456.5 | 5 |
| 403 | 2.25 | 420.3 | 419.5 | 5 |
| 404 | 2.31 | 420.3 | 419.5 | 5 |
| 405 | 2.41 | 434.2 | 433.5 | 5 |
| 406 | 2.30 | 408.1 | 407.5 | 5 |
| 407 | 2.07 | 457.1 | 456.5 | 5 |
| 408 | 2.36 | 491.1 | 490.9 | 5 |
| 409 | 2.29 | 457.2 | 456.5 | 5 |
| 410 | 2.35 | 446.2 | 445.5 | 5 |
| 411 | 2.43 | 462.2 | 461.5 | 5 |
| 412 | 2.59 | 470.2 | 469.5 | 5 |
| 413 | 2.29 | 450.3 | 449.5 | 5 |
| 414 | 2.27 | 463.2 | 462.5 | 5 |
| 415 | 2.18 | 486.1 | 485.5 | 5 |

Biologic Example

Example 13

In-Vitro Susceptibility Testing of Representative Compounds

The Minimum inhibitory concentrations (MIC) of compounds according to the invention for a number of veterinary bacterial pathogens were determined by the broth-microdilution method according to CLSI document VET01-A4.

Microdilution trays containing a doubling dilution series of the test compound were used for the tests. The MIC results were interpreted according to the CLSI documents VET01-S3. The lowest concentration of compound at which no visible growth (i.e. no turbidity) detected by the unaided eye was recorded as the MIC.

Results

MIC Data for representative compounds is shown in Table 1 below.

The following pathogens/strains were tested:

| ID | Species | Ext. RefNo. | Remarks |
|---|---|---|---|
| MH 6357 | Mannheimia haemolytica | M7/2 | Reference strain (cattle infection strain) |
| MH 6374 | Mannheimia haemolytica | ATCC 33396 | Reference strain |
| MH 10720 | Mannheimia haemolytica | 154 | BRD field isolate |
| MH 12587 | Mannheimia haemolytica | 1071 | BRD field isolate, macrolide-resistance: erm+, E+ |
| MH 13065 | Mannheimia haemolytica | XB0446-6003.9 | BRD field isolate |
| MH 13093 | Mannheimia haemolytica | XB0472-6014.1 | BRD field isolate |
| PM 6267 | Pasteurella multocida | P 2225 (L386) | Reference strain (mouse infection strain) |
| PM 6391 | Pasteurella multocida | ATCC 43137 | Reference strain |
| PM 10775 | Pasteurella multocida | 080130003051 | BRD field isolate |
| PM 12080 | Pasteurella multocida | IV102277-0093 | BRD field isolate |

| No | MH 6357 | MH 6374 | MH 10720 | MH 12587 | MH 13065 | MH 13093 | PM 6267 | PM 6391 | PM 10775 | PM 12080 |
|---|---|---|---|---|---|---|---|---|---|---|
| 26 | 12.5 | 6.3 | 3.1 | 25 | 12.5 | 12.5 | 3.1 | NT | 0.8 | 6.3 |
| 27 | 12.5 | 12.5 | 3.1 | 25 | 25 | 25 | 3.1 | NT | 0.8 | 6.3 |
| 32 | 6.3 | 6.3 | 3.1 | 12.5 | 6.3 | 6.3 | 1.6 | NT | 0.4 | 3.1 |
| 40 | 6.3 | 3.1 | 6.3 | 12.5 | 6.3 | 6.3 | 3.1 | NT | 0.8 | 6.3 |
| 43 | 6.3 | 6.3 | 1.6 | 12.5 | 6.3 | 12.5 | 3.1 | NT | 0.4 | 3.1 |
| 46 | 6.3 | 6.3 | 1.6 | 12.5 | 6.3 | 6.3 | 1.6 | NT | 0.2 | 6.3 |
| 49 | 12.5 | 12.5 | 6.3 | 25 | 12.5 | 12.5 | 3.1 | NT | 0.8 | 12.5 |
| 71 | 1.6 | 0.8 | 0.4 | 1.6 | 0.8 | 3.1 | 0.2 | NT | <=0.1 | 0.4 |
| 72 | 12.5 | 12.5 | 6.3 | 25 | 12.5 | 12.5 | 1.6 | NT | 0.8 | 12.5 |
| 73 | 3.1 | 3.1 | 3.1 | 6.3 | 3.1 | 3.1 | 0.4 | NT | <=0.1 | 1.6 |
| 74 | 3.1 | 3.1 | 3.1 | 12.5 | 6.3 | 12.5 | 0.8 | NT | <=0.1 | 3.1 |
| 76 | 12.5 | 25 | 6.3 | 25 | 12.5 | 25 | 0.4 | NT | 0.2 | 3.1 |
| 77 | 6.3 | 1.6 | 0.8 | 3.1 | 3.1 | 3.1 | <=0.1 | NT | <=0.1 | 0.8 |
| 78 | 6.3 | 6.3 | 3.1 | 12.5 | 6.3 | 6.3 | <=0.1 | NT | <=0.1 | 0.8 |
| 79 | 12.5 | 25 | 3.1 | 25 | 12.5 | 25 | 0.4 | NT | <=0.1 | 1.6 |
| 80 | 1.6 | 1.6 | 0.8 | 3.1 | 1.6 | 6.3 | <=0.1 | NT | <=0.1 | 0.8 |
| 81 | 3.1 | 3.1 | 0.8 | 25 | 3.1 | 6.3 | <=0.1 | NT | <=0.1 | 0.8 |
| 82 | 1.6 | 0.8 | 0.4 | 3.1 | 6.3 | 3.1 | <=0.1 | NT | <=0.1 | 0.8 |
| 83 | 25 | 0.8 | 0.4 | 1.6 | 0.8 | 1.6 | <=0.1 | NT | <=0.1 | 0.8 |
| 84 | 3.1 | 3.1 | 0.8 | 3.1 | 3.1 | 3.1 | <=0.1 | NT | <=0.1 | 0.4 |
| 85 | 3.1 | 0.8 | 1.6 | 3.1 | 1.6 | 3.1 | <=0.1 | NT | <=0.1 | 0.8 |
| 86 | 1.6 | 0.8 | 0.4 | 3.1 | 1.6 | 3.1 | <=0.1 | NT | <=0.1 | 0.8 |
| 87 | 3.1 | 0.8 | 1.6 | 6.3 | 3.1 | 3.1 | 0.2 | NT | <=0.1 | 1.6 |
| 88 | 6.3 | 1.6 | 1.6 | 6.3 | 3.1 | 12.5 | 0.2 | NT | <=0.1 | 1.6 |
| 89 | 6.3 | 3.1 | 1.6 | 12.5 | 6.3 | 6.3 | 0.4 | NT | <=0.1 | 1.6 |
| 90 | 3.1 | 1.6 | 1.6 | 3.1 | 1.6 | 1.6 | <=0.1 | NT | <=0.1 | 0.8 |
| 91 | 6.3 | 3.1 | 1.6 | 12.5 | 6.3 | 12.5 | 0.4 | NT | <=0.1 | 1.6 |
| 92 | 0.8 | <=0.1 | <=0.1 | 0.2 | <=0.1 | 0.2 | <=0.1 | NT | <=0.1 | <=0.1 |
| 93 | 6.3 | 6.3 | 3.1 | 12.5 | 6.3 | 12.5 | <=0.1 | NT | <=0.1 | 1.6 |
| 94 | 12.5 | 0.8 | 0.8 | 1.6 | 0.8 | 1.6 | <=0.1 | NT | <=0.1 | 0.8 |
| 95 | 1.6 | 3.1 | 0.8 | 6.3 | 3.1 | 3.1 | <=0.1 | NT | <=0.1 | 0.4 |
| 96 | 3.1 | 0.8 | 0.8 | 1.6 | 1.6 | 3.1 | 0.2 | NT | <=0.1 | 0.8 |
| 97 | 12.5 | 12.5 | 3.1 | 12.5 | 12.5 | 12.5 | 0.2 | NT | <=0.1 | 0.8 |
| 98 | 0.8 | 1.6 | 0.4 | 1.6 | 1.6 | 1.6 | <=0.1 | NT | <=0.1 | <=0.1 |
| 99 | 3.1 | 6.3 | 0.8 | 12.5 | 6.3 | 6.3 | <=0.1 | NT | <=0.1 | 0.2 |
| 100 | 3.1 | 6.3 | 0.8 | 12.5 | 3.1 | 6.3 | 0.4 | NT | <=0.1 | 0.8 |
| 101 | 3.1 | 3.1 | 0.8 | 12.5 | 3.1 | 3.1 | 0.4 | NT | <=0.1 | 0.8 |
| 102 | 3.1 | 3.1 | 0.8 | 12.5 | 3.1 | 6.3 | 0.4 | NT | <=0.1 | 0.8 |
| 104 | 0.4 | 0.4 | <=0.1 | 1.6 | 0.4 | 0.8 | <=0.1 | NT | <=0.1 | 0.4 |
| 105 | 6.3 | 3.1 | 0.8 | 6.3 | 3.1 | 3.1 | 0.2 | NT | <=0.1 | 0.8 |
| 106 | 0.8 | 0.8 | 0.2 | 1.6 | 0.8 | 1.6 | 0.2 | NT | <=0.1 | 0.8 |
| 107 | 3.1 | 0.8 | 0.4 | 3.1 | 0.8 | 0.8 | 0.2 | NT | <=0.1 | 0.4 |
| 108 | 3.1 | 1.6 | 1.6 | 3.1 | 1.6 | 3.1 | 0.4 | NT | <=0.1 | 1.6 |
| 110 | 1.6 | 0.4 | <=0.1 | 0.8 | 0.4 | 0.4 | <=0.1 | NT | <=0.1 | 0.2 |
| 111 | 3.1 | 3.1 | 0.8 | 12.5 | 3.1 | 3.1 | 0.8 | NT | 0.4 | 1.6 |

-continued

| No | MH 6357 | MH 6374 | MH 10720 | MH 12587 | MH 13065 | MH 13093 | PM 6267 | PM 6391 | PM 10775 | PM 12080 |
|---|---|---|---|---|---|---|---|---|---|---|
| 112 | 1.6 | 0.4 | <=0.1 | 0.8 | 0.4 | 0.4 | <=0.1 | NT | <=0.1 | 0.2 |
| 113 | 3.1 | 0.8 | 0.4 | 3.1 | 1.6 | 3.1 | 0.4 | NT | <=0.1 | 0.8 |
| 114 | 6.3 | 12.5 | 1.6 | 12.5 | 6.3 | 6.3 | 0.2 | NT | <=0.1 | 0.8 |
| 115 | 6.3 | 1.6 | 0.8 | 6.3 | 3.1 | 3.1 | 0.4 | NT | <=0.1 | 1.6 |
| 116 | 25 | 25 | 3.1 | 1 | 25 | 25 | 0.8 | NT | 0.4 | 3.1 |
| 118 | 6.3 | 12.5 | 3.1 | 25 | 12.5 | 12.5 | 0.4 | NT | 0.2 | 1.6 |
| 119 | 1.6 | 1.6 | 0.4 | 3.1 | 1.6 | 3.1 | <=0.1 | NT | <=0.1 | <=0.1 |
| 124 | 6.3 | 12.5 | 3.1 | 25 | 12.5 | 12.5 | 3.1 | NT | 0.8 | 3.1 |
| 126 | 3.1 | 1.6 | 0.4 | 1.6 | 1.6 | 1.6 | 0.4 | NT | <=0.1 | 0.8 |
| 127 | 3.1 | 6.3 | 1.6 | 25 | 6.3 | 12.5 | 1.6 | NT | 0.4 | 1.6 |
| 128 | 3.1 | 3.1 | 0.8 | 12.5 | 3.1 | 6.3 | 3.1 | NT | 0.4 | 3.1 |
| 129 | 1.6 | 1.6 | 0.4 | 3.1 | 1.6 | 3.1 | 0.8 | NT | <=0.1 | 1.6 |
| 130 | 3.1 | 3.1 | 1.6 | 12.5 | 6.3 | 6.3 | 3.1 | NT | 0.4 | 3.1 |
| 132 | 1.6 | 0.8 | 0.2 | 0.8 | 0.8 | 0.8 | <=0.1 | NT | <=0.1 | 0.4 |
| 134 | 25 | 6.3 | 6.3 | 12.5 | 12.5 | 25 | 0.8 | NT | <=0.1 | 3.1 |
| 135 | 3.1 | 6.3 | 0.8 | 1 | 25 | 25 | 0.8 | NT | <=0.1 | 0.8 |
| 136 | 3.1 | 12.5 | 1.6 | 25 | 12.5 | 25 | 0.4 | 0.8 | <=0.1 | 0.8 |
| 141 | 6.3 | 12.5 | 1.6 | 12.5 | 6.3 | 12.5 | 1.6 | 3.1 | 0.2 | 3.1 |
| 142 | 6.3 | 12.5 | 3.1 | 25 | 12.5 | 12.5 | 0.2 | 0.4 | <=0.1 | 0.4 |
| 144 | 6.3 | 12.5 | 1.6 | 25 | 12.5 | 12.5 | 3.1 | 12.5 | 0.4 | 3.1 |
| 145 | 6.3 | 25 | 3.1 | 25 | 12.5 | 12.5 | 3.1 | 6.3 | 0.2 | 6.3 |
| 146 | 6.3 | 25 | 1.6 | 25 | 12.5 | 25 | 0.8 | 1.6 | <=0.1 | <=0.1 |
| 147 | 3.1 | 6.3 | 3.1 | 6.3 | 6.3 | 6.3 | 0.4 | 1.6 | <=0.1 | 1.6 |
| 148 | 6.3 | 25 | 1.6 | 25 | 12.5 | 12.5 | 0.8 | 1.6 | <=0.1 | 1.6 |
| 149 | 12.5 | 25 | 3.1 | 25 | 25 | 25 | 0.8 | 1.6 | <=0.1 | 1.6 |
| 150 | 6.3 | 25 | 3.1 | 25 | 12.5 | 25 | 6.3 | 25 | <=0.1 | <=0.1 |
| 151 | 6.3 | 25 | 3.1 | 25 | 25 | 25 | 3.1 | 12.5 | <=0.1 | 6.3 |
| 152 | 3.1 | 25 | 3.1 | 12.5 | 12.5 | 12.5 | 1.6 | 6.3 | 0.2 | 3.1 |
| 153 | 12.5 | 25 | 6.3 | 25 | 12.5 | 25 | 1.6 | 6.3 | <=0.1 | 0.8 |
| 154 | 3.1 | 12.5 | 1.6 | 12.5 | 6.3 | 6.3 | 0.2 | 1.6 | <=0.1 | 0.8 |
| 155 | 12.5 | 12.5 | 1.6 | 25 | 12.5 | 25 | <=0.1 | 0.4 | <=0.1 | 0.4 |
| 156 | 6.3 | 6.3 | 1.6 | 12.5 | 12.5 | 12.5 | 0.8 | 1.6 | <=0.1 | 1.6 |
| 157 | 1.6 | 1.6 | 0.8 | 6.3 | 3.1 | 6.3 | 0.4 | 0.8 | <=0.1 | 0.8 |
| 158 | 1.6 | 3.1 | 0.8 | 6.3 | 6.3 | 6.3 | 0.4 | 0.8 | <=0.1 | 0.8 |
| 159 | 1.6 | 1.6 | 0.4 | 3.1 | 3.1 | 3.1 | 0.2 | 0.8 | <=0.1 | 0.4 |
| 160 | 0.8 | 0.8 | 0.4 | 3.1 | 1.6 | 3.1 | <=0.1 | 0.4 | <=0.1 | 0.2 |
| 161 | 1.6 | 1.6 | 0.8 | 6.3 | 3.1 | 6.3 | 0.2 | 0.8 | <=0.1 | 0.2 |
| 162 | 6.3 | 12.5 | 3.1 | 12.5 | 12.5 | 12.5 | 0.8 | 3.1 | <=0.1 | 1.6 |
| 164 | 6.3 | 12.5 | 1.6 | 25 | 12.5 | 25 | 0.4 | 1.6 | <=0.1 | 1.6 |
| 165 | 6.3 | 12.5 | 3.1 | 25 | 12.5 | 12.5 | <=0.1 | 0.2 | <=0.1 | <=0.1 |
| 166 | 3.1 | 6.3 | 0.8 | 6.3 | 6.3 | 6.3 | 0.2 | 0.8 | <=0.1 | 0.4 |
| 167 | 0.4 | 0.4 | <=0.1 | 0.8 | 0.8 | 0.8 | <=0.1 | 0.4 | <=0.1 | 0.2 |
| 168 | 0.4 | 0.8 | 0.2 | 1.6 | 0.8 | 0.8 | <=0.1 | 0.4 | <=0.1 | 0.2 |
| 169 | 0.4 | 0.8 | 0.2 | 1.6 | 0.8 | 0.8 | <=0.1 | 0.4 | <=0.1 | 0.4 |
| 170 | 0.2 | 0.4 | <=0.1 | 0.4 | 0.4 | 0.4 | <=0.1 | 0.4 | <=0.1 | 0.2 |
| 171 | 0.2 | 0.4 | <=0.1 | 0.8 | 0.2 | 0.4 | <=0.1 | 0.2 | <=0.1 | <=0.1 |
| 172 | 0.4 | 0.8 | 0.4 | 1.6 | 0.8 | 0.8 | 0.2 | 0.4 | <=0.1 | 0.4 |
| 173 | 3.1 | 3.1 | 0.8 | 6.3 | 6.3 | 6.3 | <=0.1 | 0.8 | <=0.1 | 0.4 |
| 174 | 3.1 | 6.3 | 0.8 | 6.3 | 6.3 | 6.3 | 0.4 | 1.6 | <=0.1 | 1.6 |
| 175 | 6.3 | 12.5 | 3.1 | 25 | 12.5 | 12.5 | 0.4 | 1.6 | <=0.1 | 0.8 |
| 176 | 3.1 | 6.3 | 3.1 | 12.5 | 6.3 | 12.5 | 0.8 | 3.1 | <=0.1 | 1.6 |
| 177 | 3.1 | 6.3 | 1.6 | 12.5 | 6.3 | 6.3 | 0.8 | 3.1 | <=0.1 | 1.6 |
| 178 | 1.6 | 3.1 | 0.8 | 6.3 | 1.6 | 3.1 | 0.2 | 0.8 | <=0.1 | 0.4 |
| 179 | 0.4 | 0.8 | <=0.1 | 1.6 | 0.8 | 0.8 | 0.2 | 1.6 | <=0.1 | 0.4 |
| 180 | 0.8 | 1.6 | 0.2 | 3.1 | 1.6 | 1.6 | 0.4 | 1.6 | <=0.1 | 0.8 |
| 181 | 0.4 | 0.8 | <=0.1 | 1.6 | 0.8 | 0.8 | 0.4 | 0.8 | <=0.1 | 0.4 |
| 182 | 0.4 | 1.6 | 0.2 | 1.6 | 0.8 | 0.8 | 0.2 | 0.8 | <=0.1 | 0.2 |
| 183 | 1.6 | 3.1 | 0.8 | 1.6 | 3.1 | 3.1 | 0.4 | 1.6 | <=0.1 | 0.8 |
| 184 | 12.5 | 6.3 | 0.8 | 12.5 | 6.3 | 6.3 | 0.4 | 3.1 | <=0.1 | 1.6 |
| 185 | 3.1 | 6.3 | 0.8 | 6.3 | 3.1 | 6.3 | <=0.1 | 0.8 | <=0.1 | 0.4 |
| 186 | 1.6 | 6.3 | 1.6 | 6.3 | 3.1 | 3.1 | <=0.1 | 0.4 | <=0.1 | 0.2 |
| 187 | 3.1 | 12.5 | 1.6 | 12.5 | 6.3 | 6.3 | 0.4 | 1.6 | <=0.1 | 0.8 |
| 188 | 0.8 | 1.6 | <=0.1 | 3.1 | 0.8 | 0.8 | <=0.1 | NT | <=0.1 | <=0.1 |
| 189 | 1.6 | 3.1 | NT | 3.1 | 1.6 | 3.1 | 0.2 | NT | <=0.1 | 0.4 |
| 190 | 1.6 | 3.1 | 0.4 | 3.1 | 1.6 | 1.6 | <=0.1 | 0.4 | <=0.1 | 0.2 |
| 191 | 6.3 | 25 | 1.6 | 25 | 6.3 | 12.5 | <=0.1 | <=0.1 | <=0.1 | <=0.1 |
| 192 | 0.8 | 1.6 | 0.2 | 3.1 | 0.8 | 0.8 | <=0.1 | NT | <=0.1 | <=0.1 |
| 193 | 6.3 | 6.3 | 0.8 | 6.3 | 3.1 | 3.1 | 0.4 | 0.8 | <=0.1 | 0.4 |
| 194 | 6.3 | 25 | NT | 25 | 6.3 | 12.5 | 0.4 | 1.6 | <=0.1 | 1.6 |
| 195 | 6.3 | 12.5 | 1.6 | 12.5 | 6.3 | 12.5 | 0.2 | 0.8 | <=0.1 | 0.4 |
| 196 | 6.3 | 12.5 | 1.6 | 12.5 | 6.3 | 12.5 | 0.2 | 0.8 | <=0.1 | 0.4 |
| 197 | 1.6 | 3.1 | 0.4 | 6.3 | 1.6 | 3.1 | <=0.1 | 0.4 | <=0.1 | 0.2 |
| 198 | 3.1 | 6.3 | 0.8 | 12.5 | 3.1 | 6.3 | <=0.1 | 0.4 | <=0.1 | 0.2 |
| 199 | 0.2 | 0.4 | <=0.1 | 0.4 | 0.2 | 0.4 | <=0.1 | <=0.1 | <=0.1 | <=0.1 |
| 200 | 6.3 | 3.1 | 0.8 | 6.3 | 1.6 | 3.1 | <=0.1 | 0.2 | <=0.1 | 0.2 |
| 201 | 12.5 | 6.3 | 3.1 | 12.5 | 6.3 | 6.3 | 0.4 | 0.8 | <=0.1 | 0.4 |

-continued

| No | MH 6357 | MH 6374 | MH 10720 | MH 12587 | MH 13065 | MH 13093 | PM 6267 | PM 6391 | PM 10775 | PM 12080 |
|---|---|---|---|---|---|---|---|---|---|---|
| 202 | 0.8 | 3.1 | 0.2 | 3.1 | 1.6 | 1.6 | <=0.1 | NT | <=0.1 | <=0.1 |
| 203 | 1.6 | 1.6 | 0.2 | 3.1 | 0.8 | 1.6 | <=0.1 | NT | <=0.1 | <=0.1 |
| 204 | 0.4 | 0.4 | <=0.1 | 0.8 | 0.2 | 0.4 | <=0.1 | NT | <=0.1 | <=0.1 |
| 205 | 1.6 | 3.1 | 0.8 | 6.3 | 1.6 | 3.1 | 0.2 | 0.4 | <=0.1 | 0.4 |
| 206 | 3.1 | 3.1 | 0.8 | 6.3 | 3.1 | 6.3 | <=0.1 | 0.4 | <=0.1 | 0.2 |
| 207 | 12.5 | 12.5 | 3.1 | 12.5 | 6.3 | 12.5 | 0.2 | 0.8 | <=0.1 | 0.8 |
| 208 | 12.5 | 12.5 | 3.1 | 25 | 12.5 | 12.5 | 0.2 | 0.4 | <=0.1 | 0.2 |
| 209 | 3.1 | 6.3 | 1.6 | 12.5 | 6.3 | 12.5 | <=0.1 | 0.4 | <=0.1 | 0.2 |
| 210 | 1.6 | 3.1 | 0.8 | 6.3 | 1.6 | 3.1 | <=0.1 | 0.2 | <=0.1 | <=0.1 |
| 211 | 3.1 | 12.5 | 1.6 | 12.5 | 6.3 | 6.3 | <=0.1 | 0.2 | <=0.1 | <=0.1 |
| 212 | 3.1 | 6.3 | 0.8 | 12.5 | 3.1 | 12.5 | 0.2 | 0.4 | <=0.1 | 0.2 |
| 213 | 1.6 | 1.6 | 0.8 | 3.1 | 1.6 | 3.1 | <=0.1 | 0.4 | <=0.1 | 0.2 |
| 214 | 1.6 | 1.6 | 0.8 | 6.3 | 3.1 | 3.1 | 0.2 | 0.4 | <=0.1 | 0.4 |
| 215 | 3.1 | 3.1 | 0.8 | 6.3 | 3.1 | 6.3 | <=0.1 | <=0.1 | <=0.1 | <=0.1 |
| 216 | 1.6 | 3.1 | 0.8 | 3.1 | 1.6 | 3.1 | <=0.1 | 0.2 | <=0.1 | <=0.1 |
| 218 | 0.4 | 0.4 | <=0.1 | 0.8 | 0.4 | 0.4 | 0.4 | NT | NT | <=0.1 |
| 219 | 1.6 | 0.4 | <=0.1 | 1.6 | 0.4 | 0.8 | <=0.1 | <=0.1 | <=0.1 | <=0.1 |
| 220 | 3.1 | 0.8 | <=0.1 | 3.1 | 0.8 | 1.6 | <=0.1 | 0.4 | <=0.1 | 0.4 |
| 221 | 0.8 | 0.8 | <=0.1 | 3.1 | 1.6 | 1.6 | <=0.1 | 0.4 | <=0.1 | 0.4 |
| 222 | 0.8 | 1.6 | 0.2 | 1.6 | 1.6 | 1.6 | <=0.1 | <=0.1 | <=0.1 | 0.2 |
| 223 | 0.8 | 0.4 | <=0.1 | 0.8 | 0.4 | 0.4 | <=0.1 | <=0.1 | <=0.1 | <=0.1 |
| 224 | 0.8 | 0.8 | <=0.1 | 1.6 | 0.8 | 0.8 | <=0.1 | 0.4 | <=0.1 | <=0.1 |
| 225 | 12.5 | 6.3 | 1.6 | 12.5 | 12.5 | 12.5 | <=0.1 | 0.8 | NT | 0.8 |
| 226 | 3.1 | 3.1 | 0.8 | 12.5 | 3.1 | 6.3 | <=0.1 | 0.4 | <=0.1 | 0.4 |
| 227 | 12.5 | 12.5 | 1.6 | 25 | 6.3 | 12.5 | 0.4 | 0.8 | 0.2 | 0.8 |
| 228 | 0.8 | 0.4 | <=0.1 | 1.6 | 0.4 | 0.8 | <=0.1 | <=0.1 | <=0.1 | <=0.1 |
| 229 | 0.4 | 0.4 | <=0.1 | 0.4 | 0.2 | 0.4 | <=0.1 | <=0.1 | <=0.1 | <=0.1 |
| 230 | 0.8 | 0.4 | <=0.1 | 1.6 | 0.8 | 0.8 | <=0.1 | <=0.1 | <=0.1 | <=0.1 |
| 231 | 0.4 | 0.2 | <=0.1 | 0.8 | 0.2 | 0.4 | <=0.1 | <=0.1 | <=0.1 | <=0.1 |
| 232 | 0.4 | <=0.1 | <=0.1 | 0.4 | <=0.1 | 0.2 | <=0.1 | <=0.1 | <=0.1 | <=0.1 |
| 233 | 0.8 | 0.4 | <=0.1 | 1.6 | 0.4 | 0.8 | <=0.1 | 0.2 | <=0.1 | <=0.1 |
| 234 | 6.3 | 3.1 | 0.4 | 6.3 | 3.1 | 6.3 | <=0.1 | 0.4 | <=0.1 | 0.2 |
| 235 | 0.4 | 0.8 | <=0.1 | 1.6 | 0.4 | 0.4 | <=0.1 | <=0.1 | <=0.1 | <=0.1 |
| 236 | 0.8 | 0.8 | <=0.1 | 1.6 | 0.8 | 0.8 | <=0.1 | 0.4 | <=0.1 | 0.4 |
| 237 | 1.6 | 1.6 | 0.2 | 3.1 | 1.6 | 1.6 | 0.2 | 0.8 | <=0.1 | 0.4 |
| 238 | 1.6 | 3.1 | 0.8 | 3.1 | 1.6 | 1.6 | <=0.1 | <=0.1 | <=0.1 | <=0.1 |
| 239 | 0.8 | 1.6 | 0.2 | 1.6 | 0.8 | 0.8 | 0.2 | 0.4 | <=0.1 | 0.4 |
| 240 | 1.6 | 1.6 | 0.4 | 1.6 | 1.6 | 1.6 | 0.2 | 0.8 | 0.2 | 0.4 |
| 241 | 0.4 | 0.8 | <=0.1 | 0.8 | 0.4 | 0.4 | <=0.1 | <=0.1 | <=0.1 | <=0.1 |
| 242 | 6.3 | 6.3 | 0.8 | 6.3 | 3.1 | 3.1 | 0.4 | 1.6 | 0.2 | 0.8 |
| 243 | 3.1 | 3.1 | 0.4 | 3.1 | 1.6 | 1.6 | 0.2 | 0.8 | <=0.1 | 0.4 |
| 244 | 3.1 | 6.3 | 1.6 | 6.3 | 3.1 | 6.3 | 0.4 | 1.6 | 0.2 | 0.8 |
| 245 | 3.1 | 3.1 | 0.4 | 3.1 | 1.6 | 3.1 | 0.4 | 0.8 | <=0.1 | 0.8 |
| 246 | 0.4 | 0.8 | <=0.1 | 0.8 | 0.8 | 0.4 | <=0.1 | 0.2 | <=0.1 | 0.2 |
| 247 | 0.4 | 0.8 | 0.2 | 0.8 | 0.4 | 0.8 | <=0.1 | 0.8 | <=0.1 | 0.2 |
| 248 | 1.6 | 1.6 | 0.4 | 1.6 | 1.6 | 1.6 | 0.4 | 0.8 | 0.2 | 0.8 |
| 249 | 0.8 | 1.6 | 0.2 | 1.6 | 0.8 | 0.8 | 0.2 | 0.8 | <=0.1 | 0.4 |
| 250 | 0.4 | 0.8 | <=0.1 | 0.8 | 0.4 | 0.4 | <=0.1 | 0.2 | <=0.1 | <=0.1 |
| 251 | 0.8 | 0.8 | <=0.1 | 1.6 | 0.8 | 0.8 | <=0.1 | 0.2 | <=0.1 | <=0.1 |
| 252 | 1.6 | 3.1 | 0.4 | 3.1 | 1.6 | 1.6 | 0.4 | 0.8 | 0.4 | 0.8 |
| 253 | 3.1 | 3.1 | 0.8 | 3.1 | 1.6 | 3.1 | <=0.1 | 0.4 | <=0.1 | 0.4 |
| 254 | 0.8 | 1.6 | 0.2 | 1.6 | 0.8 | 0.8 | <=0.1 | 0.4 | <=0.1 | <=0.1 |
| 255 | 0.8 | 0.4 | <=0.1 | 1.6 | 0.4 | 0.8 | <=0.1 | <=0.1 | <=0.1 | <=0.1 |
| 256 | 1.6 | 0.8 | <=0.1 | 1.6 | 0.8 | 0.8 | <=0.1 | <=0.1 | <=0.1 | <=0.1 |
| 257 | 3.1 | 1.6 | 0.4 | 3.1 | 1.6 | 1.6 | <=0.1 | 0.2 | <=0.1 | <=0.1 |
| 258 | 1.6 | 1.6 | 0.2 | 1.6 | 0.8 | 1.6 | <=0.1 | <=0.1 | <=0.1 | <=0.1 |
| 259 | 0.8 | 0.4 | <=0.1 | 0.8 | 0.4 | 0.8 | <=0.1 | <=0.1 | <=0.1 | <=0.1 |
| 260 | 1.6 | 0.4 | <=0.1 | 1.6 | 0.4 | 0.8 | <=0.1 | <=0.1 | <=0.1 | <=0.1 |
| 261 | 0.4 | 0.4 | <=0.1 | 0.8 | 0.4 | 0.4 | <=0.1 | <=0.1 | <=0.1 | <=0.1 |
| 262 | 12.5 | 6.3 | 1.6 | 12.5 | 6.3 | 6.3 | <=0.1 | 0.4 | <=0.1 | 0.4 |
| 263 | 6.3 | 3.1 | 0.8 | 6.3 | 3.1 | 3.1 | <=0.1 | 0.4 | <=0.1 | 0.2 |
| 264 | 12.5 | 12.5 | 1.6 | 12.5 | 6.3 | 6.3 | 0.2 | 0.8 | <=0.1 | 0.4 |
| 265 | 6.3 | 6.3 | 0.8 | 6.3 | 3.1 | 3.1 | <=0.1 | 0.8 | <=0.1 | 0.4 |
| 266 | 0.8 | 0.4 | <=0.1 | 1.6 | 0.8 | 0.8 | <=0.1 | <=0.1 | <=0.1 | <=0.1 |
| 267 | 0.8 | 0.4 | <=0.1 | 1.6 | 0.8 | 0.8 | <=0.1 | <=0.1 | <=0.1 | <=0.1 |
| 268 | 0.4 | 0.4 | <=0.1 | 0.8 | 0.2 | 0.4 | <=0.1 | <=0.1 | <=0.1 | <=0.1 |
| 269 | 1.6 | 0.4 | <=0.1 | 1.6 | 1.6 | 0.8 | <=0.1 | <=0.1 | <=0.1 | <=0.1 |
| 270 | 0.8 | 0.2 | <=0.1 | 0.8 | 0.2 | 0.4 | <=0.1 | <=0.1 | <=0.1 | <=0.1 |
| 271 | 0.4 | 0.2 | <=0.1 | 0.8 | 0.2 | 0.4 | <=0.1 | <=0.1 | <=0.1 | <=0.1 |
| 272 | 0.8 | 0.4 | <=0.1 | 1.6 | 0.2 | 0.8 | <=0.1 | 0.2 | <=0.1 | <=0.1 |
| 273 | 6.3 | 3.1 | 0.8 | 6.3 | 3.1 | 6.3 | <=0.1 | 0.2 | <=0.1 | <=0.1 |
| 274 | 0.2 | 0.2 | <=0.1 | 0.4 | 0.2 | 0.2 | <=0.1 | <=0.1 | <=0.1 | <=0.1 |
| 275 | 0.4 | 0.2 | <=0.1 | 0.4 | 0.2 | 0.4 | <=0.1 | <=0.1 | <=0.1 | <=0.1 |
| 276 | 0.8 | 0.8 | <=0.1 | 0.8 | 0.4 | 0.8 | <=0.1 | 0.4 | <=0.1 | <=0.1 |
| 277 | 1.6 | 1.6 | 0.4 | 3.1 | 1.6 | 1.6 | 0.4 | 0.8 | <=0.1 | 0.4 |
| 278 | 0.4 | 0.4 | <=0.1 | 0.8 | 0.4 | 0.4 | <=0.1 | <=0.1 | <=0.1 | <=0.1 |

-continued

| No | MH 6357 | MH 6374 | MH 10720 | MH 12587 | MH 13065 | MH 13093 | PM 6267 | PM 6391 | PM 10775 | PM 12080 |
|---|---|---|---|---|---|---|---|---|---|---|
| 279 | 3.1 | 6.3 | 1.6 | 6.3 | 6.3 | 6.3 | 0.4 | 1.6 | 0.4 | 1.6 |
| 280 | 1.6 | 0.8 | <=0.1 | 3.1 | 1.6 | 1.6 | <=0.1 | 0.4 | <=0.1 | 0.2 |
| 282 | 0.8 | 0.8 | <=0.1 | 1.6 | 0.4 | 1.6 | 0.8 | 0.4 | 0.4 | 0.2 |
| 283 | 3.1 | 3.1 | 0.2 | 6.3 | 1.6 | 3.1 | 3.1 | 1.6 | 0.2 | 0.8 |
| 284 | 0.4 | 0.8 | <=0.1 | 1.6 | 0.2 | 0.8 | 0.8 | 0.4 | <=0.1 | <=0.1 |
| 285 | 1.6 | 3.1 | <=0.1 | 6.3 | 1.6 | 3.1 | 3.1 | 1.6 | 0.2 | 0.8 |
| 286 | 0.4 | 0.8 | <=0.1 | 1.6 | 0.4 | 0.8 | 0.8 | 0.8 | <=0.1 | <=0.1 |
| 287 | 0.4 | 0.8 | <=0.1 | 1.6 | 0.8 | 0.8 | 0.8 | 0.4 | <=0.1 | <=0.1 |
| 288 | 0.4 | 0.8 | <=0.1 | 0.8 | 0.4 | 0.8 | 0.4 | <=0.1 | <=0.1 | <=0.1 |
| 289 | 0.4 | 0.8 | <=0.1 | 1.6 | 0.8 | 0.8 | 0.8 | 0.4 | 0.4 | <=0.1 |
| 290 | <=0.1 | <=0.1 | <=0.1 | 0.4 | <=0.1 | 0.2 | <=0.1 | 0.2 | <=0.1 | <=0.1 |
| 291 | <=0.1 | <=0.1 | <=0.1 | 0.8 | 0.4 | 0.4 | 0.8 | 0.4 | <=0.1 | <=0.1 |
| 292 | 0.4 | 0.8 | <=0.1 | 1.6 | 0.8 | 1.6 | 1.6 | 0.8 | <=0.1 | 0.4 |
| 293 | 0.4 | 0.8 | <=0.1 | 0.8 | 0.4 | 0.8 | 1.6 | 0.2 | <=0.1 | <=0.1 |
| 294 | <=0.1 | 0.2 | <=0.1 | 0.4 | <=0.1 | 0.4 | 0.8 | 0.2 | <=0.1 | <=0.1 |
| 295 | <=0.1 | 0.4 | <=0.1 | 0.8 | 0.2 | 0.4 | 0.8 | 0.4 | <=0.1 | <=0.1 |
| 296 | <=0.1 | 0.2 | <=0.1 | 0.4 | <=0.1 | 0.4 | 0.8 | <=0.1 | <=0.1 | <=0.1 |
| 297 | 0.2 | 0.4 | <=0.1 | 0.8 | 0.4 | 0.4 | 0.4 | <=0.1 | <=0.1 | 0.2 |
| 298 | <=0.1 | 0.2 | <=0.1 | 0.4 | 0.2 | 0.4 | 0.4 | <=0.1 | <=0.1 | <=0.1 |
| 299 | 0.2 | 0.4 | <=0.1 | 0.8 | 0.4 | 0.4 | 0.4 | <=0.1 | <=0.1 | 0.4 |
| 300 | 0.4 | 0.8 | <=0.1 | 0.8 | 0.4 | 0.8 | 0.4 | <=0.1 | <=0.1 | 0.4 |
| 301 | 0.4 | 0.8 | <=0.1 | 0.8 | 0.4 | 0.8 | 0.4 | 1.6 | <=0.1 | 0.4 |
| 302 | 0.4 | 0.8 | <=0.1 | 1.6 | 0.8 | 0.8 | 0.8 | 0.8 | <=0.1 | 0.4 |
| 303 | 0.2 | 1.6 | 0.4 | 1.6 | 1.6 | 1.6 | 1.6 | 0.4 | <=0.1 | 0.4 |
| 304 | 0.8 | 1.6 | <=0.1 | 1.6 | 1.6 | 3.1 | 1.6 | 1.6 | <=0.1 | 0.4 |
| 305 | 0.8 | 0.8 | 0.2 | 3.1 | 0.8 | 1.6 | 0.8 | 0.4 | <=0.1 | 0.4 |
| 306 | 0.8 | 0.8 | 0.2 | 3.1 | 0.8 | 0.8 | 0.8 | 0.4 | <=0.1 | 0.4 |
| 307 | 0.8 | 0.8 | <=0.1 | 1.6 | 0.8 | 1.6 | 0.8 | 0.4 | <=0.1 | 0.4 |
| 308 | 0.8 | 0.8 | <=0.1 | 1.6 | 0.8 | 1.6 | 0.8 | 0.4 | <=0.1 | 0.4 |
| 309 | 0.8 | 0.8 | <=0.1 | 1.6 | 0.8 | 1.6 | 1.6 | 0.4 | <=0.1 | 0.4 |
| 310 | 1.6 | 0.8 | 0.4 | 3.1 | 1.6 | 1.6 | 1.6 | 0.4 | 0.4 | 0.8 |
| 311 | 0.2 | <=0.1 | <=0.1 | 0.4 | <=0.1 | 0.4 | 0.4 | <=0.1 | <=0.1 | <=0.1 |
| 312 | 0.4 | 0.4 | <=0.1 | 0.8 | 0.4 | 0.8 | 0.4 | <=0.1 | <=0.1 | <=0.1 |
| 313 | 0.4 | 1.6 | <=0.1 | 1.6 | 0.4 | 0.8 | 0.2 | <=0.1 | <=0.1 | <=0.1 |
| 314 | 0.4 | 1.6 | <=0.1 | 0.8 | 0.4 | 0.8 | 0.4 | <=0.1 | <=0.1 | <=0.1 |
| 315 | <=0.1 | <=0.1 | <=0.1 | 0.4 | <=0.1 | 0.4 | 0.2 | <=0.1 | <=0.1 | <=0.1 |
| 316 | <=0.1 | 0.2 | <=0.1 | 0.8 | 0.2 | 0.4 | 0.2 | <=0.1 | <=0.1 | <=0.1 |
| 317 | 0.2 | 0.4 | <=0.1 | 0.8 | 0.4 | 0.4 | 0.2 | <=0.1 | <=0.1 | <=0.1 |
| 318 | 0.4 | 0.8 | <=0.1 | 1.6 | 0.8 | 1.6 | 0.8 | 0.8 | <=0.1 | 0.2 |
| 319 | 0.2 | 0.2 | <=0.1 | 0.8 | 0.4 | 0.4 | 0.2 | <=0.1 | <=0.1 | <=0.1 |
| 320 | 0.2 | <=0.1 | <=0.1 | 0.8 | 0.2 | 0.4 | 0.2 | <=0.1 | <=0.1 | <=0.1 |
| 321 | <=0.1 | <=0.1 | <=0.1 | 0.4 | 0.2 | 0.2 | <=0.1 | <=0.1 | <=0.1 | <=0.1 |
| 322 | 0.4 | 1.6 | <=0.1 | 1.6 | 0.8 | 0.8 | 0.4 | 0.2 | <=0.1 | <=0.1 |
| 323 | 0.2 | 0.2 | <=0.1 | 0.8 | 0.4 | 0.8 | 0.2 | <=0.1 | <=0.1 | <=0.1 |
| 324 | 0.4 | 0.8 | <=0.1 | 1.6 | 0.8 | 1.6 | 0.4 | 0.4 | <=0.1 | 0.2 |
| 325 | 0.8 | 1.6 | 0.4 | 3.1 | 1.6 | 3.1 | 1.6 | 0.8 | <=0.1 | 0.8 |
| 326 | 3.1 | 6.3 | 0.8 | 12.5 | 3.1 | 6.3 | 3.1 | 0.4 | <=0.1 | 0.4 |
| 327 | 0.8 | 0.8 | <=0.1 | 1.6 | 0.4 | 0.8 | 0.4 | <=0.1 | <=0.1 | <=0.1 |
| 328 | 0.8 | 0.8 | <=0.1 | 1.6 | 0.8 | 0.8 | 0.8 | <=0.1 | <=0.1 | <=0.1 |
| 329 | 0.8 | 1.6 | <=0.1 | 3.1 | 0.8 | 1.6 | 0.8 | 0.4 | <=0.1 | 0.4 |
| 330 | 0.8 | 0.8 | 0.2 | 3.1 | 1.6 | 1.6 | 1.6 | 0.8 | <=0.1 | 0.4 |
| 331 | 1.6 | 3.1 | 0.4 | 6.3 | 3.1 | 6.3 | 3.1 | 1.6 | 0.4 | 1.6 |
| 332 | 0.4 | 0.4 | <=0.1 | 1.6 | 0.8 | 0.8 | 0.4 | 0.4 | <=0.1 | 0.2 |
| 333 | 0.4 | 0.8 | <=0.1 | 1.6 | 0.8 | 1.6 | 0.4 | 0.4 | <=0.1 | 0.2 |
| 334 | 0.4 | 0.4 | <=0.1 | 1.6 | 0.8 | 1.6 | 0.4 | 0.4 | <=0.1 | 0.2 |
| 335 | 0.4 | 0.8 | <=0.1 | 3.1 | 0.4 | 0.8 | 0.4 | 0.4 | <=0.1 | 0.2 |
| 336 | 0.8 | 0.8 | 0.2 | 3.1 | 1.6 | 1.6 | 0.8 | 1.6 | <=0.1 | 0.8 |
| 337 | 3.1 | 3.1 | 0.8 | 6.3 | 6.3 | 3.1 | 3.1 | 1.6 | 0.2 | 0.8 |
| 338 | 3.1 | 6.3 | 0.8 | 6.3 | 3.1 | 6.3 | 3.1 | 0.8 | <=0.1 | 0.4 |
| 339 | 0.8 | 1.6 | <=0.1 | 1.6 | 0.8 | 1.6 | 0.8 | 0.8 | <=0.1 | 0.2 |
| 340 | 0.8 | 1.6 | 0.4 | 3.1 | 1.6 | 1.6 | 1.6 | 1.6 | 0.2 | 0.8 |
| 341 | 0.8 | 1.6 | 0.2 | 3.1 | 1.6 | 1.6 | 1.6 | 0.8 | 0.2 | 0.4 |
| 342 | 1.6 | 3.1 | 0.4 | 6.3 | 3.1 | 3.1 | 1.6 | 1.6 | 0.2 | 0.8 |
| 343 | 3.1 | 3.1 | 0.4 | 6.3 | 3.1 | 6.3 | 3.1 | 6.3 | 0.4 | 1.6 |
| 344 | 0.4 | 0.8 | <=0.1 | 1.6 | 0.8 | 1.6 | 0.8 | 0.8 | <=0.1 | 0.4 |
| 345 | 0.8 | 1.6 | <=0.1 | 1.6 | 0.8 | 1.6 | 0.8 | 0.8 | <=0.1 | 0.4 |
| 346 | 6.3 | 6.3 | 0.8 | 12.5 | 6.3 | 12.5 | 6.3 | 3.1 | 0.4 | 1.6 |
| 347 | 0.8 | 1.6 | 0.2 | 3.1 | 1.6 | 1.6 | 1.6 | 0.8 | <=0.1 | 0.8 |
| 348 | 0.8 | 0.8 | <=0.1 | 3.1 | 0.8 | 0.8 | 0.8 | <=0.1 | <=0.1 | <=0.1 |
| 349 | 1.6 | 3.1 | 0.8 | 6.3 | 6.3 | 3.1 | 1.6 | 0.8 | <=0.1 | 0.4 |
| 350 | 6.3 | 6.3 | 1.6 | 12.5 | 6.3 | 6.3 | 6.3 | 0.8 | <=0.1 | 0.4 |
| 351 | 0.4 | 0.4 | <=0.1 | 1.6 | 1.6 | 0.8 | 0.4 | 0.4 | <=0.1 | <=0.1 |
| 352 | 0.8 | 0.8 | 0.2 | 3.1 | 1.6 | 1.6 | 0.8 | 0.4 | <=0.1 | 0.2 |
| 353 | 3.1 | 6.3 | 0.8 | 12.5 | 6.3 | 6.3 | 3.1 | 1.6 | 0.4 | 0.8 |
| 354 | 0.4 | 0.8 | 0.2 | 1.6 | 1.6 | 0.8 | 0.8 | 0.4 | <=0.1 | 0.2 |
| 355 | 0.8 | 1.6 | <=0.1 | 1.6 | 0.8 | 1.6 | 0.8 | 0.2 | <=0.1 | <=0.1 |

-continued

| No | MH 6357 | MH 6374 | MH 10720 | MH 12587 | MH 13065 | MH 13093 | PM 6267 | PM 6391 | PM 10775 | PM 12080 |
|---|---|---|---|---|---|---|---|---|---|---|
| 356 | 6.3 | 6.3 | 3.1 | 12.5 | 6.3 | 12.5 | 6.3 | 3.1 | 0.2 | 1.6 |
| 357 | 0.8 | 0.8 | <=0.1 | 1.6 | 0.8 | 1.6 | 0.8 | 0.4 | <=0.1 | 0.2 |
| 358 | 3.1 | 1.6 | 0.8 | 6.3 | 6.3 | 6.3 | 0.8 | 1.6 | 0.2 | 0.8 |
| 359 | 0.4 | 0.2 | <=0.1 | 0.4 | 0.2 | 0.4 | <=0.1 | <=0.1 | 0.2 | <=0.1 |
| 360 | 0.8 | 1.6 | 0.8 | 6.3 | 1.6 | 6.3 | 0.4 | 1.6 | <=0.1 | 0.4 |
| 361 | 3.1 | 0.8 | 0.4 | 3.1 | 1.6 | 3.1 | 0.4 | 0.4 | <=0.1 | 0.2 |
| 362 | 3.1 | 0.8 | 0.4 | 3.1 | 1.6 | 3.1 | 0.2 | 0.4 | <=0.1 | 0.2 |
| 363 | 6.3 | 6.3 | 3.1 | 25 | 12.5 | 25 | 1.6 | 3.1 | 0.4 | 1.6 |
| 364 | 0.8 | 0.8 | 0.2 | 1.6 | 0.8 | 0.8 | 0.4 | 0.4 | <=0.1 | <=0.1 |
| 365 | 0.8 | 0.8 | 0.2 | 3.1 | 1.6 | 1.6 | 0.4 | 0.4 | <=0.1 | <=0.1 |
| 366 | 0.8 | 0.8 | 0.2 | 1.6 | 0.8 | 1.6 | 0.4 | 0.4 | <=0.1 | 0.2 |
| 367 | 0.8 | 0.8 | 0.4 | 3.1 | 1.6 | 3.1 | 0.4 | 0.4 | <=0.1 | 0.2 |
| 368 | 0.8 | 0.8 | 0.4 | 1.6 | 0.8 | 1.6 | 0.4 | 0.4 | <=0.1 | 0.2 |
| 369 | 0.4 | 0.2 | <=0.1 | 0.4 | 0.4 | 0.4 | <=0.1 | <=0.1 | <=0.1 | <=0.1 |
| 370 | 0.8 | 1.6 | 0.8 | 3.1 | 1.6 | 3.1 | 0.2 | 0.4 | <=0.1 | 0.2 |
| 371 | 1.6 | 1.6 | 0.8 | 3.1 | 1.6 | 3.1 | 0.2 | 0.2 | <=0.1 | 0.2 |
| 372 | 6.3 | 12.5 | 3.1 | 25 | 12.5 | 25 | 1.6 | 1.6 | 0.4 | 0.8 |
| 373 | 1.6 | 3.1 | 0.4 | 6.3 | 3.1 | 3.1 | 0.4 | 0.8 | <=0.1 | 0.4 |
| 374 | 0.8 | 0.8 | 0.4 | 3.1 | 1.6 | 3.1 | 0.2 | 0.2 | <=0.1 | <=0.1 |
| 375 | 1.6 | 3.1 | 0.8 | 6.3 | 3.1 | 6.3 | 0.8 | 1.6 | <=0.1 | 3.1 |
| 376 | 1.6 | 3.1 | 0.8 | 6.3 | 3.1 | 6.3 | 0.8 | 1.6 | <=0.1 | 1.6 |
| 378 | 0.8 | 0.8 | 0.4 | 0.2 | 0.8 | 0.8 | 1.6 | <=0.1 | 0.4 | 0.2 |
| 379 | 0.8 | 1.6 | 0.8 | 0.4 | 1.6 | 1.6 | 3.1 | <=0.1 | 0.4 | 0.4 |
| 380 | 3.1 | 6.3 | 3.1 | 0.8 | 3.1 | 6.3 | 6.3 | 0.2 | 1.6 | 0.8 |
| 381 | 1.6 | 3.1 | 0.4 | 1.6 | 1.6 | 1.6 | 1.6 | <=0.1 | 0.2 | 0.2 |
| 382 | 0.8 | 1.6 | 0.8 | 0.2 | 0.8 | 0.8 | 0.8 | <=0.1 | 0.4 | 0.4 |
| 383 | 0.8 | 1.6 | 0.8 | 0.4 | 1.6 | 1.6 | 6.3 | <=0.1 | 0.8 | 0.4 |
| 384 | 6.3 | 12.5 | 3.1 | 1.6 | 6.3 | 6.3 | 12.5 | 0.4 | 3.1 | 1.6 |
| 385 | 3.1 | 6.3 | 1.6 | 1.6 | 3.1 | 6.3 | 25 | 0.2 | 0.8 | 0.4 |
| 386 | 12.5 | 12.5 | 1.6 | 1.6 | 12.5 | 12.5 | 50 | 0.4 | 1.6 | 0.4 |
| 387 | 6.3 | 6.3 | 3.1 | 1.6 | 6.3 | 3.1 | 25 | 0.4 | 1.6 | 0.2 |
| 388 | 0.4 | 0.8 | 0.8 | 0.2 | 0.8 | 0.8 | 3.1 | <=0.1 | 0.2 | <=0.1 |
| 389 | 0.8 | 1.6 | 0.8 | 0.4 | 1.6 | 1.6 | 3.1 | <=0.1 | 0.4 | 0.4 |
| 390 | 0.4 | 1.6 | 0.8 | 0.2 | 0.8 | 0.8 | 3.1 | <=0.1 | 0.4 | 0.2 |
| 391 | 0.4 | 0.4 | 0.4 | <=0.1 | 0.4 | 0.4 | 1.6 | <=0.1 | 0.4 | <=0.1 |
| 392 | 0.4 | 0.4 | 0.4 | <=0.1 | 0.4 | 0.4 | 1.6 | <=0.1 | 0.4 | <=0.1 |
| 393 | 0.8 | 1.6 | 0.8 | 0.4 | 6.3 | 6.3 | 6.3 | 0.2 | 0.8 | 0.4 |
| 394 | 3.1 | 6.3 | 1.6 | 0.8 | 3.1 | 3.1 | 6.3 | 0.2 | 0.8 | 0.4 |
| 395 | 0.4 | 0.8 | 0.4 | 0.2 | 0.8 | 0.8 | 3.1 | <=0.1 | 0.2 | 0.2 |
| 396 | 1.6 | 1.6 | 1.6 | 0.4 | 3.1 | 3.1 | 12.5 | <=0.1 | 0.8 | 0.4 |
| 398 | 6.3 | 6.3 | 6.3 | 1.6 | 12.5 | 25 | 25 | 0.2 | 3.1 | 1.6 |
| 399 | 3.1 | 6.3 | 1.6 | 1.6 | 6.3 | 6.3 | 25 | <=0.1 | 0.8 | 0.4 |
| 400 | 0.8 | 1.6 | 1.6 | 0.2 | 1.6 | 1.6 | 3.1 | <=0.1 | 0.8 | 0.4 |
| 401 | 1.6 | 1.6 | 3.1 | 0.4 | 1.6 | 1.6 | 6.3 | 0.2 | 1.6 | 0.8 |
| 402 | 6.3 | 12.5 | 6.3 | 1.6 | 6.3 | 6.3 | 50 | 0.8 | 3.1 | 1.6 |
| 403 | 25 | 12.5 | 12.5 | 6.3 | 25 | 25 | 100 | 0.8 | 6.3 | 3.1 |
| 404 | 12.5 | 12.5 | 6.3 | 3.1 | 25 | 50 | 25 | 0.4 | 3.1 | 1.6 |
| 405 | 25 | 50 | 6.3 | 12.5 | 0.8 | 25 | 100 | 0.8 | 3.1 | 0.8 |
| 406 | 12.5 | 25 | 6.3 | 1.6 | 25 | 12.5 | 25 | 0.2 | 3.1 | 3.1 |
| 407 | 3.1 | 6.3 | 6.3 | 1.6 | 6.3 | 6.3 | 25 | 0.2 | 1.6 | 0.8 |
| 408 | 1.6 | 1.6 | 1.6 | 0.4 | 1.6 | 1.6 | 6.3 | <=0.1 | 0.8 | 0.4 |
| 410 | 0.8 | 1.6 | 1.6 | 0.4 | 1.6 | 1.6 | 6.3 | <=0.1 | 0.8 | 0.4 |
| 411 | 0.4 | 0.8 | 0.8 | 0.2 | 0.8 | 0.8 | 3.1 | <=0.1 | 0.4 | 0.2 |
| 412 | 1.6 | 1.6 | 1.6 | 0.4 | 1.6 | 1.6 | 6.3 | <=0.1 | 0.4 | 0.2 |
| 413 | 12.5 | 12.5 | 3.1 | 6.3 | 6.3 | 25 | 50 | 0.2 | 0.4 | 0.4 |
| 414 | 0.8 | 1.6 | 0.8 | 0.4 | 0.8 | 1.6 | 6.3 | <=0.1 | 0.4 | <=0.1 |
| 415 | 0.4 | 0.8 | 0.4 | 0.2 | 0.4 | 0.4 | 1.6 | <=0.1 | <=0.1 | <=0.1 |

NT = not tested

Example 14

In-Vitro Susceptibility Testing of Representative Compounds

The in vitro activity of representative compounds of the current invention are tested against bacterial isolates of different species:

The Minimum inhibitory concentrations (MIC) of compounds according to the invention are determined by the broth-microdilution method according to CLSI document VET01-A4.

Microdilution trays containing a doubling dilution series of the test compound are used for the tests.

The MIC results are interpreted according to the CLSI documents VET01-S3. The lowest concentration of compound at which no visible growth (i.e. no turbidity) detected by the unaided eye is recorded as the MIC.

The following pathogens/strains are tested:

| ID | Species | Ext. RefNo. | Remarks |
|---|---|---|---|
| MH 6357 | Mannheimia haemolytica | M7/2 | Reference strain (cattle infection strain) |
| MH 6374 | Mannheimia haemolytica | ATCC 33396 | Reference strain |
| PM 6267 | Pasteurella multocida | P 2225 (L386) | Reference strain (mouse infection strain) |
| PM 6391 | Pasteurella multocida | ATCC 43137 | Reference strain |
| SA 5816 | Staphylococcus aureus | 2139 | Mastitis field isolate |
| SA 6114 | Staphylococcus aureus | ATCC 29213 | Reference strain |
| MH 10720 | Mannheimia haemolytica | 154 | BRD field isolate |
| MH 12180 | Mannheimia haemolytica | KLI-02944 | BRD field isolate |
| MH 12587 | Mannheimia haemolytica | 1071 | BRD field isolate, macrolide-resistance: erm+, E+ |
| PM 10775 | Pasteurella multocida | 080130003051 | BRD field isolate |
| PM 12080 | Pasteurella multocida | IV102277-0093 | BRD field isolate |
| PM 14426 | Pasteurella multocida | 0006-439 | BRD field isolate macrolide-resistant |
| AB 15919 | Acinetobacter baumanii | IV369-2012 | Dermatitis field isolate |
| AB 16496 | Acinetobacter baumanii | ATCC 19606 | Reference strain |

Example 15

In Vitro Activity Against Bacteria Isolated from Respiratory Tract of Swine and Cattle Suffering from Respiratory Disease Collected in Different European Countries The in vitro activity of compounds against 20 isolates of Actinobacillus (A.) pleuropneumoniae, 20 of Bordetella (B.) bronchiseptica, 20 of Histophilus (H.) somni, 40 of Mannheimia (M.) haemolytica and 40 of Pasteurella (P.) multocida collected in different European countries are determined. All bacteria are isolated from the respiratory tract of swine and cattle suffering from respiratory disease. All isolates were epidemiologically unrelated as specified by the different suppliers.

The minimum inhibitory concentrations (MIC) of compounds according to the invention are determined by the broth-microdilution method according to CLSI document VET01-A4.

Microdilution trays containing a doubling dilution series of the test compounds are used for the tests.

The MIC results are interpreted according to the CLSI documents VET01-S3. The lowest concentration of compound at which no visible growth (i.e. no turbidity) detected by the unaided eye is recorded as the MIC. The $MIC_{50}$ and $MIC_{90}$ represent the concentration at which minimum 50% or 90% of the isolates are inhibited.

Example 16

In Vitro Activity Haemophilus parasuis Isolated from the Respiratory Tract of Swine Suffering from Respiratory Disease The in vitro activity of representative compounds of this invention against 15 isolates of H. parasuis is determined. All strains are isolated from the respiratory tract of swine in different European countries The MICs for all isolates are determined by using the agar-dilution method according to CLSI document VET01-A4 [1] with the following modification: GC agar base is used instead of Mueller-Hinton agar base for the preparation of the agar-dilution plates.

Results are interpreted according to the CLSI document VET01-S3. The MIC is the lowest concentration of antimicrobial agent that completely inhibits colony formation, disregarding a single colony or a faint haze caused by inoculum.

Example 17

Determination of the In-Vivo Efficacy in a Mouse Septicemia Model with Pasteurella multocida The objective of this study was to determine the in-vivo efficacy of antibiotic compounds after subcutaneous (SC) administration in a septicemia mouse model with Pasteurella (P.) multocida.

Materials and Methods

BALB/c mice were allocated to groups consisting of 6 mice. The mice of all groups (excluding the uninfected control group) were infected intraperitoneally (IP) with $3.2 \times 10^2$ CFU (colony forming units) P. multocida L386, Serotype A:14, per animal in 0.2 mL PBS.

Mice of the uninfected control group received 0.2 mL of sterile Phosphate Buffered Saline (PBS) intraperitoneally.

One hour after infection, the mice were treated subcutaneously with 10 mg/kg bodyweight of a 1 mg/mL solution of compounds of the invention in a 10% solution of Captisol® in PBS. The negative control groups were treated SC with 0.2 mL of galenic diluent only. In the positive control group Enrofloxacin was used in a commercial formulation ad usum veterinarium (Baytril® 2.5%, Bayer Animal Health), that was diluted with physiological saline for injection to achieve a concentration of 1 mg/mL and was administered at a dosage of 10 mg/kg bodyweight. The clinical time course of the infection was observed.

Survival of the mice was recorded at the end of the animal phase (D+2). At this timepoint all remaining mice were euthanized. From all animals of this study, a liver tissue sample was taken for quantitative re-isolation of bacteria.

Results:

"Mouse survival" indicates the number of animals (x/6) that survived at the end of the in-vivo phase (D+2)

"Bacteriological cured" indicates that no bacteria were re-isolated from liver tissue (LOQ=100 CFU/g tissue). The following table 5-1 shows the results for representative compounds of the invention.

TABLE 5-1

| No of animals survived | | | No of animals bacteriological cured | | | | |
|---|---|---|---|---|---|---|---|
| 4 of 6 | 5 of 6 | 6 of 6 | 2 of 6 | 3 of 6 | 4 of 6 | 5 of 6 | 6 of 6 |
|  | C.236 |  |  | C.236 |  |  |  |
|  | C.237 |  | C.237 |  |  |  |  |
|  | C.255 |  |  |  | C.255 |  |  |
|  |  | C.256 |  |  |  |  |  |
|  |  | C.259 |  |  |  | C.259 |  |
|  |  | C.267 |  |  |  | C.267 |  |
| C.269 |  |  | C.269 |  |  |  |  |
|  |  | C.270 |  |  | C.270 |  |  |
|  | C.274 |  | C.274 |  |  |  |  |
| C.261 |  |  | C.261 |  |  |  |  |
| C.292 |  |  | C.292 |  |  |  |  |
| C.311 |  |  |  | C.311 |  |  |  |
|  |  | C.313 |  |  | C.313 |  |  |
| C.319 |  |  | C.319 |  |  |  |  |

Example 18

Antiinfective Efficacy of Subcutaneous Treatment in the *Mannheimia haemolytica* Cattle Lung Infection Model Material and Methods 15 male Holstein black pied cattle calves of ca. 4 months age are randomly assigned to the study groups ensuring an equal distribution of body weight. The animal weight is approximately 98-133.5 kg on D-1.

Calves are infected on Day 0 via intratracheal instillation of approximately 300 mL of a *M. haemolytica* PBS suspension containing approximately 3×10 CFU *M. haemolytica* in late log phase.

| Species | Ref.-no. | Serotype | ID | Origin/description |
|---|---|---|---|---|
| *M. haemolytica* | M7/2 | A:1 | 6357 | Isolate from cattle, United Kingdom |

Three animals each are treated one hour after infection by subcutaneous (SC) administration of a compound of the invention in an aqueous 30% (w/v) Captisol® solution for injection at a dose of 10 mg/kg BW.

The respective dose volume is injected on the sides of the thoracic wall. Injection volumes exceeding 10 mL are divided into one portion of 10 mL administered to the left side and the remaining rest administered at different injection sites on the other side. Animals in one control group are treated with a commercially available Enrofloxacin solution (Baytril® 10%, Bayer Animal Health) at the recommended dose of 10 mg/kg BW. The second control group is treated with the galenic diluent (30% (w/v) Captisol®, dissolved in water) as placebo.

Animals are observed for clinical parameters for two days. Food consumption is measured. Single individual blood samples are collected from the 12 animals at the following time points: D-1 (predose), 30 minutes, 2, 4, 6, 24 h and at D2 (ca. 45 h) after administration. After the day 2 blood sampling, the infected cattle are slaughtered. The lungs are weighted. Lung states and lung scores are observed morpholog ically.

At necropsy from animals treated with test items or the positive control, samples of epithelial lining fluid (ELF), lung tissue, and additionally tissue of liver and kidney are collected. From each lung two bacteriological swaps are taken from the left and right bronchus.

Epithelial lining fluid is collected by inserting sterile paper strips caudally behind the tracheal bifurcation directly onto the bronchial mucous membrane in the left and right bronchus and allowed to moisten with bronchial fluid. The paper strip is left in place (resting on the bronchial mucosa) for approximately 1 minute before being placed back into the plastic container.

From each lung two tissue samples are collected by clipping from at least two locations, one from morphologically unchanged tissue, one from the edge of pathomorphologically changed areas.

Plasma, ELF, lung tissue and additional tissue samples are analyzed for concentrations of Compound of the invention and Enrofloxacin/Ciprofloxacin respectively using a HPLC-MS/MS method.

Example 19

Antiinfective Efficacy of Subcutaneous Treatment in the *Mannheimia haemolytica* Cattle Lung Infection Model Unless otherwise described the study is conducted as described in Example 16.

Calves are infected via intratracheal instillation of appr. 300 mL of *M. haemolytica* PBS suspension containing approximately 4×10$^9$ CFU *M. haemolytica* in late log phase on Day 0.

Three animals each are treated one hour after infection by a single subcutaneous injection with 10 mg/kg of Compound of the invention, F40 (80 mg/mL in 10% Poloxamer 188).

Example 20

Antiinfective Efficacy of Subcutaneous Treatment in the *Mannheimia haemolytica* Cattle Lung Infection Model Material and Methods Unless otherwise described the study was conducted as described in Clinical Example 15

Calves are infected via intratracheal instillation of appr. 300 mL of *M. haemolytica* PBS suspension containing approximately 4×10$^9$ CFU *M. haemolytica* in late log phase on Day 0.

One hour later three animals each are treated with 10 mg/kg of Compound of the invention (80 mg/mL in 10% Poloxamer 188), . . . .

The invention claimed is:

1. A compound according to formula A:

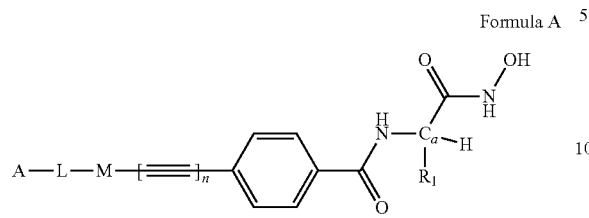

Formula A or a stereoisomer, pharmaceutically acceptable salt thereof, wherein the compound is selected from the group consisting of

| No | A | L | M |
|---|---|---|---|
| 1 | cyclopropylamine | —CH$_2$— | meta phenyl |
| 2 | (CH$_3$)$_2$CHNH— | —CH$_2$— | meta phenyl |
| 3 | CH$_2$CHCH$_2$NH— | —CH$_2$— | meta phenyl |
| 4 | (CH$_3$)$_3$CCH$_2$NH— | —CH$_2$— | meta phenyl |
| 5 | CH$_3$O(CH$_2$)$_2$NH— | —CH$_2$— | meta phenyl |
| 6 | (CH$_3$)$_2$N(CH$_2$)$_2$NH— | —CH$_2$— | meta phenyl |
| 7 | CO$_2$HCH$_2$NH— | —CH$_2$— | meta phenyl |
| 8 | (C$_2$H$_5$)$_2$N— | —CH$_2$— | meta phenyl |
| 9 | morpholine | —CH$_2$— | meta phenyl |
| 10 | 4-tert-butyl-piperidine | —CH$_2$— | meta phenyl |
| 11 | 4-phenyl-piperidine | —CH$_2$— | meta phenyl |
| 12 | 4-phenyl-piperazine | —CH$_2$— | meta phenyl |
| 13 | 1-(pyridin-2-yl)-piperazine | —CH$_2$— | meta phenyl |
| 14 | 1,2,3,4-tetrahydro-isoquinoline | —CH$_2$— | meta phenyl |
| 15 | heliamine | —CH$_2$— | meta phenyl |
| 16 | benzylamine | —CH$_2$— | meta phenyl |
| 17 | N-methylbenzylamine | —CH$_2$— | meta phenyl |
| 18 | 4-chlorobenzylamine | —CH$_2$— | meta phenyl |
| 19 | 4-methoxybenzylamine | —CH$_2$— | meta phenyl |
| 20 | 4-dimethylaminobenzylamine | —CH$_2$— | meta phenyl |
| 21 | 4-trifluoromethylbenzylamine | —CH$_2$— | meta phenyl |
| 22 | 4-pyridylmethanamine | —CH$_2$— | meta phenyl |
| 23 | 3,4-dimethylbenzylamine | —CH$_2$— | meta phenyl |
| 24 | cyclopropylamine | —CH$_2$— | meta phenyl |
| 25 | (CH$_3$)$_2$CHNH— | —CH$_2$— | meta phenyl |
| 26 | CH$_2$CHCH$_2$NH— | —CH$_2$— | meta phenyl |
| 27 | (CH$_3$)$_3$CCH$_2$NH— | —CH$_2$— | meta phenyl |
| 28 | CH$_3$O(CH$_2$)$_2$NH— | —CH$_2$— | meta phenyl |
| 29 | (CH$_3$)$_2$N(CH$_2$)$_2$NH— | —CH$_2$— | meta phenyl |
| 30 | CO$_2$HCH$_2$NH— | —CH$_2$— | meta phenyl |
| 31 | (C$_2$H$_5$)$_2$N— | —CH$_2$— | meta phenyl |
| 32 | morpholine | —CH$_2$— | meta phenyl |
| 33 | 1,1-dioxo-thiomorpholine | —CH$_2$— | meta phenyl |
| 34 | 4-tert-butyl-piperidine | —CH$_2$— | meta phenyl |
| 35 | 4-phenyl-piperidine | —CH$_2$— | meta phenyl |
| 36 | 4-phenyl-piperazine | —CH$_2$— | meta phenyl |
| 37 | 1-(pyridin-2-yl)-piperazine | —CH$_2$— | meta phenyl |
| 38 | 1,2,3,4-tetrahydro-isoquinoline | —CH$_2$— | meta phenyl |
| 39 | heliamine | —CH$_2$— | meta phenyl |
| 40 | benzylamine | —CH$_2$— | meta phenyl |
| 41 | N-methylbenzylamine | —CH$_2$— | meta phenyl |
| 42 | 4-chlorobenzylamine | —CH$_2$— | meta phenyl |
| 43 | 4-methoxybenzylamine | —CH$_2$— | meta phenyl |
| 44 | 4-dimethylaminobenzylamine | —CH$_2$— | meta phenyl |
| 45 | 4-trifluoromethylbenzylamine | —CH$_2$— | meta phenyl |
| 46 | 4-pyridylmethanamine | —CH$_2$— | meta phenyl |
| 47 | 3,4-dimethylbenzylamine | —CH$_2$— | meta phenyl |
| 48 | (CH$_3$)$_2$CHNH— | —CH$_2$— | meta phenyl |
| 49 | CH$_2$CHCH$_2$NH— | —CH$_2$— | meta phenyl |
| 50 | (CH$_3$)$_3$CCH$_2$NH— | —CH$_2$— | meta phenyl |
| 51 | CH$_3$O(CH$_2$)$_2$NH— | —CH$_2$— | meta phenyl |
| 52 | (CH$_3$)$_2$N(CH$_2$)$_2$NH— | —CH$_2$— | meta phenyl |
| 53 | CO$_2$HCH$_2$NH— | —CH$_2$— | meta phenyl |
| 54 | (C$_2$H$_5$)$_2$N— | —CH$_2$— | meta phenyl |
| 55 | morpholine | —CH$_2$— | meta phenyl |
| 56 | 1,1-dioxo-thiomorpholine | —CH$_2$— | meta phenyl |
| 57 | 4-tert-butyl-piperidine | —CH$_2$— | meta phenyl |
| 58 | 4-phenyl-piperidine | —CH$_2$— | meta phenyl |
| 59 | 4-phenyl-piperazine | —CH$_2$— | meta phenyl |
| 60 | 1-(pyridin-2-yl)-piperazine | —CH$_2$— | meta phenyl |
| 61 | 1,2,3,4-tetrahydro-isoquinoline | —CH$_2$— | meta phenyl |
| 62 | heliamine | —CH$_2$— | meta phenyl |
| 63 | benzylamine | —CH$_2$— | meta phenyl |
| 64 | N-methylbenzylamine | —CH$_2$— | meta phenyl |
| 65 | 4-chlorobenzylamine | —CH$_2$— | meta phenyl |
| 66 | 4-methoxybenzylamine | —CH$_2$— | meta phenyl |
| 67 | 4-dimethylaminobenzylamine | —CH$_2$— | meta phenyl |
| 68 | 4-trifluoromethylbenzylamine | —CH$_2$— | meta phenyl |
| 69 | 4-pyridylmethanamine | —CH$_2$— | meta phenyl |
| 70 | 3,4-dimethylbenzylamine | —CH$_2$— | meta phenyl |
| 71 | cyclopropylamine | —CH$_2$— | para phenyl |
| 72 | (CH$_3$)$_2$CHNH— | —CH$_2$— | para phenyl |
| 73 | CH$_2$CHCH$_2$NH— | —CH$_2$— | para phenyl |
| 74 | CH$_3$O(CH$_2$)$_2$NH— | —CH$_2$— | para phenyl |
| 75 | (CH$_3$)$_2$N(CH$_2$)$_2$NH— | —CH$_2$— | para phenyl |
| 76 | (C$_2$H$_5$)$_2$N— | —CH$_2$— | para phenyl |
| 77 | morpholine | —CH$_2$— | para phenyl |
| 78 | 1,1-dioxo-thiomorpholine | —CH$_2$— | para phenyl |
| 79 | 4-tert-butyl-piperidine | —CH$_2$— | para phenyl |
| 80 | 4-phenyl-piperidine | —CH$_2$— | para phenyl |
| 81 | 4-phenyl-piperazine | —CH$_2$— | para phenyl |
| 82 | 1-(pyridin-2-yl)-piperazine | —CH$_2$— | para phenyl |
| 83 | 1,2,3,4-tetrahydro-isoquinoline | —CH$_2$— | para phenyl |
| 84 | heliamine | —CH$_2$— | para phenyl |
| 85 | benzylamine | —CH$_2$— | para phenyl |
| 86 | N-methylbenzylamine | —CH$_2$— | para phenyl |
| 87 | 4-chlorobenzylamine | —CH$_2$— | para phenyl |
| 88 | 4-methoxybenzylamine | —CH$_2$— | para phenyl |
| 89 | 4-trifluoromethylbenzylamine | —CH$_2$— | para phenyl |
| 90 | 4-pyridylmethanamine | —CH$_2$— | para phenyl |
| 91 | 3,4-dimethylbenzylamine | —CH$_2$— | para phenyl |
| 92 | cyclopropylamine | —CH$_2$— | para phenyl |
| 93 | (CH$_3$)$_2$CHNH— | —CH$_2$— | para phenyl |
| 94 | CH$_2$CHCH$_2$NH— | —CH$_2$— | para phenyl |
| 95 | (CH$_3$)$_3$CCH$_2$NH— | —CH$_2$— | para phenyl |
| 96 | CH$_3$O(CH$_2$)$_2$NH— | —CH$_2$— | para phenyl |
| 97 | (C$_2$H$_5$)$_2$N— | —CH$_2$— | para phenyl |
| 98 | morpholine | —CH$_2$— | para phenyl |
| 99 | 1,1-dioxo-thiomorpholine | —CH$_2$— | para phenyl |
| 100 | 4-phenyl-piperidine | —CH$_2$— | para phenyl |
| 101 | 1-(pyridin-2-yl)-piperazine | —CH$_2$— | para phenyl |
| 102 | 1,2,3,4-tetrahydro-isoquinoline | —CH$_2$— | para phenyl |
| 103 | heliamine | —CH$_2$— | para phenyl |
| 104 | benzylamine | —CH$_2$— | para phenyl |
| 105 | N-methylbenzylamine | —CH$_2$— | para phenyl |
| 106 | 4-chlorobenzylamine | —CH$_2$— | para phenyl |
| 107 | 4-methoxybenzylamine | —CH$_2$— | para phenyl |
| 108 | 4-dimethylaminobenzylamine | —CH$_2$— | para phenyl |
| 109 | 4-trifluoromethylbenzylamine | —CH$_2$— | para phenyl |
| 110 | 4-pyridylmethanamine | —CH$_2$— | para phenyl |
| 111 | 3,4-dimethylbenzylamine | —CH$_2$— | para phenyl |
| 112 | cyclopropylamine | —CH$_2$— | para phenyl |
| 113 | CH$_2$CHCH$_2$NH— | —CH$_2$— | para phenyl |
| 114 | (CH$_3$)$_3$CCH$_2$NH— | —CH$_2$— | para phenyl |
| 115 | CH$_3$O(CH$_2$)$_2$NH— | —CH$_2$— | para phenyl |
| 116 | (CH$_3$)$_2$N(CH$_2$)$_2$NH— | —CH$_2$— | para phenyl |
| 117 | CO$_2$HCH$_2$NH— | —CH$_2$— | para phenyl |
| 118 | (C$_2$H$_5$)$_2$N— | —CH$_2$— | para phenyl |
| 119 | morpholine | —CH$_2$— | para phenyl |
| 120 | 4-tert-butyl-piperidine | —CH$_2$— | para phenyl |
| 121 | 4-phenyl-piperidine | —CH$_2$— | para phenyl |
| 122 | 4-phenyl-piperazine | —CH$_2$— | para phenyl |
| 123 | 1-(pyridin-2-yl)-piperazine | —CH$_2$— | para phenyl |
| 124 | 1,2,3,4-tetrahydro-isoquinoline | —CH$_2$— | para phenyl |
| 125 | heliamine | —CH$_2$— | para phenyl |
| 126 | benzylamine | —CH$_2$— | para phenyl |
| 127 | N-methylbenzylamine | —CH$_2$— | para phenyl |
| 128 | 4-chlorobenzylamine | —CH$_2$— | para phenyl |
| 129 | 4-methoxybenzylamine | —CH$_2$— | para phenyl |
| 130 | 4-dimethylaminobenzylamine | —CH$_2$— | para phenyl |

-continued

| | | | |
|---|---|---|---|
| 131 | 4-trifluoromethylbenzylamine | —CH$_2$— | para phenyl |
| 132 | 4-pyridylmethanamine | —CH$_2$— | para phenyl |
| 133 | 3,4-dimethylbenzylamine | —CH$_2$— | para phenyl |
| 134 | 4-dimethylaminobenzylamine | —CH$_2$— | para phenyl |
| 135 | 4-phenyl-piperazine | —CH$_2$— | para phenyl |
| 136 | (CH$_3$)$_3$CCH$_2$NH— | —CH$_2$— | para phenyl |
| 137 | CO$_2$HCH$_2$NH— | —CH$_2$— | para phenyl |
| 138 | (CH$_3$)$_2$N(CH$_2$)$_2$NH— | —CH$_2$— | para phenyl |
| 139 | CO$_2$HCH$_2$NH— | —CH$_2$— | para phenyl |
| 140 | 4-tert-butyl-piperidine | —CH$_2$— | para phenyl |
| 141 | (CH$_3$)$_2$CHNH— | —CH$_2$— | para phenyl |
| 142 | 1,1-dioxo-thiomorpholine | —CH$_2$— | para phenyl |
| 143 | 1,1-dioxo-thiomorpholine | —CH$_2$— | meta phenyl |
| 144 | cyclopropylamine | —CH$_2$— | meta phenyl |
| 145 | pyrrolidine | —CH$_2$— | para phenyl |
| 146 | N-methylpiperazine | —CH$_2$— | para phenyl |
| 147 | cyclobutylamine | —CH$_2$— | para phenyl |
| 148 | cyclopentylamine | —CH$_2$— | para phenyl |
| 149 | cyclohexylamine | —CH$_2$— | para phenyl |
| 150 | CH$_3$NH— | —CH$_2$— | para phenyl |
| 151 | C$_2$H$_5$NH— | —CH$_2$— | para phenyl |
| 152 | CH$_3$(CH$_2$)$_2$NH— | —CH$_2$— | para phenyl |
| 153 | CH$_3$O(CH$_2$)$_3$NH— | —CH$_2$— | para phenyl |
| 154 | CH$_3$O(CH$_2$)$_2$N(CH$_3$)— | —CH$_2$— | para phenyl |
| 155 | 2,6-dimethylmorpholine | —CH$_2$— | para phenyl |
| 156 | piperidine | —CH$_2$— | para phenyl |
| 157 | 3-pyridylmethanamine | —CH$_2$— | para phenyl |
| 158 | 2-pyridylmethanamine | —CH$_2$— | para phenyl |
| 159 | furfurylamine | —CH$_2$— | para phenyl |
| 160 | 2-thienylmethanamine | —CH$_2$— | para phenyl |
| 161 | 4-methylbenzylamine | —CH$_2$— | para phenyl |
| 162 | tetrahydrofurfurylamine | —CH$_2$— | para phenyl |
| 163 | imidazol-2-ylmethanamine | —CH$_2$— | para phenyl |
| 164 | CH$_3$OCH$_2$CH(CH$_3$)NH— | —CH$_2$— | para phenyl |
| 165 | 2,6-dimethylmorpholine | —CH$_2$— | para phenyl |
| 166 | piperidine | —CH$_2$— | para phenyl |
| 167 | 3-pyridylmethanamine | —CH$_2$— | para phenyl |
| 168 | (2-chloro-4-pyridyl)methanamine | —CH$_2$— | para phenyl |
| 169 | 2-pyridylmethanamine | —CH$_2$— | para phenyl |
| 170 | furfurylamine | —CH$_2$— | para phenyl |
| 171 | 2-thienylmethanamine | —CH$_2$— | para phenyl |
| 172 | 4-methylbenzylamine | —CH$_2$— | para phenyl |
| 173 | imidazol-2-ylmethanamine | —CH$_2$— | para phenyl |
| 174 | pyrrolidine | —CH$_2$— | para phenyl |
| 175 | N-methylpiperazine | —CH$_2$— | para phenyl |
| 176 | C$_2$H$_5$NH— | —CH$_2$— | para phenyl |
| 177 | CH$_3$O(CH$_2$)$_3$NH— | —CH$_2$— | para phenyl |
| 178 | CH$_3$O(CH$_2$)$_2$N(CH$_3$)— | —CH$_2$— | para phenyl |
| 179 | 3-pyridylmethanamine | —CH$_2$— | para phenyl |
| 180 | 2-pyridylmethanamine | —CH$_2$— | para phenyl |
| 181 | furfurylamine | —CH$_2$— | para phenyl |
| 182 | 2-thienylmethanamine | —CH$_2$— | para phenyl |
| 183 | tetrahydrofurfurylamine | —CH$_2$— | para phenyl |
| 184 | imidazol-2-ylmethanamine | —CH$_2$— | para phenyl |
| 185 | CH$_3$OCH$_2$CH(CH$_3$)NH— | —CH$_2$— | para phenyl |
| 186 | 1,4-oxazepane | —CH$_2$— | para phenyl |
| 187 | piperidine | —CH$_2$— | para phenyl |
| 188 | thiazol-2-ylmethanamine | —CH$_2$— | para phenyl |
| 189 | 4-methylbenzylamine | —CH$_2$— | para phenyl |
| 190 | (2-chloro-4-pyridyl)methanamine | —CH$_2$— | para phenyl |
| 191 | 2,6-dimethylmorpholine | —CH$_2$— | para phenyl |
| 192 | NCCH$_2$NH— | —CH$_2$— | para phenyl |
| 193 | CH$_3$(CH$_2$)$_2$NH— | —CH$_2$— | para phenyl |
| 194 | CH$_3$NH— | —CH$_2$— | para phenyl |
| 195 | cyclohexylamine | —CH$_2$— | para phenyl |
| 196 | cyclopentylamine | —CH$_2$— | para phenyl |
| 197 | cyclobutylamine | —CH$_2$— | para phenyl |
| 198 | CH$_3$OCH$_2$CH(CH$_3$)NH— | —CH$_2$— | para phenyl |
| 199 | thiazol-2-ylmethanamine | —CH$_2$— | para phenyl |
| 200 | tetrahydrofurfurylamine | —CH$_2$— | para phenyl |
| 201 | C$_2$H$_5$NH— | —CH$_2$— | para phenyl |
| 202 | 1,4-oxazepane | —CH$_2$— | para phenyl |
| 203 | CH$_3$O(CH$_2$)$_2$N(CH$_3$) | —CH$_2$— | para phenyl |
| 204 | NCCH$_2$NH— | —CH$_2$— | para phenyl |
| 205 | CH$_3$O(CH$_2$)$_3$NH— | —CH$_2$— | para phenyl |
| 206 | CH$_3$(CH$_2$)$_2$NH— | —CH$_2$— | para phenyl |
| 207 | CH$_3$NH— | —CH$_2$— | para phenyl |
| 208 | cyclohexylamine | —CH$_2$— | para phenyl |
| 209 | cyclopentylamine | —CH$_2$— | para phenyl |
| 210 | cyclobutylamine | —CH$_2$— | para phenyl |
| 211 | N-methylpiperazine | —CH$_2$— | para phenyl |
| 212 | pyrrolidine | —CH$_2$— | para phenyl |
| 213 | thiazol-2-ylmethanamine | —CH$_2$— | para phenyl |
| 214 | (2-chloro-4-pyridyl)methanamine | | |
| 215 | 1,4-oxazepane | —CH$_2$— | para phenyl |
| 216 | NCCH$_2$NH— | —CH$_2$— | para phenyl |
| 217 | morpholine | —CH$_2$— | ethenyl |
| 218 | cyclopropylamine | —CH$_2$— | para phenyl |
| 219 | cyclopropylamine | —CH$_2$— | para phenyl |
| 220 | CH$_2$CHCH$_2$NH— | —CH$_2$— | para phenyl |
| 221 | CH$_3$O(CH$_2$)$_2$NH— | —CH$_2$— | para phenyl |
| 222 | morpholine | —CH$_2$— | para phenyl |
| 223 | benzylamine | —CH$_2$— | para phenyl |
| 224 | 4-methoxybenzylamine | —CH$_2$— | para phenyl |
| 225 | pyrrolidine | —CH$_2$— | para phenyl |
| 226 | cyclobutylamine | —CH$_2$— | para phenyl |
| 227 | cyclopentylamine | —CH$_2$— | para phenyl |
| 228 | 3-pyridylmethanamine | —CH$_2$— | para phenyl |
| 229 | (2-chloro-4-pyridyl)methanamine | —CH$_2$— | para phenyl |
| 230 | 2-pyridylmethanamine | —CH$_2$— | para phenyl |
| 231 | furfurylamine | —CH$_2$— | para phenyl |
| 232 | 2-thienylmethanamine | —CH$_2$— | para phenyl |
| 233 | 4-methylbenzylamine | —CH$_2$— | para phenyl |
| 234 | tetrahydrofurfurylamine | —CH$_2$— | para phenyl |
| 235 | cyclopropylamine | —CH$_2$— | para phenyl |
| 236 | CH$_2$CHCH$_2$NH— | —CH$_2$— | para phenyl |
| 237 | CH$_3$O(CH$_2$)$_2$NH— | —CH$_2$— | para phenyl |
| 238 | morpholine | —CH$_2$— | para phenyl |
| 239 | benzylamine | —CH$_2$— | para phenyl |
| 240 | 4-methoxybenzylamine | —CH$_2$— | para phenyl |
| 241 | 4-pyridylmethanamine | —CH$_2$— | para phenyl |
| 242 | pyrrolidine | —CH$_2$— | para phenyl |
| 243 | cyclobutylamine | —CH$_2$— | para phenyl |
| 244 | cyclopentylamine | —CH$_2$— | para phenyl |
| 245 | CH$_3$(CH$_2$)$_2$NH— | —CH$_2$— | para phenyl |
| 246 | NCCH$_2$NH— | —CH$_2$— | para phenyl |
| 247 | 3-pyridylmethanamine | —CH$_2$— | para phenyl |
| 248 | (2-chloro-4-pyridyl)methanamine | —CH$_2$— | para phenyl |
| 249 | 2-pyridylmethanamine | —CH$_2$— | para phenyl |
| 250 | furfurylamine | —CH$_2$— | para phenyl |
| 251 | 2-thienylmethanamine | —CH$_2$— | para phenyl |
| 252 | 4-methylbenzylamine | —CH$_2$— | para phenyl |
| 253 | tetrahydrofurfurylamine | —CH$_2$— | para phenyl |
| 254 | thiazol-2-ylmethanamine | —CH$_2$— | para phenyl |
| 255 | cyclopropylamine | —CH$_2$— | para phenyl |
| 256 | CH$_2$CHCH$_2$NH— | —CH$_2$— | para phenyl |
| 257 | CH$_3$O(CH$_2$)$_2$NH— | —CH$_2$— | para phenyl |
| 258 | morpholine | —CH$_2$— | para phenyl |
| 259 | benzylamine | —CH$_2$— | para phenyl |
| 260 | 4-methoxybenzylamine | —CH$_2$— | para phenyl |
| 261 | 4-pyridylmethanamine | —CH$_2$— | para phenyl |
| 262 | pyrrolidine | —CH$_2$— | para phenyl |
| 263 | cyclobutylamine | —CH$_2$— | para phenyl |
| 264 | cyclopentylamine | —CH$_2$— | para phenyl |
| 265 | CH$_3$(CH$_2$)$_2$NH— | —CH$_2$— | para phenyl |
| 266 | NCCH$_2$NH— | —CH$_2$— | para phenyl |
| 267 | 3-pyridylmethanamine | —CH$_2$— | para phenyl |
| 268 | (2-chloro-4-pyridyl)methanamine | —CH$_2$— | para phenyl |
| 269 | 2-pyridylmethanamine | —CH$_2$— | para phenyl |
| 270 | furfurylamine | —CH$_2$— | para phenyl |
| 271 | 2-thienylmethanamine | —CH$_2$— | para phenyl |
| 272 | 4-methylbenzylamine | —CH$_2$— | para phenyl |
| 273 | tetrahydrofurfurylamine | —CH$_2$— | para phenyl |
| 274 | thiazol-2-ylmethanamine | —CH$_2$— | para phenyl |
| 275 | 4-pyridylmethanamine | —CH$_2$— | para phenyl |
| 276 | benzylamine | —CH$_2$— | para phenyl |
| 277 | 4-chlorobenzylamine | —CH$_2$— | para phenyl |
| 278 | 4-pyridylmethanamine | —CH$_2$— | para phenyl |
| 279 | 4-trifluoromethylbenzylamine | —CH$_2$— | para phenyl |
| 280 | CH$_2$CHCH$_2$NH— | —CH$_2$— | para phenyl |
| 281 | (CH$_3$)$_2$CHNH— | —CH$_2$— | para phenyl |
| 282 | 2-pyridylmethanamine | —CH$_2$— | para phenyl |

-continued

| No | | | |
|---|---|---|---|
| 283 | 4-methylbenzylamine | —CH$_2$— | para phenyl |
| 284 | 4-fluorobenzylamine | —CH$_2$— | para phenyl |
| 285 | CH$_3$O(CH$_2$)$_3$NH— | —CH$_2$— | para phenyl |
| 286 | 3-pyridylmethanamine | —CH$_2$— | para phenyl |
| 287 | furfurylamine | —CH$_2$— | para phenyl |
| 288 | CF$_3$CH$_2$NH— | —CH$_2$— | para phenyl |
| 289 | 2-thienylmethanamine | —CH$_2$— | para phenyl |
| 290 | cyclopropylamine | | thiophene |
| 291 | CH$_2$CHCH$_2$NH— | —CH$_2$— | thiophene |
| 292 | CH$_3$O(CH$_2$)$_2$NH— | —CH$_2$— | thiophene |
| 293 | morpholine | —CH$_2$— | thiophene |
| 294 | benzylamine | —CH$_2$— | thiophene |
| 295 | 4-methoxybenzylamine | —CH$_2$— | thiophene |
| 296 | 3-pyridylmethanamine | —CH$_2$— | thiophene |
| 297 | 2-pyridylmethanamine | —CH$_2$— | thiophene |
| 298 | furfurylamine | —CH$_2$— | thiophene |
| 299 | (5-methyloxazol-2-yl)methanamine | —CH$_2$— | thiophene |
| 300 | cyclopropylamine | —CH$_2$— | thiophene |
| 301 | CH$_2$CHCH$_2$NH— | —CH$_2$— | thiophene |
| 302 | CH$_3$O(CH$_2$)$_2$NH— | —CH$_2$— | thiophene |
| 303 | morpholine | —CH$_2$— | thiophene |
| 304 | benzylamine | —CH$_2$— | thiophene |
| 305 | 4-methoxybenzylamine | —CH$_2$— | thiophene |
| 306 | 3-pyridylmethanamine | —CH$_2$— | thiophene |
| 307 | 2-pyridylmethanamine | —CH$_2$— | thiophene |
| 308 | furfurylamine | —CH$_2$— | thiophene |
| 309 | CF$_3$CH$_2$NH— | —CH$_2$— | thiophene |
| 310 | (5-methyloxazol-2-yl)methanamine | —CH$_2$— | thiophene |
| 311 | cyclopropylamine | —CH$_2$— | thiophene |
| 312 | CH$_2$CHCH$_2$NH— | —CH$_2$— | thiophene |
| 313 | CH$_3$O(CH$_2$)$_2$NH— | —CH$_2$— | thiophene |
| 314 | morpholine | —CH$_2$— | thiophene |
| 315 | benzylamine | —CH$_2$— | thiophene |
| 316 | 4-methoxybenzylamine | —CH$_2$— | thiophene |
| 317 | 4-pyridylmethanamine | —CH$_2$— | thiophene |
| 318 | NCCH$_2$NH— | —CH$_2$— | thiophene |
| 319 | 3-pyridylmethanamine | —CH$_2$— | thiophene |
| 320 | 2-pyridylmethanamine | —CH$_2$— | thiophene |
| 321 | furfurylamine | —CH$_2$— | thiophene |
| 322 | 2-pyrimidinylmethanamine | —CH$_2$— | thiophene |
| 323 | (5-methyloxazol-2-yl)methanamine | —CH$_2$— | thiophene |
| 324 | cyclopropylamine | —CH$_2$— | pyridine |
| 325 | CH$_3$O(CH$_2$)$_2$NH— | —CH$_2$— | pyridine |
| 326 | morpholine | —CH$_2$— | pyridine |
| 327 | benzylamine | —CH$_2$— | pyridine |
| 328 | 4-methoxybenzylamine | —CH$_2$— | pyridine |
| 329 | 4-pyridylmethanamine | —CH$_2$— | pyridine |
| 330 | 3-pyridylmethanamine | —CH$_2$— | pyridine |
| 331 | 2-pyridylmethanamine | —CH$_2$— | pyridine |
| 332 | furfurylamine | —CH$_2$— | pyridine |
| 333 | CF$_3$CH$_2$NH— | —CH$_2$— | pyridine |
| 334 | (5-methyloxazol-2-yl)methanamine | —CH$_2$— | pyridine |
| 335 | cyclopropylamine | —CH$_2$— | pyridine |
| 336 | CH$_2$CHCH$_2$NH— | —CH$_2$— | pyridine |
| 337 | CH$_3$O(CH$_2$)$_2$NH— | —CH$_2$— | pyridine |
| 338 | morpholine | —CH$_2$— | pyridine |
| 339 | benzylamine | —CH$_2$— | pyridine |
| 340 | 4-methoxybenzylamine | —CH$_2$— | pyridine |
| 341 | 4-pyridylmethanamine | —CH$_2$— | pyridine |
| 342 | NCCH$_2$NH— | —CH$_2$— | pyridine |
| 343 | 2-pyridylmethanamine | —CH$_2$— | pyridine |
| 344 | furfurylamine | —CH$_2$— | pyridine |
| 345 | CF$_3$CH$_2$NH— | —CH$_2$— | pyridine |
| 346 | 2-pyrimidinylmethanamine | —CH$_2$— | pyridine |
| 347 | (5-methyloxazol-2-yl)methanamine | —CH$_2$— | pyridine |
| 348 | cyclopropylamine | —CH$_2$— | pyridine |
| 349 | CH$_3$O(CH$_2$)$_2$NH— | —CH$_2$— | pyridine |
| 350 | morpholine | —CH$_2$— | pyridine |
| 351 | benzylamine | —CH$_2$— | pyridine |
| 352 | 4-methoxybenzylamine | —CH$_2$— | pyridine |
| 353 | 2-pyridylmethanamine | —CH$_2$— | pyridine |
| 354 | furfurylamine | —CH$_2$— | pyridine |
| 355 | CF$_3$CH$_2$NH— | —CH$_2$— | pyridine |
| 356 | 2-pyrimidinylmethanamine | —CH$_2$— | pyridine |
| 357 | (5-methyloxazol-2-yl)methanamine | —CH$_2$— | pyridine |
| 358 | NCCH$_2$NH— | —CH$_2$— | thiophene |
| 359 | thiazol-2-ylmethanamine | —CH$_2$— | thiophene |
| 360 | 2-pyrimidinylmethanamine | —CH$_2$— | thiophene |
| 361 | CH$_2$CHCH$_2$NH— | —CH$_2$— | pyridine |
| 362 | thiazol-2-ylmethanamine | —CH$_2$— | pyridine |
| 363 | 2-pyrimidinylmethanamine | —CH$_2$— | pyridine |
| 364 | 4-pyridylmethanamine | —CH$_2$— | thiophene |
| 365 | thiazol-2-ylmethanamine | —CH$_2$— | thiophene |
| 366 | 2-pyrimidinylmethanamine | —CH$_2$— | thiophene |
| 367 | 3-pyridylmethanamine | —CH$_2$— | pyridine |
| 368 | thiazol-2-ylmethanamine | —CH$_2$— | pyridine |
| 369 | thiazol-2-ylmethanamine | —CH$_2$— | thiophene |
| 370 | CH$_2$CHCH$_2$NH— | —CH$_2$— | pyridine |
| 371 | 4-pyridylmethanamine | —CH$_2$— | pyridine |
| 372 | NCCH$_2$NH— | —CH$_2$— | pyridine |
| 373 | 3-pyridylmethanamine | —CH$_2$— | pyridine |
| 374 | thiazol-2-ylmethanamine | —CH$_2$— | pyridine |
| 375 | NO$_2$ | — | para phenyl |
| 376 | NH$_2$ | — | para phenyl |
| 377 | NO$_2$ | — | para phenyl |
| 378 | cyclopropylamine | —CH$_2$— | para phenyl |
| 379 | CH$_2$CHCH$_2$NH— | —CH$_2$— | para phenyl |
| 380 | CH$_3$O(CH$_2$)$_2$NH— | —CH$_2$— | para phenyl |
| 381 | morpholine | —CH$_2$— | para phenyl |
| 382 | benzylamine | —CH$_2$— | para phenyl |
| 383 | 4-methoxybenzylamine | —CH$_2$— | para phenyl |
| 384 | pyrrolidine | —CH$_2$— | para phenyl |
| 385 | cyclobutylamine | —CH$_2$— | para phenyl |
| 386 | cyclopentylamine | —CH$_2$— | para phenyl |
| 387 | CH$_3$(CH$_2$)$_2$NH— | —CH$_2$— | para phenyl |
| 388 | 3-pyridylmethanamine | —CH$_2$— | para phenyl |
| 389 | (2-chloro-4-pyridyl)methanamine | —CH$_2$— | para phenyl |
| 390 | 2-pyridylmethanamine | —CH$_2$— | para phenyl |
| 391 | furfurylamine | —CH$_2$— | para phenyl |
| 392 | 2-thienylmethanamine | —CH$_2$— | para phenyl |
| 393 | 4-methylbenzylamine | —CH$_2$— | para phenyl |
| 394 | tetrahydrofurfurylamine | —CH$_2$— | para phenyl |
| 395 | thiazol-2-ylmethanamine | —CH$_2$— | para phenyl |
| 396 | cyclopropylamine | —CH$_2$— | para phenyl |
| 397 | CH$_2$CHCH$_2$NH— | —CH$_2$— | para phenyl |
| 398 | CH$_3$O(CH$_2$)$_2$NH— | —CH$_2$— | para phenyl |
| 399 | morpholine | —CH$_2$— | para phenyl |
| 400 | benzylamine | —CH$_2$— | para phenyl |
| 401 | 4-methoxybenzylamine | —CH$_2$— | para phenyl |
| 402 | 4-pyridylmethanamine | —CH$_2$— | para phenyl |
| 403 | pyrrolidine | —CH$_2$— | para phenyl |
| 404 | cyclobutylamine | —CH$_2$— | para phenyl |
| 405 | cyclopentylamine | —CH$_2$— | para phenyl |
| 406 | CH$_3$(CH$_2$)$_2$NH— | —CH$_2$— | para phenyl |
| 407 | 3-pyridylmethanamine | —CH$_2$— | para phenyl |
| 408 | (2-chloro-4-pyridyl)methanamine | —CH$_2$— | para phenyl |
| 409 | 2-pyridylmethanamine | —CH$_2$— | para phenyl |
| 410 | furfurylamine | —CH$_2$— | para phenyl |
| 411 | 2-thienylmethanamine | —CH$_2$— | para phenyl |
| 412 | 4-methylbenzylamine | —CH$_2$— | para phenyl |
| 413 | tetrahydrofurfurylamine | —CH$_2$— | para phenyl |
| 414 | thiazol-2-ylmethanamine and | —CH$_2$— | para phenyl |
| 415 | 4-pyridylmethanamine | —CH$_2$— | para phenyl |

| No | n | R$_1$ | C$_a$ |
|---|---|---|---|
| 1 | 1 | —CH$_2$OH | (S) |
| 2 | 1 | —CH$_2$OH | (S) |
| 3 | 1 | —CH$_2$OH | (S) |
| 4 | 1 | —CH$_2$OH | (S) |
| 5 | 1 | —CH$_2$OH | (S) |
| 6 | 1 | —CH$_2$OH | (S) |
| 7 | 1 | —CH$_2$OH | (S) |
| 8 | 1 | —CH$_2$OH | (S) |
| 9 | 1 | —CH$_2$OH | (S) |
| 10 | 1 | —CH$_2$OH | (S) |
| 11 | 1 | —CH$_2$OH | (S) |
| 12 | 1 | —CH$_2$OH | (S) |
| 13 | 1 | —CH$_2$OH | (S) |

| | | | |
|---|---|---|---|
| 14 | 1 | —CH$_2$OH | (S) |
| 15 | 1 | —CH$_2$OH | (S) |
| 16 | 1 | —CH$_2$OH | (S) |
| 17 | 1 | —CH$_2$OH | (S) |
| 18 | 1 | —CH$_2$OH | (S) |
| 19 | 1 | —CH$_2$OH | (S) |
| 20 | 1 | —CH$_2$OH | (S) |
| 21 | 1 | —CH$_2$OH | (S) |
| 22 | 1 | —CH$_2$OH | (S) |
| 23 | 1 | —CH$_2$OH | (S) |
| 24 | 1 | —CH(CH$_3$)$_2$ | (S) |
| 25 | 1 | —CH(CH$_3$)$_2$ | (S) |
| 26 | 1 | —CH(CH$_3$)$_2$ | (S) |
| 27 | 1 | —CH(CH$_3$)$_2$ | (S) |
| 28 | 1 | —CH(CH$_3$)$_2$ | (S) |
| 29 | 1 | —CH(CH$_3$)$_2$ | (S) |
| 30 | 1 | —CH(CH$_3$)$_2$ | (S) |
| 31 | 1 | —CH(CH$_3$)$_2$ | (S) |
| 32 | 1 | —CH(CH$_3$)$_2$ | (S) |
| 33 | 1 | —CH(CH$_3$)$_2$ | (S) |
| 34 | 1 | —CH(CH$_3$)$_2$ | (S) |
| 35 | 1 | —CH(CH$_3$)$_2$ | (S) |
| 36 | 1 | —CH(CH$_3$)$_2$ | (S) |
| 37 | 1 | —CH(CH$_3$)$_2$ | (S) |
| 38 | 1 | —CH(CH$_3$)$_2$ | (S) |
| 39 | 1 | —CH(CH$_3$)$_2$ | (S) |
| 40 | 1 | —CH(CH$_3$)$_2$ | (S) |
| 41 | 1 | —CH(CH$_3$)$_2$ | (S) |
| 42 | 1 | —CH(CH$_3$)$_2$ | (S) |
| 43 | 1 | —CH(CH$_3$)$_2$ | (S) |
| 44 | 1 | —CH(CH$_3$)$_2$ | (S) |
| 45 | 1 | —CH(CH$_3$)$_2$ | (S) |
| 46 | 1 | —CH(CH$_3$)$_2$ | (S) |
| 47 | 1 | —CH(CH$_3$)$_2$ | (S) |
| 48 | 1 | (S)—CH(CH$_3$)C$_2$H$_5$ | (S) |
| 49 | 1 | (S)—CH(CH$_3$)C$_2$H$_5$ | (S) |
| 50 | 1 | (S)—CH(CH$_3$)C$_2$H$_5$ | (S) |
| 51 | 1 | (S)—CH(CH$_3$)C$_2$H$_5$ | (S) |
| 52 | 1 | (S)—CH(CH$_3$)C$_2$H$_5$ | (S) |
| 53 | 1 | (S)—CH(CH$_3$)C$_2$H$_5$ | (S) |
| 54 | 1 | (S)—CH(CH$_3$)C$_2$H$_5$ | (S) |
| 55 | 1 | (S)—CH(CH$_3$)C$_2$H$_5$ | (S) |
| 56 | 1 | (S)—CH(CH$_3$)C$_2$H$_5$ | (S) |
| 57 | 1 | (S)—CH(CH$_3$)C$_2$H$_5$ | (S) |
| 58 | 1 | (S)—CH(CH$_3$)C$_2$H$_5$ | (S) |
| 59 | 1 | (S)—CH(CH$_3$)C$_2$H$_5$ | (S) |
| 60 | 1 | (S)—CH(CH$_3$)C$_2$H$_5$ | (S) |
| 61 | 1 | (S)—CH(CH$_3$)C$_2$H$_5$ | (S) |
| 62 | 1 | (S)—CH(CH$_3$)C$_2$H$_5$ | (S) |
| 63 | 1 | (S)—CH(CH$_3$)C$_2$H$_5$ | (S) |
| 64 | 1 | (S)—CH(CH$_3$)C$_2$H$_5$ | (S) |
| 65 | 1 | (S)—CH(CH$_3$)C$_2$H$_5$ | (S) |
| 66 | 1 | (S)—CH(CH$_3$)C$_2$H$_5$ | (S) |
| 67 | 1 | (S)—CH(CH$_3$)C$_2$H$_5$ | (S) |
| 68 | 1 | (S)—CH(CH$_3$)C$_2$H$_5$ | (S) |
| 69 | 1 | (S)—CH(CH$_3$)C$_2$H$_5$ | (S) |
| 70 | 1 | (S)—CH(CH$_3$)C$_2$H$_5$ | (S) |
| 71 | 1 | —CH$_2$OH | (S) |
| 72 | 1 | —CH$_2$OH | (S) |
| 73 | 1 | —CH$_2$OH | (S) |
| 74 | 1 | —CH$_2$OH | (S) |
| 75 | 1 | —CH$_2$OH | (S) |
| 76 | 1 | —CH$_2$OH | (S) |
| 77 | 1 | —CH$_2$OH | (S) |
| 78 | 1 | —CH$_2$OH | (S) |
| 79 | 1 | —CH$_2$OH | (S) |
| 80 | 1 | —CH$_2$OH | (S) |
| 81 | 1 | —CH$_2$OH | (S) |
| 82 | 1 | —CH$_2$OH | (S) |
| 83 | 1 | —CH$_2$OH | (S) |
| 84 | 1 | —CH$_2$OH | (S) |
| 85 | 1 | —CH$_2$OH | (S) |
| 86 | 1 | —CH$_2$OH | (S) |
| 87 | 1 | —CH$_2$OH | (S) |
| 88 | 1 | —CH$_2$OH | (S) |
| 89 | 1 | —CH$_2$OH | (S) |
| 90 | 1 | —CH$_2$OH | (S) |
| 91 | 1 | —CH$_2$OH | (S) |
| 92 | 1 | —CH(CH$_3$)$_2$ | (S) |
| 93 | 1 | —CH(CH$_3$)$_2$ | (S) |
| 94 | 1 | —CH(CH$_3$)$_2$ | (S) |
| 95 | 1 | —CH(CH$_3$)$_2$ | (S) |
| 96 | 1 | —CH(CH$_3$)$_2$ | (S) |
| 97 | 1 | —CH(CH$_3$)$_2$ | (S) |
| 98 | 1 | —CH(CH$_3$)$_2$ | (S) |
| 99 | 1 | —CH(CH$_3$)$_2$ | (S) |
| 100 | 1 | —CH(CH$_3$)$_2$ | (S) |
| 101 | 1 | —CH(CH$_3$)$_2$ | (S) |
| 102 | 1 | —CH(CH$_3$)$_2$ | (S) |
| 103 | 1 | —CH(CH$_3$)$_2$ | (S) |
| 104 | 1 | —CH(CH$_3$)$_2$ | (S) |
| 105 | 1 | —CH(CH$_3$)$_2$ | (S) |
| 106 | 1 | —CH(CH$_3$)$_2$ | (S) |
| 107 | 1 | —CH(CH$_3$)$_2$ | (S) |
| 108 | 1 | —CH(CH$_3$)$_2$ | (S) |
| 109 | 1 | —CH(CH$_3$)$_2$ | (S) |
| 110 | 1 | —CH(CH$_3$)$_2$ | (S) |
| 111 | 1 | —CH(CH$_3$)$_2$ | (S) |
| 112 | 1 | (S)—CH(CH$_3$)C$_2$H$_5$ | (S) |
| 113 | 1 | (S)—CH(CH$_3$)C$_2$H$_5$ | (S) |
| 114 | 1 | (S)—CH(CH$_3$)C$_2$H$_5$ | (S) |
| 115 | 1 | (S)—CH(CH$_3$)C$_2$H$_5$ | (S) |
| 116 | 1 | (S)—CH(CH$_3$)C$_2$H$_5$ | (S) |
| 117 | 1 | (S)—CH(CH$_3$)C$_2$H$_5$ | (S) |
| 118 | 1 | (S)—CH(CH$_3$)C$_2$H$_5$ | (S) |
| 119 | 1 | (S)—CH(CH$_3$)C$_2$H$_5$ | (S) |
| 120 | 1 | (S)—CH(CH$_3$)C$_2$H$_5$ | (S) |
| 121 | 1 | (S)—CH(CH$_3$)C$_2$H$_5$ | (S) |
| 122 | 1 | (S)—CH(CH$_3$)C$_2$H$_5$ | (S) |
| 123 | 1 | (S)—CH(CH$_3$)C$_2$H$_5$ | (S) |
| 124 | 1 | (S)—CH(CH$_3$)C$_2$H$_5$ | (S) |
| 125 | 1 | (S)—CH(CH$_3$)C$_2$H$_5$ | (S) |
| 126 | 1 | (S)—CH(CH$_3$)C$_2$H$_5$ | (S) |
| 127 | 1 | (S)—CH(CH$_3$)C$_2$H$_5$ | (S) |
| 128 | 1 | (S)—CH(CH$_3$)C$_2$H$_5$ | (S) |
| 129 | 1 | (S)—CH(CH$_3$)C$_2$H$_5$ | (S) |
| 130 | 1 | (S)—CH(CH$_3$)C$_2$H$_5$ | (S) |
| 131 | 1 | (S)—CH(CH$_3$)C$_2$H$_5$ | (S) |
| 132 | 1 | (S)—CH(CH$_3$)C$_2$H$_5$ | (S) |
| 133 | 1 | (S)—CH(CH$_3$)C$_2$H$_5$ | (S) |
| 134 | 1 | —CH$_2$OH | (S) |
| 135 | 1 | —CH(CH$_3$)$_2$ | (S) |
| 136 | 1 | —CH$_2$OH | (S) |
| 137 | 1 | —CH$_2$OH | (S) |
| 138 | 1 | —CH(CH$_3$)$_2$ | (S) |
| 139 | 1 | —CH(CH$_3$)$_2$ | (S) |
| 140 | 1 | —CH(CH$_3$)$_2$ | (S) |
| 141 | 1 | (S)—CH(CH$_3$)C$_2$H$_5$ | (S) |
| 142 | 1 | (S)—CH(CH$_3$)C$_2$H$_5$ | (S) |
| 143 | 1 | —CH$_2$OH | (S) |
| 144 | 1 | (S)—CH(CH$_3$)C$_2$H$_5$ | (S) |
| 145 | 1 | —CH$_2$OH | (S) |
| 146 | 1 | —CH$_2$OH | (S) |
| 147 | 1 | —CH$_2$OH | (S) |
| 148 | 1 | —CH$_2$OH | (S) |
| 149 | 1 | —CH$_2$OH | (S) |
| 150 | 1 | —CH$_2$OH | (S) |
| 151 | 1 | —CH$_2$OH | (S) |
| 152 | 1 | —CH$_2$OH | (S) |
| 153 | 1 | —CH$_2$OH | (S) |
| 154 | 1 | —CH$_2$OH | (S) |
| 155 | 1 | —CH$_2$OH | (S) |
| 156 | 1 | —CH$_2$OH | (S) |
| 157 | 1 | —CH$_2$OH | (S) |
| 158 | 1 | —CH$_2$OH | (S) |
| 159 | 1 | —CH$_2$OH | (S) |
| 160 | 1 | —CH$_2$OH | (S) |
| 161 | 1 | —CH$_2$OH | (S) |
| 162 | 1 | —CH$_2$OH | (S) |
| 163 | 1 | —CH$_2$OH | (S) |
| 164 | 1 | —CH$_2$OH | (S) |
| 165 | 1 | —CH(CH$_3$)$_2$ | (S) |
| 166 | 1 | —CH(CH$_3$)$_2$ | (S) |
| 167 | 1 | —CH(CH$_3$)$_2$ | (S) |
| 168 | 1 | —CH(CH$_3$)$_2$ | (S) |
| 169 | 1 | —CH(CH$_3$)$_2$ | (S) |
| 170 | 1 | —CH(CH$_3$)$_2$ | (S) |
| 171 | 1 | —CH(CH$_3$)$_2$ | (S) |

| | | | |
|---|---|---|---|
| 172 | 1 | —CH(CH₃)₂ | (S) |
| 173 | 1 | —CH(CH₃)₂ | (S) |
| 174 | 1 | (S)—CH(CH₃)C₂H₅ | (S) |
| 175 | 1 | (S)—CH(CH₃)C₂H₅ | (S) |
| 176 | 1 | (S)—CH(CH₃)C₂H₅ | (S) |
| 177 | 1 | (S)—CH(CH₃)C₂H₅ | (S) |
| 178 | 1 | (S)—CH(CH₃)C₂H₅ | (S) |
| 179 | 1 | (S)—CH(CH₃)C₂H₅ | (S) |
| 180 | 1 | (S)—CH(CH₃)C₂H₅ | (S) |
| 181 | 1 | (S)—CH(CH₃)C₂H₅ | (S) |
| 182 | 1 | (S)—CH(CH₃)C₂H₅ | (S) |
| 183 | 1 | (S)—CH(CH₃)C₂H₅ | (S) |
| 184 | 1 | (S)—CH(CH₃)C₂H₅ | (S) |
| 185 | 1 | (S)—CH(CH₃)C₂H₅ | (S) |
| 186 | 1 | (S)—CH(CH₃)C₂H₅ | (S) |
| 187 | 1 | (S)—CH(CH₃)C₂H₅ | (S) |
| 188 | 1 | (S)—CH(CH₃)C₂H₅ | (S) |
| 189 | 1 | (S)—CH(CH₃)C₂H₅ | (S) |
| 190 | 1 | (S)—CH(CH₃)C₂H₅ | (S) |
| 191 | 1 | (S)—CH(CH₃)C₂H₅ | (S) |
| 192 | 1 | (S)—CH(CH₃)C₂H₅ | (S) |
| 193 | 1 | (S)—CH(CH₃)C₂H₅ | (S) |
| 194 | 1 | (S)—CH(CH₃)C₂H₅ | (S) |
| 195 | 1 | (S)—CH(CH₃)C₂H₅ | (S) |
| 196 | 1 | (S)—CH(CH₃)C₂H₅ | (S) |
| 197 | 1 | (S)—CH(CH₃)C₂H₅ | (S) |
| 198 | 1 | —CH(CH₃)₂ | (S) |
| 199 | 1 | —CH(CH₃)₂ | (S) |
| 200 | 1 | —CH(CH₃)₂ | (S) |
| 201 | 1 | —CH(CH₃)₂ | (S) |
| 202 | 1 | —CH(CH₃)₂ | (S) |
| 203 | 1 | —CH(CH₃)₂ | (S) |
| 204 | 1 | —CH(CH₃)₂ | (S) |
| 205 | 1 | —CH(CH₃)₂ | (S) |
| 206 | 1 | —CH(CH₃)₂ | (S) |
| 207 | 1 | —CH(CH₃)₂ | (S) |
| 208 | 1 | —CH(CH₃)₂ | (S) |
| 209 | 1 | —CH(CH₃)₂ | (S) |
| 210 | 1 | —CH(CH₃)₂ | (S) |
| 211 | 1 | —CH(CH₃)₂ | (S) |
| 212 | 1 | —CH(CH₃)₂ | (S) |
| 213 | 1 | —CH₂OH | (S) |
| 214 | 1 | —CH₂OH | (S) |
| 215 | 1 | —CH₂OH | (S) |
| 216 | 1 | —CH₂OH | (S) |
| 217 | 1 | —CH(CH₃)₂ | (S) |
| 218 | 1 | —C(CH₃)₂NO₂ | |
| 219 | 1 | —C(CH₃)₂OH | (S) |
| 220 | 1 | —C(CH₃)₂OH | (S) |
| 221 | 1 | —C(CH₃)₂OH | (S) |
| 222 | 1 | —C(CH₃)₂OH | (S) |
| 223 | 1 | —C(CH₃)₂OH | (S) |
| 224 | 1 | —C(CH₃)₂OH | (S) |
| 225 | 1 | —C(CH₃)₂OH | (S) |
| 226 | 1 | —C(CH₃)₂OH | (S) |
| 227 | 1 | —C(CH₃)₂OH | (S) |
| 228 | 1 | —C(CH₃)₂OH | (S) |
| 229 | 1 | —C(CH₃)₂OH | (S) |
| 230 | 1 | —C(CH₃)₂OH | (S) |
| 231 | 1 | —C(CH₃)₂OH | (S) |
| 232 | 1 | —C(CH₃)₂OH | (S) |
| 233 | 1 | —C(CH₃)₂OH | (S) |
| 234 | 1 | —C(CH₃)₂OH | (S) |
| 235 | 1 | —C(CH₃)₂SCH₃ | (R) |
| 236 | 1 | —C(CH₃)₂SCH₃ | (R) |
| 237 | 1 | —C(CH₃)₂SCH₃ | (R) |
| 238 | 1 | —C(CH₃)₂SCH₃ | (R) |
| 239 | 1 | —C(CH₃)₂SCH₃ | (R) |
| 240 | 1 | —C(CH₃)₂SCH₃ | (R) |
| 241 | 1 | —C(CH₃)₂SCH₃ | (R) |
| 242 | 1 | —C(CH₃)₂SCH₃ | (R) |
| 243 | 1 | —C(CH₃)₂SCH₃ | (R) |
| 244 | 1 | —C(CH₃)₂SCH₃ | (R) |
| 245 | 1 | —C(CH₃)₂SCH₃ | (R) |
| 246 | 1 | —C(CH₃)₂SCH₃ | (R) |
| 247 | 1 | —C(CH₃)₂SCH₃ | (R) |
| 248 | 1 | —C(CH₃)₂SCH₃ | (R) |
| 249 | 1 | —C(CH₃)₂SCH₃ | (R) |
| 250 | 1 | —C(CH₃)₂SCH₃ | (R) |
| 251 | 1 | —C(CH₃)₂SCH₃ | (R) |
| 252 | 1 | —C(CH₃)₂SCH₃ | (R) |
| 253 | 1 | —C(CH₃)₂SCH₃ | (R) |
| 254 | 1 | —C(CH₃)₂SCH₃ | (R) |
| 255 | 1 | —C(CH₃)₂SO₂CH₃ | (R) |
| 256 | 1 | —C(CH₃)₂SO₂CH₃ | (R) |
| 257 | 1 | —C(CH₃)₂SO₂CH₃ | (R) |
| 258 | 1 | —C(CH₃)₂SO₂CH₃ | (R) |
| 259 | 1 | —C(CH₃)₂SO₂CH₃ | (R) |
| 260 | 1 | —C(CH₃)₂SO₂CH₃ | (R) |
| 261 | 1 | —C(CH₃)₂SO₂CH₃ | (R) |
| 262 | 1 | —C(CH₃)₂SO₂CH₃ | (R) |
| 263 | 1 | —C(CH₃)₂SO₂CH₃ | (R) |
| 264 | 1 | —C(CH₃)₂SO₂CH₃ | (R) |
| 265 | 1 | —C(CH₃)₂SO₂CH₃ | (R) |
| 266 | 1 | —C(CH₃)₂SO₂CH₃ | (R) |
| 267 | 1 | —C(CH₃)₂SO₂CH₃ | (R) |
| 268 | 1 | —C(CH₃)₂SO₂CH₃ | (R) |
| 269 | 1 | —C(CH₃)₂SO₂CH₃ | (R) |
| 270 | 1 | —C(CH₃)₂SO₂CH₃ | (R) |
| 271 | 1 | —C(CH₃)₂SO₂CH₃ | (R) |
| 272 | 1 | —C(CH₃)₂SO₂CH₃ | (R) |
| 273 | 1 | —C(CH₃)₂SO₂CH₃ | (R) |
| 274 | 1 | —C(CH₃)₂SO₂CH₃ | (R) |
| 275 | 1 | —C(CH₃)₂OH | (S) |
| 276 | 1 | —C(CH₃)₂NO₂ | |
| 277 | 1 | —C(CH₃)₂NO₂ | |
| 278 | 1 | —C(CH₃)₂NO₂ | |
| 279 | 1 | —C(CH₃)₂NO₂ | |
| 280 | 1 | —C(CH₃)₂NO₂ | |
| 281 | 1 | —C(CH₃)₂NO₂ | |
| 282 | 1 | —C(CH₃)₂NO₂ | |
| 283 | 1 | —C(CH₃)₂NO₂ | |
| 284 | 1 | —C(CH₃)₂NO₂ | |
| 285 | 1 | —C(CH₃)₂NO₂ | |
| 286 | 1 | —C(CH₃)₂NO₂ | |
| 287 | 1 | —C(CH₃)₂NO₂ | |
| 288 | 1 | —C(CH₃)₂NO₂ | |
| 289 | 1 | —C(CH₃)₂NO₂ | |
| 290 | 1 | —C(CH₃)₂OH | (S) |
| 291 | 1 | —C(CH₃)₂OH | (S) |
| 292 | 1 | —C(CH₃)₂OH | (S) |
| 293 | 1 | —C(CH₃)₂OH | (S) |
| 294 | 1 | —C(CH₃)₂OH | (S) |
| 295 | 1 | —C(CH₃)₂OH | (S) |
| 296 | 1 | —C(CH₃)₂OH | (S) |
| 297 | 1 | —C(CH₃)₂OH | (S) |
| 298 | 1 | —C(CH₃)₂OH | (S) |
| 299 | 1 | —C(CH₃)₂OH | (S) |
| 300 | 1 | —C(CH₃)₂SCH₃ | (R) |
| 301 | 1 | —C(CH₃)₂SCH₃ | (R) |
| 302 | 1 | —C(CH₃)₂SCH₃ | (R) |
| 303 | 1 | —C(CH₃)₂SCH₃ | (R) |
| 304 | 1 | —C(CH₃)₂SCH₃ | (R) |
| 305 | 1 | —C(CH₃)₂SCH₃ | (R) |
| 306 | 1 | —C(CH₃)₂SCH₃ | (R) |
| 307 | 1 | —C(CH₃)₂SCH₃ | (R) |
| 308 | 1 | —C(CH₃)₂SCH₃ | (R) |
| 309 | 1 | —C(CH₃)₂SCH₃ | (R) |
| 310 | 1 | —C(CH₃)₂SCH₃ | (R) |
| 311 | 1 | —C(CH₃)₂SO₂CH₃ | (R) |
| 312 | 1 | —C(CH₃)₂SO₂CH₃ | (R) |
| 313 | 1 | —C(CH₃)₂SO₂CH₃ | (R) |
| 314 | 1 | —C(CH₃)₂SO₂CH₃ | (R) |
| 315 | 1 | —C(CH₃)₂SO₂CH₃ | (R) |
| 316 | 1 | —C(CH₃)₂SO₂CH₃ | (R) |
| 317 | 1 | —C(CH₃)₂SO₂CH₃ | (R) |
| 318 | 1 | —C(CH₃)₂SO₂CH₃ | (R) |
| 319 | 1 | —C(CH₃)₂SO₂CH₃ | (R) |
| 320 | 1 | —C(CH₃)₂SO₂CH₃ | (R) |
| 321 | 1 | —C(CH₃)₂SO₂CH₃ | (R) |
| 322 | 1 | —C(CH₃)₂SO₂CH₃ | (R) |
| 323 | 1 | —C(CH₃)₂SO₂CH₃ | (R) |
| 324 | 1 | —C(CH₃)₂OH | (S) |
| 325 | 1 | —C(CH₃)₂OH | (S) |
| 326 | 1 | —C(CH₃)₂OH | (S) |
| 327 | 1 | —C(CH₃)₂OH | (S) |
| 328 | 1 | —C(CH₃)₂OH | (S) |
| 329 | 1 | —C(CH₃)₂OH | (S) |

| | | | |
|---|---|---|---|
| 330 | 1 | —C(CH₃)₂OH | (S) |
| 331 | 1 | —C(CH₃)₂OH | (S) |
| 332 | 1 | —C(CH₃)₂OH | (S) |
| 333 | 1 | —C(CH₃)₂OH | (S) |
| 334 | 1 | —C(CH₃)₂OH | (S) |
| 335 | 1 | —C(CH₃)₂SCH₃ | (R) |
| 336 | 1 | —C(CH₃)₂SCH₃ | (R) |
| 337 | 1 | —C(CH₃)₂SCH₃ | (R) |
| 338 | 1 | —C(CH₃)₂SCH₃ | (R) |
| 339 | 1 | —C(CH₃)₂SCH₃ | (R) |
| 340 | 1 | —C(CH₃)₂SCH₃ | (R) |
| 341 | 1 | —C(CH₃)₂SCH₃ | (R) |
| 342 | 1 | —C(CH₃)₂SCH₃ | (R) |
| 343 | 1 | —C(CH₃)₂SCH₃ | (R) |
| 344 | 1 | —C(CH₃)₂SCH₃ | (R) |
| 345 | 1 | —C(CH₃)₂SCH₃ | (R) |
| 346 | 1 | —C(CH₃)₂SCH₃ | (R) |
| 347 | 1 | —C(CH₃)₂SCH₃ | (R) |
| 348 | 1 | —C(CH₃)₂SO₂CH₃ | (R) |
| 349 | 1 | —C(CH₃)₂SO₂CH₃ | (R) |
| 350 | 1 | —C(CH₃)₂SO₂CH₃ | (R) |
| 351 | 1 | —C(CH₃)₂SO₂CH₃ | (R) |
| 352 | 1 | —C(CH₃)₂SO₂CH₃ | (R) |
| 353 | 1 | —C(CH₃)₂SO₂CH₃ | (R) |
| 354 | 1 | —C(CH₃)₂SO₂CH₃ | (R) |
| 355 | 1 | —C(CH₃)₂SO₂CH₃ | (R) |
| 356 | 1 | —C(CH₃)₂SO₂CH₃ | (R) |
| 357 | 1 | —C(CH₃)₂SO₂CH₃ | (R) |
| 358 | 1 | —C(CH₃)₂OH | (S) |
| 359 | 1 | —C(CH₃)₂OH | (S) |
| 360 | 1 | —C(CH₃)₂OH | (S) |
| 361 | 1 | —C(CH₃)₂OH | (S) |
| 362 | 1 | —C(CH₃)₂OH | (S) |
| 363 | 1 | —C(CH₃)₂OH | (S) |
| 364 | 1 | —C(CH₃)₂SCH₃ | (R) |
| 365 | 1 | —C(CH₃)₂SCH₃ | (R) |
| 366 | 1 | —C(CH₃)₂SCH₃ | (R) |
| 367 | 1 | —C(CH₃)₂SCH₃ | (R) |
| 368 | 1 | —C(CH₃)₂SCH₃ | (R) |
| 369 | 1 | —C(CH₃)₂SO₂CH₃ | (R) |
| 370 | 1 | —C(CH₃)₂SO₂CH₃ | (R) |
| 371 | 1 | —C(CH₃)₂SO₂CH₃ | (R) |
| 372 | 1 | —C(CH₃)₂SO₂CH₃ | (R) |
| 373 | 1 | —C(CH₃)₂SO₂CH₃ | (R) |
| 374 | 1 | —C(CH₃)₂SO₂CH₃ | (R) |
| 375 | 1 | —CH₂OH | (S) |
| 376 | 1 | —CH₂OH | (S) |
| 377 | 1 | —CH(CH₃)₂ | (S) |
| 378 | 1 | —C(=NOCH₃)CH₃ | (S) |
| 379 | 1 | —C(=NOCH₃)CH₃ | (S) |
| 380 | 1 | —C(=NOCH₃)CH₃ | (S) |
| 381 | 1 | —C(=NOCH₃)CH₃ | (S) |
| 382 | 1 | —C(=NOCH₃)CH₃ | (S) |
| 383 | 1 | —C(=NOCH₃)CH₃ | (S) |
| 384 | 1 | —C(=NOCH₃)CH₃ | (S) |
| 385 | 1 | —C(=NOCH₃)CH₃ | (S) |
| 386 | 1 | —C(=NOCH₃)CH₃ | (S) |
| 387 | 1 | —C(=NOCH₃)CH₃ | (S) |
| 388 | 1 | —C(=NOCH₃)CH₃ | (S) |
| 389 | 1 | —C(=NOCH₃)CH₃ | (S) |
| 390 | 1 | —C(=NOCH₃)CH₃ | (S) |
| 391 | 1 | —C(=NOCH₃)CH₃ | (S) |
| 392 | 1 | —C(=NOCH₃)CH₃ | (S) |
| 393 | 1 | —C(=NOCH₃)CH₃ | (S) |
| 394 | 1 | —C(=NOCH₃)CH₃ | (S) |
| 395 | 1 | —C(=NOCH₃)CH₃ | (S) |
| 396 | 1 | —COCH₃ | (S) |
| 397 | 1 | —COCH₃ | (S) |
| 398 | 1 | —COCH₃ | (S) |
| 399 | 1 | —COCH₃ | (S) |
| 400 | 1 | —COCH₃ | (S) |
| 401 | 1 | —COCH₃ | (S) |
| 402 | 1 | —COCH₃ | (S) |
| 403 | 1 | —COCH₃ | (S) |
| 404 | 1 | —COCH₃ | (S) |
| 405 | 1 | —COCH₃ | (S) |
| 406 | 1 | —COCH₃ | (S) |
| 407 | 1 | —COCH₃ | (S) |
| 408 | 1 | —COCH₃ | (S) |
| 409 | 1 | —COCH₃ | (S) |
| 410 | 1 | —COCH₃ | (S) |
| 411 | 1 | —COCH₃ | (S) |
| 412 | 1 | —COCH₃ | (S) |
| 413 | 1 | —COCH₃ | (S) |
| 414 | 1 | —COCH₃ | (S) |
| 415 | 1 | —C(=NOCH₃)CH₃ | (S). |

2. A pharmaceutical composition comprising a compound according to claim 1 and a pharmaceutical acceptable carrier.

3. A method of treating an infection caused by a bacteria in an animal wherein the bacteria is at least one of the bacteria selected from the group *Pasteurella multocida*, *Mannheimia haemolytica* and *Histophilus somni*, comprising administering to an animal in need thereof an effective amount of the compound according to claim 1.

4. The method of treating according to claim 3 wherein the bacteria causes bovine respiratory disease or swine respiratory disease.

\* \* \* \* \*